US009909170B2

(12) United States Patent
Mitra et al.

(10) Patent No.: US 9,909,170 B2
(45) Date of Patent: *Mar. 6, 2018

(54) METHOD FOR MULTIPLEXED NUCLEIC ACID PATCH POLYMERASE CHAIN REACTION

(71) Applicant: Washington University, St. Louis, MO (US)

(72) Inventors: Robi M. Mitra, St. Louis, MO (US); Katherine E. Varley, St. Louis, MO (US)

(73) Assignee: WASHINGTON UNIVERSITY, Saint Louis, MO (US)

(*) Notice: Subject to any disclaimer, the term of this patent is extended or adjusted under 35 U.S.C. 154(b) by 427 days.

This patent is subject to a terminal disclaimer.

(21) Appl. No.: 14/599,056

(22) Filed: Jan. 16, 2015

(65) Prior Publication Data

US 2015/0197788 A1 Jul. 16, 2015

Related U.S. Application Data

(63) Continuation-in-part of application No. 13/556,590, filed on Jul. 24, 2012, now Pat. No. 8,936,912, which is a continuation of application No. 12/555,627, filed on Sep. 8, 2009, now Pat. No. 8,586,310.

(60) Provisional application No. 61/094,660, filed on Sep. 5, 2008.

(51) Int. Cl.
*C12Q 1/68* (2006.01)
*C12P 19/34* (2006.01)

(52) U.S. Cl.
CPC .............. *C12Q 1/686* (2013.01); *C12P 19/34* (2013.01); *C12Q 1/6853* (2013.01)

(58) Field of Classification Search
None
See application file for complete search history.

(56) References Cited

U.S. PATENT DOCUMENTS

| 6,143,527 | A | 11/2000 | Pachuk et al. |
|---|---|---|---|
| 6,221,598 | B1 * | 4/2001 | Schumm .............. C12Q 1/6827 435/6.11 |
| 2004/0058373 | A1 | 3/2004 | Winkler et al. |
| 2004/0068096 | A1 | 4/2004 | Tsuchihashi et al. |
| 2005/0084896 | A1 | 4/2005 | Yerramilli et al. |
| 2005/0100911 | A1 | 5/2005 | Patil et al. |
| 2005/0181394 | A1 | 8/2005 | Steemers et al. |
| 2005/0202519 | A1 | 9/2005 | Barthe et al. |
| 2006/0063163 | A1 | 3/2006 | Chen et al. |
| 2008/0194416 | A1 | 8/2008 | Chen |

(Continued)

FOREIGN PATENT DOCUMENTS

EP  0 744 470 A1  11/1996

OTHER PUBLICATIONS

NEBuffer Activity Chart for Restriction Enzymes [online] [retrieved on Aug. 16, 2005] retrieved from http://www.neb.com/nebecomm/tech_reference/restriction_enzymes/buffer_activity_restriction_enzymes.asp.*

(Continued)

*Primary Examiner* — Samuel C Woolwine
(74) *Attorney, Agent, or Firm* — Polsinelli PC

(57) ABSTRACT

The invention encompasses a method for amplifying at least two different nucleic acid sequences. In particular, the method encompasses a multiplexed nucleic acid patch polymerase chain reaction.

21 Claims, 22 Drawing Sheets
(2 of 22 Drawing Sheet(s) Filed in Color)

(56) References Cited

U.S. PATENT DOCUMENTS

| | | |
|---|---|---|
| 2010/0129874 A1 | 5/2010 | Mitra et al. |
| 2010/0143908 A1 | 6/2010 | Gillevet |
| 2012/0289414 A1 | 11/2012 | Mitra et al. |

OTHER PUBLICATIONS

Schwarz et al. Nucleic Acids Research 27(24):4792-4800 (1999).*
Notice of Allowance from related U.S. Appl. No. 13/556,590, dated Sep. 8, 2014; 5 pgs.
Office Action from related U.S. Appl. No. 13/556,590, dated Feb. 7, 2013; 16 pgs.
Office Action from related U.S. Appl. No. 13/556,590, dated Nov. 8, 2013; 10 pgs.
Office Action from related U.S. Appl. No. 13/556,590, dated Mar. 28, 2014; 10 pgs.
Okou et al., "Microarray-based genomic selection for high-throughput resequencing," Nature Methods, 2007, pp. 907-909, vol. 4, No. 11.
Parameswaran et al., "A pyrosequencing-tailored nucleotide barcode design unveils opportunities for large-scale sample multiplexing," Nucleic Acids Research, 2007, e130, 9 pgs., vol. 35, No. 19.
Porreca et al., "Multiplex amplification of large sets of human exons," Nature Methods, 2007, pp. 931-936, vol. 4, No. 11.
Reisinger et al., "Total synthesis of multi-kilobase DNA sequences from oligonucleotides," Nature Protocols, 2006, pp. 2596-2603, vol. 1, No. 6.
Ronaghi et al., "A Sequencing Method Based on Real-Time Pyrophosphate," Science, 1998, pp. 363-365, vol. 281, No. 5375.
Sjoblom et al., "The Consensus Coding Sequences of Human Breast and Colorectal Cancers," Science, 2006, pp. 268-274, vol. 314.
Suzuki et al., "Frequent epigenetic inactivation of Wnt antagonist genes in breast cancer," British Journal of Cancer, 2008, pp. 1147-1156, vol. 98, No. 6.
Taylor et al., "Ultradeep Bisulfite Sequencing Analysis of DNA Methylation Patterns in Multiple Gene Promoters by 454 Sequencing," Cancer Research, 2007, pp. 8511-8518, vol. 67, No. 18.
Tomii et al., "Aberrant promoter methylation of insulin-like growth factor binding protein-3 gene in human cancers," International Journal of Cancer, 2006, pp. 566-573, vol. 120.
Ushijima, "Detection and interpretation of altered methylation patterns in cancer cells," Nature Reviews, 2005, pp. 223-231, vol. 5.
Varley et al., "Nested Patch PCR enables highly multiplexed mutation discovery in candidate genes," Genome Research, 2008, pp. 1844-1850, vol. 18.
Varley et al., "Intra-tumor heterogeneity of MLH1 promoter methylation revealed by deep single molecule bisulfite sequencing," Nucleic Acids Research, 2009, pp. 4603-4612, vol. 37, No. 14.
Veigl et al., "Biallelic inactivation of hMLH1 by epigenetic gene silencing, a novel mechanism causing human MSI cancers," Proc. Natl. Acad. Sci. USA, 1998, pp. 8698-8702, vol. 95.
Weinstein, "Selected Genetic Disorders Affecting Ashkenazi Jewish Families," Family & Community Health, 2007, pp. 50-62, vol. 30, No. 1.
Widschwendter et al., "Association of Breast Cancer DNA Methylation Profiles with Hormone Receptor Status and Response to Tamoxifen," Cancer Research, 2004, pp. 3807-3813, vol. 64.
Wood et al., "The Genomic Landscapes of Human Breast and Colorectal Cancers," Science, 2007, pp. 1108-1113, vol. 318.
Akhras et al., "PathogenMip Assay: A Multiplex Pathogen Detection Assay," PloS ONE, 2007, e223, pp. 1-11, Issue 2.
Akhras et al., "Connector Inversion Probe Technology: A Powerful One-Primer Multiplex DNA Amplification System for Numerous Scientific Applications," PloS ONE, 2007, e915, pp. 1-6, Issue 9.
Albert et al., "Direct selection of human genomic loci by microarray hybridization," Nature Methods, 2007, pp. 903-905, vol. 4, No. 11.
Ball et al., "Targeted and genome-scale strategies reveal gene-body methylation signatures in human cells," Nature Biotechnology, 2009, pp. 361-368, vol. 27, No. 4.

Barany, "Genetic disease detection and DNA amplification using cloned thermostable ligase," Proc. Natl. Acad. Sci. USA, 1991, pp. 189-193, vol. 88.
Bashiardes et al., "Direct genomic selection," Nature Methods, 2005, pp. 63-69, vol. 2, No. 1.
Baylin et al., "Alterations in DNA Methylation: A Fundamental Aspect of Neoplasia," Advances in Cancer Research, 1998, pp. 141-196, vol. 72.
Chan et al., "Convergence of Mutation and Epigenetic Alterations Identifies Common Genes in Cancer That Predict for Poor Prognosis," PloS Medicine, 2008, e114, pp. 08023-0838, vol. 5, Issue 5.
Cokus et al., "Shotgun bisulfite sequencing of the *Arabidopsis* genome reveals DNA methylation patterning," Nature, 2008, pp. 215-219, vol. 452, No. 7184.
Dahl et al., "Multiplex amplification enabled by selective circularization of large sets of genomic DNA fragments," Nucleic Acids Research, 2005, e71, 7 pgs., vol. 33, No. 8.
Dahl et al., "Multigene amplification and massively parallel sequencing for cancer mutation discovery," PNAS, 2007, pp. 9387-9392, vol. 104, No. 22.
Deng et al., "Targeted bisulfite sequencing reveals changes in DNA methylation associated with nuclear reprogramming," Nature Biotechnology, 2009, pp. 353-360, vol. 27, No. 4.
Eads et al., "MethyLight: a high-throughput assay to measure DNA methylation," Nucleic Acids Research, 2000, e32, pp. i-viii, vol. 28, No. 8.
Ehrich et al., "Quantitative high-thoughput analysis of DNA methylation patterns by base-specific cleavage and mass spectrometry," PNAS, 2005, pp. 15785-15790, vol. 102, No. 44.
Elnifro et al., "Multiplex PCR: Optimization and Application in Diagnostic Virology," Clinical Microbiology Reviews, 2000, pp. 559-570, vol. 13, No. 4.
Esteller et al., "Inactivation of the DNA-Repair Gene MGMT and the Clinical Response of Gliomas to Alkylating Agents," The New England Journal of Medicine, 2000, pp. 1350-1354, vol. 343, No. 19.
Ewing et al., "Base-Calling of Automated Sequencer Traces Using Phred. I. Accuracy Assessment," Genome Research, 1998, pp. 175-185, vol. 8.
Ewing et al., "Base-Calling of Automated Sequencer Traces Using Phred. II. Error Probabilities," Genome Research, 1998, pp. 186-194, vol. 8.
Fackler et al., "Quantitative Multiplex Methylation-Specific PCR Analysis Doubles Detection of Tumor Cells in Breast Ductal Fluid," Clinical Cancer Research, 2006, pp. 3306-3310, vol. 12, No. 11.
Fan et al., "Highly parallel genomic assays," Nature Reviews, 2006, pp. 632-644, vol. 7.
Forster et al., "Synthetic biology projects in vitro," Genome Research, 2007, pp. 1-6, vol. 17.
Fredriksson et al., "Multiplex amplification of all coding sequences within 10 cancer genes by Gene-Collector," Nucleic Acids Research, 2007, e47, 6 pgs., vol. 35, No. 7.
Frommer et al., "A genomic sequencing protocol that yields a positive display of 5-methylcytosine residues in individual DNA strands," Proc. Natl. Acad. Sci. USA, 1992, pp. 1827-1831, vol. 89.
Furuyama et al., "DNA Sequencing Directly from a Mixture Using Terminal-Base-Selective Primers", DNA Research, 1994, pp. 231-237, vol. 1.
Greenman et al., "Patterns of somatic mutation in human cancer genomes," Nature, 2007, pp. 153-158, vol. 446.
Han et al., "Simultaneous Amplification and Identification of 25 Human Papillomavirus Types with Templex Technology," Journal of Clinical Microbiology, 2006, pp. 4157-4162, vol. 44, No. 11.
Hodges et al., "Genome-wide in situ exon capture for selective resequencing," Nature Genetics, 2007, pp. 1522-1527, vol. 39, No. 12.
Hodges et al., "High definition profiling of mammalian DNA methylation by array capture and single molecule bisulfite sequencing," Genome Research, 2009, pp. 1593-1605, vol. 19.
Jun et al., "Epigenetic Regulation of c-ROS Receptor Tyrosine Kinase Expression in Malignant Gliomas," Cancer Research, 2009, pp. 2180-2184, vol. 69.

(56) References Cited

OTHER PUBLICATIONS

Kent, "BLAT—The BLAST-Like Alignment Tool," Genome Research, 2002, pp. 656-664, vol. 12.
Kent et al., "The Human Genome Browser at UCSC," Genome Research, 2002, pp. 996-1006, vol. 12.
Kim et al., "Human hair genealogies and stem cell latency," BMC Biology, 2006, pp. 1-10, vol. 4, No. 2.
Klarmann et al., "Epigenetic gene silencing in the Wnt pathway in breast cancer," Epigenetics, 2008, pp. 59-63, vol. 3, No. 2.
Korshunova et al., "Massively parallel bisulphite pyrosequencing reveals the molecular complexity of breast cancer-associated cytosine-methylation patterns obtained from tissue and serum DNA," Genome Research, 2008, pp. 19-29, vol. 18.
Laird, "Cancer epigenetics," Human Molecular Genetics, 2005, pp. R65-R76, vol. 14, No. 1.
Larkin et al., "Clustal W and Clustal X version 2.0," Bioinformatics, 2007, pp. 2947-2948, vol. 23, No. 21.
Lyko et al., "DNA Methyltransferase Inhibitors and the Development of Epigenetic Cancer Therapies," Journal of the National Cancer Institute, 2005, pp. 1498-1506, vol. 97, No. 20.
Marsh et al., "Genetic insights into familial cancers—update and recent discoveries," Cancer Letters, 2002, pp. 125-164, vol. 181.
Marsh et al., "Pharmacogenomics: from bedside to clinical practice," Human Molecular Genetics, 2006, pp. R89-R93, vol. 15, No. 1.
McLendon, "Comprehensive genomic characterization defines human glioblastoma genes and core pathways," Nature, 2008, pp. 1061-1068, vol. 455, No. 7216.
Meissner et al., "Genome-scale DNA methylation maps of pluripotent and differentiated cells," Nature, 2008, pp. 766-770, vol. 454, No. 7205.
Metzker, "Emerging technologies in DNA sequencing," Genome Research, 2005, pp. 1767-1776, vol. 15.
Meuzelaar et al., "MegaPlex PCR: a strategy for multiplex amplification," Nature Methods, 2007, pp. 835-837, vol. 4, No. 10.
Munson et al., "Recovery of bisulfite-converted genomic sequences in the methylation-sensitive QPCR," Nucleic Acids Research, 2007, pp. 2893-2903, vol. 35, No. 9.
Nabilsi et al., "DNA methylation inhibits p53-mediated survivin repression", Oncogene, 2009, pp. 2046-2050, vol. 28.
Nickerson et al., "PolyPhred: automating the detection and genotyping of single nucleotide substitutions using fluorescence-based resequencing," Nucleic Acids Research, 1997, pp. 2745-2751, vol. 25, No. 14.

* cited by examiner

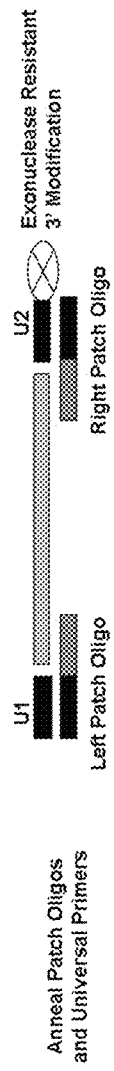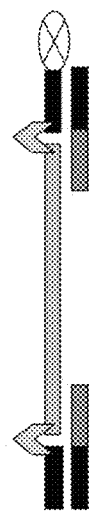
FIG. 7A Genomic DNA
FIG. 7B Restriction Digest
FIG. 7C Anneal Patch Oligos and Universal Primers (Left Patch Oligo, U1, U2, Right Patch Oligo, Exonuclease Resistant 3' Modification)
FIG. 7D Ligate Universal Primers To Targeted Fragments
FIG. 7E Degrade Unselected DNA with Exo I & III

```
                              SEQUENCE LISTING

<160> NUMBER OF SEQ ID NOS: 675

<210> SEQ ID NO 1
<211> LENGTH: 28
<212> TYPE: DNA
<213> ORGANISM: Homo sapiens

<400> SEQUENCE: 1
tcttaagagt tttgtttcct ttaccccu                                          28

<210> SEQ ID NO 2
<211> LENGTH: 25
<212> TYPE: DNA
<213> ORGANISM: Homo sapiens

<400> SEQUENCE: 2
cgtgctttga gagtgatctg aattu                                             25

<210> SEQ ID NO 3
<211> LENGTH: 32
<212> TYPE: DNA
<213> ORGANISM: Homo sapiens

<400> SEQUENCE: 3
ttgtggttaa aatgtaaacc taatatttca cu                                     32

<210> SEQ ID NO 4
<211> LENGTH: 28
<212> TYPE: DNA
<213> ORGANISM: Homo sapiens

<400> SEQUENCE: 4
ggtagagaag tttgcaataa caactgau                                          28

<210> SEQ ID NO 5
<211> LENGTH: 26
<212> TYPE: DNA
<213> ORGANISM: Homo sapiens

<400> SEQUENCE: 5
aaataatttt ctcatgcacc atgacu                                            26

<210> SEQ ID NO 6
<211> LENGTH: 28
<212> TYPE: DNA
<213> ORGANISM: Homo sapiens

<400> SEQUENCE: 6
ttaaatgaga atgatttgac ataacccu                                          28

<210> SEQ ID NO 7
<211> LENGTH: 25
<212> TYPE: DNA
<213> ORGANISM: Homo sapiens

<400> SEQUENCE: 7
aaaaagcctt gggctaagaa agccu                                             25
```

```
<210> SEQ ID NO 8
<211> LENGTH: 34
<212> TYPE: DNA
<213> ORGANISM: Homo sapiens

<400> SEQUENCE: 8
aatggtcata cttttatgat gtatttaatt gttu                        34

<210> SEQ ID NO 9
<211> LENGTH: 31
<212> TYPE: DNA
<213> ORGANISM: Homo sapiens

<400> SEQUENCE: 9
gcttttggat attaaagtcg taattttgtt u                           31

<210> SEQ ID NO 10
<211> LENGTH: 25
<212> TYPE: DNA
<213> ORGANISM: Homo sapiens

<400> SEQUENCE: 10
atttgttgat ccactaaaat tccgu                                  25

<210> SEQ ID NO 11
<211> LENGTH: 25
<212> TYPE: DNA
<213> ORGANISM: Homo sapiens

<400> SEQUENCE: 11
tgattgtctt tttcctcttg ccctu                                  25

<210> SEQ ID NO 12
<211> LENGTH: 25
<212> TYPE: DNA
<213> ORGANISM: Homo sapiens

<400> SEQUENCE: 12
aaagcttggc ttcaagttgt ctttu                                  25

<210> SEQ ID NO 13
<211> LENGTH: 26
<212> TYPE: DNA
<213> ORGANISM: Homo sapiens

<400> SEQUENCE: 13
aaagtgatag gattacaggc gtgagu                                 26

<210> SEQ ID NO 14
<211> LENGTH: 29
<212> TYPE: DNA
<213> ORGANISM: Homo sapiens

<400> SEQUENCE: 14
gaagttaatg agagacaaat tccaactcu                              29

<210> SEQ ID NO 15
<211> LENGTH: 24
<212> TYPE: DNA
<213> ORGANISM: Homo sapiens

<400> SEQUENCE: 15
ccgttgagca tctagacgtt tccu                                   24
```

<210> SEQ ID NO 16
<211> LENGTH: 29
<212> TYPE: DNA
<213> ORGANISM: Homo sapiens

<400> SEQUENCE: 16
cctgtaagac aaaggaaaaa cacgttaau                              29

<210> SEQ ID NO 17
<211> LENGTH: 25
<212> TYPE: DNA
<213> ORGANISM: Homo sapiens

<400> SEQUENCE: 17
tggattaaat caagaaaatg ggaau                                  25

<210> SEQ ID NO 18
<211> LENGTH: 26
<212> TYPE: DNA
<213> ORGANISM: Homo sapiens

<400> SEQUENCE: 18
cagcagttca gataaccttt cccttu                                 26

<210> SEQ ID NO 19
<211> LENGTH: 28
<212> TYPE: DNA
<213> ORGANISM: Homo sapiens

<400> SEQUENCE: 19
tgttgatatg attttctctt ttccctu                                28

<210> SEQ ID NO 20
<211> LENGTH: 28
<212> TYPE: DNA
<213> ORGANISM: Homo sapiens

<400> SEQUENCE: 20
tggattcact atcttaagac ctcgcttu                               28

<210> SEQ ID NO 21
<211> LENGTH: 25
<212> TYPE: DNA
<213> ORGANISM: Homo sapiens

<400> SEQUENCE: 21
gggctctgac atctagtgtg tgttu                                  25

<210> SEQ ID NO 22
<211> LENGTH: 25
<212> TYPE: DNA
<213> ORGANISM: Homo sapiens

<400> SEQUENCE: 22
tccttgtgtc ttctgctgtt tgttu                                  25

<210> SEQ ID NO 23
<211> LENGTH: 24
<212> TYPE: DNA
<213> ORGANISM: Homo sapiens

<400> SEQUENCE: 23
gaggacctca aatggaccaa gtcu                                   24

<210> SEQ ID NO 24
<211> LENGTH: 27
<212> TYPE: DNA
<213> ORGANISM: Homo sapiens

<400> SEQUENCE: 24
ggtgatttca tgactttgtg tgaatgu                                27

<210> SEQ ID NO 25
<211> LENGTH: 25
<212> TYPE: DNA
<213> ORGANISM: Homo sapiens

<400> SEQUENCE: 25
atcttctggc caccacatac accau                                  25

<210> SEQ ID NO 26
<211> LENGTH: 25
<212> TYPE: DNA
<213> ORGANISM: Homo sapiens

<400> SEQUENCE: 26
gctccatttg gggacctgta tatcu                                  25

<210> SEQ ID NO 27
<211> LENGTH: 27
<212> TYPE: DNA
<213> ORGANISM: Homo sapiens

<400> SEQUENCE: 27
gctctgtaga accagcacag agaagtu                                27

<210> SEQ ID NO 28
<211> LENGTH: 27
<212> TYPE: DNA
<213> ORGANISM: Homo sapiens

<400> SEQUENCE: 28
gctctgtaga accagcacag agaagtu                                27

<210> SEQ ID NO 29
<211> LENGTH: 25
<212> TYPE: DNA
<213> ORGANISM: Homo sapiens

<400> SEQUENCE: 29
tctcatccat gtttcaggga ttacu                                  25

<210> SEQ ID NO 30
<211> LENGTH: 25
<212> TYPE: DNA
<213> ORGANISM: Homo sapiens

<400> SEQUENCE: 30
ttgctccttc atgttcttgc ttctu                                  25

<210> SEQ ID NO 31
<211> LENGTH: 25
<212> TYPE: DNA
<213> ORGANISM: Homo sapiens

<400> SEQUENCE: 31

```
atcaagtaac gtggtcaccc agagu                                      25

<210> SEQ ID NO 32
<211> LENGTH: 24
<212> TYPE: DNA
<213> ORGANISM: Homo sapiens

<400> SEQUENCE: 32
cagcaatatt cagcagtccc attu                                       24

<210> SEQ ID NO 33
<211> LENGTH: 25
<212> TYPE: DNA
<213> ORGANISM: Homo sapiens

<400> SEQUENCE: 33
atcagccagg acaccagtgt atgtu                                      25

<210> SEQ ID NO 34
<211> LENGTH: 21
<212> TYPE: DNA
<213> ORGANISM: Homo sapiens

<400> SEQUENCE: 34
gaagtgacgt tttcccgcgg u                                          21

<210> SEQ ID NO 35
<211> LENGTH: 36
<212> TYPE: DNA
<213> ORGANISM: Homo sapiens

<400> SEQUENCE: 35
gatcttaaag tatttaataa tgttctttt cacagu                           36

<210> SEQ ID NO 36
<211> LENGTH: 31
<212> TYPE: DNA
<213> ORGANISM: Homo sapiens

<400> SEQUENCE: 36
ccatcagaag gatgtgttac aaatatacag u                               31

<210> SEQ ID NO 37
<211> LENGTH: 30
<212> TYPE: DNA
<213> ORGANISM: Homo sapiens

<400> SEQUENCE: 37
aattccttcc aaaggatata gtagtgattu                                 30

<210> SEQ ID NO 38
<211> LENGTH: 34
<212> TYPE: DNA
<213> ORGANISM: Homo sapiens

<400> SEQUENCE: 38
tcttaaaaga agataaataa agcatgagaa aacu                            34

<210> SEQ ID NO 39
<211> LENGTH: 25
<212> TYPE: DNA
<213> ORGANISM: Homo sapiens

<400> SEQUENCE: 39
```

```
gcacaaaaag aaacacccaa aagau                                          25

<210> SEQ ID NO 40
<211> LENGTH: 27
<212> TYPE: DNA
<213> ORGANISM: Homo sapiens

<400> SEQUENCE: 40
catgctgata gtgattgttg aatgaau                                        27

<210> SEQ ID NO 41
<211> LENGTH: 34
<212> TYPE: DNA
<213> ORGANISM: Homo sapiens

<400> SEQUENCE: 41
ggatgtacaa ttgttcttat ctaatttacc actu                                34

<210> SEQ ID NO 42
<211> LENGTH: 24
<212> TYPE: DNA
<213> ORGANISM: Homo sapiens

<400> SEQUENCE: 42
catgggggat tgacacctct aacu                                           24

<210> SEQ ID NO 43
<211> LENGTH: 28
<212> TYPE: DNA
<213> ORGANISM: Homo sapiens

<400> SEQUENCE: 43
aaaattcttt aatgaaatct gtgcctcu                                       28

<210> SEQ ID NO 44
<211> LENGTH: 31
<212> TYPE: DNA
<213> ORGANISM: Homo sapiens

<400> SEQUENCE: 44
ttatatgatt ttatgagaca acagaagcat u                                   31

<210> SEQ ID NO 45
<211> LENGTH: 26
<212> TYPE: DNA
<213> ORGANISM: Homo sapiens

<400> SEQUENCE: 45
aaccacagtc ttatttgagg gaatgu                                         26

<210> SEQ ID NO 46
<211> LENGTH: 27
<212> TYPE: DNA
<213> ORGANISM: Homo sapiens

<400> SEQUENCE: 46
cgacattgat ttctgttttt acctccu                                        27

<210> SEQ ID NO 47
<211> LENGTH: 20
<212> TYPE: DNA
<213> ORGANISM: Homo sapiens
```

```
<400> SEQUENCE: 47
tgagccaaga ttgtgccatu                                            20

<210> SEQ ID NO 48
<211> LENGTH: 28
<212> TYPE: DNA
<213> ORGANISM: Homo sapiens

<400> SEQUENCE: 48
aattatctgt ttcaggaaga agaacgau                                   28

<210> SEQ ID NO 49
<211> LENGTH: 31
<212> TYPE: DNA
<213> ORGANISM: Homo sapiens

<400> SEQUENCE: 49
tggtttaacc tttctactgt tttctttgtc u                               31

<210> SEQ ID NO 50
<211> LENGTH: 26
<212> TYPE: DNA
<213> ORGANISM: Homo sapiens

<400> SEQUENCE: 50
ttcattctga cttttaaatt gccacu                                     26

<210> SEQ ID NO 51
<211> LENGTH: 26
<212> TYPE: DNA
<213> ORGANISM: Homo sapiens

<400> SEQUENCE: 51
tctgggtgta caaccttgaa gtgtau                                     26

<210> SEQ ID NO 52
<211> LENGTH: 23
<212> TYPE: DNA
<213> ORGANISM: Homo sapiens

<400> SEQUENCE: 52
tctgggggaa agaaaagagt ggu                                        23

<210> SEQ ID NO 53
<211> LENGTH: 34
<212> TYPE: DNA
<213> ORGANISM: Homo sapiens

<400> SEQUENCE: 53
aaagaaataa ctctgtagat taaacctttc tttu                            34

<210> SEQ ID NO 54
<211> LENGTH: 30
<212> TYPE: DNA
<213> ORGANISM: Homo sapiens

<400> SEQUENCE: 54
tttcctttat aatatgtgct tcttaccagu                                 30

<210> SEQ ID NO 55
<211> LENGTH: 26
<212> TYPE: DNA
<213> ORGANISM: Homo sapiens
```

-continued

<400> SEQUENCE: 55
tcttcatgca gagactgaaa acaaau                                          26

<210> SEQ ID NO 56
<211> LENGTH: 30
<212> TYPE: DNA
<213> ORGANISM: Homo sapiens

<400> SEQUENCE: 56
tttggtattc ctaatagttc agaatgatgu                                      30

<210> SEQ ID NO 57
<211> LENGTH: 24
<212> TYPE: DNA
<213> ORGANISM: Homo sapiens

<400> SEQUENCE: 57
ctttgcctga tttttgacac accu                                            24

<210> SEQ ID NO 58
<211> LENGTH: 29
<212> TYPE: DNA
<213> ORGANISM: Homo sapiens

<400> SEQUENCE: 58
aatagcataa agtaagtcat cgaaagcau                                       29

<210> SEQ ID NO 59
<211> LENGTH: 29
<212> TYPE: DNA
<213> ORGANISM: Homo sapiens

<400> SEQUENCE: 59
tgtcaaatac tagaatgaag accactgcu                                       29

<210> SEQ ID NO 60
<211> LENGTH: 22
<212> TYPE: DNA
<213> ORGANISM: Homo sapiens

<400> SEQUENCE: 60
gtctcagaca ctggcatggt gu                                              22

<210> SEQ ID NO 61
<211> LENGTH: 28
<212> TYPE: DNA
<213> ORGANISM: Homo sapiens

<400> SEQUENCE: 61
cattttcaga cctatggaaa ctgtgagu                                        28

<210> SEQ ID NO 62
<211> LENGTH: 25
<212> TYPE: DNA
<213> ORGANISM: Homo sapiens

<400> SEQUENCE: 62
acaacgttct ggtaaggaca agggu                                           25

<210> SEQ ID NO 63
<211> LENGTH: 25
<212> TYPE: DNA

```
<213> ORGANISM: Homo sapiens

<400> SEQUENCE: 63
aggtgcttac gcatgtttgt ttctu                                              25

<210> SEQ ID NO 64
<211> LENGTH: 23
<212> TYPE: DNA
<213> ORGANISM: Homo sapiens

<400> SEQUENCE: 64
agtcacagca catgacggag gtu                                                23

<210> SEQ ID NO 65
<211> LENGTH: 20
<212> TYPE: DNA
<213> ORGANISM: Homo sapiens

<400> SEQUENCE: 65
tgagctgaga tcacgccacu                                                    20

<210> SEQ ID NO 66
<211> LENGTH: 22
<212> TYPE: DNA
<213> ORGANISM: Homo sapiens

<400> SEQUENCE: 66
ctccagaaag gacaagggtg gu                                                 22

<210> SEQ ID NO 67
<211> LENGTH: 25
<212> TYPE: DNA
<213> ORGANISM: Homo sapiens

<400> SEQUENCE: 67
tatcaccttt ccttgcctct ttccu                                              25

<210> SEQ ID NO 68
<211> LENGTH: 25
<212> TYPE: DNA
<213> ORGANISM: Homo sapiens

<400> SEQUENCE: 68
tacttacttc tccccctcct ctgtu                                              25

<210> SEQ ID NO 69
<211> LENGTH: 24
<212> TYPE: DNA
<213> ORGANISM: Homo sapiens

<400> SEQUENCE: 69
caccatcttg atttgaattc ccgu                                               24

<210> SEQ ID NO 70
<211> LENGTH: 19
<212> TYPE: DNA
<213> ORGANISM: Homo sapiens

<400> SEQUENCE: 70
cgagcgcgtt ccatcctcu                                                     19

<210> SEQ ID NO 71
<211> LENGTH: 23
```

<212> TYPE: DNA
<213> ORGANISM: Homo sapiens

<400> SEQUENCE: 71
cccaaagtgc tgggattaca ggu                                          23

<210> SEQ ID NO 72
<211> LENGTH: 25
<212> TYPE: DNA
<213> ORGANISM: Homo sapiens

<400> SEQUENCE: 72
aagcctcttg ttcgttcctt gtacu                                        25

<210> SEQ ID NO 73
<211> LENGTH: 32
<212> TYPE: DNA
<213> ORGANISM: Homo sapiens

<400> SEQUENCE: 73
ggtttgtatt attctaaaac cttccaaatc tu                                32

<210> SEQ ID NO 74
<211> LENGTH: 29
<212> TYPE: DNA
<213> ORGANISM: Homo sapiens

<400> SEQUENCE: 74
ttattgagcc tcatttattt tctttttcu                                    29

<210> SEQ ID NO 75
<211> LENGTH: 26
<212> TYPE: DNA
<213> ORGANISM: Homo sapiens

<400> SEQUENCE: 75
gctcttaagg gcagttgtga gattau                                       26

<210> SEQ ID NO 76
<211> LENGTH: 26
<212> TYPE: DNA
<213> ORGANISM: Homo sapiens

<400> SEQUENCE: 76
tgctgagtgt gtttctcaaa caattu                                       26

<210> SEQ ID NO 77
<211> LENGTH: 27
<212> TYPE: DNA
<213> ORGANISM: Homo sapiens

<400> SEQUENCE: 77
tcacaggtaa ccttaatgca ttgtctu                                      27

<210> SEQ ID NO 78
<211> LENGTH: 25
<212> TYPE: DNA
<213> ORGANISM: Homo sapiens

<400> SEQUENCE: 78
tcttcaggag gaaaagcaca gaacu                                        25

<210> SEQ ID NO 79

```
<211> LENGTH: 26
<212> TYPE: DNA
<213> ORGANISM: Homo sapiens

<400> SEQUENCE: 79
ttaactagca ttgtacctgc cacagu                                         26

<210> SEQ ID NO 80
<211> LENGTH: 26
<212> TYPE: DNA
<213> ORGANISM: Homo sapiens

<400> SEQUENCE: 80
aaaggagaga gcagctttca ctaacu                                         26

<210> SEQ ID NO 81
<211> LENGTH: 28
<212> TYPE: DNA
<213> ORGANISM: Homo sapiens

<400> SEQUENCE: 81
tgacaattca gttttgagt accttgtu                                        28

<210> SEQ ID NO 82
<211> LENGTH: 27
<212> TYPE: DNA
<213> ORGANISM: Homo sapiens

<400> SEQUENCE: 82
ccaaagcaag gaatttaatc attttgu                                        27

<210> SEQ ID NO 83
<211> LENGTH: 25
<212> TYPE: DNA
<213> ORGANISM: Homo sapiens

<400> SEQUENCE: 83
attttcttgg tgccatttat cgttu                                          25

<210> SEQ ID NO 84
<211> LENGTH: 31
<212> TYPE: DNA
<213> ORGANISM: Homo sapiens

<400> SEQUENCE: 84
tcactatcag aacaaagcag taaagtagat u                                   31

<210> SEQ ID NO 85
<211> LENGTH: 27
<212> TYPE: DNA
<213> ORGANISM: Homo sapiens

<400> SEQUENCE: 85
tgatctctct gacatgagct gtttcau                                        27

<210> SEQ ID NO 86
<211> LENGTH: 28
<212> TYPE: DNA
<213> ORGANISM: Homo sapiens

<400> SEQUENCE: 86
tgtgtaaatt aaacttctcc cattcctu                                       28
```

```
<210> SEQ ID NO 87
<211> LENGTH: 24
<212> TYPE: DNA
<213> ORGANISM: Homo sapiens

<400> SEQUENCE: 87
gtagaacgtg caggattgct acau                                          24

<210> SEQ ID NO 88
<211> LENGTH: 25
<212> TYPE: DNA
<213> ORGANISM: Homo sapiens

<400> SEQUENCE: 88
aaatccagat tgatcttggg agtgu                                         25

<210> SEQ ID NO 89
<211> LENGTH: 25
<212> TYPE: DNA
<213> ORGANISM: Homo sapiens

<400> SEQUENCE: 89
agccttatta aagggctgtg gcttu                                         25

<210> SEQ ID NO 90
<211> LENGTH: 24
<212> TYPE: DNA
<213> ORGANISM: Homo sapiens

<400> SEQUENCE: 90
ctaggattac aggggtgagc cacu                                          24

<210> SEQ ID NO 91
<211> LENGTH: 25
<212> TYPE: DNA
<213> ORGANISM: Homo sapiens

<400> SEQUENCE: 91
attttccttc tctccattcc cctgu                                         25

<210> SEQ ID NO 92
<211> LENGTH: 23
<212> TYPE: DNA
<213> ORGANISM: Homo sapiens

<400> SEQUENCE: 92
ccttcatccg gagagtgtag ggu                                           23

<210> SEQ ID NO 93
<211> LENGTH: 27
<212> TYPE: DNA
<213> ORGANISM: Homo sapiens

<400> SEQUENCE: 93
tcctactttg acactttgaa tgctctu                                       27

<210> SEQ ID NO 94
<211> LENGTH: 28
<212> TYPE: DNA
<213> ORGANISM: Homo sapiens

<400> SEQUENCE: 94
ttgacactaa tctctgcttg tgttctcu                                      28
```

-continued

<210> SEQ ID NO 95
<211> LENGTH: 32
<212> TYPE: DNA
<213> ORGANISM: Homo sapiens

<400> SEQUENCE: 95
aauggauaaa cuacaatuaa aagucacagu cu                          32

<210> SEQ ID NO 96
<211> LENGTH: 25
<212> TYPE: DNA
<213> ORGANISM: Homo sapiens

<400> SEQUENCE: 96
cacccaaauc gagagaagcu guacu                                  25

<210> SEQ ID NO 97
<211> LENGTH: 32
<212> TYPE: DNA
<213> ORGANISM: Homo sapiens

<400> SEQUENCE: 97
cacaaggcaa ugutuacuau augaagaaaa gu                          32

<210> SEQ ID NO 98
<211> LENGTH: 29
<212> TYPE: DNA
<213> ORGANISM: Homo sapiens

<400> SEQUENCE: 98
aaagutucaa auaagtugua cugccaagu                              29

<210> SEQ ID NO 99
<211> LENGTH: 28
<212> TYPE: DNA
<213> ORGANISM: Homo sapiens

<400> SEQUENCE: 99
tucgcugutt uaucactuag aaacaagu                               28

<210> SEQ ID NO 100
<211> LENGTH: 25
<212> TYPE: DNA
<213> ORGANISM: Homo sapiens

<400> SEQUENCE: 100
uacccacaaa caagaaaggc aautu                                  25

<210> SEQ ID NO 101
<211> LENGTH: 25
<212> TYPE: DNA
<213> ORGANISM: Homo sapiens

<400> SEQUENCE: 101
gacagcacat ugguacugaa ugctu                                  25

<210> SEQ ID NO 102
<211> LENGTH: 23
<212> TYPE: DNA
<213> ORGANISM: Homo sapiens

<400> SEQUENCE: 102
cccaaaaugc ugggatuaca ggu                                    23

<210> SEQ ID NO 103
<211> LENGTH: 28
<212> TYPE: DNA
<213> ORGANISM: Homo sapiens

<400> SEQUENCE: 103
utucugutua aaaautucac autugctu                                      28

<210> SEQ ID NO 104
<211> LENGTH: 26
<212> TYPE: DNA
<213> ORGANISM: Homo sapiens

<400> SEQUENCE: 104
cagaggaagc agcugauaac agaagu                                        26

<210> SEQ ID NO 105
<211> LENGTH: 25
<212> TYPE: DNA
<213> ORGANISM: Homo sapiens

<400> SEQUENCE: 105
gcgaauguga agcacaggut tuuau                                         25

<210> SEQ ID NO 106
<211> LENGTH: 21
<212> TYPE: DNA
<213> ORGANISM: Homo sapiens

<400> SEQUENCE: 106
ggcugaagug ggaggatugc u                                             21

<210> SEQ ID NO 107
<211> LENGTH: 33
<212> TYPE: DNA
<213> ORGANISM: Homo sapiens

<400> SEQUENCE: 107
ugaauaauac acagguaaga aatuaggaaa ucu                                33

<210> SEQ ID NO 108
<211> LENGTH: 34
<212> TYPE: DNA
<213> ORGANISM: Homo sapiens

<400> SEQUENCE: 108
gctuaaaacu tucaugatua uauaaaacat ugcu                               34

<210> SEQ ID NO 109
<211> LENGTH: 21
<212> TYPE: DNA
<213> ORGANISM: Homo sapiens

<400> SEQUENCE: 109
gcaugcgcug uacaugccuc u                                             21

<210> SEQ ID NO 110
<211> LENGTH: 26
<212> TYPE: DNA
<213> ORGANISM: Homo sapiens

<400> SEQUENCE: 110
gccuagutuc cagaacagag aaaggu                                        26

<210> SEQ ID NO 111
<211> LENGTH: 31
<212> TYPE: DNA
<213> ORGANISM: Homo sapiens

<400> SEQUENCE: 111
ggaggauaut tuacacautu ctugaaucut u                                  31

<210> SEQ ID NO 112
<211> LENGTH: 26
<212> TYPE: DNA
<213> ORGANISM: Homo sapiens

<400> SEQUENCE: 112
cacuggugtu gagacaggat uacucu                                        26

<210> SEQ ID NO 113
<211> LENGTH: 25
<212> TYPE: DNA
<213> ORGANISM: Homo sapiens

<400> SEQUENCE: 113
gctucaacaa utuacucucc caugu                                         25

<210> SEQ ID NO 114
<211> LENGTH: 22
<212> TYPE: DNA
<213> ORGANISM: Homo sapiens

<400> SEQUENCE: 114
ucucagagac ccacucccag au                                            22

<210> SEQ ID NO 115
<211> LENGTH: 26
<212> TYPE: DNA
<213> ORGANISM: Homo sapiens

<400> SEQUENCE: 115
ggcugagacu gaaacaucau aacctu                                        26

<210> SEQ ID NO 116
<211> LENGTH: 25
<212> TYPE: DNA
<213> ORGANISM: Homo sapiens

<400> SEQUENCE: 116
caaaucugaa gcauaaaaca agccu                                         25

<210> SEQ ID NO 117
<211> LENGTH: 25
<212> TYPE: DNA
<213> ORGANISM: Homo sapiens

<400> SEQUENCE: 117
utuccauggu cccauaaaat ucccu                                         25

<210> SEQ ID NO 118
<211> LENGTH: 25
<212> TYPE: DNA
<213> ORGANISM: Homo sapiens

<400> SEQUENCE: 118

-continued cuguaagaag ggacagaaca ucctu                                                25

<210> SEQ ID NO 119
<211> LENGTH: 25
<212> TYPE: DNA
<213> ORGANISM: Homo sapiens

<400> SEQUENCE: 119
aauaacaggc aaaaaucugg gcucu                                                25

<210> SEQ ID NO 120
<211> LENGTH: 24
<212> TYPE: DNA
<213> ORGANISM: Homo sapiens

<400> SEQUENCE: 120
gcuguacutt ucccaaaagg ccau                                                 24

<210> SEQ ID NO 121
<211> LENGTH: 24
<212> TYPE: DNA
<213> ORGANISM: Homo sapiens

<400> SEQUENCE: 121
aaacctuggc agtugaggcc cuau                                                 24

<210> SEQ ID NO 122
<211> LENGTH: 26
<212> TYPE: DNA
<213> ORGANISM: Homo sapiens

<400> SEQUENCE: 122
ggautugaaa ccacaugugu cugacu                                               26

<210> SEQ ID NO 123
<211> LENGTH: 30
<212> TYPE: DNA
<213> ORGANISM: Homo sapiens

<400> SEQUENCE: 123
gaaautucag aagugaaaag gaucuaaacu                                           30

<210> SEQ ID NO 124
<211> LENGTH: 22
<212> TYPE: DNA
<213> ORGANISM: Homo sapiens

<400> SEQUENCE: 124
accccaagtu aucugcccac cu                                                   22

<210> SEQ ID NO 125
<211> LENGTH: 22
<212> TYPE: DNA
<213> ORGANISM: Homo sapiens

<400> SEQUENCE: 125 aaagggguggu cautugcccu tu                                                  22

<210> SEQ ID NO 126
<211> LENGTH: 25
<212> TYPE: DNA
<213> ORGANISM: Homo sapiens

```
<400> SEQUENCE: 126
tuguaugagg uccuguccua guccu                                          25

<210> SEQ ID NO 127
<211> LENGTH: 27
<212> TYPE: DNA
<213> ORGANISM: Homo sapiens

<400> SEQUENCE: 127
ucggaauaca gagaaagaag aacacau                                        27

<210> SEQ ID NO 128
<211> LENGTH: 18
<212> TYPE: DNA
<213> ORGANISM: Homo sapiens

<400> SEQUENCE: 128
acggcggcuc ugcucgcu                                                  18

<210> SEQ ID NO 129
<211> LENGTH: 31
<212> TYPE: DNA
<213> ORGANISM: Homo sapiens

<400> SEQUENCE: 129
tucaauttuu guauagugau tugaagtugt u                                   31

<210> SEQ ID NO 130
<211> LENGTH: 25
<212> TYPE: DNA
<213> ORGANISM: Homo sapiens

<400> SEQUENCE: 130
tugagaggaa aauccagaat ucgtu                                          25

<210> SEQ ID NO 131
<211> LENGTH: 27
<212> TYPE: DNA
<213> ORGANISM: Homo sapiens

<400> SEQUENCE: 131
ugagcuaaca tuaaaaggga caagucu                                        27

<210> SEQ ID NO 132
<211> LENGTH: 28
<212> TYPE: DNA
<213> ORGANISM: Homo sapiens

<400> SEQUENCE: 132
ucuacacagg actuaaaucu augggctu                                       28

<210> SEQ ID NO 133
<211> LENGTH: 25
<212> TYPE: DNA
<213> ORGANISM: Homo sapiens

<400> SEQUENCE: 133
gcagagaaug agggaggagu acatu                                          25

<210> SEQ ID NO 134
<211> LENGTH: 25
<212> TYPE: DNA
<213> ORGANISM: Homo sapiens
```

```
<400> SEQUENCE: 134
aucauccugu cagccuuaga accau                                         25

<210> SEQ ID NO 135
<211> LENGTH: 30
<212> TYPE: DNA
<213> ORGANISM: Homo sapiens

<400> SEQUENCE: 135
aaaaacaugc ucauaacaaa agaaguaaau                                    30

<210> SEQ ID NO 136
<211> LENGTH: 25
<212> TYPE: DNA
<213> ORGANISM: Homo sapiens

<400> SEQUENCE: 136
gacaauuauc cucccuccac agucu                                         25

<210> SEQ ID NO 137
<211> LENGTH: 34
<212> TYPE: DNA
<213> ORGANISM: Homo sapiens

<400> SEQUENCE: 137
ccuauaucua aagcaaauca aucaaauaua ccau                               34

<210> SEQ ID NO 138
<211> LENGTH: 29
<212> TYPE: DNA
<213> ORGANISM: Homo sapiens

<400> SEQUENCE: 138
ugaauacaua aagaaacgug aacaaaucu                                     29

<210> SEQ ID NO 139
<211> LENGTH: 35
<212> TYPE: DNA
<213> ORGANISM: Homo sapiens

<400> SEQUENCE: 139
ucaagutucu tugccaagau auacaauaa auaau                               35

<210> SEQ ID NO 140
<211> LENGTH: 26
<212> TYPE: DNA
<213> ORGANISM: Homo sapiens

<400> SEQUENCE: 140
cgaacuggaa agaugcugcu uuaau                                         26

<210> SEQ ID NO 141
<211> LENGTH: 21
<212> TYPE: DNA
<213> ORGANISM: Homo sapiens

<400> SEQUENCE: 141
agcgcacgcc aauaaagaca u                                             21

<210> SEQ ID NO 142
<211> LENGTH: 26
<212> TYPE: DNA
```

-continued

<213> ORGANISM: Homo sapiens

<400> SEQUENCE: 142
gcatucctuc ucctuaaccu cacacu                                              26

<210> SEQ ID NO 143
<211> LENGTH: 30
<212> TYPE: DNA
<213> ORGANISM: Homo sapiens

<400> SEQUENCE: 143
agaugtuaag aaacaccucu cacuaacaau                                          30

<210> SEQ ID NO 144
<211> LENGTH: 26
<212> TYPE: DNA
<213> ORGANISM: Homo sapiens

<400> SEQUENCE: 144
ugcagutuga auggucaaca uaacau                                              26

<210> SEQ ID NO 145
<211> LENGTH: 25
<212> TYPE: DNA
<213> ORGANISM: Homo sapiens

<400> SEQUENCE: 145
aacaugautu gaacccaguc agccu                                               25

<210> SEQ ID NO 146
<211> LENGTH: 25
<212> TYPE: DNA
<213> ORGANISM: Homo sapiens

<400> SEQUENCE: 146
gaggagagaa ggugaagugc tugau                                               25

<210> SEQ ID NO 147
<211> LENGTH: 36
<212> TYPE: DNA
<213> ORGANISM: Homo sapiens

<400> SEQUENCE: 147
ugaatuaccu augtuaugtu auggauaugg autuau                                   36

<210> SEQ ID NO 148
<211> LENGTH: 25
<212> TYPE: DNA
<213> ORGANISM: Homo sapiens

<400> SEQUENCE: 148
aagggctucg aggaauguga gguau                                               25

<210> SEQ ID NO 149
<211> LENGTH: 26
<212> TYPE: DNA
<213> ORGANISM: Homo sapiens

<400> SEQUENCE: 149
ucaaaauaau cccccucuca tucutu                                              26

<210> SEQ ID NO 150
<211> LENGTH: 25

```
<212> TYPE: DNA
<213> ORGANISM: Homo sapiens

<400> SEQUENCE: 150
uaugcaauau gccuggauga ggugu                                 25

<210> SEQ ID NO 151
<211> LENGTH: 25
<212> TYPE: DNA
<213> ORGANISM: Homo sapiens

<400> SEQUENCE: 151
aactuggcau gaaagaaatu gguau                                 25

<210> SEQ ID NO 152
<211> LENGTH: 25
<212> TYPE: DNA
<213> ORGANISM: Homo sapiens

<400> SEQUENCE: 152
aaacaaaccu gccaacugaa gaaau                                 25

<210> SEQ ID NO 153
<211> LENGTH: 25
<212> TYPE: DNA
<213> ORGANISM: Homo sapiens

<400> SEQUENCE: 153
ugugagagac aaugaaucca gaggu                                 25

<210> SEQ ID NO 154
<211> LENGTH: 21
<212> TYPE: DNA
<213> ORGANISM: Homo sapiens

<400> SEQUENCE: 154
acaggucucu gcuagggggc u                                     21

<210> SEQ ID NO 155
<211> LENGTH: 24
<212> TYPE: DNA
<213> ORGANISM: Homo sapiens

<400> SEQUENCE: 155
gacagcauca aaucauccat ugcu                                  24

<210> SEQ ID NO 156
<211> LENGTH: 25
<212> TYPE: DNA
<213> ORGANISM: Homo sapiens

<400> SEQUENCE: 156
ucccaaagtu ccaaacaaaa gaaau                                 25

<210> SEQ ID NO 157
<211> LENGTH: 22
<212> TYPE: DNA
<213> ORGANISM: Homo sapiens

<400> SEQUENCE: 157
gcaaautucc tuccacucgg au                                    22

<210> SEQ ID NO 158
```

-continued

```
<211> LENGTH: 21
<212> TYPE: DNA
<213> ORGANISM: Homo sapiens

<400> SEQUENCE: 158
cuccucccag agacccccagt u                                             21

<210> SEQ ID NO 159
<211> LENGTH: 21
<212> TYPE: DNA
<213> ORGANISM: Homo sapiens

<400> SEQUENCE: 159
ggucagaggc aagcagaggc u                                              21

<210> SEQ ID NO 160
<211> LENGTH: 24
<212> TYPE: DNA
<213> ORGANISM: Homo sapiens

<400> SEQUENCE: 160
gaaucugagg cauaacugca cccu                                           24

<210> SEQ ID NO 161
<211> LENGTH: 25
<212> TYPE: DNA
<213> ORGANISM: Homo sapiens

<400> SEQUENCE: 161
agcuacaacc aggagccatu guctu                                          25

<210> SEQ ID NO 162
<211> LENGTH: 22
<212> TYPE: DNA
<213> ORGANISM: Homo sapiens

<400> SEQUENCE: 162
caaccuagga aggcagggga gu                                             22

<210> SEQ ID NO 163
<211> LENGTH: 21
<212> TYPE: DNA
<213> ORGANISM: Homo sapiens

<400> SEQUENCE: 163
cgggacaaag caaauggaag u                                              21

<210> SEQ ID NO 164
<211> LENGTH: 23
<212> TYPE: DNA
<213> ORGANISM: Homo sapiens

<400> SEQUENCE: 164
ctucagaccg ugcuaucguc ccu                                            23

<210> SEQ ID NO 165
<211> LENGTH: 25
<212> TYPE: DNA
<213> ORGANISM: Homo sapiens

<400> SEQUENCE: 165
aaagatugga uaacgugccu gacau                                          25
```

```
<210> SEQ ID NO 166
<211> LENGTH: 26
<212> TYPE: DNA
<213> ORGANISM: Homo sapiens

<400> SEQUENCE: 166
gaaacuaagg aaggaaccag uccugu                                        26

<210> SEQ ID NO 167
<211> LENGTH: 28
<212> TYPE: DNA
<213> ORGANISM: Homo sapiens

<400> SEQUENCE: 167
cccaaauuaa uacacucuug ugcugacu                                      28

<210> SEQ ID NO 168
<211> LENGTH: 25
<212> TYPE: DNA
<213> ORGANISM: Homo sapiens

<400> SEQUENCE: 168
uggagccaca uaacacauuc aaacu                                         25

<210> SEQ ID NO 169
<211> LENGTH: 27
<212> TYPE: DNA
<213> ORGANISM: Homo sapiens

<400> SEQUENCE: 169
tucuacuuuu uccacugug gtugcuu                                        27

<210> SEQ ID NO 170
<211> LENGTH: 25
<212> TYPE: DNA
<213> ORGANISM: Homo sapiens

<400> SEQUENCE: 170 agcacugag ugucauucuu gggau                                          25

<210> SEQ ID NO 171
<211> LENGTH: 22
<212> TYPE: DNA
<213> ORGANISM: Homo sapiens

<400> SEQUENCE: 171
ggcuaaggca ggaggacugc uu                                            22

<210> SEQ ID NO 172
<211> LENGTH: 26
<212> TYPE: DNA
<213> ORGANISM: Homo sapiens

<400> SEQUENCE: 172
ucaccauagg gcucauaaaa tucacu                                        26

<210> SEQ ID NO 173
<211> LENGTH: 28
<212> TYPE: DNA
<213> ORGANISM: Homo sapiens

<400> SEQUENCE: 173
ggaaaauacc agcuucauag acaaaggu                                      28
```

```
<210> SEQ ID NO 174
<211> LENGTH: 25
<212> TYPE: DNA
<213> ORGANISM: Homo sapiens

<400> SEQUENCE: 174
aacucugcca agagauuug ugggu                                    25

<210> SEQ ID NO 175
<211> LENGTH: 26
<212> TYPE: DNA
<213> ORGANISM: Homo sapiens

<400> SEQUENCE: 175
gcuguaauga gcuggcauga guautu                                  26

<210> SEQ ID NO 176
<211> LENGTH: 26
<212> TYPE: DNA
<213> ORGANISM: Homo sapiens

<400> SEQUENCE: 176
tugugccatu aatucaaaga gaugau                                  26

<210> SEQ ID NO 177
<211> LENGTH: 25
<212> TYPE: DNA
<213> ORGANISM: Homo sapiens

<400> SEQUENCE: 177
aaggcuccau aatuacccau gugcu                                   25

<210> SEQ ID NO 178
<211> LENGTH: 27
<212> TYPE: DNA
<213> ORGANISM: Homo sapiens

<400> SEQUENCE: 178
ccacagcauc utuacatuga ugutucu                                 27

<210> SEQ ID NO 179
<211> LENGTH: 27
<212> TYPE: DNA
<213> ORGANISM: Homo sapiens

<400> SEQUENCE: 179
ugutugtucc aauacagcag augaaau                                 27

<210> SEQ ID NO 180
<211> LENGTH: 33
<212> TYPE: DNA
<213> ORGANISM: Homo sapiens

<400> SEQUENCE: 180
ugtugtuaag uctuagucat uagggagaua cau                          33

<210> SEQ ID NO 181
<211> LENGTH: 23
<212> TYPE: DNA
<213> ORGANISM: Homo sapiens

<400> SEQUENCE: 181
caaagugcug cgatuacagg cau                                     23
```

<210> SEQ ID NO 182
<211> LENGTH: 27
<212> TYPE: DNA
<213> ORGANISM: Homo sapiens

<400> SEQUENCE: 182
gguguaaaaa ugcaaucucg aggugtu                                        27

<210> SEQ ID NO 183
<211> LENGTH: 25
<212> TYPE: DNA
<213> ORGANISM: Homo sapiens

<400> SEQUENCE: 183
utugugcatu gtuaaggaaa guggu                                          25

<210> SEQ ID NO 184
<211> LENGTH: 25
<212> TYPE: DNA
<213> ORGANISM: Homo sapiens

<400> SEQUENCE: 184 gguggggguga gauuuuguc aactu                                          25

<210> SEQ ID NO 185
<211> LENGTH: 25
<212> TYPE: DNA
<213> ORGANISM: Homo sapiens

<400> SEQUENCE: 185
uccacuaugu aagacaaagg cuggu                                          25

<210> SEQ ID NO 186
<211> LENGTH: 23
<212> TYPE: DNA
<213> ORGANISM: Homo sapiens

<400> SEQUENCE: 186
gaggcuacag uaggggcauc cau                                            23

<210> SEQ ID NO 187
<211> LENGTH: 25
<212> TYPE: DNA
<213> ORGANISM: Homo sapiens

<400> SEQUENCE: 187
caaaaggacc ccauauagca caggu                                          25

<210> SEQ ID NO 188
<211> LENGTH: 22
<212> TYPE: DNA
<213> ORGANISM: Homo sapiens

<400> SEQUENCE: 188 ggggguccugu ggcucuguac cu                                            22

<210> SEQ ID NO 189
<211> LENGTH: 57
<212> TYPE: DNA
<213> ORGANISM: Homo sapiens

<400> SEQUENCE: 189
ttagtggctg cttgttttta agaagatcg gaagagcgtc gtgtagggaa agagtgt        57

<210> SEQ ID NO 190
<211> LENGTH: 48
<212> TYPE: DNA
<213> ORGANISM: Homo sapiens

<400> SEQUENCE: 190
caagcagaag acggcatacg atgataccctt catattagat gcctcagt              48

<210> SEQ ID NO 191
<211> LENGTH: 61
<212> TYPE: DNA
<213> ORGANISM: Homo sapiens

<400> SEQUENCE: 191
tttcttgaca tttaagtatg ctgagaaaag atcggaagag cgtcgtgtag ggaaagagtg   60
t                                                                   61

<210> SEQ ID NO 192
<211> LENGTH: 46
<212> TYPE: DNA
<213> ORGANISM: Homo sapiens

<400> SEQUENCE: 192
caagcagaag acggcatacg atggatctac acacctaaag atgaca                 46

<210> SEQ ID NO 193
<211> LENGTH: 75
<212> TYPE: DNA
<213> ORGANISM: Homo sapiens

<400> SEQUENCE: 193
gctttaagca gtctaaaata ttcttaatgt tatattattt taagatcgga agagcgtcgt   60
gtagggaaag agtgt                                                    75

<210> SEQ ID NO 194
<211> LENGTH: 52
<212> TYPE: DNA
<213> ORGANISM: Homo sapiens

<400> SEQUENCE: 194
caagcagaag acggcatacg atacctctct ttctcaagtt cttctaaata tc          52

<210> SEQ ID NO 195
<211> LENGTH: 57
<212> TYPE: DNA
<213> ORGANISM: Homo sapiens

<400> SEQUENCE: 195
aagactgcag aagagcaata cttacgatcg gaagagcgtc gtgtagggaa agagtgt     57

<210> SEQ ID NO 196
<211> LENGTH: 53
<212> TYPE: DNA
<213> ORGANISM: Homo sapiens

<400> SEQUENCE: 196
caagcagaag acggcatacg atacttacat tttcagttaa aggaagacta tct         53

<210> SEQ ID NO 197
<211> LENGTH: 63

<212> TYPE: DNA
<213> ORGANISM: Homo sapiens

<400> SEQUENCE: 197
ccaataaaga aaatgaataa gcaaatacgt cgatcggaag agcgtcgtgt agggaaagag    60
tgt                                                                  63

<210> SEQ ID NO 198
<211> LENGTH: 46
<212> TYPE: DNA
<213> ORGANISM: Homo sapiens

<400> SEQUENCE: 198
caagcagaag acggcatacg aaacttacct gtgctcgttt ttccat                   46

<210> SEQ ID NO 199
<211> LENGTH: 57
<212> TYPE: DNA
<213> ORGANISM: Homo sapiens

<400> SEQUENCE: 199
tactatggct accacttaaa agctcgatcg gaagagcgtc gtgtagggaa agagtgt       57

<210> SEQ ID NO 200
<211> LENGTH: 45
<212> TYPE: DNA
<213> ORGANISM: Homo sapiens

<400> SEQUENCE: 200
caagcagaag acggcatacg aactaacctc tgcttctgtt gcttg                    45

<210> SEQ ID NO 201
<211> LENGTH: 57
<212> TYPE: DNA
<213> ORGANISM: Homo sapiens

<400> SEQUENCE: 201
acatcagtac atgcaaaaat ggtgtgatcg gaagagcgtc gtgtagggaa agagtgt       57

<210> SEQ ID NO 202
<211> LENGTH: 47
<212> TYPE: DNA
<213> ORGANISM: Homo sapiens

<400> SEQUENCE: 202
caagcagaag acggcatacg actggaaata tgcattcagg actaaga                  47

<210> SEQ ID NO 203
<211> LENGTH: 57
<212> TYPE: DNA
<213> ORGANISM: Homo sapiens

<400> SEQUENCE: 203
actccaaatg aagtgtctgt atgatgatcg gaagagcgtc gtgtagggaa agagtgt       57

<210> SEQ ID NO 204
<211> LENGTH: 39
<212> TYPE: DNA
<213> ORGANISM: Homo sapiens

<400> SEQUENCE: 204
caagcagaag acggcatacg agtgagccac tgcacctgg                           39

<210> SEQ ID NO 205
<211> LENGTH: 56
<212> TYPE: DNA
<213> ORGANISM: Homo sapiens

<400> SEQUENCE: 205
cacctgtggg ccaaatgagt ttaggatcgg aagagcgtcg tgtagggaaa gagtgt      56

<210> SEQ ID NO 206
<211> LENGTH: 46
<212> TYPE: DNA
<213> ORGANISM: Homo sapiens

<400> SEQUENCE: 206
caagcagaag acggcatacg atgaaacatg cactacgatg tacact                 46

<210> SEQ ID NO 207
<211> LENGTH: 60
<212> TYPE: DNA
<213> ORGANISM: Homo sapiens

<400> SEQUENCE: 207
gcagggatca ctaatataac cctaattcga tcggaagagc gtcgtgtagg gaaagagtgt  60

<210> SEQ ID NO 208
<211> LENGTH: 46
<212> TYPE: DNA
<213> ORGANISM: Homo sapiens

<400> SEQUENCE: 208
caagcagaag acggcatacg atggtggcct tatatcctaa ttcatc                 46

<210> SEQ ID NO 209
<211> LENGTH: 57
<212> TYPE: DNA
<213> ORGANISM: Homo sapiens

<400> SEQUENCE: 209
tggcctgtag tcccccctaat ttaaagatcg gaagagcgtc gtgtagggaa agagtgt    57

<210> SEQ ID NO 210
<211> LENGTH: 47
<212> TYPE: DNA
<213> ORGANISM: Homo sapiens

<400> SEQUENCE: 210
caagcagaag acggcatacg acagtcattg tttaatgagg agagtga                47

<210> SEQ ID NO 211
<211> LENGTH: 66
<212> TYPE: DNA
<213> ORGANISM: Homo sapiens

<400> SEQUENCE: 211
gcctgtaaat taaatacaga atagaggatc attagatcgg aagagcgtcg tgtagggaaa  60
gagtgt                                                             66

<210> SEQ ID NO 212
<211> LENGTH: 40
<212> TYPE: DNA
<213> ORGANISM: Homo sapiens

<400> SEQUENCE: 212

```
caagcagaag acggcatacg atgaaccctg gaggcagagg                              40
```

<210> SEQ ID NO 213
<211> LENGTH: 54
<212> TYPE: DNA
<213> ORGANISM: Homo sapiens

<400> SEQUENCE: 213

```
gaaattctgg ctagccgtgg tggatcggaa gagcgtcgtg tagggaaaga gtgt             54
```

<210> SEQ ID NO 214
<211> LENGTH: 46
<212> TYPE: DNA
<213> ORGANISM: Homo sapiens

<400> SEQUENCE: 214

```
caagcagaag acggcatacg acatggctaa agaaggcag caaaaa                       46
```

<210> SEQ ID NO 215
<211> LENGTH: 62
<212> TYPE: DNA
<213> ORGANISM: Homo sapiens

<400> SEQUENCE: 215

```
agtaagaaac agaatatggg tcatctaatt gatcggaaga gcgtcgtgta gggaaagagt       60
gt                                                                      62
```

<210> SEQ ID NO 216
<211> LENGTH: 52
<212> TYPE: DNA
<213> ORGANISM: Homo sapiens

<400> SEQUENCE: 216

```
caagcagaag acggcatacg atacaattag gtcttttga gagtatgaat tc                52
```

<210> SEQ ID NO 217
<211> LENGTH: 49
<212> TYPE: DNA
<213> ORGANISM: Homo sapiens

<400> SEQUENCE: 217

```
tggcgccaga agagccagat cggaagagcg tcgtgtaggg aaagagtgt                   49
```

<210> SEQ ID NO 218
<211> LENGTH: 37
<212> TYPE: DNA
<213> ORGANISM: Homo sapiens

<400> SEQUENCE: 218

```
caagcagaag acggcatacg agcccgggca aagaggc                                37
```

<210> SEQ ID NO 219
<211> LENGTH: 57
<212> TYPE: DNA
<213> ORGANISM: Homo sapiens

<400> SEQUENCE: 219

```
ctccaaatac aaacaatagt gcctcgatcg gaagagcgtc gtgtagggaa agagtgt          57
```

<210> SEQ ID NO 220
<211> LENGTH: 42
<212> TYPE: DNA

<213> ORGANISM: Homo sapiens

<400> SEQUENCE: 220
caagcagaag acggcatacg acctgactct tccatgaagc gc                          42

<210> SEQ ID NO 221
<211> LENGTH: 61
<212> TYPE: DNA
<213> ORGANISM: Homo sapiens

<400> SEQUENCE: 221
atgttactca tttttccaaa tctctttgag atcggaagag cgtcgtgtag ggaaagagtg       60
t                                                                      61

<210> SEQ ID NO 222
<211> LENGTH: 43
<212> TYPE: DNA
<213> ORGANISM: Homo sapiens

<400> SEQUENCE: 222
caagcagaag acggcatacg aagcttacct cacctcgaaa gcc                         43

<210> SEQ ID NO 223
<211> LENGTH: 52
<212> TYPE: DNA
<213> ORGANISM: Homo sapiens

<400> SEQUENCE: 223
tcacccactg tcacctcacc gatcggaaga gcgtcgtgta gggaaagagt gt               52

<210> SEQ ID NO 224
<211> LENGTH: 48
<212> TYPE: DNA
<213> ORGANISM: Homo sapiens

<400> SEQUENCE: 224
caagcagaag acggcatacg agagacctag gcaaaaaata catttcag                    48

<210> SEQ ID NO 225
<211> LENGTH: 60
<212> TYPE: DNA
<213> ORGANISM: Homo sapiens

<400> SEQUENCE: 225
atccagtaga gagatagata ctaatcccga tcggaagagc gtcgtgtagg gaaagagtgt       60

<210> SEQ ID NO 226
<211> LENGTH: 45
<212> TYPE: DNA
<213> ORGANISM: Homo sapiens

<400> SEQUENCE: 226
caagcagaag acggcatacg aaccattctt accgtgatct gggtc                       45

<210> SEQ ID NO 227
<211> LENGTH: 57
<212> TYPE: DNA
<213> ORGANISM: Homo sapiens

<400> SEQUENCE: 227
aaataaaacc caagatgtcc tggcagatcg gaagagcgtc gtgtagggaa agagtgt         57

```
<210> SEQ ID NO 228
<211> LENGTH: 45
<212> TYPE: DNA
<213> ORGANISM: Homo sapiens

<400> SEQUENCE: 228
caagcagaag acggcatacg atttggactg tacctgccaa caact            45

<210> SEQ ID NO 229
<211> LENGTH: 58
<212> TYPE: DNA
<213> ORGANISM: Homo sapiens

<400> SEQUENCE: 229
caaaagagta agaaaagagt tgccaagatc ggaagagcgt cgtgtaggga aagagtgt  58

<210> SEQ ID NO 230
<211> LENGTH: 48
<212> TYPE: DNA
<213> ORGANISM: Homo sapiens

<400> SEQUENCE: 230
caagcagaag acggcatacg aatctccacc agcaaactat taaaaatc         48

<210> SEQ ID NO 231
<211> LENGTH: 56
<212> TYPE: DNA
<213> ORGANISM: Homo sapiens

<400> SEQUENCE: 231
cagctactgt ctctccttgc tgatgatcgg aagagcgtcg tgtagggaaa gagtgt   56

<210> SEQ ID NO 232
<211> LENGTH: 50
<212> TYPE: DNA
<213> ORGANISM: Homo sapiens

<400> SEQUENCE: 232
caagcagaag acggcatacg agtgtatttg actaaagcaa actcttaaca          50

<210> SEQ ID NO 233
<211> LENGTH: 53
<212> TYPE: DNA
<213> ORGANISM: Homo sapiens

<400> SEQUENCE: 233
tttgtgaaat gagggccccg agatcggaag agcgtcgtgt agggaaagag tgt      53

<210> SEQ ID NO 234
<211> LENGTH: 44
<212> TYPE: DNA
<213> ORGANISM: Homo sapiens

<400> SEQUENCE: 234
caagcagaag acggcatacg agtgggtgtt tcctgtgagt ggat             44

<210> SEQ ID NO 235
<211> LENGTH: 51
<212> TYPE: DNA
<213> ORGANISM: Homo sapiens

<400> SEQUENCE: 235
ggggtgaggt cacaggtgtg atcggaagag cgtcgtgtag ggaaagagtg t        51
```

<210> SEQ ID NO 236
<211> LENGTH: 44
<212> TYPE: DNA
<213> ORGANISM: Homo sapiens

<400> SEQUENCE: 236
caagcagaag acggcatacg attgccagtg gtgtatggga ttca         44

<210> SEQ ID NO 237
<211> LENGTH: 53
<212> TYPE: DNA
<213> ORGANISM: Homo sapiens

<400> SEQUENCE: 237 aggggagaa aaagcccaca tgatcggaag agcgtcgtgt agggaaagag tgt         53

<210> SEQ ID NO 238
<211> LENGTH: 36
<212> TYPE: DNA
<213> ORGANISM: Homo sapiens

<400> SEQUENCE: 238
caagcagaag acggcatacg acacgtctgg ccgggc         36

<210> SEQ ID NO 239
<211> LENGTH: 59
<212> TYPE: DNA
<213> ORGANISM: Homo sapiens

<400> SEQUENCE: 239
agtggagaga ctcagaataa gaagtatgat cggaagagcg tcgtgtaggg aaagagtgt         59

<210> SEQ ID NO 240
<211> LENGTH: 43
<212> TYPE: DNA
<213> ORGANISM: Homo sapiens

<400> SEQUENCE: 240
caagcagaag acggcatacg aacctggggt tgctggaagt agg         43

<210> SEQ ID NO 241
<211> LENGTH: 54
<212> TYPE: DNA
<213> ORGANISM: Homo sapiens

<400> SEQUENCE: 241 gttgcattt ggaggagcaa gcgatcggaa gagcgtcgtg tagggaaaga gtgt         54

<210> SEQ ID NO 242
<211> LENGTH: 37
<212> TYPE: DNA
<213> ORGANISM: Homo sapiens

<400> SEQUENCE: 242
caagcagaag acggcatacg agcatcccag gcaggcc         37

<210> SEQ ID NO 243
<211> LENGTH: 54
<212> TYPE: DNA
<213> ORGANISM: Homo sapiens

<400> SEQUENCE: 243
aagcaccagg caccagaact aggatcggaa gagcgtcgtg tagggaaaga gtgt         54

<210> SEQ ID NO 244
<211> LENGTH: 39
<212> TYPE: DNA
<213> ORGANISM: Homo sapiens

<400> SEQUENCE: 244
caagcagaag acggcatacg accaaagcct gtgccctcc                                39

<210> SEQ ID NO 245
<211> LENGTH: 56
<212> TYPE: DNA
<213> ORGANISM: Homo sapiens

<400> SEQUENCE: 245
aaccagttgg gacaaaatgg gagagatcgg aagagcgtcg tgtagggaaa gagtgt         56

<210> SEQ ID NO 246
<211> LENGTH: 46
<212> TYPE: DNA
<213> ORGANISM: Homo sapiens

<400> SEQUENCE: 246
caagcagaag acggcatacg ataccgataa cctgagaaca ccaaaa                    46

<210> SEQ ID NO 247
<211> LENGTH: 49
<212> TYPE: DNA
<213> ORGANISM: Homo sapiens

<400> SEQUENCE: 247
cggtgctggc tcctagggat cggaagagcg tcgtgtaggg aaagagtgt                 49

<210> SEQ ID NO 248
<211> LENGTH: 40
<212> TYPE: DNA
<213> ORGANISM: Homo sapiens

<400> SEQUENCE: 248
caagcagaag acggcatacg acagcctccc aaagtgctgg                           40

<210> SEQ ID NO 249
<211> LENGTH: 52
<212> TYPE: DNA
<213> ORGANISM: Homo sapiens

<400> SEQUENCE: 249
gccttgtgct cctatctgcc gatcggaaga gcgtcgtgta gggaaagagt gt             52

<210> SEQ ID NO 250
<211> LENGTH: 41
<212> TYPE: DNA
<213> ORGANISM: Homo sapiens

<400> SEQUENCE: 250
caagcagaag acggcatacg accctccagc acacatgcat g                         41

<210> SEQ ID NO 251
<211> LENGTH: 58
<212> TYPE: DNA
<213> ORGANISM: Homo sapiens

<400> SEQUENCE: 251

```
tgtgatactt taggcgttaa aactgtgatc ggaagagcgt cgtgtaggga aagagtgt        58

<210> SEQ ID NO 252
<211> LENGTH: 39
<212> TYPE: DNA
<213> ORGANISM: Homo sapiens

<400> SEQUENCE: 252
caagcagaag acggcatacg aggggtgcca gtgtgcatc                            39

<210> SEQ ID NO 253
<211> LENGTH: 51
<212> TYPE: DNA
<213> ORGANISM: Homo sapiens

<400> SEQUENCE: 253
gcctccctgt ttgcatcccg atcggaagag cgtcgtgtag ggaaagagtg t              51

<210> SEQ ID NO 254
<211> LENGTH: 47
<212> TYPE: DNA
<213> ORGANISM: Homo sapiens

<400> SEQUENCE: 254
caagcagaag acggcatacg acccacagtg cataaataac catattt                   47

<210> SEQ ID NO 255
<211> LENGTH: 50
<212> TYPE: DNA
<213> ORGANISM: Homo sapiens

<400> SEQUENCE: 255
aactgagcgc cgcgtccaga tcggaagagc gtcgtgtagg gaaagagtgt                50

<210> SEQ ID NO 256
<211> LENGTH: 41
<212> TYPE: DNA
<213> ORGANISM: Homo sapiens

<400> SEQUENCE: 256
caagcagaag acggcatacg acacctgacg agaggcaggt c                        41

<210> SEQ ID NO 257
<211> LENGTH: 58
<212> TYPE: DNA
<213> ORGANISM: Homo sapiens

<400> SEQUENCE: 257
tgtttcaata gtttgcacat aacactgatc ggaagagcgt cgtgtaggga aagagtgt       58

<210> SEQ ID NO 258
<211> LENGTH: 58
<212> TYPE: DNA
<213> ORGANISM: Homo sapiens

<400> SEQUENCE: 258
caagcagaag acggcatacg atttaaaatg agaaaaaaaa atttcaaaac gttttaag       58

<210> SEQ ID NO 259
<211> LENGTH: 67
<212> TYPE: DNA
<213> ORGANISM: Homo sapiens

<400> SEQUENCE: 259
```
tttcttattc agcatacaaa ataaatgttt gtaatgatcg aagagcgtc gtgtagggaa    60 agagtgt                                                              67

<210> SEQ ID NO 260
<211> LENGTH: 46
<212> TYPE: DNA
<213> ORGANISM: Homo sapiens

<400> SEQUENCE: 260
caagcagaag acggcatacg atcctttat ggcagaggct tatatt                    46

<210> SEQ ID NO 261
<211> LENGTH: 62
<212> TYPE: DNA
<213> ORGANISM: Homo sapiens

<400> SEQUENCE: 261
ttcaattcaa aagattatca gctctacatc gatcggaaga gcgtcgtgta gggaaagagt    60
gt                                                                   62

<210> SEQ ID NO 262
<211> LENGTH: 64
<212> TYPE: DNA
<213> ORGANISM: Homo sapiens

<400> SEQUENCE: 262
caagcagaag acggcatacg aaagaattaa tacttactaa ctttactaaa tgtgttaaat    60
aatt                                                                 64

<210> SEQ ID NO 263
<211> LENGTH: 67
<212> TYPE: DNA
<213> ORGANISM: Homo sapiens

<400> SEQUENCE: 263
tttttaacat tttttcgtaa tttagaagtc atagtgatcg aagagcgtc gtgtagggaa    60 agagtgt                                                              67

<210> SEQ ID NO 264
<211> LENGTH: 49
<212> TYPE: DNA
<213> ORGANISM: Homo sapiens

<400> SEQUENCE: 264
caagcagaag acggcatacg aaatttatga agtagcctgc tataatcga                49

<210> SEQ ID NO 265
<211> LENGTH: 62
<212> TYPE: DNA
<213> ORGANISM: Homo sapiens

<400> SEQUENCE: 265
tgtatcactg aaagaaagtt ttccagatat gatcggaaga gcgtcgtgta gggaaagagt    60
gt                                                                   62

<210> SEQ ID NO 266
<211> LENGTH: 49
<212> TYPE: DNA
<213> ORGANISM: Homo sapiens -continued

<400> SEQUENCE: 266
caagcagaag acggcatacg aactcaataa aaattgggga atttagtcc                49

<210> SEQ ID NO 267
<211> LENGTH: 59
<212> TYPE: DNA
<213> ORGANISM: Homo sapiens

<400> SEQUENCE: 267
cgcagggtag agtatatcca taaatttgat cggaagagcg tcgtgtaggg aaagagtgt    59

<210> SEQ ID NO 268
<211> LENGTH: 46
<212> TYPE: DNA
<213> ORGANISM: Homo sapiens

<400> SEQUENCE: 268
caagcagaag acggcatacg agtttggtac ccactagaca ttcaat                  46

<210> SEQ ID NO 269
<211> LENGTH: 57
<212> TYPE: DNA
<213> ORGANISM: Homo sapiens

<400> SEQUENCE: 269
atgggtataa cagctgtttc tgtaagatcg gaagagcgtc gtgtagggaa agagtgt      57

<210> SEQ ID NO 270
<211> LENGTH: 50
<212> TYPE: DNA
<213> ORGANISM: Homo sapiens

<400> SEQUENCE: 270
caagcagaag acggcatacg aattgttagg gagaacttac atctaaatct              50

<210> SEQ ID NO 271
<211> LENGTH: 57
<212> TYPE: DNA
<213> ORGANISM: Homo sapiens

<400> SEQUENCE: 271
cttgactctt gaacaatgca gggtagatcg gaagagcgtc gtgtagggaa agagtgt      57

<210> SEQ ID NO 272
<211> LENGTH: 61
<212> TYPE: DNA
<213> ORGANISM: Homo sapiens

<400> SEQUENCE: 272
caagcagaag acggcatacg acaaaacatt aatattttat taaatttcct ttcagattac   60
c                                                                   61

<210> SEQ ID NO 273
<211> LENGTH: 57
<212> TYPE: DNA
<213> ORGANISM: Homo sapiens

<400> SEQUENCE: 273
catgtcatta catctctcag cacacgatcg gaagagcgtc gtgtagggaa agagtgt      57

<210> SEQ ID NO 274
<211> LENGTH: 47

<212> TYPE: DNA
<213> ORGANISM: Homo sapiens

<400> SEQUENCE: 274
caagcagaag acggcatacg agtgcaatac ctgtctatag aatcagt     47

<210> SEQ ID NO 275
<211> LENGTH: 58
<212> TYPE: DNA
<213> ORGANISM: Homo sapiens

<400> SEQUENCE: 275
tgctttatgc atcaaaaaag cagtatgatc ggaagagcgt cgtgtaggga aagagtgt     58

<210> SEQ ID NO 276
<211> LENGTH: 52
<212> TYPE: DNA
<213> ORGANISM: Homo sapiens

<400> SEQUENCE: 276
caagcagaag acggcatacg agaaacacta taaagccatg aataacaaaa tt     52

<210> SEQ ID NO 277
<211> LENGTH: 53
<212> TYPE: DNA
<213> ORGANISM: Homo sapiens

<400> SEQUENCE: 277
cactgcctcc cacttgtctc tgatcggaag agcgtcgtgt agggaaagag tgt     53

<210> SEQ ID NO 278
<211> LENGTH: 51
<212> TYPE: DNA
<213> ORGANISM: Homo sapiens

<400> SEQUENCE: 278
caagcagaag acggcatacg agtttcatat atggcttacg ttaaaatagg a     51

<210> SEQ ID NO 279
<211> LENGTH: 57
<212> TYPE: DNA
<213> ORGANISM: Homo sapiens

<400> SEQUENCE: 279
ttttggattc actgtgcagt tctttgatcg gaagagcgtc gtgtagggaa agagtgt     57

<210> SEQ ID NO 280
<211> LENGTH: 54
<212> TYPE: DNA
<213> ORGANISM: Homo sapiens

<400> SEQUENCE: 280
caagcagaag acggcatacg aattattact ctatagtacc acgaattaca atga     54

<210> SEQ ID NO 281
<211> LENGTH: 49
<212> TYPE: DNA
<213> ORGANISM: Homo sapiens

<400> SEQUENCE: 281
ttgccaggct ggggtgagat cggaagagcg tcgtgtaggg aaagagtgt     49

<210> SEQ ID NO 282

```
<211> LENGTH: 50
<212> TYPE: DNA
<213> ORGANISM: Homo sapiens

<400> SEQUENCE: 282
caagcagaag acggcatacg aatgaaaaat gttgtcattc agaagtttgc      50

<210> SEQ ID NO 283
<211> LENGTH: 71
<212> TYPE: DNA
<213> ORGANISM: Homo sapiens

<400> SEQUENCE: 283
actaaaagta aaaatttac ctaaaatttt gaatggatag atcggaagag cgtcgtgtag      60
ggaaagagtg t                                                          71

<210> SEQ ID NO 284
<211> LENGTH: 39
<212> TYPE: DNA
<213> ORGANISM: Homo sapiens

<400> SEQUENCE: 284
caagcagaag acggcatacg aatccctctc ccccgacca                  39

<210> SEQ ID NO 285
<211> LENGTH: 63
<212> TYPE: DNA
<213> ORGANISM: Homo sapiens

<400> SEQUENCE: 285
tgagctaggt attttttgg aagttattat cgatcggaag agcgtcgtgt agggaaagag      60
tgt                                                                   63

<210> SEQ ID NO 286
<211> LENGTH: 46
<212> TYPE: DNA
<213> ORGANISM: Homo sapiens

<400> SEQUENCE: 286
caagcagaag acggcatacg aaatttgtta gccatatgca catgaa          46

<210> SEQ ID NO 287
<211> LENGTH: 60
<212> TYPE: DNA
<213> ORGANISM: Homo sapiens

<400> SEQUENCE: 287
agtactatga attttaggca caattgacga tcggaagagc gtcgtgtagg gaaagagtgt     60

<210> SEQ ID NO 288
<211> LENGTH: 47
<212> TYPE: DNA
<213> ORGANISM: Homo sapiens

<400> SEQUENCE: 288
caagcagaag acggcatacg aatatttgc ttacatatct gctgcag          47

<210> SEQ ID NO 289
<211> LENGTH: 60
<212> TYPE: DNA
<213> ORGANISM: Homo sapiens

<400> SEQUENCE: 289
```

```
caagttggct aagaatcaca gattatacga tcggaagagc gtcgtgtagg gaaagagtgt    60
```

<210> SEQ ID NO 290
<211> LENGTH: 46
<212> TYPE: DNA
<213> ORGANISM: Homo sapiens

<400> SEQUENCE: 290

```
caagcagaag acggcatacg aagtttcaga gtccatgctc ttgaaa                   46
```

<210> SEQ ID NO 291
<211> LENGTH: 60
<212> TYPE: DNA
<213> ORGANISM: Homo sapiens

<400> SEQUENCE: 291

```
gtagcatttt aacagaaacc tcttttctga tcggaagagc gtcgtgtagg gaaagagtgt    60
```

<210> SEQ ID NO 292
<211> LENGTH: 46
<212> TYPE: DNA
<213> ORGANISM: Homo sapiens

<400> SEQUENCE: 292

```
caagcagaag acggcatacg atttcttact tggtccaaat gcctgt                   46
```

<210> SEQ ID NO 293
<211> LENGTH: 60
<212> TYPE: DNA
<213> ORGANISM: Homo sapiens

<400> SEQUENCE: 293

```
aataccattt tctttctttt agcctcaaga tcggaagagc gtcgtgtagg gaaagagtgt    60
```

<210> SEQ ID NO 294
<211> LENGTH: 53
<212> TYPE: DNA
<213> ORGANISM: Homo sapiens

<400> SEQUENCE: 294

```
caagcagaag acggcatacg acaaaaaaac ttactatgga aaattaccta cct           53
```

<210> SEQ ID NO 295
<211> LENGTH: 73
<212> TYPE: DNA
<213> ORGANISM: Homo sapiens

<400> SEQUENCE: 295

```
accttagat tttcttttct aatagtttat aatactttt ggatcggaag agcgtcgtgt      60
agggaaagag tgt                                                       73
```

<210> SEQ ID NO 296
<211> LENGTH: 40
<212> TYPE: DNA
<213> ORGANISM: Homo sapiens

<400> SEQUENCE: 296

```
caagcagaag acggcatacg atggtgacaa ggtaggggc                           40
```

<210> SEQ ID NO 297
<211> LENGTH: 56
<212> TYPE: DNA

<213> ORGANISM: Homo sapiens

<400> SEQUENCE: 297
cctggtggaa gcatactgca aaatgatcgg aagagcgtcg tgtagggaaa gagtgt           56

<210> SEQ ID NO 298
<211> LENGTH: 47
<212> TYPE: DNA
<213> ORGANISM: Homo sapiens

<400> SEQUENCE: 298
caagcagaag acggcatacg aactacttcc ctaaagagaa aacacac                    47

<210> SEQ ID NO 299
<211> LENGTH: 58
<212> TYPE: DNA
<213> ORGANISM: Homo sapiens

<400> SEQUENCE: 299
acaattttgc agagatgagc ataaatgatc ggaagagcgt cgtgtaggga aagagtgt        58

<210> SEQ ID NO 300
<211> LENGTH: 52
<212> TYPE: DNA
<213> ORGANISM: Homo sapiens

<400> SEQUENCE: 300
caagcagaag acggcatacg attgaataac tgcatttgga aattcaaatt at              52

<210> SEQ ID NO 301
<211> LENGTH: 61
<212> TYPE: DNA
<213> ORGANISM: Homo sapiens

<400> SEQUENCE: 301
catagttagc aacctcaagt tatagtttgg atcggaagag cgtcgtgtag ggaaagagtg     60
t                                                                      61

<210> SEQ ID NO 302
<211> LENGTH: 40
<212> TYPE: DNA
<213> ORGANISM: Homo sapiens

<400> SEQUENCE: 302
caagcagaag acggcatacg aaagccagga gcagtgctga                            40

<210> SEQ ID NO 303
<211> LENGTH: 60
<212> TYPE: DNA
<213> ORGANISM: Homo sapiens

<400> SEQUENCE: 303
tggaaaactc aaatttccag taactatgga tcggaagagc gtcgtgtagg gaaagagtgt     60

<210> SEQ ID NO 304
<211> LENGTH: 56
<212> TYPE: DNA
<213> ORGANISM: Homo sapiens

<400> SEQUENCE: 304
caagcagaag acggcatacg atatacattc ttttatataa cgaaaagact tcttgc         56

```
<210> SEQ ID NO 305
<211> LENGTH: 51
<212> TYPE: DNA
<213> ORGANISM: Homo sapiens

<400> SEQUENCE: 305
gcgctcagga ccttgcaaag atcggaagag cgtcgtgtag ggaaagagtg t      51

<210> SEQ ID NO 306
<211> LENGTH: 43
<212> TYPE: DNA
<213> ORGANISM: Homo sapiens

<400> SEQUENCE: 306
caagcagaag acggcatacg agtacacagt gtccaccaag gtc              43

<210> SEQ ID NO 307
<211> LENGTH: 48
<212> TYPE: DNA
<213> ORGANISM: Homo sapiens

<400> SEQUENCE: 307 ggaacccct cccccagatc ggaagagcgt cgtgtaggga aagagtgt          48

<210> SEQ ID NO 308
<211> LENGTH: 36
<212> TYPE: DNA
<213> ORGANISM: Homo sapiens

<400> SEQUENCE: 308
caagcagaag acggcatacg aggggttggg gtgggg                      36

<210> SEQ ID NO 309
<211> LENGTH: 52
<212> TYPE: DNA
<213> ORGANISM: Homo sapiens

<400> SEQUENCE: 309
cctgcccttc caatggatcc gatcggaaga gcgtcgtgta gggaaagagt gt    52

<210> SEQ ID NO 310
<211> LENGTH: 37
<212> TYPE: DNA
<213> ORGANISM: Homo sapiens

<400> SEQUENCE: 310
caagcagaag acggcatacg atgggacggc aaggggg                     37

<210> SEQ ID NO 311
<211> LENGTH: 48
<212> TYPE: DNA
<213> ORGANISM: Homo sapiens

<400> SEQUENCE: 311
ccaggtcccc agcccagatc ggaagagcgt cgtgtaggga aagagtgt         48

<210> SEQ ID NO 312
<211> LENGTH: 38
<212> TYPE: DNA
<213> ORGANISM: Homo sapiens

<400> SEQUENCE: 312
caagcagaag acggcatacg agcaggggga tacggcca                    38
```

<210> SEQ ID NO 313
<211> LENGTH: 51
<212> TYPE: DNA
<213> ORGANISM: Homo sapiens

<400> SEQUENCE: 313
caactggaag acggcagcag atcggaagag cgtcgtgtag ggaaagagtg t    51

<210> SEQ ID NO 314
<211> LENGTH: 40
<212> TYPE: DNA
<213> ORGANISM: Homo sapiens

<400> SEQUENCE: 314
caagcagaag acggcatacg aaagatgctg aggaggggcc    40

<210> SEQ ID NO 315
<211> LENGTH: 47
<212> TYPE: DNA
<213> ORGANISM: Homo sapiens

<400> SEQUENCE: 315
ggggcagcgc ctcacgatcg gaagagcgtc gtgtagggaa agagtgt    47

<210> SEQ ID NO 316
<211> LENGTH: 40
<212> TYPE: DNA
<213> ORGANISM: Homo sapiens

<400> SEQUENCE: 316
caagcagaag acggcatacg agcaaaccag acctcaggcg    40

<210> SEQ ID NO 317
<211> LENGTH: 48
<212> TYPE: DNA
<213> ORGANISM: Homo sapiens

<400> SEQUENCE: 317
gcccaggctg gagtgcgatc ggaagagcgt cgtgtaggga agagtgt    48

<210> SEQ ID NO 318
<211> LENGTH: 36
<212> TYPE: DNA
<213> ORGANISM: Homo sapiens

<400> SEQUENCE: 318
caagcagaag acggcatacg aggggcacag caggcc    36

<210> SEQ ID NO 319
<211> LENGTH: 53
<212> TYPE: DNA
<213> ORGANISM: Homo sapiens

<400> SEQUENCE: 319
accaggctcc atctactccc agatcggaag agcgtcgtgt agggaaagag tgt    53

<210> SEQ ID NO 320
<211> LENGTH: 40
<212> TYPE: DNA
<213> ORGANISM: Homo sapiens

<400> SEQUENCE: 320
caagcagaag acggcatacg atggtctcct ccaccgcttc    40

<210> SEQ ID NO 321
<211> LENGTH: 51
<212> TYPE: DNA
<213> ORGANISM: Homo sapiens

<400> SEQUENCE: 321
ggtgttgttg ggcagtgctg atcggaagag cgtcgtgtag ggaaagagtg t        51

<210> SEQ ID NO 322
<211> LENGTH: 39
<212> TYPE: DNA
<213> ORGANISM: Homo sapiens

<400> SEQUENCE: 322
caagcagaag acggcatacg atgaggcatc actgccccc                       39

<210> SEQ ID NO 323
<211> LENGTH: 49
<212> TYPE: DNA
<213> ORGANISM: Homo sapiens

<400> SEQUENCE: 323
gcccacggat ctgcagcgat cggaagagcg tcgtgtaggg aaagagtgt            49

<210> SEQ ID NO 324
<211> LENGTH: 37
<212> TYPE: DNA
<213> ORGANISM: Homo sapiens

<400> SEQUENCE: 324
caagcagaag acggcatacg aagggccagg aaggggc                         37

<210> SEQ ID NO 325
<211> LENGTH: 50
<212> TYPE: DNA
<213> ORGANISM: Homo sapiens

<400> SEQUENCE: 325
gggcctaagg ctgggacaga tcggaagagc gtcgtgtagg gaaagagtgt           50

<210> SEQ ID NO 326
<211> LENGTH: 39
<212> TYPE: DNA
<213> ORGANISM: Homo sapiens

<400> SEQUENCE: 326
caagcagaag acggcatacg acctgggtgc ttctgacgc                       39

<210> SEQ ID NO 327
<211> LENGTH: 50
<212> TYPE: DNA
<213> ORGANISM: Homo sapiens

<400> SEQUENCE: 327
tcttcgcgcg cgctcggtga tcggaagagc gtcgtgtagg gaaagagtgt           50

<210> SEQ ID NO 328
<211> LENGTH: 38
<212> TYPE: DNA
<213> ORGANISM: Homo sapiens

<400> SEQUENCE: 328
caagcagaag acggcatacg agctgggtcg ggcctaag    38

<210> SEQ ID NO 329
<211> LENGTH: 47
<212> TYPE: DNA
<213> ORGANISM: Homo sapiens

<400> SEQUENCE: 329
ggcacggtgg cccacgatcg gaagagcgtc gtgtagggaa agagtgt    47

<210> SEQ ID NO 330
<211> LENGTH: 46
<212> TYPE: DNA
<213> ORGANISM: Homo sapiens

<400> SEQUENCE: 330
caagcagaag acggcatacg acaggcaaaa attgagaact gggctt    46

<210> SEQ ID NO 331
<211> LENGTH: 54
<212> TYPE: DNA
<213> ORGANISM: Homo sapiens

<400> SEQUENCE: 331
ctcagtggca gactagggtc tcgatcggaa gagcgtcgtg tagggaaaga gtgt    54

<210> SEQ ID NO 332
<211> LENGTH: 47
<212> TYPE: DNA
<213> ORGANISM: Homo sapiens

<400> SEQUENCE: 332
caagcagaag acggcatacg aatctagatc aagactcatc agtacca    47

<210> SEQ ID NO 333
<211> LENGTH: 72
<212> TYPE: DNA
<213> ORGANISM: Homo sapiens

<400> SEQUENCE: 333
atgacaactt cattttatca ttttaaaata aagtaaattt gatcggaaga gcgtcgtgta    60
gggaaagagt gt    72

<210> SEQ ID NO 334
<211> LENGTH: 46
<212> TYPE: DNA
<213> ORGANISM: Homo sapiens

<400> SEQUENCE: 334
caagcagaag acggcatacg ataccagatg ggacactcta agattt    46

<210> SEQ ID NO 335
<211> LENGTH: 50
<212> TYPE: DNA
<213> ORGANISM: Homo sapiens

<400> SEQUENCE: 335
ctagcagggt aggggggggga tcggaagagc gtcgtgtagg gaaagagtgt    50

<210> SEQ ID NO 336
<211> LENGTH: 46
<212> TYPE: DNA
<213> ORGANISM: Homo sapiens

<400> SEQUENCE: 336
caagcagaag acggcatacg atacttgcaa aatatgtggt cacact                46

<210> SEQ ID NO 337
<211> LENGTH: 57
<212> TYPE: DNA
<213> ORGANISM: Homo sapiens

<400> SEQUENCE: 337
tcaaaaggca aatagccatg aaaaggatcg gaagagcgtc gtgtagggaa agagtgt    57

<210> SEQ ID NO 338
<211> LENGTH: 51
<212> TYPE: DNA
<213> ORGANISM: Homo sapiens

<400> SEQUENCE: 338
caagcagaag acggcatacg accaacctag catcattacc aaattatata c          51

<210> SEQ ID NO 339
<211> LENGTH: 57
<212> TYPE: DNA
<213> ORGANISM: Homo sapiens

<400> SEQUENCE: 339
tactttcttg taggctcctg aaattgatcg gaagagcgtc gtgtagggaa agagtgt    57

<210> SEQ ID NO 340
<211> LENGTH: 46
<212> TYPE: DNA
<213> ORGANISM: Homo sapiens

<400> SEQUENCE: 340
caagcagaag acggcatacg aattcaacac ttacactcca aacctg                46

<210> SEQ ID NO 341
<211> LENGTH: 57
<212> TYPE: DNA
<213> ORGANISM: Homo sapiens

<400> SEQUENCE: 341
ccctatgtat gctctttgtt gtgttgatcg gaagagcgtc gtgtagggaa agagtgt    57

<210> SEQ ID NO 342
<211> LENGTH: 39
<212> TYPE: DNA
<213> ORGANISM: Homo sapiens

<400> SEQUENCE: 342
caagcagaag acggcatacg actagcctgg gccacagag                        39

<210> SEQ ID NO 343
<211> LENGTH: 57
<212> TYPE: DNA
<213> ORGANISM: Homo sapiens

<400> SEQUENCE: 343
aagaacagtc aagcaattgt tggccgatcg gaagagcgtc gtgtagggaa agagtgt    57

<210> SEQ ID NO 344
<211> LENGTH: 45
<212> TYPE: DNA

<213> ORGANISM: Homo sapiens

<400> SEQUENCE: 344
caagcagaag acggcatacg atcccaaagc tgcctaccac aaata    45

<210> SEQ ID NO 345
<211> LENGTH: 65
<212> TYPE: DNA
<213> ORGANISM: Homo sapiens

<400> SEQUENCE: 345
agatattcaa ctagaaatat ttactgagca tctgatcgga agagcgtcgt gtagggaaag    60
agtgt    65

<210> SEQ ID NO 346
<211> LENGTH: 46
<212> TYPE: DNA
<213> ORGANISM: Homo sapiens

<400> SEQUENCE: 346
caagcagaag acggcatacg atctctttga ctcacctgca ataagt    46

<210> SEQ ID NO 347
<211> LENGTH: 60
<212> TYPE: DNA
<213> ORGANISM: Homo sapiens

<400> SEQUENCE: 347
gattacagaa agctgaccaa tcttatttga tcggaagagc gtcgtgtagg gaaagagtgt    60

<210> SEQ ID NO 348
<211> LENGTH: 46
<212> TYPE: DNA
<213> ORGANISM: Homo sapiens

<400> SEQUENCE: 348
caagcagaag acggcatacg atgtaaaggt cccaaatggt cttcag    46

<210> SEQ ID NO 349
<211> LENGTH: 60
<212> TYPE: DNA
<213> ORGANISM: Homo sapiens

<400> SEQUENCE: 349
tcacaagcag ctgaaaatat acaaaaatga tcggaagagc gtcgtgtagg gaaagagtgt    60

<210> SEQ ID NO 350
<211> LENGTH: 41
<212> TYPE: DNA
<213> ORGANISM: Homo sapiens

<400> SEQUENCE: 350
caagcagaag acggcatacg agtgccacat ggctccacat g    41

<210> SEQ ID NO 351
<211> LENGTH: 57
<212> TYPE: DNA
<213> ORGANISM: Homo sapiens

<400> SEQUENCE: 351
aggactggat ttactttcat gtcacgatcg gaagagcgtc gtgtagggaa agagtgt    57

```
<210> SEQ ID NO 352
<211> LENGTH: 46
<212> TYPE: DNA
<213> ORGANISM: Homo sapiens

<400> SEQUENCE: 352
caagcagaag acggcatacg agtcagcaaa cctaagaatg tgggat            46

<210> SEQ ID NO 353
<211> LENGTH: 56
<212> TYPE: DNA
<213> ORGANISM: Homo sapiens

<400> SEQUENCE: 353
ttgcatggta tccctctgct tcaagatcgg aagagcgtcg tgtagggaaa gagtgt    56

<210> SEQ ID NO 354
<211> LENGTH: 46
<212> TYPE: DNA
<213> ORGANISM: Homo sapiens

<400> SEQUENCE: 354
caagcagaag acggcatacg agagcaagga tcataaaatg ttggag            46

<210> SEQ ID NO 355
<211> LENGTH: 58
<212> TYPE: DNA
<213> ORGANISM: Homo sapiens

<400> SEQUENCE: 355
actgctttaa atggaatgag aaaacagatc ggaagagcgt cgtgtaggga aagagtgt   58

<210> SEQ ID NO 356
<211> LENGTH: 46
<212> TYPE: DNA
<213> ORGANISM: Homo sapiens

<400> SEQUENCE: 356
caagcagaag acggcatacg ataccttttcc actcctggtt ctttat            46

<210> SEQ ID NO 357
<211> LENGTH: 52
<212> TYPE: DNA
<213> ORGANISM: Homo sapiens

<400> SEQUENCE: 357
gctgggcagc caaagcataa gatcggaaga gcgtcgtgta gggaaagagt gt       52

<210> SEQ ID NO 358
<211> LENGTH: 46
<212> TYPE: DNA
<213> ORGANISM: Homo sapiens

<400> SEQUENCE: 358
caagcagaag acggcatacg aattacctag atcttgcctt ggcaag            46

<210> SEQ ID NO 359
<211> LENGTH: 53
<212> TYPE: DNA
<213> ORGANISM: Homo sapiens

<400> SEQUENCE: 359
caggtaaggg gttccctctg agatcggaag agcgtcgtgt agggaaagag tgt      53
```

<210> SEQ ID NO 360
<211> LENGTH: 47
<212> TYPE: DNA
<213> ORGANISM: Homo sapiens

<400> SEQUENCE: 360
caagcagaag acggcatacg aatggataca ctcacaaatt cttctgg                47

<210> SEQ ID NO 361
<211> LENGTH: 57
<212> TYPE: DNA
<213> ORGANISM: Homo sapiens

<400> SEQUENCE: 361
attccaccat ggcatatgtt tacctgatcg gaagagcgtc gtgtagggaa agagtgt     57

<210> SEQ ID NO 362
<211> LENGTH: 36
<212> TYPE: DNA
<213> ORGANISM: Homo sapiens

<400> SEQUENCE: 362
caagcagaag acggcatacg agcgccaccg tgcctc                            36

<210> SEQ ID NO 363
<211> LENGTH: 57
<212> TYPE: DNA
<213> ORGANISM: Homo sapiens

<400> SEQUENCE: 363
agaagctaaa gagcctcagt tttttgatcg gaagagcgtc gtgtagggaa agagtgt     57

<210> SEQ ID NO 364
<211> LENGTH: 46
<212> TYPE: DNA
<213> ORGANISM: Homo sapiens

<400> SEQUENCE: 364
caagcagaag acggcatacg aaaagggagg aggggagaaa tagtat                 46

<210> SEQ ID NO 365
<211> LENGTH: 54
<212> TYPE: DNA
<213> ORGANISM: Homo sapiens

<400> SEQUENCE: 365
cagaggagag gtccttccct ctgatcggaa gagcgtcgtg tagggaaaga gtgt        54

<210> SEQ ID NO 366
<211> LENGTH: 46
<212> TYPE: DNA
<213> ORGANISM: Homo sapiens

<400> SEQUENCE: 366
caagcagaag acggcatacg agcattgatg gaaggaagca aataca                 46

<210> SEQ ID NO 367
<211> LENGTH: 48
<212> TYPE: DNA
<213> ORGANISM: Homo sapiens

<400> SEQUENCE: 367
cattcaggcc aggcgcgatc ggaagagcgt cgtgtaggga aagagtgt               48

<210> SEQ ID NO 368
<211> LENGTH: 45
<212> TYPE: DNA
<213> ORGANISM: Homo sapiens

<400> SEQUENCE: 368
caagcagaag acggcatacg agagggaggg agctttacct ttctg    45

<210> SEQ ID NO 369
<211> LENGTH: 57
<212> TYPE: DNA
<213> ORGANISM: Homo sapiens

<400> SEQUENCE: 369
tggaagaaga gaggaagaga gaggggatcg gaagagcgtc gtgtagggaa agagtgt    57

<210> SEQ ID NO 370
<211> LENGTH: 42
<212> TYPE: DNA
<213> ORGANISM: Homo sapiens

<400> SEQUENCE: 370
caagcagaag acggcatacg agctggaact ctggggttct cc    42

<210> SEQ ID NO 371
<211> LENGTH: 54
<212> TYPE: DNA
<213> ORGANISM: Homo sapiens

<400> SEQUENCE: 371
gcatacttaa cccaggccct ctgatcggaa gagcgtcgtg tagggaaaga gtgt    54

<210> SEQ ID NO 372
<211> LENGTH: 40
<212> TYPE: DNA
<213> ORGANISM: Homo sapiens

<400> SEQUENCE: 372
caagcagaag acggcatacg aagggactga caggtgccag    40

<210> SEQ ID NO 373
<211> LENGTH: 51
<212> TYPE: DNA
<213> ORGANISM: Homo sapiens

<400> SEQUENCE: 373
cctggatccc caggaaggag atcggaagag cgtcgtgtag ggaaagagtg t    51

<210> SEQ ID NO 374
<211> LENGTH: 42
<212> TYPE: DNA
<213> ORGANISM: Homo sapiens

<400> SEQUENCE: 374
caagcagaag acggcatacg aacatgcagg caccttacca tg    42

<210> SEQ ID NO 375
<211> LENGTH: 54
<212> TYPE: DNA
<213> ORGANISM: Homo sapiens

<400> SEQUENCE: 375
catctgccca attgctggag acgatcggaa gagcgtcgtg tagggaaaga gtgt       54

<210> SEQ ID NO 376
<211> LENGTH: 39
<212> TYPE: DNA
<213> ORGANISM: Homo sapiens

<400> SEQUENCE: 376
caagcagaag acggcatacg agtggctggc tgcagtcag                        39

<210> SEQ ID NO 377
<211> LENGTH: 32
<212> TYPE: DNA
<213> ORGANISM: Homo sapiens

<400> SEQUENCE: 377
acactctttc cctacacgac gctcttccga tc                               32

<210> SEQ ID NO 378
<211> LENGTH: 21
<212> TYPE: DNA
<213> ORGANISM: Homo sapiens

<400> SEQUENCE: 378
tcgtatgccg tcttctgctt g                                           21

<210> SEQ ID NO 379
<211> LENGTH: 40
<212> TYPE: DNA
<213> ORGANISM: Homo sapiens

<400> SEQUENCE: 379
gcctccctcg cgccatcagc tacacgacgc tcttccgatc                       40

<210> SEQ ID NO 380
<211> LENGTH: 40
<212> TYPE: DNA
<213> ORGANISM: Homo sapiens

<400> SEQUENCE: 380
gccttgccag cccgctcagc aagcagaaga cggcatacga                       40

<210> SEQ ID NO 381
<211> LENGTH: 46
<212> TYPE: DNA
<213> ORGANISM: Homo sapiens

<400> SEQUENCE: 381
gcctccctcg cgccatcagg tcacactaca cgacgctctt ccgatc                46

<210> SEQ ID NO 382
<211> LENGTH: 46
<212> TYPE: DNA
<213> ORGANISM: Homo sapiens

<400> SEQUENCE: 382
gccttgccag cccgctcagc agtcacaagc agaagacggc atacga                46

<210> SEQ ID NO 383
<211> LENGTH: 24
<212> TYPE: DNA
<213> ORGANISM: Homo sapiens

<400> SEQUENCE: 383

```
cgccagggtt tcccagtca cgac                                                   24
```

<210> SEQ ID NO 384
<211> LENGTH: 22
<212> TYPE: DNA
<213> ORGANISM: Homo sapiens

<400> SEQUENCE: 384

```
tcacacagga aacagctatg ac                                                    22
```

<210> SEQ ID NO 385
<211> LENGTH: 42
<212> TYPE: DNA
<213> ORGANISM: Homo sapiens

<400> SEQUENCE: 385

```
taggtgggcg gggtttgaga tcaccaacta cccacacaca cc                              42
```

<210> SEQ ID NO 386
<211> LENGTH: 37
<212> TYPE: DNA
<213> ORGANISM: Homo sapiens

<400> SEQUENCE: 386

```
gcaccggcgc ggagatcacc aactacccac acacacc                                    37
```

<210> SEQ ID NO 387
<211> LENGTH: 42
<212> TYPE: DNA
<213> ORGANISM: Homo sapiens

<400> SEQUENCE: 387

```
ttgcccacct ggagagcaga tcaccaacta cccacacaca cc                              42
```

<210> SEQ ID NO 388
<211> LENGTH: 43
<212> TYPE: DNA
<213> ORGANISM: Homo sapiens

<400> SEQUENCE: 388

```
ggggagaggt ctggggaaag atcaccaact acccacacac acc                             43
```

<210> SEQ ID NO 389
<211> LENGTH: 48
<212> TYPE: DNA
<213> ORGANISM: Homo sapiens

<400> SEQUENCE: 389

```
attctcagag tcactgctaa tagagatcac caactaccca cacacacc                        48
```

<210> SEQ ID NO 390
<211> LENGTH: 46
<212> TYPE: DNA
<213> ORGANISM: Homo sapiens

<400> SEQUENCE: 390

```
gcatcaccgc catcattgct tagatcacca actacccaca cacacc                          46
```

<210> SEQ ID NO 391
<211> LENGTH: 40
<212> TYPE: DNA
<213> ORGANISM: Homo sapiens

<400> SEQUENCE: 391
cctcaggcca cgctgagatc accaactacc cacacacacc            40

<210> SEQ ID NO 392
<211> LENGTH: 44
<212> TYPE: DNA
<213> ORGANISM: Homo sapiens

<400> SEQUENCE: 392
ggggaaacag aggggagaa gatcaccaac tacccacaca cacc        44

<210> SEQ ID NO 393
<211> LENGTH: 48
<212> TYPE: DNA
<213> ORGANISM: Homo sapiens

<400> SEQUENCE: 393
gggacagtgg atttctgaca aagagatcac caactaccca cacacacc   48

<210> SEQ ID NO 394
<211> LENGTH: 48
<212> TYPE: DNA
<213> ORGANISM: Homo sapiens

<400> SEQUENCE: 394 cttttttcg ttatttgctg ggaagatcac caactaccca cacacacc   48

<210> SEQ ID NO 395
<211> LENGTH: 39
<212> TYPE: DNA
<213> ORGANISM: Homo sapiens

<400> SEQUENCE: 395
cagcgtccgg gagcagatca ccaactaccc acacacacc             39

<210> SEQ ID NO 396
<211> LENGTH: 44
<212> TYPE: DNA
<213> ORGANISM: Homo sapiens

<400> SEQUENCE: 396
ccattctcag cccctaccca gatcaccaac tacccacaca cacc       44

<210> SEQ ID NO 397
<211> LENGTH: 48
<212> TYPE: DNA
<213> ORGANISM: Homo sapiens

<400> SEQUENCE: 397
tgtcaatact ctcggattta caaagatcac caactaccca cacacacc  48

<210> SEQ ID NO 398
<211> LENGTH: 48
<212> TYPE: DNA
<213> ORGANISM: Homo sapiens

<400> SEQUENCE: 398
aatgcttaac catctcgcta gacagatcac caactaccca cacacacc  48

<210> SEQ ID NO 399
<211> LENGTH: 48
<212> TYPE: DNA
<213> ORGANISM: Homo sapiens

```
<400> SEQUENCE: 399
ggtaattggc tttttaacgg ttgagatcac caactaccca cacacacc                48

<210> SEQ ID NO 400
<211> LENGTH: 48
<212> TYPE: DNA
<213> ORGANISM: Homo sapiens

<400> SEQUENCE: 400
cactgggaat tgtgtactga tgcagatcac caactaccca cacacacc                48

<210> SEQ ID NO 401
<211> LENGTH: 48
<212> TYPE: DNA
<213> ORGANISM: Homo sapiens

<400> SEQUENCE: 401
tctagtccct attcttgttc caaagatcac caactaccca cacacacc                48

<210> SEQ ID NO 402
<211> LENGTH: 45
<212> TYPE: DNA
<213> ORGANISM: Homo sapiens

<400> SEQUENCE: 402
gaaggacttg gctgggagaa agatcaccaa ctacccacac acacc                   45

<210> SEQ ID NO 403
<211> LENGTH: 40
<212> TYPE: DNA
<213> ORGANISM: Homo sapiens

<400> SEQUENCE: 403
ccgactggcc ctccaagatc accaactacc cacacacacc                         40

<210> SEQ ID NO 404
<211> LENGTH: 47
<212> TYPE: DNA
<213> ORGANISM: Homo sapiens

<400> SEQUENCE: 404
gaaagtcagt gccaaaacag caagatcacc aactacccac acacacc                 47

<210> SEQ ID NO 405
<211> LENGTH: 42
<212> TYPE: DNA
<213> ORGANISM: Homo sapiens

<400> SEQUENCE: 405
ggaggcccga aagaagcaga tcaccaacta cccacacaca cc                      42

<210> SEQ ID NO 406
<211> LENGTH: 48
<212> TYPE: DNA
<213> ORGANISM: Homo sapiens

<400> SEQUENCE: 406
ttagatgtag gttggctatt ggtagatcac caactaccca cacacacc                48

<210> SEQ ID NO 407
<211> LENGTH: 37
<212> TYPE: DNA
```

<213> ORGANISM: Homo sapiens

<400> SEQUENCE: 407
cgggcgggga gcagatcacc aactacccac acacacc                              37

<210> SEQ ID NO 408
<211> LENGTH: 40
<212> TYPE: DNA
<213> ORGANISM: Homo sapiens

<400> SEQUENCE: 408
gtgcccgagg cctacagatc accaactacc cacacacacc                           40

<210> SEQ ID NO 409
<211> LENGTH: 44
<212> TYPE: DNA
<213> ORGANISM: Homo sapiens

<400> SEQUENCE: 409
aggactcaac cagtccagca gatcaccaac tacccacaca cacc                      44

<210> SEQ ID NO 410
<211> LENGTH: 48
<212> TYPE: DNA
<213> ORGANISM: Homo sapiens

<400> SEQUENCE: 410
cgtaaattat acaggcattc ccgagatcac caactaccca cacacacc                  48

<210> SEQ ID NO 411
<211> LENGTH: 48
<212> TYPE: DNA
<213> ORGANISM: Homo sapiens

<400> SEQUENCE: 411
cctcttttct tctgtatgtc catagatcac caactaccca cacacacc                  48

<210> SEQ ID NO 412
<211> LENGTH: 48
<212> TYPE: DNA
<213> ORGANISM: Homo sapiens

<400> SEQUENCE: 412
tgctcagaac tctgaagtga catagatcac caactaccca cacacacc                  48

<210> SEQ ID NO 413
<211> LENGTH: 48
<212> TYPE: DNA
<213> ORGANISM: Homo sapiens

<400> SEQUENCE: 413
cttgaggcca caaatgcagg aatagatcac caactaccca cacacacc                  48

<210> SEQ ID NO 414
<211> LENGTH: 48
<212> TYPE: DNA
<213> ORGANISM: Homo sapiens

<400> SEQUENCE: 414
cacaactcag ttcccggaaa caaagatcac caactaccca cacacacc                  48

<210> SEQ ID NO 415
<211> LENGTH: 48

<212> TYPE: DNA
<213> ORGANISM: Homo sapiens

<400> SEQUENCE: 415
ctggatttcc taattttcac tacagatcac caactaccca cacacacc         48

<210> SEQ ID NO 416
<211> LENGTH: 48
<212> TYPE: DNA
<213> ORGANISM: Homo sapiens

<400> SEQUENCE: 416
gttttatttg ggaggaagta aagagatcac caactaccca cacacacc         48

<210> SEQ ID NO 417
<211> LENGTH: 48
<212> TYPE: DNA
<213> ORGANISM: Homo sapiens

<400> SEQUENCE: 417
tacgatgtaa ccctttttca ggcagatcac caactaccca cacacacc         48

<210> SEQ ID NO 418
<211> LENGTH: 48
<212> TYPE: DNA
<213> ORGANISM: Homo sapiens

<400> SEQUENCE: 418
tagaactact atgtaaactt gggagatcac caactaccca cacacacc         48

<210> SEQ ID NO 419
<211> LENGTH: 45
<212> TYPE: DNA
<213> ORGANISM: Homo sapiens

<400> SEQUENCE: 419
ttgtgagaga cgcttgggtg agatcaccaa ctacccacac acacc            45

<210> SEQ ID NO 420
<211> LENGTH: 42
<212> TYPE: DNA
<213> ORGANISM: Homo sapiens

<400> SEQUENCE: 420
ggtcctagtc ccgagcgaga tcaccaacta cccacacaca cc               42

<210> SEQ ID NO 421
<211> LENGTH: 40
<212> TYPE: DNA
<213> ORGANISM: Homo sapiens

<400> SEQUENCE: 421
ggcccgaggg accgtagatc accaactacc cacacacacc                  40

<210> SEQ ID NO 422
<211> LENGTH: 41
<212> TYPE: DNA
<213> ORGANISM: Homo sapiens

<400> SEQUENCE: 422
cagagcccgg gcgactagat caccaactac ccacacacac c                41

<210> SEQ ID NO 423

```
<211> LENGTH: 47
<212> TYPE: DNA
<213> ORGANISM: Homo sapiens

<400> SEQUENCE: 423 cgggaactttt cccttccttc ctagatcacc aactacccac acacacc                47

<210> SEQ ID NO 424
<211> LENGTH: 48
<212> TYPE: DNA
<213> ORGANISM: Homo sapiens

<400> SEQUENCE: 424
ctaccctcac gtggttaaga gtgagatcac caactaccca cacacacc               48

<210> SEQ ID NO 425
<211> LENGTH: 48
<212> TYPE: DNA
<213> ORGANISM: Homo sapiens

<400> SEQUENCE: 425
tgtgctaatg gcagatgaaa aggagatcac caactaccca cacacacc               48

<210> SEQ ID NO 426
<211> LENGTH: 48
<212> TYPE: DNA
<213> ORGANISM: Homo sapiens

<400> SEQUENCE: 426
ctggctgaga tgccatgata ataagatcac caactaccca cacacacc               48

<210> SEQ ID NO 427
<211> LENGTH: 37
<212> TYPE: DNA
<213> ORGANISM: Homo sapiens

<400> SEQUENCE: 427
gccgcgaccc gcagatcacc aactacccac acacacc                           37

<210> SEQ ID NO 428
<211> LENGTH: 38
<212> TYPE: DNA
<213> ORGANISM: Homo sapiens

<400> SEQUENCE: 428
tcggggcgcg gagagatcac caactaccca cacacacc                          38

<210> SEQ ID NO 429
<211> LENGTH: 45
<212> TYPE: DNA
<213> ORGANISM: Homo sapiens

<400> SEQUENCE: 429
caagtctctt tgctgccagc agatcaccaa ctacccacac acacc                  45

<210> SEQ ID NO 430
<211> LENGTH: 48
<212> TYPE: DNA
<213> ORGANISM: Homo sapiens

<400> SEQUENCE: 430
aaaggaaaaa gcaaagtccc attagatcac caactaccca cacacacc               48
```

-continued

<210> SEQ ID NO 431
<211> LENGTH: 45
<212> TYPE: DNA
<213> ORGANISM: Homo sapiens

<400> SEQUENCE: 431
ccacacgcca acagtacaag agatcaccaa ctacccacac acacc        45

<210> SEQ ID NO 432
<211> LENGTH: 41
<212> TYPE: DNA
<213> ORGANISM: Homo sapiens

<400> SEQUENCE: 432
ccccgtgaac tccgcaagat caccaactac ccacacacac c            41

<210> SEQ ID NO 433
<211> LENGTH: 43
<212> TYPE: DNA
<213> ORGANISM: Homo sapiens

<400> SEQUENCE: 433
ctcagccaga gagccccaag atcaccaact acccacacac acc          43

<210> SEQ ID NO 434
<211> LENGTH: 41
<212> TYPE: DNA
<213> ORGANISM: Homo sapiens

<400> SEQUENCE: 434
cagcccatgc tcagccagat caccaactac ccacacacac c            41

<210> SEQ ID NO 435
<211> LENGTH: 46
<212> TYPE: DNA
<213> ORGANISM: Homo sapiens

<400> SEQUENCE: 435
ctccactccg actctcggaa aagatcacca actacccaca cacacc       46

<210> SEQ ID NO 436
<211> LENGTH: 43
<212> TYPE: DNA
<213> ORGANISM: Homo sapiens

<400> SEQUENCE: 436
ttctacgagc agcaggcgag atcaccaact acccacacac acc          43

<210> SEQ ID NO 437
<211> LENGTH: 44
<212> TYPE: DNA
<213> ORGANISM: Homo sapiens

<400> SEQUENCE: 437
ccgcagccgg ttgatcatta gatcaccaac tacccacaca cacc         44

<210> SEQ ID NO 438
<211> LENGTH: 41
<212> TYPE: DNA
<213> ORGANISM: Homo sapiens

<400> SEQUENCE: 438
cacgggacga ggcagaagat caccaactac ccacacacac c            41

<210> SEQ ID NO 439
<211> LENGTH: 48
<212> TYPE: DNA
<213> ORGANISM: Homo sapiens

<400> SEQUENCE: 439
acaatgatga tagtggcaca taaagatcac caactaccca cacacacc                48

<210> SEQ ID NO 440
<211> LENGTH: 48
<212> TYPE: DNA
<213> ORGANISM: Homo sapiens

<400> SEQUENCE: 440
gaattaaaaa tagttaccag aaaagatcac caactaccca cacacacc                48

<210> SEQ ID NO 441
<211> LENGTH: 48
<212> TYPE: DNA
<213> ORGANISM: Homo sapiens

<400> SEQUENCE: 441
cttctgtcct tgattactgc aggagatcac caactaccca cacacacc                48

<210> SEQ ID NO 442
<211> LENGTH: 46
<212> TYPE: DNA
<213> ORGANISM: Homo sapiens

<400> SEQUENCE: 442
caagtaacac aggcacagga cagatcacca actacccaca cacacc                  46

<210> SEQ ID NO 443
<211> LENGTH: 41
<212> TYPE: DNA
<213> ORGANISM: Homo sapiens

<400> SEQUENCE: 443
ctggcagggg ctttgcagat caccaactac ccacacacac c                       41

<210> SEQ ID NO 444
<211> LENGTH: 48
<212> TYPE: DNA
<213> ORGANISM: Homo sapiens

<400> SEQUENCE: 444
attgatgaag aaaagacagt ataagatcac caactaccca cacacacc                48

<210> SEQ ID NO 445
<211> LENGTH: 45
<212> TYPE: DNA
<213> ORGANISM: Homo sapiens

<400> SEQUENCE: 445
cattcgtgtg tacctcgtgg agatcaccaa ctacccacac acacc                   45

<210> SEQ ID NO 446
<211> LENGTH: 48
<212> TYPE: DNA
<213> ORGANISM: Homo sapiens

<400> SEQUENCE: 446
ctaaaacagt ggggctccta ctcagatcac caactaccca cacacacc                48

```
<210> SEQ ID NO 447
<211> LENGTH: 40
<212> TYPE: DNA
<213> ORGANISM: Homo sapiens

<400> SEQUENCE: 447 ccggggagg cactcagatc accaactacc cacacacacc                              40

<210> SEQ ID NO 448
<211> LENGTH: 43
<212> TYPE: DNA
<213> ORGANISM: Homo sapiens

<400> SEQUENCE: 448
caccgcgctc aacaggaaag atcaccaact acccacacac acc                         43

<210> SEQ ID NO 449
<211> LENGTH: 48
<212> TYPE: DNA
<213> ORGANISM: Homo sapiens

<400> SEQUENCE: 449
acaatgacac aaaaggaaga gaaagatcac caactaccca cacacacc                    48

<210> SEQ ID NO 450
<211> LENGTH: 48
<212> TYPE: DNA
<213> ORGANISM: Homo sapiens

<400> SEQUENCE: 450
gaggaaagcc agtttaaaga ggcagatcac caactaccca cacacacc                    48

<210> SEQ ID NO 451
<211> LENGTH: 48
<212> TYPE: DNA
<213> ORGANISM: Homo sapiens

<400> SEQUENCE: 451
ggctcgtttg ccctaaaaat gaaagatcac caactaccca cacacacc                    48

<210> SEQ ID NO 452
<211> LENGTH: 39
<212> TYPE: DNA
<213> ORGANISM: Homo sapiens

<400> SEQUENCE: 452
caggggggcc ctggagatca ccaactaccc acacacacc                              39

<210> SEQ ID NO 453
<211> LENGTH: 40
<212> TYPE: DNA
<213> ORGANISM: Homo sapiens

<400> SEQUENCE: 453
caggaggcgg ggaagagatc accaactacc cacacacacc                             40

<210> SEQ ID NO 454
<211> LENGTH: 41
<212> TYPE: DNA
<213> ORGANISM: Homo sapiens

<400> SEQUENCE: 454
```
gcgagcaggg cgagaaagat caccaactac ccacacacac c     41

<210> SEQ ID NO 455
<211> LENGTH: 41
<212> TYPE: DNA
<213> ORGANISM: Homo sapiens

<400> SEQUENCE: 455
cccatcctgc tggagcagat caccaactac ccacacacac c     41

<210> SEQ ID NO 456
<211> LENGTH: 48
<212> TYPE: DNA
<213> ORGANISM: Homo sapiens

<400> SEQUENCE: 456
tgtcttcacc tacccacccc tatagatcac caactaccca cacacacc     48

<210> SEQ ID NO 457
<211> LENGTH: 48
<212> TYPE: DNA
<213> ORGANISM: Homo sapiens

<400> SEQUENCE: 457
attagccact ccctagtcct agcagatcac caactaccca cacacacc     48

<210> SEQ ID NO 458
<211> LENGTH: 48
<212> TYPE: DNA
<213> ORGANISM: Homo sapiens

<400> SEQUENCE: 458
cacgtttcaa ttttttttcaa aacagatcac caactaccca cacacacc     48

<210> SEQ ID NO 459
<211> LENGTH: 48
<212> TYPE: DNA
<213> ORGANISM: Homo sapiens

<400> SEQUENCE: 459
ggctacatag aatataaaaa cttagatcac caactaccca cacacacc     48

<210> SEQ ID NO 460
<211> LENGTH: 39
<212> TYPE: DNA
<213> ORGANISM: Homo sapiens

<400> SEQUENCE: 460
cgcacccggg catcagatca ccaactaccc acacacacc     39

<210> SEQ ID NO 461
<211> LENGTH: 40
<212> TYPE: DNA
<213> ORGANISM: Homo sapiens

<400> SEQUENCE: 461
aggaggcctt cgccgagatc accaactacc cacacacacc     40

<210> SEQ ID NO 462
<211> LENGTH: 44
<212> TYPE: DNA
<213> ORGANISM: Homo sapiens

<400> SEQUENCE: 462

```
cacagaacac gccgttgaca gatcaccaac tacccacaca cacc                    44
```

<210> SEQ ID NO 463
<211> LENGTH: 39
<212> TYPE: DNA
<213> ORGANISM: Homo sapiens

<400> SEQUENCE: 463

```
ctggcgctgg gctcagatca ccaactaccc acacacacc                          39
```

<210> SEQ ID NO 464
<211> LENGTH: 47
<212> TYPE: DNA
<213> ORGANISM: Homo sapiens

<400> SEQUENCE: 464

```
gattccgaga aactatgtgc ccagatcacc aactacccac acacacc                 47
```

<210> SEQ ID NO 465
<211> LENGTH: 40
<212> TYPE: DNA
<213> ORGANISM: Homo sapiens

<400> SEQUENCE: 465

```
caaggagcgc gggagagatc accaactacc cacacacacc                         40
```

<210> SEQ ID NO 466
<211> LENGTH: 45
<212> TYPE: DNA
<213> ORGANISM: Homo sapiens

<400> SEQUENCE: 466

```
ccacccctct caactcacaa agatcaccaa ctacccacac acacc                   45
```

<210> SEQ ID NO 467
<211> LENGTH: 44
<212> TYPE: DNA
<213> ORGANISM: Homo sapiens

<400> SEQUENCE: 467

```
ggggctagga actcgaggaa gatcaccaac tacccacaca cacc                    44
```

<210> SEQ ID NO 468
<211> LENGTH: 44
<212> TYPE: DNA
<213> ORGANISM: Homo sapiens

<400> SEQUENCE: 468

```
tctttcttgg agccctggca gatcaccaac tacccacaca cacc                    44
```

<210> SEQ ID NO 469
<211> LENGTH: 44
<212> TYPE: DNA
<213> ORGANISM: Homo sapiens

<400> SEQUENCE: 469

```
agggagcccc taacaaagca gatcaccaac tacccacaca cacc                    44
```

<210> SEQ ID NO 470
<211> LENGTH: 39
<212> TYPE: DNA
<213> ORGANISM: Homo sapiens -continued

```
<400> SEQUENCE: 470
gggcgctgcc acgaagatca ccaactaccc acacacacc                      39

<210> SEQ ID NO 471
<211> LENGTH: 47
<212> TYPE: DNA
<213> ORGANISM: Homo sapiens

<400> SEQUENCE: 471
ccctttctcg cgtcagtgtt taagatcacc aactacccac acacacc             47

<210> SEQ ID NO 472
<211> LENGTH: 45
<212> TYPE: DNA
<213> ORGANISM: Homo sapiens

<400> SEQUENCE: 472
ctgaccggtc tccacagaga agatcaccaa ctacccacac acacc               45

<210> SEQ ID NO 473
<211> LENGTH: 43
<212> TYPE: DNA
<213> ORGANISM: Homo sapiens

<400> SEQUENCE: 473
ccgaaaaaga gcggaggcag atcaccaact acccacacac acc                 43

<210> SEQ ID NO 474
<211> LENGTH: 45
<212> TYPE: DNA
<213> ORGANISM: Homo sapiens

<400> SEQUENCE: 474
gattcccatc cagttgaccg agatcaccaa ctacccacac acacc               45

<210> SEQ ID NO 475
<211> LENGTH: 41
<212> TYPE: DNA
<213> ORGANISM: Homo sapiens

<400> SEQUENCE: 475
cccccgagag tcagggagat caccaactac ccacacacac c                   41

<210> SEQ ID NO 476
<211> LENGTH: 44
<212> TYPE: DNA
<213> ORGANISM: Homo sapiens

<400> SEQUENCE: 476
ctccttcttg accttgccca gatcaccaac tacccacaca cacc                44

<210> SEQ ID NO 477
<211> LENGTH: 47
<212> TYPE: DNA
<213> ORGANISM: Homo sapiens

<400> SEQUENCE: 477
gattccgaga aactatgtgc ccagatcacc aactacccac acacacc             47

<210> SEQ ID NO 478
<211> LENGTH: 43
<212> TYPE: DNA
<213> ORGANISM: Homo sapiens
```

<400> SEQUENCE: 478
ttctacgagc agcaggcgag atcaccaact acccacacac acc    43

<210> SEQ ID NO 479
<211> LENGTH: 48
<212> TYPE: DNA
<213> ORGANISM: Homo sapiens

<400> SEQUENCE: 479
acagcaaaaa ctacccttga tcaagatcac caactaccca cacacacc    48

<210> SEQ ID NO 480
<211> LENGTH: 47
<212> TYPE: DNA
<213> ORGANISM: Homo sapiens

<400> SEQUENCE: 480
ggtggaaaat tctgcaagcc agagatcacc aactacccac acacacc    47

<210> SEQ ID NO 481
<211> LENGTH: 38
<212> TYPE: DNA
<213> ORGANISM: Homo sapiens

<400> SEQUENCE: 481
ctaccccacc ttcctcattc tctctaggca ggcggggc    38

<210> SEQ ID NO 482
<211> LENGTH: 42
<212> TYPE: DNA
<213> ORGANISM: Homo sapiens

<400> SEQUENCE: 482
ctaccccacc ttcctcattc tctcttttgg ccctccctct cg    42

<210> SEQ ID NO 483
<211> LENGTH: 41
<212> TYPE: DNA
<213> ORGANISM: Homo sapiens

<400> SEQUENCE: 483
ctaccccacc ttcctcattc tctcttacct tgtgccgggc c    41

<210> SEQ ID NO 484
<211> LENGTH: 41
<212> TYPE: DNA
<213> ORGANISM: Homo sapiens

<400> SEQUENCE: 484
ctaccccacc ttcctcattc tctctgcggc ggtgttcatg g    41

<210> SEQ ID NO 485
<211> LENGTH: 47
<212> TYPE: DNA
<213> ORGANISM: Homo sapiens

<400> SEQUENCE: 485
ctaccccacc ttcctcattc tctcttcagg gcatgaagag ttcttgg    47

<210> SEQ ID NO 486
<211> LENGTH: 44
<212> TYPE: DNA

```
<213> ORGANISM: Homo sapiens

<400> SEQUENCE: 486 ctacccccacc ttcctcattc tctctggtag accctcacag cgtc                44

<210> SEQ ID NO 487
<211> LENGTH: 38
<212> TYPE: DNA
<213> ORGANISM: Homo sapiens

<400> SEQUENCE: 487 ctacccccacc ttcctcattc tctctccacc cgcagggg                       38

<210> SEQ ID NO 488
<211> LENGTH: 47
<212> TYPE: DNA
<213> ORGANISM: Homo sapiens

<400> SEQUENCE: 488 ctacccccacc ttcctcattc tctctgcctt tatcttgctg gctagtg             47

<210> SEQ ID NO 489
<211> LENGTH: 47
<212> TYPE: DNA
<213> ORGANISM: Homo sapiens

<400> SEQUENCE: 489 ctacccccacc ttcctcattc tctcttcagg cccatcatct cttactt             47

<210> SEQ ID NO 490
<211> LENGTH: 47
<212> TYPE: DNA
<213> ORGANISM: Homo sapiens

<400> SEQUENCE: 490 ctacccccacc ttcctcattc tctcttcatt aacacttccc tctccct             47

<210> SEQ ID NO 491
<211> LENGTH: 44
<212> TYPE: DNA
<213> ORGANISM: Homo sapiens

<400> SEQUENCE: 491 ctacccccacc ttcctcattc tctctcacgt cagtcactca cgca                44

<210> SEQ ID NO 492
<211> LENGTH: 44
<212> TYPE: DNA
<213> ORGANISM: Homo sapiens

<400> SEQUENCE: 492 ctacccccacc ttcctcattc tctcttcagc cccatgctta gcac                44

<210> SEQ ID NO 493
<211> LENGTH: 47
<212> TYPE: DNA
<213> ORGANISM: Homo sapiens

<400> SEQUENCE: 493 ctacccccacc ttcctcattc tctctgttgc cttcttagtc agatggg             47

<210> SEQ ID NO 494
<211> LENGTH: 47
```

<212> TYPE: DNA
<213> ORGANISM: Homo sapiens

<400> SEQUENCE: 494
ctaccccacc ttcctcattc tctctcttca gtcaatgcta gaaatgg         47

<210> SEQ ID NO 495
<211> LENGTH: 47
<212> TYPE: DNA
<213> ORGANISM: Homo sapiens

<400> SEQUENCE: 495
ctaccccacc ttcctcattc tctctgggag taatgccttt caggttt         47

<210> SEQ ID NO 496
<211> LENGTH: 46
<212> TYPE: DNA
<213> ORGANISM: Homo sapiens

<400> SEQUENCE: 496
ctaccccacc ttcctcattc tctctgttcc ttagccttgg tgctga          46

<210> SEQ ID NO 497
<211> LENGTH: 38
<212> TYPE: DNA
<213> ORGANISM: Homo sapiens

<400> SEQUENCE: 497
ctaccccacc ttcctcattc tctctgccgg tcgcaggc                   38

<210> SEQ ID NO 498
<211> LENGTH: 44
<212> TYPE: DNA
<213> ORGANISM: Homo sapiens

<400> SEQUENCE: 498
ctaccccacc ttcctcattc tctctgacag atggaccagg gcag            44

<210> SEQ ID NO 499
<211> LENGTH: 47
<212> TYPE: DNA
<213> ORGANISM: Homo sapiens

<400> SEQUENCE: 499
ctaccccacc ttcctcattc tctctgtgat tggaggatat gttgtca         47

<210> SEQ ID NO 500
<211> LENGTH: 47
<212> TYPE: DNA
<213> ORGANISM: Homo sapiens

<400> SEQUENCE: 500
ctaccccacc ttcctcattc tctcttagga acagtgtaag agcctgg         47

<210> SEQ ID NO 501
<211> LENGTH: 44
<212> TYPE: DNA
<213> ORGANISM: Homo sapiens

<400> SEQUENCE: 501
ctaccccacc ttcctcattc tctctcccac cctgttccag ttgt            44

<210> SEQ ID NO 502

<211> LENGTH: 41
<212> TYPE: DNA
<213> ORGANISM: Homo sapiens

<400> SEQUENCE: 502
ctaccccacc ttcctcattc tctctcgggc tgagtagtgg c    41

<210> SEQ ID NO 503
<211> LENGTH: 38
<212> TYPE: DNA
<213> ORGANISM: Homo sapiens

<400> SEQUENCE: 503
ctaccccacc ttcctcattc tctctgagcc gcgcgtcc    38

<210> SEQ ID NO 504
<211> LENGTH: 42
<212> TYPE: DNA
<213> ORGANISM: Homo sapiens

<400> SEQUENCE: 504
ctaccccacc ttcctcattc tctcttgggg tagaaggcgg ag    42

<210> SEQ ID NO 505
<211> LENGTH: 38
<212> TYPE: DNA
<213> ORGANISM: Homo sapiens

<400> SEQUENCE: 505
ctaccccacc ttcctcattc tctctcccac ctgcccgg    38

<210> SEQ ID NO 506
<211> LENGTH: 44
<212> TYPE: DNA
<213> ORGANISM: Homo sapiens

<400> SEQUENCE: 506
ctaccccacc ttcctcattc tctctgctcg agtcacgtgg ctta    44

<210> SEQ ID NO 507
<211> LENGTH: 46
<212> TYPE: DNA
<213> ORGANISM: Homo sapiens

<400> SEQUENCE: 507
ctaccccacc ttcctcattc tctctagaaa aaacgagggg cgcaag    46

<210> SEQ ID NO 508
<211> LENGTH: 47
<212> TYPE: DNA
<213> ORGANISM: Homo sapiens

<400> SEQUENCE: 508
ctaccccacc ttcctcattc tctctcgaca gatttgttgc ttaaatt    47

<210> SEQ ID NO 509
<211> LENGTH: 41
<212> TYPE: DNA
<213> ORGANISM: Homo sapiens

<400> SEQUENCE: 509
ctaccccacc ttcctcattc tctctggcgg tgggaacctt c    41

<210> SEQ ID NO 510
<211> LENGTH: 45
<212> TYPE: DNA
<213> ORGANISM: Homo sapiens

<400> SEQUENCE: 510
ctaccccacc ttcctcattc tctcttaaag ggcccgtacc tctcc                45

<210> SEQ ID NO 511
<211> LENGTH: 47
<212> TYPE: DNA
<213> ORGANISM: Homo sapiens

<400> SEQUENCE: 511
ctaccccacc ttcctcattc tctcttgcca gagtaaacag aacacca              47

<210> SEQ ID NO 512
<211> LENGTH: 38
<212> TYPE: DNA
<213> ORGANISM: Homo sapiens

<400> SEQUENCE: 512
ctaccccacc ttcctcattc tctctggacc ggtccccg                        38

<210> SEQ ID NO 513
<211> LENGTH: 47
<212> TYPE: DNA
<213> ORGANISM: Homo sapiens

<400> SEQUENCE: 513
ctaccccacc ttcctcattc tctctaggtc cgaggtgcaa tcctaaa               47

<210> SEQ ID NO 514
<211> LENGTH: 47
<212> TYPE: DNA
<213> ORGANISM: Homo sapiens

<400> SEQUENCE: 514
ctaccccacc ttcctcattc tctctgtaag agatcccaga ggacact               47

<210> SEQ ID NO 515
<211> LENGTH: 39
<212> TYPE: DNA
<213> ORGANISM: Homo sapiens

<400> SEQUENCE: 515
ctaccccacc ttcctcattc tctctccagg cagcaggcg                       39

<210> SEQ ID NO 516
<211> LENGTH: 41
<212> TYPE: DNA
<213> ORGANISM: Homo sapiens

<400> SEQUENCE: 516
ctaccccacc ttcctcattc tctctgcggg accgtactcg t                    41

<210> SEQ ID NO 517
<211> LENGTH: 42
<212> TYPE: DNA
<213> ORGANISM: Homo sapiens

<400> SEQUENCE: 517
ctaccccacc ttcctcattc tctctatggt ggcacgatcg gc                   42

<210> SEQ ID NO 518
<211> LENGTH: 39
<212> TYPE: DNA
<213> ORGANISM: Homo sapiens

<400> SEQUENCE: 518
ctaccccacc ttcctcattc tctctccatc ctggggcgc                     39

<210> SEQ ID NO 519
<211> LENGTH: 47
<212> TYPE: DNA
<213> ORGANISM: Homo sapiens

<400> SEQUENCE: 519
ctaccccacc ttcctcattc tctcttgagc atggcctttt tgtcctc            47

<210> SEQ ID NO 520
<211> LENGTH: 41
<212> TYPE: DNA
<213> ORGANISM: Homo sapiens

<400> SEQUENCE: 520
ctaccccacc ttcctcattc tctctcagcc cacgctgcct a                  41

<210> SEQ ID NO 521
<211> LENGTH: 45
<212> TYPE: DNA
<213> ORGANISM: Homo sapiens

<400> SEQUENCE: 521
ctaccccacc ttcctcattc tctctgccaa gacagcccag tctag              45

<210> SEQ ID NO 522
<211> LENGTH: 41
<212> TYPE: DNA
<213> ORGANISM: Homo sapiens

<400> SEQUENCE: 522
ctaccccacc ttcctcattc tctctggcag gagtgagcga c                  41

<210> SEQ ID NO 523
<211> LENGTH: 44
<212> TYPE: DNA
<213> ORGANISM: Homo sapiens

<400> SEQUENCE: 523
ctaccccacc ttcctcattc tctctggagg gagccaaatg ttcc               44

<210> SEQ ID NO 524
<211> LENGTH: 38
<212> TYPE: DNA
<213> ORGANISM: Homo sapiens

<400> SEQUENCE: 524
ctaccccacc ttcctcattc tctctcggct cctcgccg                      38

<210> SEQ ID NO 525
<211> LENGTH: 44
<212> TYPE: DNA
<213> ORGANISM: Homo sapiens

<400> SEQUENCE: 525
ctaccccacc ttcctcattc tctcttctga gatcccacgg gtcc               44

<210> SEQ ID NO 526
<211> LENGTH: 44
<212> TYPE: DNA
<213> ORGANISM: Homo sapiens

<400> SEQUENCE: 526
ctaccccacc ttcctcattc tctctagttg ctgctgcact ggtg         44

<210> SEQ ID NO 527
<211> LENGTH: 47
<212> TYPE: DNA
<213> ORGANISM: Homo sapiens

<400> SEQUENCE: 527
ctaccccacc ttcctcattc tctctcttct gacttccctc ctccttc      47

<210> SEQ ID NO 528
<211> LENGTH: 43
<212> TYPE: DNA
<213> ORGANISM: Homo sapiens

<400> SEQUENCE: 528
ctaccccacc ttcctcattc tctctggctc catccaggct tct          43

<210> SEQ ID NO 529
<211> LENGTH: 43
<212> TYPE: DNA
<213> ORGANISM: Homo sapiens

<400> SEQUENCE: 529
ctaccccacc ttcctcattc tctctgaggg agaaggcttg ggg          43

<210> SEQ ID NO 530
<211> LENGTH: 42
<212> TYPE: DNA
<213> ORGANISM: Homo sapiens

<400> SEQUENCE: 530
ctaccccacc ttcctcattc tctctcaccc ccacaggaac cc           42

<210> SEQ ID NO 531
<211> LENGTH: 38
<212> TYPE: DNA
<213> ORGANISM: Homo sapiens

<400> SEQUENCE: 531
ctaccccacc ttcctcattc tctctcgccg gcagcagc                38

<210> SEQ ID NO 532
<211> LENGTH: 41
<212> TYPE: DNA
<213> ORGANISM: Homo sapiens

<400> SEQUENCE: 532
ctaccccacc ttcctcattc tctctgagga ggggcagagc c            41

<210> SEQ ID NO 533
<211> LENGTH: 40
<212> TYPE: DNA
<213> ORGANISM: Homo sapiens

<400> SEQUENCE: 533

```
ctaccccacc ttcctcattc tctctggacg gagcaggcag                40
```

<210> SEQ ID NO 534
<211> LENGTH: 39
<212> TYPE: DNA
<213> ORGANISM: Homo sapiens

<400> SEQUENCE: 534

```
ctaccccacc ttcctcattc tctcttggtt ggggccccg                 39
```

<210> SEQ ID NO 535
<211> LENGTH: 46
<212> TYPE: DNA
<213> ORGANISM: Homo sapiens

<400> SEQUENCE: 535

```
ctaccccacc ttcctcattc tctctctgtg cccagacctt gtaaag         46
```

<210> SEQ ID NO 536
<211> LENGTH: 44
<212> TYPE: DNA
<213> ORGANISM: Homo sapiens

<400> SEQUENCE: 536

```
ctaccccacc ttcctcattc tctctgcttc tctctccgct tccc           44
```

<210> SEQ ID NO 537
<211> LENGTH: 47
<212> TYPE: DNA
<213> ORGANISM: Homo sapiens

<400> SEQUENCE: 537

```
ctaccccacc ttcctcattc tctctatgct tgagattctt ttcctga        47
```

<210> SEQ ID NO 538
<211> LENGTH: 47
<212> TYPE: DNA
<213> ORGANISM: Homo sapiens

<400> SEQUENCE: 538

```
ctaccccacc ttcctcattc tctcttttca taagaatcca ttgggct        47
```

<210> SEQ ID NO 539
<211> LENGTH: 47
<212> TYPE: DNA
<213> ORGANISM: Homo sapiens

<400> SEQUENCE: 539

```
ctaccccacc ttcctcattc tctcttcgaa ttctaaatcc ggacctg        47
```

<210> SEQ ID NO 540
<211> LENGTH: 47
<212> TYPE: DNA
<213> ORGANISM: Homo sapiens

<400> SEQUENCE: 540

```
ctaccccacc ttcctcattc tctctttttt cagtttcctt gcttta         47
```

<210> SEQ ID NO 541
<211> LENGTH: 40
<212> TYPE: DNA
<213> ORGANISM: Homo sapiens

<400> SEQUENCE: 541

```
ctaccccacc ttcctcattc tctctcgaga ctcgcccggg                   40
```

<210> SEQ ID NO 542
<211> LENGTH: 39
<212> TYPE: DNA
<213> ORGANISM: Homo sapiens

<400> SEQUENCE: 542

```
ctaccccacc ttcctcattc tctctcctgc ctgggctcg                    39
```

<210> SEQ ID NO 543
<211> LENGTH: 43
<212> TYPE: DNA
<213> ORGANISM: Homo sapiens

<400> SEQUENCE: 543

```
ctaccccacc ttcctcattc tctctgctgc aaccatggac agc                43
```

<210> SEQ ID NO 544
<211> LENGTH: 38
<212> TYPE: DNA
<213> ORGANISM: Homo sapiens

<400> SEQUENCE: 544

```
ctaccccacc ttcctcattc tctctgaggg ggcgggtg                     38
```

<210> SEQ ID NO 545
<211> LENGTH: 44
<212> TYPE: DNA
<213> ORGANISM: Homo sapiens

<400> SEQUENCE: 545

```
ctaccccacc ttcctcattc tctctcgccc tgctcagaaa gaca              44
```

<210> SEQ ID NO 546
<211> LENGTH: 39
<212> TYPE: DNA
<213> ORGANISM: Homo sapiens

<400> SEQUENCE: 546

```
ctaccccacc ttcctcattc tctctgctgc tgctgctgc                    39
```

<210> SEQ ID NO 547
<211> LENGTH: 43
<212> TYPE: DNA
<213> ORGANISM: Homo sapiens

<400> SEQUENCE: 547

```
ctaccccacc ttcctcattc tctctgagat gggtgcgttg agc                43
```

<210> SEQ ID NO 548
<211> LENGTH: 44
<212> TYPE: DNA
<213> ORGANISM: Homo sapiens

<400> SEQUENCE: 548

```
ctaccccacc ttcctcattc tctctgcctg ccttggtctc tgaa              44
```

<210> SEQ ID NO 549
<211> LENGTH: 39
<212> TYPE: DNA
<213> ORGANISM: Homo sapiens

<400> SEQUENCE: 549
ctaccccacc ttcctcattc tctctcagtg cgggacgcg                              39

<210> SEQ ID NO 550
<211> LENGTH: 43
<212> TYPE: DNA
<213> ORGANISM: Homo sapiens

<400> SEQUENCE: 550
ctaccccacc ttcctcattc tctctcaacc atagacaccg ccc                         43

<210> SEQ ID NO 551
<211> LENGTH: 41
<212> TYPE: DNA
<213> ORGANISM: Homo sapiens

<400> SEQUENCE: 551
ctaccccacc ttcctcattc tctctcgggt cggactgagg g                           41

<210> SEQ ID NO 552
<211> LENGTH: 41
<212> TYPE: DNA
<213> ORGANISM: Homo sapiens

<400> SEQUENCE: 552
ctaccccacc ttcctcattc tctctgccct tccaacccct c                           41

<210> SEQ ID NO 553
<211> LENGTH: 47
<212> TYPE: DNA
<213> ORGANISM: Homo sapiens

<400> SEQUENCE: 553
ctaccccacc ttcctcattc tctctctttc aggcaatgat gtcatct                     47

<210> SEQ ID NO 554
<211> LENGTH: 47
<212> TYPE: DNA
<213> ORGANISM: Homo sapiens

<400> SEQUENCE: 554
ctaccccacc ttcctcattc tctctgcaag attcctgcga atgtgta                     47

<210> SEQ ID NO 555
<211> LENGTH: 42
<212> TYPE: DNA
<213> ORGANISM: Homo sapiens

<400> SEQUENCE: 555
ctaccccacc ttcctcattc tctctccgtg aaacaggggc ct                          42

<210> SEQ ID NO 556
<211> LENGTH: 42
<212> TYPE: DNA
<213> ORGANISM: Homo sapiens

<400> SEQUENCE: 556
ctaccccacc ttcctcattc tctctccact tactgagccc gc                          42

<210> SEQ ID NO 557
<211> LENGTH: 40
<212> TYPE: DNA
<213> ORGANISM: Homo sapiens -continued

<400> SEQUENCE: 557
ctaccccacc ttcctcattc tctctgtgtg cggatggggc                         40

<210> SEQ ID NO 558
<211> LENGTH: 42
<212> TYPE: DNA
<213> ORGANISM: Homo sapiens

<400> SEQUENCE: 558
ctaccccacc ttcctcattc tctcttccag cccagggtcc tc                      42

<210> SEQ ID NO 559
<211> LENGTH: 44
<212> TYPE: DNA
<213> ORGANISM: Homo sapiens

<400> SEQUENCE: 559
ctaccccacc ttcctcattc tctctagaga ttgagagcgc ggct                    44

<210> SEQ ID NO 560
<211> LENGTH: 40
<212> TYPE: DNA
<213> ORGANISM: Homo sapiens

<400> SEQUENCE: 560
ctaccccacc ttcctcattc tctcttggcc tctgggtccc                         40

<210> SEQ ID NO 561
<211> LENGTH: 43
<212> TYPE: DNA
<213> ORGANISM: Homo sapiens

<400> SEQUENCE: 561
ctaccccacc ttcctcattc tctctttcct ttctcccggc tgc                     43

<210> SEQ ID NO 562
<211> LENGTH: 42
<212> TYPE: DNA
<213> ORGANISM: Homo sapiens

<400> SEQUENCE: 562
ctaccccacc ttcctcattc tctcttgggg agaagggggc ag                      42

<210> SEQ ID NO 563
<211> LENGTH: 40
<212> TYPE: DNA
<213> ORGANISM: Homo sapiens

<400> SEQUENCE: 563
ctaccccacc ttcctcattc tctctctgcc gggtccctgg                         40

<210> SEQ ID NO 564
<211> LENGTH: 38
<212> TYPE: DNA
<213> ORGANISM: Homo sapiens

<400> SEQUENCE: 564
ctaccccacc ttcctcattc tctctcggga ggcgggct                           38

<210> SEQ ID NO 565
<211> LENGTH: 39
<212> TYPE: DNA

```
<213> ORGANISM: Homo sapiens

<400> SEQUENCE: 565 ctacccacc ttcctcattc tctctccgat tgggccgcc                    39

<210> SEQ ID NO 566
<211> LENGTH: 47
<212> TYPE: DNA
<213> ORGANISM: Homo sapiens

<400> SEQUENCE: 566 ctacccacc ttcctcattc tctctatgtt ctgctacaag tctaaga           47

<210> SEQ ID NO 567
<211> LENGTH: 38
<212> TYPE: DNA
<213> ORGANISM: Homo sapiens

<400> SEQUENCE: 567 ctacccacc ttcctcattc tctctgcccg tccagccg                     38

<210> SEQ ID NO 568
<211> LENGTH: 41
<212> TYPE: DNA
<213> ORGANISM: Homo sapiens

<400> SEQUENCE: 568 ctacccacc ttcctcattc tctctatcga tgcgttccgc g                 41

<210> SEQ ID NO 569
<211> LENGTH: 42
<212> TYPE: DNA
<213> ORGANISM: Homo sapiens

<400> SEQUENCE: 569 ctacccacc ttcctcattc tctctactgc gtgccccaag tc                42

<210> SEQ ID NO 570
<211> LENGTH: 38
<212> TYPE: DNA
<213> ORGANISM: Homo sapiens

<400> SEQUENCE: 570 ctacccacc ttcctcattc tctctgcggg tccctggg                     38

<210> SEQ ID NO 571
<211> LENGTH: 45
<212> TYPE: DNA
<213> ORGANISM: Homo sapiens

<400> SEQUENCE: 571 ctacccacc ttcctcattc tctctaagac accaggctgc aggat             45

<210> SEQ ID NO 572
<211> LENGTH: 38
<212> TYPE: DNA
<213> ORGANISM: Homo sapiens

<400> SEQUENCE: 572 ctacccacc ttcctcattc tctcttcctg cgcgctgc                     38

<210> SEQ ID NO 573
<211> LENGTH: 40
```

<212> TYPE: DNA
<213> ORGANISM: Homo sapiens

<400> SEQUENCE: 573
ctaccccacc ttcctcattc tctcttggcc tctgggtccc                                40

<210> SEQ ID NO 574
<211> LENGTH: 41
<212> TYPE: DNA
<213> ORGANISM: Homo sapiens

<400> SEQUENCE: 574
ctaccccacc ttcctcattc tctctgagga ggggcagagc c                              41

<210> SEQ ID NO 575
<211> LENGTH: 46
<212> TYPE: DNA
<213> ORGANISM: Homo sapiens

<400> SEQUENCE: 575
ctaccccacc ttcctcattc tctctcctag aacgcaacca acaaga                         46

<210> SEQ ID NO 576
<211> LENGTH: 43
<212> TYPE: DNA
<213> ORGANISM: Homo sapiens

<400> SEQUENCE: 576
ctaccccacc ttcctcattc tctctggaca gtcgccatga caa                            43

<210> SEQ ID NO 577
<211> LENGTH: 23
<212> TYPE: DNA
<213> ORGANISM: Homo sapiens

<400> SEQUENCE: 577
ggtgtgtgtg ggtagttggt gat                                                  23

<210> SEQ ID NO 578
<211> LENGTH: 23
<212> TYPE: DNA
<213> ORGANISM: Homo sapiens

<400> SEQUENCE: 578
agagaatgag gaaggtgggg tag                                                  23

<210> SEQ ID NO 579
<211> LENGTH: 23
<212> TYPE: DNA
<213> ORGANISM: Homo sapiens

<400> SEQUENCE: 579
ctaccccacc ttcctcattc tct                                                  23

<210> SEQ ID NO 580
<211> LENGTH: 47
<212> TYPE: DNA
<213> ORGANISM: Homo sapiens
<220> FEATURE:
<221> NAME/KEY: MISC_FEATURE
<222> LOCATION: (20)..(24)
<223> OTHER INFORMATION: n = a, c, g, or t

<400> SEQUENCE: 580

```
gcctccctcg cgccatcagn nnnnggtgtg tgtgggtagt tggtgat      47
```

<210> SEQ ID NO 581
<211> LENGTH: 47
<212> TYPE: DNA
<213> ORGANISM: Homo sapiens
<220> FEATURE:
<221> NAME/KEY: MISC_FEATURE
<222> LOCATION: (20)..(24)
<223> OTHER INFORMATION: n = a, c, g, or t

<400> SEQUENCE: 581

```
gccttgccag cccgctcagn nnnctaccc caccttcctc attctct        47
```

<210> SEQ ID NO 582
<211> LENGTH: 302
<212> TYPE: DNA
<213> ORGANISM: Homo sapiens

<400> SEQUENCE: 582

```
ctgctggcag caaagagact tgcaggattt ggcctaccca tggccactta ccgcgcacgc    60
tcaggaccgg gggcttggtg ggaaaggaag gagggactta gggtgcgcct gcgcatcagg   120
ggcgcgcgca aggggctgat ttggtgatcc ctttaagaaa ccgcaggcgg aggaatttct   180
ctgagagaaa ataatcctac tcacggggcc ccttggaggc cattaacccc ccgagtcccg   240
gcccccaccc cgtccccggg caggccctcc cgcccacgcg cggacccgtg ggatctcaga   300
ag                                                                 302
```

<210> SEQ ID NO 583
<211> LENGTH: 256
<212> TYPE: DNA
<213> ORGANISM: Homo sapiens

<400> SEQUENCE: 583

```
ctaatgggac tttgcttttt cctttgtcgg gtcatttatt tcacttttcc tggcgctgag    60
atggcctgag tctgtgtatg tgtgcacacg tgtgtggcca ctgcttttct tccaaaggac   120
tcacctctct tctgccattt tactaggaca caggaggcgg ctctctgctc tcgctctccc   180
tctcttttc tccctgcccc caactcagcc tgggcttttt cctgtctctt aactccacca   240
gtgcagcagc aactag                                                  256
```

<210> SEQ ID NO 584
<211> LENGTH: 161
<212> TYPE: DNA
<213> ORGANISM: Homo sapiens

<400> SEQUENCE: 584

```
ctcttgtact gttggcgtgt gggaggcatt tgggatgggg tgagggtcag agtgggcttg    60
tgggaccgaa tgtccccagt ctgttattcc tgcccccact tcagagtcct gccactcaca   120
agtgtgagac gatggatgaa ggaggaggga agtcagaaga g                       161
```

<210> SEQ ID NO 585
<211> LENGTH: 189
<212> TYPE: DNA
<213> ORGANISM: Homo sapiens

<400> SEQUENCE: 585

```
cttgcggagt tcacgggggt cactcgggca caggcttgtg acccaggcgc ggagaatgat    60
tcacggggtg gctctttgca ttctttgtcg ggtagtcacg tcgggccggg caccccgccg   120
```

```
acggatacct gcggatggaa agacacccgg cccgacgcca gcgagcggga gaagcctgga    180
tggagccag                                                           189

<210> SEQ ID NO 586
<211> LENGTH: 419
<212> TYPE: DNA
<213> ORGANISM: Homo sapiens

<400> SEQUENCE: 586 cttgggctc tctggctgag tgatctgggg gccattcaac cggttttttc ctggagaaat    60
gggaatctta aggcctctct ggaaagggtg tgaggggtc gagggggagc gggcccggg     120 ccttcagcgc ttcagcaggt ggcttccctt tgcgagcccg gggtccctct tctgggaagc   180
atgggctggg acaaggcagg cgccggtttt ctgcatccca aatgtcctgg gcatgtgtc    240 ccttccttgc tgaccgtggg tccgggccag agcgcaaggt ccaaagccgg cggcttggct   300
ccaccgccag gggcaaatac cagggcggga tgcgtgctgc ggggcgcccc ggggctccc    360 ccttgggact tctagggtcc aggggtcccc gcgggcgcgc cccaagcctt ctccctcag    419

<210> SEQ ID NO 587
<211> LENGTH: 511
<212> TYPE: DNA
<213> ORGANISM: Homo sapiens

<400> SEQUENCE: 587
ctggctgagc atgggctgct gagtggaggg cagatdggga ggcagggagg gtggatgggg    60
gttggcgggc aggaccagcg gctcaggagt ggctggggct agtgagggga tgtgggtctg    120
gtgggctagc agggtgcctg tagcgagtca gagccccatg agcgccctgg agttggaaag    180
gtggaggcag gaacagacag acccattcag gggctgccct gccttccgcc gaccagcacc    240
ccaggagcct ctgaatgaaa cacactgggc tcgcaggcgg gggactcgtt cacgtgtgcc    300
tttggatttg cttcagaacc tctgatagag cccaggtccc ggggctcatg gtggcctgga    360
cttccaggtt gtgatgccag gagggtccca gccgggaagc cccgagcagg gctcaggccg    420
cccatggggg gtcagtggcc agcaccttcc cttccgcctg caggctgctg atatgcagga    480
ggaaatcctg gcgggttcct gtgggggtga g                                  511

<210> SEQ ID NO 588
<211> LENGTH: 304
<212> TYPE: DNA
<213> ORGANISM: Homo sapiens

<400> SEQUENCE: 588
cttttccgag agtcggagtg gaggcgcggg gctggagggc tctccggagc cgcccaccag    60
ggtcctctgg gggcccggtc ccgactgggc aggggacct ggacagggcc ccggagcgtg     120
gagacggctg aggaaagttg ggggtcgggg ccttggggcg gggagcgcgg aacccggcgc    180
cgatgcccgc gttcatgaat atgcacgagc cacctccctc cctccgtgac gtcacgggcc    240
gtcccggggt gagcgcctga gccgctccgg gtccgcgcca gtgagcgcgg ctgctgccgg    300
cgag                                                                304

<210> SEQ ID NO 589
<211> LENGTH: 157
<212> TYPE: DNA
<213> ORGANISM: Homo sapiens
```

<400> SEQUENCE: 589

| ctaatgatca accggctgcg gtgtctgtgc agccgccctg ggcctgcctc tccgtcaccg | 60 |
| gccctcaggc gcagggagga agtagggcag gaagcagggg gcggaggccg ctgtgcagtc | 120 |
| agcctggctg tgggcggccc ctgcctgctc cgtccag | 157 |

<210> SEQ ID NO 590
<211> LENGTH: 204
<212> TYPE: DNA
<213> ORGANISM: Homo sapiens

<400> SEQUENCE: 590

| cttctgcctc gtcccgtggg gcgtggggcg agaccccaa ggtgtaggga gggggtccc | 60 |
| agccgcagcg acacatgcgg gagccggag cggggcggc gccgagcgga gccggccggg | 120 |
| tccctcgcct tgccgccgac tcggccaccc gcccggggcc gtagcatctt gccccggagt | 180 |
| gtatgaaccg gggccccaac caag | 204 |

<210> SEQ ID NO 591
<211> LENGTH: 371
<212> TYPE: DNA
<213> ORGANISM: Homo sapiens

<400> SEQUENCE: 591

| ctttatgtgc cactatcatc attgtctgtt atccttgatc tcctttggtg aggggaaggc | 60 |
| gggaaagaga ggacctctcc gacccttgga ttttttcttt aagcagaggc taataaaaca | 120 |
| aagcgcaaac tgactgtcct gaggagtctg ctcacaccgc tgccccgcag atcattccac | 180 |
| agaccccttg tcccatccct tctggacaga cccaggactg atgagggttc gggttcggga | 240 |
| ggtgtggtgt ggtgggggct tgtgtggctg tagcggccgg cttttcctaaa ccccagagcg | 300 |
| ggatactcgg gatctgagca gaggggaaag tcatctaaga ggctgctgct ttacaaggtc | 360 |
| tgggcacaga g | 371 |

<210> SEQ ID NO 592
<211> LENGTH: 395
<212> TYPE: DNA
<213> ORGANISM: Homo sapiens

<400> SEQUENCE: 592

| cttttctggt aactattttt aattcaaata taattcgagt gatctatcta acaagtcatc | 60 |
| actctgacaa ctcagtgact tgtaatgtaa aattattcat tgtaattcat ttaatattat | 120 |
| tgtttctctg tgctgcaaaa atcatagcaa tcgagatgta atttattact ctccctccca | 180 |
| cctccggcat cttgtgctaa tccttctgcc ctgcggacct cccccgactc tttactatgc | 240 |
| gtgtcaactg ccatcaactt ccttgcttgc tggggactgg ggccgcgagg gcataccccc | 300 |
| gagggtacg gggctagggc taggcaggct gtgcggttgg gcggggccct gtgccccact | 360 |
| gcggagtgcg ggtcgggaag cggagagaga agcag | 395 |

<210> SEQ ID NO 593
<211> LENGTH: 247
<212> TYPE: DNA
<213> ORGANISM: Homo sapiens

<400> SEQUENCE: 593

| ctcctgcagt aatcaaggac agaagcaatt gttaaatgca cctcttaggc tgttatcagt | 60 |
| agaaatacga aataaaagat aaatatgcaa aaacattaat ggcacaataa acactcacgg | 120 | tttttgccttt agacttgaga tacactaaaa tctagattta attaatcgac ttggacgttg     180 gaataagata gtaaaactca caacaaaact ttgtagaact tagtcaggaa aagaatctca     240 agcatag                                                                247

<210> SEQ ID NO 594
<211> LENGTH: 208
<212> TYPE: DNA
<213> ORGANISM: Homo sapiens

<400> SEQUENCE: 594
ctgtcctgtg cctgtgttac ttgctacagt tagaaacaaa cttcatgccc aaaccaagga     60
acccagtgtc ttttctcttg caaaaatcaa agcatgaact catgggcaaa ttttaaaaa      120 taactttcac tggatactta gtagaaattt atcgcgacac gctactaact aacatgatgc     180
cctcagccca atggattctt atgaaaag                                         208

<210> SEQ ID NO 595
<211> LENGTH: 273
<212> TYPE: DNA
<213> ORGANISM: Homo sapiens

<400> SEQUENCE: 595
ctgcaaagcc cctgccagaa ccaaaccgaa ctcgcgcctc ggagaggggc ttctggggcc     60
gtttcgctgc agggcgtggg gagtggagag agggaagggg aagcctgggg ctgggtgtgc     120
gcgcgtggga gcgcgcctcg gagcgccccg cactccccca ctctatcccc gggggcagtt     180
tgggaaggag ggagtggtag tcgcgggaat gagggagcaa gagaaaccct ctcaaagtga     240
cgccccaaac aggtccggat ttagaattcg aag                                  273

<210> SEQ ID NO 596
<211> LENGTH: 345
<212> TYPE: DNA
<213> ORGANISM: Homo sapiens

<400> SEQUENCE: 596
cttatactgt cttttcttca tcaatattca tttattcctg tacgtgtggt tttagaacta     60
tctggaaata taggaacatt gggaaaaatt gaactccaca taaacctaat gtagaaacat     120
tagttttaca gaatactaaa gaaaagcatt tctgcttata ttcattttcg tattttattg     180
gattttttaa aaaatcactt gcacttaagg caaaaacttc gcacatagac atccggcaga     240 gaaccctct ttcatttaaa tacaaaccct aacacatttt ggcatcatca gataaatttg      300
atttaaagcc tgacaaaatt ctaaaagcaa ggaaactgaa aaaag                     345

<210> SEQ ID NO 597
<211> LENGTH: 276
<212> TYPE: DNA
<213> ORGANISM: Homo sapiens

<400> SEQUENCE: 597
ctccacgagg tacacacgaa tgcggagcgc tgtatgccag tttccccgac accggctcgc     60
cgcagggaga cctcaccccg agagcggaag gggtaagggc ggcggggtca aggagatcgg     120
gggtgctgag ttggccagga gtgactgggg tgaccggggg tgctgaggtg gcctggagtg     180
ccggggtggc cggcacacc ttggttcttg tagacgacaa ggtgacccgg gctccgggcg      240
tgcgcacgag gagcaggtgc ccgggcgagt ctcgag                               276

<210> SEQ ID NO 598
<211> LENGTH: 172
<212> TYPE: DNA
<213> ORGANISM: Homo sapiens

<400> SEQUENCE: 598
ctgagtagga gccccactgt tttagttcct agagttaaag ccgaagagga gggaggcgcg    60
agggggtgtg tgcagggctc tgccctgccc tgaactgcca cggtccgcca gttgcgcttc   120
gctccgcggg tgtccgaccc aagccgagcc cgagcccgag cccaggcagg ag           172

<210> SEQ ID NO 599
<211> LENGTH: 235
<212> TYPE: DNA
<213> ORGANISM: Homo sapiens

<400> SEQUENCE: 599
ctgagtgcct cccccggcca ggccagccga ccagatcatt aagtgaccgc cggagtgctc    60
cgtaacgcgc cagccagcca gtgaggcgct gggcgaggcg ggggctctcc tgggacccgt   120
ctccctcttc ccaccttccc ccgctgaccg cggcggtgcc tgcggcagag cctccctctg   180
cagcagcccc ttgcacttgg ctcgcacttc tgggcgctgt ccatggttgc agcag        235

<210> SEQ ID NO 600
<211> LENGTH: 185
<212> TYPE: DNA
<213> ORGANISM: Homo sapiens

<400> SEQUENCE: 600 cttttcctgtt gagcgcggtg gagcgcacac atttccttca gttctttctc ggaagtttag    60
gccgcaccca cccgcgcccc ctttccagga ttatacaagt gcacgccagg gtttcttatt   120
tttggtgtgt ttttgagacc aaagaaccat atccgctaag cctgaggagg cacccgcccc   180
ctcag                                                              185

<210> SEQ ID NO 601
<211> LENGTH: 374
<212> TYPE: DNA
<213> ORGANISM: Homo sapiens

<400> SEQUENCE: 601
ctttctcttc cttttgtgtc attgttccct aaataaagca acacatgaaa ttcctgacgg    60
caaaaatcag actcagatcc caaaacctct gtctttatgc aagatttatc ttttgcattg   120
gaaacggcca aggaatatga agaggggaaa gaagaggcaa acagacaagc atgcaggctc   180
tgaggaataa atgcccctca ggacgctgtc cctggggaa ttgcaaacct cagtccgttt    240
ctgaggaagt gcggtctctg catttctgaa agaggtattt ccccccttg acacaaggag    300 catggtaatg aattgactag ttaaaaactg ttggttggaa aaacccgtcc ctgtgtcttt   360
ctgagcaggg cgag                                                    374

<210> SEQ ID NO 602
<211> LENGTH: 315
<212> TYPE: DNA
<213> ORGANISM: Homo sapiens

<400> SEQUENCE: 602
ctgcctcttt aaactggctt tcctccccg aggagggagc agggagagag ggtggagtgt     60
ggtttgcggc caaacctaaa ggctgcaatt aaccagccgc ccggccttcg ctactccgga   120

```
cagacgaacg tcttaaagga cgtcttcgct cctcgggagt cgcggctgcg ctcgcggtgc    180
gggtctgggc gcgcgccccg cgcctccggg cgaagcggtc gaggaggagc cagtgccggg    240
aggcgggaac gacctgcggc gggtgagact atggagcagc gtcttcggcg ccgcggcgg     300 cagcagcagc agcag                                                    315
```

<210> SEQ ID NO 603
<211> LENGTH: 412
<212> TYPE: DNA
<213> ORGANISM: Homo sapiens

<400> SEQUENCE: 603

```
ctttcatttt tagggcaaac gagccgagtt accggggaag cgagaggtgg ggcgctgcaa    60
gggagccgga tgaggtgata cacgctggcg acacaatagc aggttgctct ttgtgctaag    120
actgacacca tgaggacaca gatttggggg aaggggaat ctctaggcaa aggctgttac     180
agtcaaatct ctgcgaacga ttgtgatccg acagcggtgc aaaaggaaag agcgaatgca    240
gtccacgccg cggaaatcta ggggtagagg caagggggga gggtattccc cttgcaggga    300
ccgtccctgc atttccctct acactgagca gcgtggtcac ctggtccttt tcacctgtgc    360
acaggtaacc tcagactcga gtcagtgaca ctgctcaacg cacccatctc ag            412
```

<210> SEQ ID NO 604
<211> LENGTH: 235
<212> TYPE: DNA
<213> ORGANISM: Homo sapiens

<400> SEQUENCE: 604

```
ctccagggcc cccctgtagc cacagcctta ggcggatcaa aaatgagact aatacaggtc    60
ctggtaatac tgggggtgac caaggcgaaa gaatcgattt ttaagttaag ttttgaggtg    120
tgactgtatc agagggaaag aaaccatgcc aattgaacga ctcacagccc tgtcgttcct    180
gacttgctta ttttcttggc tttgccagaa cttcttcaga gaccaaggca ggcag         235
```

<210> SEQ ID NO 605
<211> LENGTH: 412
<212> TYPE: DNA
<213> ORGANISM: Homo sapiens

<400> SEQUENCE: 605

```
ctcttccccg cctcctgcct ccggccccag cagaggccgc gctcccactg cgcctctcgc    60
ctctgagaaa tggcgcagca gcgctccgc ggagagcctg gaggcgggc gcccttctct      120 gagtccgcgg ggtcgcaccc cgagccagtc ggccagacct gcatcccgcg tagcatccct    180
gccctctctg tgcagcggaa agggcaaaag gcagggactg caagcgggcg cgcaccgggt    240
aggaagagcg gctctgcgta ggtgcgcgga cccgggctcc tgggttccat ccccgccgcg    300
cacctcgggg tccgcacccg gctcctgccg ggcccttttc ggccgcaccc cgctcccgca    360
ccccgctcct ccccaagccc cacccggccc aagccgcgcg tcccgcactg ag            412
```

<210> SEQ ID NO 606
<211> LENGTH: 171
<212> TYPE: DNA
<213> ORGANISM: Homo sapiens

<400> SEQUENCE: 606

```
ctttctcgcc ctgctcgcac gcaagtagaa aggcgctgct gagcccgtcc ctccaaacca    60
```
cgtggtcttg cccgtgctta aaaacaaacg ctgagccagg cgcatgcgcc acgggcctcc    120
ccgcaccagc agaagtcgga gtcgctgttg ggggcggtgt ctatggttga g             171

<210> SEQ ID NO 607
<211> LENGTH: 313
<212> TYPE: DNA
<213> ORGANISM: Homo sapiens

<400> SEQUENCE: 607
ctgctccagc aggatgggcg ccaaaatgtt gcccctgtcc ttcccttccc ctgaaagcgt    60
ctcctctgga gtgggctggc tggacgcttg gccttttccct tttgcctcgg aacttcctaa   120
ataaactcgg agaaaggaca acatggaccc taaccccccac ttcacactgt caggtttccc   180
caaggtggct ccaggggggag gcctctcgcc ccccagcccc gagcccttct ccccaccagc   240
gccgccggga cccatctgct cccgagggcc gaggataagg cgtttggggt tggggccctc    300
agtccgaccc gag                                                        313

<210> SEQ ID NO 608
<211> LENGTH: 205
<212> TYPE: DNA
<213> ORGANISM: Homo sapiens

<400> SEQUENCE: 608
ctataggggt gggtaggtga agacaaagga ggaagataac acaggtagcg tagacattaa    60
actgctcatt gtgaataacc gtttaaatag tcacaatgtg ccaagtgctg aggaaaattc   120
gaacagcgtg ccaggggggtg gctggactca tctggggttc tccggagggc aggcttgcgg   180
aagtcacgag gggttggaag ggcag                                           205

<210> SEQ ID NO 609
<211> LENGTH: 382
<212> TYPE: DNA
<213> ORGANISM: Homo sapiens

<400> SEQUENCE: 609
ctgctaggac tagggagtgg ctaatagttg gaagacgcca aacacaatct atctgcttta    60
ttaaaaagga gtaattaaag gaaaagggag aactgcaaag aacctgggga agggaagagg   120
agtcctcttg ggcccccctc cccttgcgct gacatttgga tcacctcact gagtgatgag   180
gtgaagacag gaacaggtgc gcctcatccc tacccccattt gccctaaaca gggattatct   240
tgctgagttt gctgtgtccg gggccaatta atcaaggcta gacaaaggat agacagcgag   300
aactggaagg catggggtct gggaggcgaa gccaggaacc gcgtacggcg cgccttgcag   360
atgacatcat tgcctgaaag ag                                              382

<210> SEQ ID NO 610
<211> LENGTH: 269
<212> TYPE: DNA
<213> ORGANISM: Homo sapiens

<400> SEQUENCE: 610
ctgttttgaa aaaaattgaa acgtgtagat aatgtctttt ctctatgttt tgattacgct    60
gtgttggcgg atgtgtgggg tttaataatt aggcgaaaaa ctctccatcc ttcacccat    120 ccaatccccg aaaacaattt ggggatttaa aaaatcgcct ttccgtatct tcctcttctg   180
tctccactat tccgctttcc tttagatttt ccagatcct cgatacttgt agtaaactac    240
cttcctacac attcgcagga atcttgcag                                       269

<210> SEQ ID NO 611
<211> LENGTH: 163
<212> TYPE: DNA
<213> ORGANISM: Homo sapiens

<400> SEQUENCE: 611

```
ctaagtttt  atattctatg  tagccccagc  ctaggacgta  aattccacga  gaccaaaagc      60
cttgtgatga  ttccccgagg  ttgctgaccc  tcccggtgtg  tcccgggcct  gctctggggg     120
acacagcggc  gaatacgttg  aacgaggccc  ctgtttcacg  gag                        163
```

<210> SEQ ID NO 612
<211> LENGTH: 353
<212> TYPE: DNA
<213> ORGANISM: Homo sapiens

<400> SEQUENCE: 612

```
ctgatgcccg  ggtgcgtggc  gagggcccgc  cagagaaact  cctgcgtgca  gggttccaaa      60
ggcagcggga  agggcggcac  tcgcgtctcc  agccggctcc  acagcgctgg  cagacacagg     120
ccatcgagcc  cctccagagc  gacttcgtcc  aacaacgact  ccagcgcgtc  cattgctact     180
tcagtcggcg  gcgcccgggg  cgcatgcgca  acgcaccgcc  aagggccttg  gtccatcgcg     240
cctgcgcaca  acgatccggg  gcccggggag  gtgggtcaga  cccagggttc  ggaggaggag     300
ttccagcgcg  ccggcatgac  gtcactcccc  ggggggcgggc  tcagtaagtg  gag            353
```

<210> SEQ ID NO 613
<211> LENGTH: 242
<212> TYPE: DNA
<213> ORGANISM: Homo sapiens

<400> SEQUENCE: 613

```
ctcggcgaag  gcctcctcca  ggtcccattt  cctaaggtgc  cttctaagcc  cagggaagaa      60
gtagaaagaa  agcggagagc  cgaggatggt  gcgagcccgg  acgccccacg  ccgcgcgtac     120
gcacctcctt  ggcaatcacc  gcgatgcaca  ccgccatctt  gggaggctcg  gcgccaggca     180
ccgcgtcacg  tgaccgccg   ctggtcacgc  ggcctccaaa  gccccgcccc  atccgcacac     240
ag                                                                          242
```

<210> SEQ ID NO 614
<211> LENGTH: 349
<212> TYPE: DNA
<213> ORGANISM: Homo sapiens

<400> SEQUENCE: 614

```
ctgtcaacgg  cgtgttctgt  ggaatgctgg  gatgcatcac  aggtatgctg  gaagatgtat      60
agaattttac  ttctgttatt  ctggtaactc  agagtcctgt  tcagtcagtt  tccacgtcag     120
gttgctgtcc  tggtttttaaa  gagaatgaac  gcagccgaag  ttgaatcgag  gcagtgattt    180
cactcagtgc  gttgggtctt  tccactcacc  tggccctcca  gaaccccagg  gccttgagtg     240
catgggctgg  tacaagagcc  cagttttttgg  ctgggggaggc  acttcctatg  ggaggggggac   300 gcctgtctca  gtgctgaggc  aaccaccacc  gaggaccctg  ggctggaag                  349
```

<210> SEQ ID NO 615
<211> LENGTH: 198
<212> TYPE: DNA
<213> ORGANISM: Homo sapiens

```
<400> SEQUENCE: 615
ctgagcccag cgccagtcta ggtgagcccc acggcggtga gggacgctcg ccagacggcc      60
cagaggagtt agatgacgtc acctccagga ggactcgctt tttcattaat gaaaccggcc     120
ggcgcgggcg catgcgcggc aggccgcctt ccctctcgct tcccccctccc ctttcccagc   180 cgcgctctca atctctag                                                  198

<210> SEQ ID NO 616
<211> LENGTH: 217
<212> TYPE: DNA
<213> ORGANISM: Homo sapiens

<400> SEQUENCE: 616
ctctcccgcg ctccttggat acttttttgc aacgagatgc caatttcccc ggcgaccact      60
ccctcaaaca ggccttcgcc tccgcccgcg ctgaggccca ggcccaggtc cagattcaga    120
gccgcccgcc ggctggcgct gccctgtagg cgcctgcgca gagcgaccct ccccgtcact    180
cggagcggga ggcgggggca gccgggagaa aggaaag                             217

<210> SEQ ID NO 617
<211> LENGTH: 418
<212> TYPE: DNA
<213> ORGANISM: Homo sapiens

<400> SEQUENCE: 617
ctttgtgagt tgagaggggt gggagtgatt atccccaacc acaagcaagg cttccgggct      60
tcaagggttg gagaccaccc agggctcggc cagcatcaga accaacggct tctaattcca    120
aatcaaatga tggtttatgc cacactacaa ccctaaacaa atgaactgtg atgtgtctca    180
cttccctgtg caagtggaag atgctaatac atgtgtatca tgagaaagga cctcacaatt    240
ttcttcttct gggttctgct gagacgtttc tttgattcag agagaacttc ccaggatcag    300
caagaaaagc atgtcatcat ttcctaaacc ctacaatcca ggaaatagtc catcatttta    360
taaaattata aaagcgaact atttgagttt ctttattatc tgccccttc tccccaag      418

<210> SEQ ID NO 618
<211> LENGTH: 172
<212> TYPE: DNA
<213> ORGANISM: Homo sapiens

<400> SEQUENCE: 618
cttcctcgag ttcctagccc ccaaagcccc tgctcactcc atggcatgcc tccgaggctc      60
ctcatgccat gagaaagaga atggagccaa aatcaagccg gcagtatctc ggggctgtaa    120
cgtcttcccc ccgtcgctgt ttccacagtg ctgagccagg gacccggcag ag             172

<210> SEQ ID NO 619
<211> LENGTH: 338
<212> TYPE: DNA
<213> ORGANISM: Homo sapiens

<400> SEQUENCE: 619
ctgccagggc tccaagaaag acccatggag ggagagggga acgtccgggg aggcgaaggc      60
tgcgagtgag acccggagag gctgatgtcg gcgggtctgc gcgctcgcaa cgcgacctcc    120
gcccggtcag caagacctcg gcgcgcgatc ctcagattct gcgaaacaag acaagcgact    180
gggtccgaga ccgcggtccc catcaaaacg agcatcaacc aatcgctggg agaaatccgc    240
agcctcgttt taagccacca agcagagacc gcggcgacct attatgataa cctcgagaac    300
```

```
caatgaaaaa cgggggattcg ctcagcccgc ctcccgag                            338
```

<210> SEQ ID NO 620
<211> LENGTH: 283
<212> TYPE: DNA
<213> ORGANISM: Homo sapiens

<400> SEQUENCE: 620

```
ctgctttgtt aggggctccc tggtcgtccc ccggcccgcc gcgcctccgc tgcctgcggg      60
cgatctcccc gggccgcgct gacggagcct cgcaggaagg catctctgga gcgcgcgccg    120
cccgcgcccc tccagccgcg cgctccgagc ctggctgcgg cgcggatacc cggcgtgcgc    180
ccatagtcgc tctacagccc aactccgaac gccccgctcc tgcatccacc gcctcggatt    240
ggctggccgg aggcggagcg attgtcaggc ggcccaatcg gag                      283
```

<210> SEQ ID NO 621
<211> LENGTH: 488
<212> TYPE: DNA
<213> ORGANISM: Homo sapiens

<400> SEQUENCE: 621

```
cttcgtggca gcgccctcgt ccttccagcc cgctcgaggg tggccgccag ggcgcgatga      60
aggaatgtga gaaagtgctt agcgctccag ccgctccgag ggaagccagg tgggaggaga    120
tcccgaaacg ctaaggtttt gacagcgtta cagtgaattc tccggctgta gagattggag    180
gaagtcggga gaaattcgtc tctaagttgt aaggtggaac agcattcatt ttcttactgc    240
caatggaggt ttttcatgaa tttactaact cagtaaaaag attcggcttt ttttttttta    300
atcttaaagg atcacgcttt aaacctctgt aacaaagtaa ttatttgtac cactctctac    360
cccacccttc aacaaaataa cctatcggct ctcagaaaat aataacccttt tgcctgcctt    420
tgaaatagtt atcctttag tatgacagtg ttcaaaaatt ctttttcttag acttgtagca    480
gaacatag                                                              488
```

<210> SEQ ID NO 622
<211> LENGTH: 397
<212> TYPE: DNA
<213> ORGANISM: Homo sapiens

<400> SEQUENCE: 622

```
cttaaacact gacgcgagaa aggggtggag tcgagggagg ggacgtggtc tcaggaacaa     60
agaggagggc ggagaggggc tgtcctgaag gctctgagac tcctacgacc ccaggaaact    120
tacctcggct cggggcgccc ccccgactt ggcgcagagc ctgcgtcccc ctgccgatgc     180
ccacccgact cgctaaagcc accgaggcag acgaccccaa gactcccaat ttccgacctc    240
cctggcccgc gaggggcggg gccttcctct cggggcgtgg ccgtcaaatt gaattttccc    300
aatgggcac gagagtggga ggtacccaat cgagggttgg ctggcgcgtc ggggcagggc    360
ggggccagcc gggctgctgg cgcggctgga cgggcag                             397
```

<210> SEQ ID NO 623
<211> LENGTH: 415
<212> TYPE: DNA
<213> ORGANISM: Homo sapiens

<400> SEQUENCE: 623

```
cttctctgtg gagaccggtc agcggggcgg cgtggccgct cgcggcgtct ccctggtggc      60
```

| | |
|---|---|
| atccgcacag cccgccgcgg tccggtcccg ctccgggtca gaattggcgg ctgcggggac | 120 |
| agccttgcgg ctaggcaggg ggcggccgc cgcgtgggtc cggcagtccc tcctcccgcc | 180 |
| aaggcgccgc ccagacccgc tctccagccg gcccggctcg ccaccctaga ccgcccagc | 240 |
| caccccttcc tccgccggcc cggccccgc tcctccccg ccggcccggc ccggcccct | 300 |
| ccttctcccc gccggcgctc gctgcctccc cctcttccct cttcccacac cgccctcagc | 360 |
| cgctccctct cgtacgcccg tctgaagaag aatcgagcgc ggaacgcatc gatag | 415 |

<210> SEQ ID NO 624
<211> LENGTH: 214
<212> TYPE: DNA
<213> ORGANISM: Homo sapiens

<400> SEQUENCE: 624

| | |
|---|---|
| ctcaaacccc gcccacctac ttggtggatg gatggaggaa catctactat ttcatccttg | 60 |
| aggagttcct gaaatgcag ttgcccctca acaatgtat ctacatctcg cggggtttct | 120 |
| gtggaagaaa agaaaaagtg caagttgttg cttggagcgc ggactgcttt tacctttgcc | 180 |
| tggggatccc tcctatctgg ccccgcctgc ctag | 214 |

<210> SEQ ID NO 625
<211> LENGTH: 581
<212> TYPE: DNA
<213> ORGANISM: Homo sapiens

<400> SEQUENCE: 625

| | |
|---|---|
| ctccgcgccg gtgccccgcg gatcctgcag gctcccgggt cccaggagaa gggcgggctg | 60 |
| ggctgggctg gggtggggag ggcggtgaat gcaaggatat tgccgcaggc aggagtccac | 120 |
| ctcgccctcg tcgggcccgg cctggccgtc gcccccatct tcttcgtcca cgaacttgtt | 180 |
| ctcgtcatat tcatccacgt ccaccttccg gaagcgggcc gacgacactg tgttcttcga | 240 |
| catcccaatc ccgaccagcg gcaaaggcct cttcttggcg ctgcctctac ctcagcaagc | 300 |
| ccagcccagc aacccactac ccggcgcctg attcacttcc ctcttccgct ctgaggcgtc | 360 |
| gccgactgcc gcggctcgga ccgttctggg cctgcgcgct agccccgttt cttcctcctc | 420 |
| aggttcgcgc tcccttggcg cctcccacgc tgcccctgct cttccacgga gagcgcgcgc | 480 |
| gagggaagga gcgcgcagga cacagcgcgc aggcgcgggc tctccgcagg caaggggcgg | 540 |
| ggctgggcga aggaggcggg ggcgagaggg agggccaaaa g | 581 |

<210> SEQ ID NO 626
<211> LENGTH: 267
<212> TYPE: DNA
<213> ORGANISM: Homo sapiens

<400> SEQUENCE: 626

| | |
|---|---|
| ctgctctcca ggtgggcaaa gtgatgtccc ttcacccccc gccccccac ccccccgcca | 60 |
| cctcatccca tgtctccctc taaccccaga cctcactgct acttcctgcc aaccttgggc | 120 |
| tgctcactga ctcccatttc tccccagtgc cccagaccag ccccccaatt ccttctacat | 180 |
| ggtccgtatc atttccaagg ccccatgcat ggttcttcgc ctgggttttc ccattggcac | 240 |
| accagcaccg gcccggcaca aggtaag | 267 |

<210> SEQ ID NO 627
<211> LENGTH: 245
<212> TYPE: DNA
<213> ORGANISM: Homo sapiens

```
<400> SEQUENCE: 627
ctttccccag acctctcccc gctttacagt tattcgccac agcccgggag agtctgggga      60
cggccgcctg ggaggggacg gccgcctggg aggggacggc ccggagcaga cgccaggttt     120
cccgcggctc aggagaccgg tgccgcctcg gagagcgcgc gaaggtgccg ccggccgccc     180
gacccgcccg aggaacggac atctcccgcc cgggcccgca aggacgacca tgaacaccgc     240
cgcag                                                                 245

<210> SEQ ID NO 628
<211> LENGTH: 276
<212> TYPE: DNA
<213> ORGANISM: Homo sapiens

<400> SEQUENCE: 628
ctctattagc agtgactctg agaatagtcc tttccctcct ctgtcttccc cttctctgtc      60
ttgcagcaag tgggaggacg aagcaggttt cataagagca gcgcccaaga cccacagtcg     120
cctagtgcca agtcaacaac cttactgata tctggatgta gtttcctgtg ctctttgaca     180
caggtgtgga gattgtaatt tgctgtgtgt gattgtttgc acttccttga ttatgtaaac     240
cagtggcttt tgccaagaac tcttcatgcc ctgaag                              276

<210> SEQ ID NO 629
<211> LENGTH: 212
<212> TYPE: DNA
<213> ORGANISM: Homo sapiens

<400> SEQUENCE: 629
ctaagcaatg atggcggtga tgcagcaaag cctatttgtt tgagatcctg gcttttttgat     60 ccgttggtgc cacccacgct atgtgctgga tgggggtaat caatatacca ccttctctgc    120
tactttgggc tcaggtggaa ggaatttat tccactctct gcaaatcttc ccggtgcctc     180
agtgggaagt ggacgctgtg agggtctacc ag                                   212

<210> SEQ ID NO 630
<211> LENGTH: 165
<212> TYPE: DNA
<213> ORGANISM: Homo sapiens

<400> SEQUENCE: 630
ctcagcgtgg cctgagggtg atggatgtgg gggagccggg aactcatacc ctcgcccagc      60
cccgggcagg tccccccccg gaggggaccc cctcttcggg tcgaccccta ctgggcgcgg     120
catcctcccc ggagcgcccg cttcccacgg cccctgcggg tggag                    165

<210> SEQ ID NO 631
<211> LENGTH: 173
<212> TYPE: DNA
<213> ORGANISM: Homo sapiens

<400> SEQUENCE: 631
cttctccccc tctgtttccc ctccccagcc caaaggacat gtaactgatt ccccaggatg      60
gaagagtgac ttccacaaga cctaaaaata accgaaccac ttaatactcg aacatagcc     120 tctcccaccc gccccacca cggcccaccc actagccagc aagataaagg cag             173

<210> SEQ ID NO 632
<211> LENGTH: 195
<212> TYPE: DNA
```

<213> ORGANISM: Homo sapiens

<400> SEQUENCE: 632

```
ctctttgtca gaaatccact gtcccaaagt cttaaattaa cacaatggcg caatttctgt      60
aggttcattt tcaccccttta tttgtttatt tttaaaaaat aaaacaaagc cttaagccgt    120
caaatgcctg agatatacag gagcaatgac gttgcatttc atcagccaat caagtaagag    180
atgatgggcc tgaag                                                      195
```

<210> SEQ ID NO 633
<211> LENGTH: 210
<212> TYPE: DNA
<213> ORGANISM: Homo sapiens

<400> SEQUENCE: 633

```
cttcccagca ataacgaaa aaagagagt acgtatgttg tgaagtttgt tctgtttatt      60
agcaacttcc cgcatacttc aactttcaac aattttactc tagaggcaga gtaaagggat    120
actttcttta ggaggtgact cttactggac gaacactcag tgtttccaaa acgtttgtga    180
gatctcaggg agagggaagt gttaatgaag                                      210
```

<210> SEQ ID NO 634
<211> LENGTH: 163
<212> TYPE: DNA
<213> ORGANISM: Homo sapiens

<400> SEQUENCE: 634

```
ctgctcccgg acgctgtggt ctctcgctag agtggatccg aactctgcgt gacgctggga      60
acggccagcg tctgttgcct cacgaaaaca tctcccacaa ggtggccgcc tcgcgcgagg    120
tcagcagcag ggcaaacagg gatgcgtgag tgactgacgt gag                      163
```

<210> SEQ ID NO 635
<211> LENGTH: 165
<212> TYPE: DNA
<213> ORGANISM: Homo sapiens

<400> SEQUENCE: 635

```
ctgggtaggg gctgagaatg gcctggaata agtggtcatg gagccgagat gggggggctgt     60
ggttgggaat tgggaactgg gatcaggatg agactgggat gggttggact gaagatgtgc    120
cgtgacacat gttgggggg acacgtgcta agcatggggc tgaag                     165
```

<210> SEQ ID NO 636
<211> LENGTH: 175
<212> TYPE: DNA
<213> ORGANISM: Homo sapiens

<400> SEQUENCE: 636

```
ctttgtaaat ccgagagtat tgacacaatg atacgaggga aggtgaagg tgatatttca      60
tccagtgttc ccggttcatc ctctccttac ctgacctctg aaatggagcc attggccttg    120
aaaagcctgg tgtctaaaat taatattctt ccccatctga ctaagaaggc aacag         175
```

<210> SEQ ID NO 637
<211> LENGTH: 225
<212> TYPE: DNA
<213> ORGANISM: Homo sapiens

<400> SEQUENCE: 637

```
ctgtctagcg agatggttaa gcatttactg tgtctctaac accgaccagg ggaaaaatca      60
```

```
tcaattcgtt tgcccgagtt taagagaatt ttcacctaac ttctaatctc cacagccaat    120
cagttcttgg aaccgcacac ccgatgccga catccctctc ttgttggctc ccctcgttag    180
cgggattcaa taactaaacg tccatttcta gcattgactg aagag                    225

<210> SEQ ID NO 638
<211> LENGTH: 168
<212> TYPE: DNA
<213> ORGANISM: Homo sapiens

<400> SEQUENCE: 638
ctcaaccgtt aaaagccaa ttacctactc gtgaacgttt gccacataca ataatacttt     60
gaagacactt catgatcaga agtgagaaac tctaggcatt tgcatccaac cgtcatttta   120
tctgtgaaac tgctagtaaa acataaacct gaaaggcatt actcccag                168

<210> SEQ ID NO 639
<211> LENGTH: 434
<212> TYPE: DNA
<213> ORGANISM: Homo sapiens

<400> SEQUENCE: 639
ctgcatcagt acacaattcc cagtgaagac aggaagttac ataaggaggg agaatttgtg    60
agtgggtgaa tagagcagaa ggtgacttta ctaacgtctt tcgcgcattc attagccctc   120
agcatgctta aaggtgaagt ttaaggatga ttaaaggtga ggttttcttc ttaccccaca   180
gtagtggctg ttgacatttg atattttttgc tcttaaaggt gtgagatgct ctttgcatta   240
cagcctagtg ccttacagga aagaatttca gagaaactaa aattcgtttt agtccatatt   300
tcaagtagtg tgttttagtc catatttcaa gtagtgtgat ggtactgctt aacaatgaac   360
agacattgct gttccgggtt aacaggacta agaatttgtt cccacattcg gtcagcacca   420
aggctaagga acag                                                     434

<210> SEQ ID NO 640
<211> LENGTH: 334
<212> TYPE: DNA
<213> ORGANISM: Homo sapiens

<400> SEQUENCE: 640
ctttggaaca agaataggga ctagaactca ggaggtatcg tgagaggtca cgtagaccct    60
caaacggcgg gcaccattta cagtcagaac tgcgctccac acttgtctca ggggcctccc   120
tcctcccgtc gcctagtccg cagtccgcgt ctcgggacta aatttccctg cgggccgttc   180
ccgcaaactc cgccccgccg ccgctgccgc gaaatcccgg agtggatttt gggaaggggc   240
gcgcgagcgg cgccctgggc atgcgcgagc gcgtcccggg cccggcgagt cgagggttca   300
ggtggtgcgc cgtggcgccg cctgcgaccg gcag                               334

<210> SEQ ID NO 641
<211> LENGTH: 207
<212> TYPE: DNA
<213> ORGANISM: Homo sapiens

<400> SEQUENCE: 641
ctttctccca gccaagtcct tcctcctttc tgaatctggt cagggtctca agatcgtta     60 aaaagccgcc aaagtttgca actcgtcttg agtggctgct cctcccaaac ggttctgcct   120
ctggtgtctt gttctaggag cggttgaatt ctctgttttg ctgtgggtgc cagcctctat   180
```

```
cagcccctgc cctggtccat ctgtcag                                          207
```

<210> SEQ ID NO 642
<211> LENGTH: 179
<212> TYPE: DNA
<213> ORGANISM: Homo sapiens

<400> SEQUENCE: 642

```
cttggagggc cagtcgggcc acaccctttg gacgtcaccc ggagcccaca ggagcacctg       60
gcaaaagcca ggcccacttc ctgctcggct ccgcccagag caggggggcgg gcggataggc     120
gattccctcc aatcacagtt ccaaaaggag ggggctgaca acatatcctc caatcacag      179
```

<210> SEQ ID NO 643
<211> LENGTH: 330
<212> TYPE: DNA
<213> ORGANISM: Homo sapiens

<400> SEQUENCE: 643

```
cttgctgttt tggcactgac tttccgttga agaaaatttc ctttaaaacc atcttacaaa      60
gaaatttagg gtaaaatagt acattaatac ctacccttag ttccactctc ctgggaaact     120
agaggtctct tttctagtgg tagcatatgg ccatatgcga ttgtattggg gtgaactgaa     180
taatatgttg aaaatggtaa tgaaagccca ggacccaacg ttgaccacac tcctgggcta     240
ggagtaatgc cctgagaggt atgccaacac ttttcctctc actaccaccc ctccccattt     300
ttctttccag gctcttacac tgttcctaag                                      330
```

<210> SEQ ID NO 644
<211> LENGTH: 221
<212> TYPE: DNA
<213> ORGANISM: Homo sapiens

<400> SEQUENCE: 644

```
ctgcttcttt cgggcctcca cgtgctgcct cctgcccgat gcaataccat catgtttcct      60
tctctgcttt cttccgggag atggaaaaca gttcccccacc tttccctgg tgtcccccac    120
tcaggacctg tgttcctgc ccagtaccac ggtgggcggg cgctccccc aatcctgcag      180
gcctgtcatg gcccacccag acaactggaa cagggtggga g                         221
```

<210> SEQ ID NO 645
<211> LENGTH: 201
<212> TYPE: DNA
<213> ORGANISM: Homo sapiens

<400> SEQUENCE: 645

```
ctaccaatag ccaacctaca tctaagggga actgtaagat ttcagaagaa caagaagcat      60
aggtcgctta ggcgtgggcc acccaagaag agagacttaa cactaggtaa gcccgcgctg    120
gctgcgaagg cgggagcggc accaggacca tccagggcgc aggcgcaggg acctcacggc    180
cacgccacta ctcagcccga g                                               201
```

<210> SEQ ID NO 646
<211> LENGTH: 282
<212> TYPE: DNA
<213> ORGANISM: Homo sapiens

<400> SEQUENCE: 646

```
ctgctccccg cccggcccag cgcacggtgc acacggctgt ccgcggcctc gccctcccca      60
ttccgccccg ggctcctccg cttattcaca tgcaaatttc agtcgccagt tgtcgccgag    120
```

```
cgcggcaacc gccagagccg gatccttccg cagccccggc tcaaactttt ggcctctgaa      180
aactttcaaa cgagaagtag tcccaggcgc ccgctcccga cccacgccgc gccgccgggt      240
ccctcctccc cggagaggct gggctcggga cgcgcggctc ag                        282

<210> SEQ ID NO 647
<211> LENGTH: 297
<212> TYPE: DNA
<213> ORGANISM: Homo sapiens

<400> SEQUENCE: 647
ctgtaggcct cgggcaccta tccactgtcc ctctacggcc gggattcccc gccggcggct       60
ttccatagcc ctctccggac ccgcctccca ggctcaattc tcctcagcct caacgcagc      120 gaaagtgacg cacccaccc cgtggcactg tgggacttgg agttccctcc aactgagaag      180
aggcttgggt gcagcgccac gtcccagggg ctatgcaaat gtaggggacg ccctgctgc      240 cgcctcgcac cccgagggcg ggggttccgg ggctccggct ccgccttcta ccccaag       297

<210> SEQ ID NO 648
<211> LENGTH: 221
<212> TYPE: DNA
<213> ORGANISM: Homo sapiens

<400> SEQUENCE: 648
ctgctggact ggttgagtcc tgaccttggc cagcaccacg ctattgccag aggcacagtg       60
agaggccacg gcggcctctg cccgccccac actgccgagc agagtcctgg tggggtgcct      120
gggtccctcc ccattccagt gggagcctcc ccttcaccag gcagggcagg gcaggtgga      180 agagcctgac cttgtgtctg agggagccgg gcaggtggga g                         221

<210> SEQ ID NO 649
<211> LENGTH: 153
<212> TYPE: DNA
<213> ORGANISM: Homo sapiens

<400> SEQUENCE: 649
ctcgggaatg cctgtataat ttacgtcaag tctctccttg ggacggaccg gtgaaattgc       60
acgcagcaca aagaccggct cttaccctta cttccgggta ttgtggtaca ggaacccgag      120
gttgcctgcg cgtaagccac gtgactcgag cag                                  153

<210> SEQ ID NO 650
<211> LENGTH: 246
<212> TYPE: DNA
<213> ORGANISM: Homo sapiens

<400> SEQUENCE: 650
ctatggacat acagaagaaa agaggttaat tcggccggtg atgggatca gaagccctag        60 tcctcgtcca atattacgtc actgggtgac ctcgagggac gcttcgcgga gggcctcatt      120
tttctccact ggcgaatgca atctaagggt cttcggaaac tgtgggagcc cttgggcgca      180
cctatccgcc tcacctcgag gcttctcacc cgctggccgc ccccttgcgc ccctcgtttt      240
ttctag                                                                246

<210> SEQ ID NO 651
<211> LENGTH: 383
<212> TYPE: DNA
<213> ORGANISM: Homo sapiens
```

<400> SEQUENCE: 651

```
ctatgtcact tcagagttct gagcacgatg aaaatgcaga ctttacaagc acttcaagtc      60
aagacaagtg attagcattg ctccaaggg tttaaaagga actcagccaa aaactgttca     120
aaactggcca tttcatctga actgggacag cagggcacaa ggagagaaaa ggctggttgg     180
attaatgcag cccccgcttt ccatggctct actgtatttc actgagagtt gctaccaact     240
cctgcgcgcg ccccccacccg cccactccac taatctcgtg tcttaatcag agatacaggg    300
aacccgtgga gaagatgaag tacaactggg ataagaagat cgtaggtgtt ttacgtttga    360
atttaagcaa caaatctgtc gag                                              383
```

<210> SEQ ID NO 652
<211> LENGTH: 252
<212> TYPE: DNA
<213> ORGANISM: Homo sapiens

<400> SEQUENCE: 652

```
ctattcctgc atttgtggcc tcaagggcta aagtgggaca acgctggtat ttttggtgat     60
gaggaaacac tttttttttg ttaagggagg ttgggtgatc gttgaactgg gacagaggtc    120
acagcagagg tcacattggc gattcgagcg gcggtggggg gttggctttg ggtcgggcat    180
cctgcgcccc ccactcggga aaggtggcgg agacttcgag gttggggggcc catcgaaggt    240
tcccaccgcc ag                                                         252
```

<210> SEQ ID NO 653
<211> LENGTH: 182
<212> TYPE: DNA
<213> ORGANISM: Homo sapiens

<400> SEQUENCE: 653

```
ctttgtttcc gggaactgag ttgtgtttac cttggcttcc gactatgttg gcaacaggtt     60
tcctgcaaga acaggcgcg tctccacacc ctcgtccctc ctcccacccc cctgcctttc    120
aatagccatc ttcctggagc cggaggcatc ccagattaag ggagaggtac gggcccttta    180
ag                                                                    182
```

<210> SEQ ID NO 654
<211> LENGTH: 393
<212> TYPE: DNA
<213> ORGANISM: Homo sapiens

<400> SEQUENCE: 654

```
ctgtagtgaa aattaggaaa tccaggtctc actggggtgt ggtttctgct gcagagacac     60
aacccgggac ctgcatgcat ctttagcgtt gggtcctagt tttcagcgct ttatttgatg    120
cagagggat accttttcctt tacgcatacc actctcactg atcctaaata attacttgac    180
agtttgaatg atctcattac acttccgac tggcttcttc tgggcatcta atttgttcat    240
gaagtgttga acttcggagg acctgccagc attcagggga tttcagcccg actcagcact   300
gttgatgttg ttatgtgaat ttgttctatg acggttttga tggtcttggg attagccact    360
aaacacacct ggtgttctgt ttactctggc aag                                   393
```

<210> SEQ ID NO 655
<211> LENGTH: 308
<212> TYPE: DNA
<213> ORGANISM: Homo sapiens

<400> SEQUENCE: 655

```
ctctttactt cctcccaaat aaaacctaac ttttctaact aactatttaa gacttggaat      60
agtccgcttg actagaagaa ggggaagaat gtttgtaaat tcacctctaa tcggactttg     120
attctactat aattcagcag aaaattcata gcgctgtgat ttttagatcg acctcacata     180
aaacagtccc tgcactcgct tccctttttcc ttcttcttc accaatctcc gccccagttc     240
gctcggagtc acgtggacca gcccggctcg ccccgcctcg ctcttcgcgc aggcggggac     300
cggtccag                                                              308

<210> SEQ ID NO 656
<211> LENGTH: 190
<212> TYPE: DNA
<213> ORGANISM: Homo sapiens

<400> SEQUENCE: 656
ctgcctgaaa aagggttaca tcgtaagaca taaggataca gggctcattg ggatgtgtag      60
agagggcaat gggtacaagt gtatactaga atgcagggct gtgagggtaa cagaccaaat    120
gtgcatgaat tcctgtgaga gtttgaaatc cgcaggtcat caagagttta ggattgcacc    180
tcggacctag                                                            190

<210> SEQ ID NO 657
<211> LENGTH: 562
<212> TYPE: DNA
<213> ORGANISM: Homo sapiens

<400> SEQUENCE: 657
ctcccaagtt tacatagtag ttctagccat ccccagaggc taatttaaac ttctcagttt      60
tattttcaac ctcctaggag atagaatctg attggttcag cgagggtcat ttgtcttggg    120
tcattcgatt aaccctggtc caatcagcaa tggcttcggg gactggattg taggctataa    180
actgattcct ggggagtcag tccctgtaaa ttgagtggag agagggatag aggcctatt     240 cgcagagaaa agggatggtc atcggcttcc aggctgagca gacacttaaa aaaatgatcc    300
gaaatgatat ccatcaattc cataatcata aaaactgatt ttcattttgg atcaagtcat    360
tcctactgaa tacttgttgt tactctttag tgtagagttg tccacactac catgagaatg    420
actctgacat gtcatatacc atcatgaaag tgctgagaaa ttcctgctac aacttatgta    480
cacgtttcag aagacatcct aaagttgcat gtaactgact ggacttttcc tttatttcag    540
tgtcctctgg gatctcttac ag                                              562

<210> SEQ ID NO 658
<211> LENGTH: 304
<212> TYPE: DNA
<213> ORGANISM: Homo sapiens

<400> SEQUENCE: 658
ctcacccaag cgtctctcac aaactgttgt ttgacttggg ttgagaaaat gacaggctgg      60
gttctgcacc aagaagagaa gaaaaaaaga gggggaaaaa aggagttttc ttttccctcc    120
gctgccaatc tccatccccc tcaactcctc ccctaggcct gggtggaccc tgcctgggta    180
atagttccct gctatatttta aaaccacag atgtgtttgg tggagactta atttcggaat    240
tgcaggcagc gtctcctgag gacaaggga aagccggtgc cgcgcgcccg cctgctgcct    300
ggag                                                                  304

<210> SEQ ID NO 659
```

```
<211> LENGTH: 287
<212> TYPE: DNA
<213> ORGANISM: Homo sapiens

<400> SEQUENCE: 659
ctcgctcggg actaggaccg ccccgtacat gtcccggtgc cctcggggct cgaacatgag      60
ccgtcgccgc acgtggtcaa ggtgctggcg catgtagcgc cgcttggcca gcagggtggg     120
cccagacacc tccggacacc ccgccagcac gatacgcaag ggctcgccgc ccgtgtgcat     180
gtccaccacc gacagcaccg gcgtccctgg atcatgcggg ggcagccggg gcaccgccag     240
cgcgctctcc atggtctgcg tcggggggaga cgagtacggt cccgcag                  287

<210> SEQ ID NO 660
<211> LENGTH: 382
<212> TYPE: DNA
<213> ORGANISM: Homo sapiens

<400> SEQUENCE: 660
ctacggtccc tcgggcctat cagatgacaa ccttaacacc ctggaggcgt ggttatcgtc      60
ttggggctct gggaagtgca gttccatggg ggaccaggcc tgataatacc ataaaaggct     120
tggttctctc aattctgaag ccatgttctg ttgaccttcc tctaaaagcg gtacccgcaa     180
ttgtgcggat tccgtggttc cctagtccca agccgtctgc ttcctgggcc ctttcattgg     240
ctccgccccc gtaaaccttg ctcgtccact ctggaagcgc tctcctgact acaggccgcg     300
cccctcgcgt cggctccgcc cacccagccc gcggcttggc ccaggcggta gttcgcgttt     360
tgagccgatc gtgccaccat ag                                              382

<210> SEQ ID NO 661
<211> LENGTH: 259
<212> TYPE: DNA
<213> ORGANISM: Homo sapiens

<400> SEQUENCE: 661
ctagtcgccc gggctctggg ggacaggtcc agccccgcgg cgcctctggc cttccggccc      60
ccgtgacctc agggctgggg tcgcagcgct tctcacgcga gccgggactc agtaaccccg     120
ggaaggaggt caccacgggg cagccccgcc ccgcctgcc gagtcctggt aggctgtagc     180 gctgggagg catctgcacg cccagcgttc cagtgggtgc aaaaatgacg aagaggagtc     240
cccgcgcccc aggatggag                                                  259

<210> SEQ ID NO 662
<211> LENGTH: 202
<212> TYPE: DNA
<213> ORGANISM: Homo sapiens

<400> SEQUENCE: 662
ctaggaagga agggaaagtt cccggggaac ctccagccta tggcggcaga gaagcatctt      60
gcaagaggtc tctgtgtgtg ctgaggcaag gggacgccag gcaggctgac ggtatacgcc     120
cgccttgtgt tagtctgggg ccaggtcacc ggcaatgtct tcaagaacca gaaggtggga     180
ggacaaaaag gccatgctca ag                                              202

<210> SEQ ID NO 663
<211> LENGTH: 170
<212> TYPE: DNA
<213> ORGANISM: Homo sapiens

<400> SEQUENCE: 663
```

```
ctcactctta accacgtgag ggtagggtat ccaaccaata aagacattca gagttggaga    60
gcgggcgagt ggagtgtcct ttagactccg cggactcgac gggagggacc ctgcaatgct   120
taattagaac cggttgccat ggcgacagtc tctaggcagc gtgggctgag               170
```

<210> SEQ ID NO 664
<211> LENGTH: 220
<212> TYPE: DNA
<213> ORGANISM: Homo sapiens

<400> SEQUENCE: 664

```
ctccttttca tctgccatta gcacagactt tgcactttcg gcacggacgt tctcatcctt    60
aaagcctttc ggactctaaa accaacgttt ccctgtaagc ctggactgcg cctaagcccc   120
cagttctccc accgcagagg cccccaccca gggctgcgcc agcgccgtgg ggtcgctggg   180
cggcgggttt tggcgtcgct agactgggct gtcttggcag                        220
```

<210> SEQ ID NO 665
<211> LENGTH: 178
<212> TYPE: DNA
<213> ORGANISM: Homo sapiens

<400> SEQUENCE: 665

```
cttattatca tggcatctca gccagggctg gggtaggggt ttgggaaggg caacccagca    60
tcccccgatc ccagagtcgc ggccggggat gacgcgagag agcgtggtcg ccccagaag   120 gccctgggcc atcatgccgg cctccacgta gaccccaggg gtcgctcact cctgccag    178
```

<210> SEQ ID NO 666
<211> LENGTH: 211
<212> TYPE: DNA
<213> ORGANISM: Homo sapiens

<400> SEQUENCE: 666

```
ctgcgggtcg cggccggcgc cggcctctcc aatggcaaat gtgtgtggct ggaggcgagc    60
gcgaggcttt cggcaaaggc agtcgagtgt ttgcagaccg gggcgagtcc tgtgaaagca   120
gataaaagaa aacatttatt aacgtgtcat tacgagggga gcgcccggcc ggggctgtcg   180
cactccccgc ggaacatttg gctccctcca g                                 211
```

<210> SEQ ID NO 667
<211> LENGTH: 368
<212> TYPE: DNA
<213> ORGANISM: Homo sapiens

<400> SEQUENCE: 667

```
ctctccgcgc cccgagtcgc cgcctcctga ttggattccc cctgtgtcaa tccttgtcct    60
agaacctggc tgtccgttgg acccgcccta gagggcgggg ctcccgccta ggaagcgcgg   120
gggaaggtgg agcgggtgga ggtgggcgg aaagaggatg ttgaatcccc acccatctgg   180
ccgcagaggc tccgcccacc cccttccac aggccaatac gtctgcccat caaggccagg   240
cgcggcctgc agtgggtgta gcaggaaggg ggcgggattg tgccccaggc tccgccccgg   300
agccggctcc cggctgggaa tggtcccgcg gctccgaggg cggggcggga aggcggcgag   360
gagccgag                                                           368
```

<210> SEQ ID NO 668
<211> LENGTH: 381
<212> TYPE: DNA

<213> ORGANISM: Homo sapiens

<400> SEQUENCE: 668

| ctgcctccgc tcttttcgg tgtccccccc agtcccgccc ttgggtgtgg ggacgcctgc | 60 |
| cccacaagtg tttagggagg tcagtgggtt cctcgcccgt agagacaccg tttatgccaa | 120 |
| atgagcactc ctcatccccg ctcttgatgg agtcatgtcc tagacgtgaa actatggggc | 180 |
| tgtgatcaca agcaaatgtg tgggcggatc cgttgcttgg gttcttcccc gccccctctt | 240 |
| tttttcggac catgacgtca aggtgggctg gtggcggcag gtgcggggtt gacaatcata | 300 |
| ctcctttaag gcggagggat ctacaggagg gcggctgtac tgtgcttcgc cttatatagg | 360 |
| gcgacttggg gcacgcagta g | 381 |

<210> SEQ ID NO 669
<211> LENGTH: 177
<212> TYPE: DNA
<213> ORGANISM: Homo sapiens

<400> SEQUENCE: 669

| ctcggtcaac tggatgggaa tcggcctggg gggctggcac cgcgcccacc aggggtttg | 60 |
| cggcacttcc ctctgcccct cagcacccca cccctactct ccaggaacgt gaggtctgag | 120 |
| ccgtgatggt ggcaggaagg ggccctctgt gccatccgag tccccaggga cccgcag | 177 |

<210> SEQ ID NO 670
<211> LENGTH: 184
<212> TYPE: DNA
<213> ORGANISM: Homo sapiens

<400> SEQUENCE: 670

| ctccctgact ctcgggggga gaagggctc ccaacatgac cctgagtccc ctggattttg | 60 |
| cattcactcc tgcggagacc taggaacttt ttctgtccca cgcgcgtttg ttcttgcgca | 120 |
| cgggagagtt tgtggcggcg attatgcagc gtgcaatgag tgatcctgca gcctggtgtc | 180 |
| ttag | 184 |

<210> SEQ ID NO 671
<211> LENGTH: 213
<212> TYPE: DNA
<213> ORGANISM: Homo sapiens

<400> SEQUENCE: 671

| ctgggcaagg tcaagaagga gcagcaggac ggcgaggcgg acgatgacaa gttccccgtg | 60 |
| tgcatccgcg aggccgtcag ccaggtgctc agcggctacg actggacgct ggtgcccatg | 120 |
| cccgtgcgcg tcaacggcgc cagcaaaagc aagccgcacg tcaagcggcc catgaacgcc | 180 |
| ttcatggtgt gggctcaggc agcgcgcagg aag | 213 |

<210> SEQ ID NO 672
<211> LENGTH: 169
<212> TYPE: DNA
<213> ORGANISM: Homo sapiens

<400> SEQUENCE: 672

| ctgggcacat agtttctcgg aatccaccct cccggacccc cgcagcccag tttctcctcc | 60 |
| cctcagccca ccttctctgc ccacctccta cccggagccg gggaggcggc cgcggtcagc | 120 |
| ccggcctccc cgacttgggg tccgcgtgcg ccgggaccca gaggccaag | 169 |

```
<210> SEQ ID NO 673
<211> LENGTH: 270
<212> TYPE: DNA
<213> ORGANISM: Homo sapiens

<400> SEQUENCE: 673
ctcgcctgct gctcgtagaa acaaatatac tacacgtacg ctgtcctagg atgacacaac      60
accctcacta ctgcagaaga cggatcatta acaaacgtc agaagagcag ccccaactgt     120
acataaactt cgggcggaaa agcaagacgc aggcgcagta gcacatattg ttaccctatt    180
tgcccactcc ctgctcctcc tcgcctcaat ttcgcttccg cttctttgcg catctgcttc    240
cgggggattg taggctctgc ccctcctcag                                      270

<210> SEQ ID NO 674
<211> LENGTH: 125
<212> TYPE: DNA
<213> ORGANISM: Homo sapiens

<400> SEQUENCE: 674
cttgatcaag ggtagttttt gctgtggccc ctgcaaatac gttgtggtgc ccagagtaga     60
tgaaaaactg tgagtttccc aatagagcgg gttcatctgg actcttgttg gttgcgttct    120
aggag                                                                 125

<210> SEQ ID NO 675
<211> LENGTH: 154
<212> TYPE: DNA
<213> ORGANISM: Homo sapiens

<400> SEQUENCE: 675
ctctggcttg cagaattttc caccccaaaa tgttagtatc tacggcacca ggtcggcgag     60
aatcctgact ctgcaccctc ctcccaact ccatttcctt tgcttcctcc ggcaggcgga    120
ttacttgccc ttacttgtca tggcgactgt ccag                                154
```

METHOD FOR MULTIPLEXED NUCLEIC ACID PATCH POLYMERASE CHAIN REACTION

CROSS REFERENCE TO RELATED APPLICATIONS

This application is a continuation-in-part of U.S. application Ser. No. 13/556,590, filed Jul. 24, 2012, now U.S. Pat. No. 8,936,912, which is a continuation of U.S. application Ser. No. 12/555,627, filed Sep. 8, 2009, now U.S. Pat. No. 8,586,310, which claims the priority of U.S. provisional application No. 61/094,660, filed Sep. 5, 2008, each of which is hereby incorporated by reference in its entirety.

GOVERNMENTAL RIGHTS

This invention was made with government support under 5P50HG003170-0 awarded by the National Institutes of Health. The government has certain rights in the invention.

FIELD OF THE INVENTION

The invention encompasses a method for a amplifying at least two different nucleic acid sequences.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

As the genes involved in various aspects of human physiology are elucidated, there are increasingly more candidate genes associated with disease. The application of this knowledge both in the clinic and to clinical research can be very powerful as the field moves toward personalized medicine. Examples of success include the sequencing of candidate disease loci in targeted populations, such as Ashkenazi Jews (Weinstein 2007), the sequencing of variants in drug metabolism genes to adjust dosage (Marsh and McLeod 2006), and the identification of genetic defects in cancer that make tumors more responsive to certain treatments (Marsh and McLeod 2006). However, the sequencing of many candidate genes across many individual samples necessitates the development of new technology to lower the cost and increase the throughput of medical re-sequencing to make clinical application more feasible.

The cost of sequencing is declining rapidly due to second generation sequencing technologies that perform a large number of sequencing reactions in parallel while using a small amount of reagent per reaction (Metzker 2005). These technologies integrate cloning and amplification into the sequencing protocol, which is essential for achieving the greater than 100-fold cost savings over traditional methods. However, this integration results in a loss of flexibility—it is not yet feasible to sequence a subset of the human genome in a large number of samples for the same cost as sequencing the complete genome of a single individual. This is a limitation, because sequencing the complete genome of a large numbers of individuals is still cost prohibitive, and the whole genome sequence of only a few individuals does not provide enough statistical power to make correlations between genotype and phenotype. The promise of personalized medicine based on genome analysis still glows on the horizon, but the significance behind observed variability is dim without an affordable technology to drive the necessary depth of patient sampling.

Current methods for analyzing sequence variation in a subset of the human genome rely on PCR to amplify the targeted sequences (Greenman et al. 2007; Sjoblom et al. 2006; Wood et al. 2007). Efforts to multiplex PCR have been hampered by the dramatic increase in the amplification of mispriming events as more primer pairs are used (Fan et al. 2006). In addition, large numbers of primer pairs often result in inter-primer interactions that prevent amplification (Han et al. 2006). Therefore, separate PCRs for each region of interest are performed, a costly approach when hundreds of individual PCRs must be performed for each sample (Greenman et al. 2007; Sjoblom et al. 2006; Wood et al. 2007). Furthermore, this strategy requires a large amount of starting DNA to supply enough template for all of the individual PCR reactions. This can be a problem as DNA is often a limiting factor when working with clinical samples.

It is important to choose the appropriate strategy for sample tracking to fully harness the throughput of second generation sequencing technologies. The sequencing capacities of these platforms are large enough that multiple samples can be sequenced with a single instrument run. To do this, one can use a separate compartment for each sample, but this only allows for a small number of samples, and there is a reduction in the total amount of sequence generated per run. Recently, Parameswaran et al. (Parameswaran et al. 2007) demonstrated the power of using DNA barcodes to label samples so that they can be pooled and sequenced together on the 454/Roche GS20 Sequencer. They were able to utilize the full capacity of the instrument and still determine from which sample each read originated. To realize the full power of second generation sequencing technologies, a multiplexing strategy should be compatible with DNA barcoding to track samples.

Therefore, there remains a need in the art for a multiplexed PCR method that simultaneously amplifies many targeted regions from a small amount of nucleic acid. The PCR method should also be compatible with next generation high throughput sequencing technologies where numerous samples can be processed in a single run. The PCR method should be specific and sensitive enough for identifying SNPs and mutations in individual samples.

SUMMARY OF THE INVENTION

One aspect of the present invention encompasses a method of amplifying at least two different nucleic acid sequences. Generally speaking, the method comprises the following steps: (a) defining the ends of at least two nucleic acid sequences; (b) annealing upstream and downstream nucleic acid patches to each nucleic acid sequence of step (a), and annealing an upstream universal primer to the upstream patch, and a downstream universal primer to the downstream patch; (c) ligating the upstream universal primer and the downstream universal primer to each nucleic acid sequence; and (d) amplifying the nucleic acid sequences of step (c).

Another aspect of the invention encompasses a method of detecting short tandem repeats. The method typically comprises the following steps: (a) defining the ends of at least two nucleic acid sequences, wherein the ends are immediately adjacent to a short tandem repeat; (b) annealing upstream and downstream nucleic acid patches to each nucleic acid sequence of step (a), and annealing an upstream universal primer to the upstream patch, and a downstream universal primer to the downstream patch; (c) ligating the upstream universal primer and the downstream universal primer to each nucleic acid sequence; (d) amplifying the nucleic acid sequences of step (c); and (e) sequencing the products of step (d) to detect the length of the short tandem repeat.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

(FIG. 1A) A PCR reaction containing primers pairs for all targets is performed on genomic DNA. The primers contain uracil substituted for thymine. The primers are then cleaved from the amplicons by the addition of heat-labile Uracil DNA Glycosylase, Endonuclease VIII, and single strand specific Exonuclease I. (FIG. 1B) The ends of the target regions are now internal to the PCR primers (nested). (FIG. 1C) Nucleic acid patch oligonucleotides are annealed to the target amplicons and serve as a patch between the correct amplicons and universal primers. The universal primers are then ligated to the amplicons. The universal primer on the 3' end of the amplicon is modified with a 3 carbon spacer that protects the selected amplicon from the final exonuclease reaction that degrades nonspecific products. (FIG. 1D) The selected amplicons are then amplified together simultaneously by PCR with universal primers.

(FIG. 3A) Uniform Exon Abundance. Graph of the number of reads obtained for each targeted exon from the colon cancer sample and adjacent normal tissue. The 90 exons for which at least 1 read was obtained are ordered by abundance in the normal sample on the x-axis. The median number of reads per exon is 145. Seventy-six percent of all exons fell within 5 fold coverage of this median. All exons are within 3 log 10 of each other. (FIG. 3B) Correlation of number of reads across samples. Each exon is depicted as a point on the graph, where the x-axis is the number of reads in the normal sample and the y-axis is the number of reads in the colon cancer sample. The correlation was high ($R^2$ of 93%), indicating high reproducibility across samples. (FIG. 3C) Fold difference in abundance across samples. We computed the fold change of abundance per exon between the two samples. 85% (77/90) of exons displayed a 2 fold or less difference in abundance between samples. 100% of exons displayed a 3 fold or less difference in abundance between samples. Dotted line indicates 3 fold change.

FIG. 7A-G depicts a schematic of multiplexed bisulfite PCR. (FIG. 7A) Genomic DNA. (FIG. 76) Restriction digest. (FIG. 7C) Anneal patch oligos and universal primers specifically to the ends of desired fragments. (FIG. 7D) Ligate universal primers (U1 & U2) to targeted fragments. (FIG. 7E) Degrade unselected DNA with exonucleases. Targeted loci are protected from exonuclease by 3-prime modification on U2. (FIG. 7F) Treat with sodium bisulfite to convert unmethylated cytosine to uracil, leaving methylated cytosine intact. (FIG. 7G) PCR all loci simultaneously with universal primers tailed with sample-specific-DNA barcodes and sequencing machine primers (454A & 454B). Pool PCR products from all samples together for sequencing.

(FIG. 9A) Number of sequencing reads per promoter for all 94 targeted promoters, order by length in base-pairs (bp) on the x-axis. Longer promoter amplicons yield fewer sequencing reads (length bias), but 87 amplicons (93%) have coverage within 10 fold of the median coverage (444 reads). The abundance of each promoter ranged from 10 to 5114 reads. (FIG. 9B) Histogram of the pair-wise squared correlation coefficients for the number of reads per promoter for all 48 samples. The mean correlation coefficient is 0.91, indicating that the number of reads per promoter is highly reproducible across patient samples.

FIG. 11A ICAM5 promoters exhibit colon and breast tumor specific methylation. FIG. 11B LAMA1 promoters exhibit colon and breast tumor specific methylation. FIG. 11C KCNQ5 promoters exhibit colon tumor specific methylation. FIG. 11D CLSTN2 promoters exhibit colon tumor specific methylation.

FIG. 15A depicts a multiplex PCR reaction. FIG. 15B depicts an embodiment where the amplified targets from the PCR reaction in FIG. 15A may be trimmed so the ends of the target regions become internal to the PCR primer sequences. FIG. 15C depicts a restriction enzyme reaction creating nucleic acid sequences with defined ends. FIG. 15D depicts an embodiment where oligonucleotides are used to direct Type IIs restriction enzymes to cut at specific sites in the nucleic acid template. This is facilitated by upstream and downstream oligonucleotides that anneal upstream and downstream of the target nucleic acid sequences and serve as a guide for digestion by the type IIs restriction endonuclease enzyme. FIG. 15E depicts single strand specific exonuclease enzyme digestion of nucleic acid templates protected by locus-specific oligonucleotides to define ends of the nucleic acid template. This is facilitated by upstream and downstream oligonucleotides that anneal upstream and downstream of the target nucleic acid sequences and serve as protection against digestion by the single strand specific exonuclease enzymes. FIG. 15F depicts the ligation of universal primer sequences to nucleic acid sequences. This is facilitated by upstream and downstream nucleic acid patch oligonucleotides that anneal upstream and downstream of the target nucleic acid sequences and serve as a patch between the desired sequence and upstream and downstream universal primers to be ligated. FIG. 15G depicts PCR amplification for 454 sequencing. The primers for the PCR amplification may be complementary to the upstream and downstream universal primer nucleotide sequences (black segments of the primers). Additionally, the PCR primers may be coupled to nucleic acid sequence barcodes (white segments of the primers). The barcodes may be internal to the primer sequence.

DETAILED DESCRIPTION OF THE INVENTION

Figure 1:
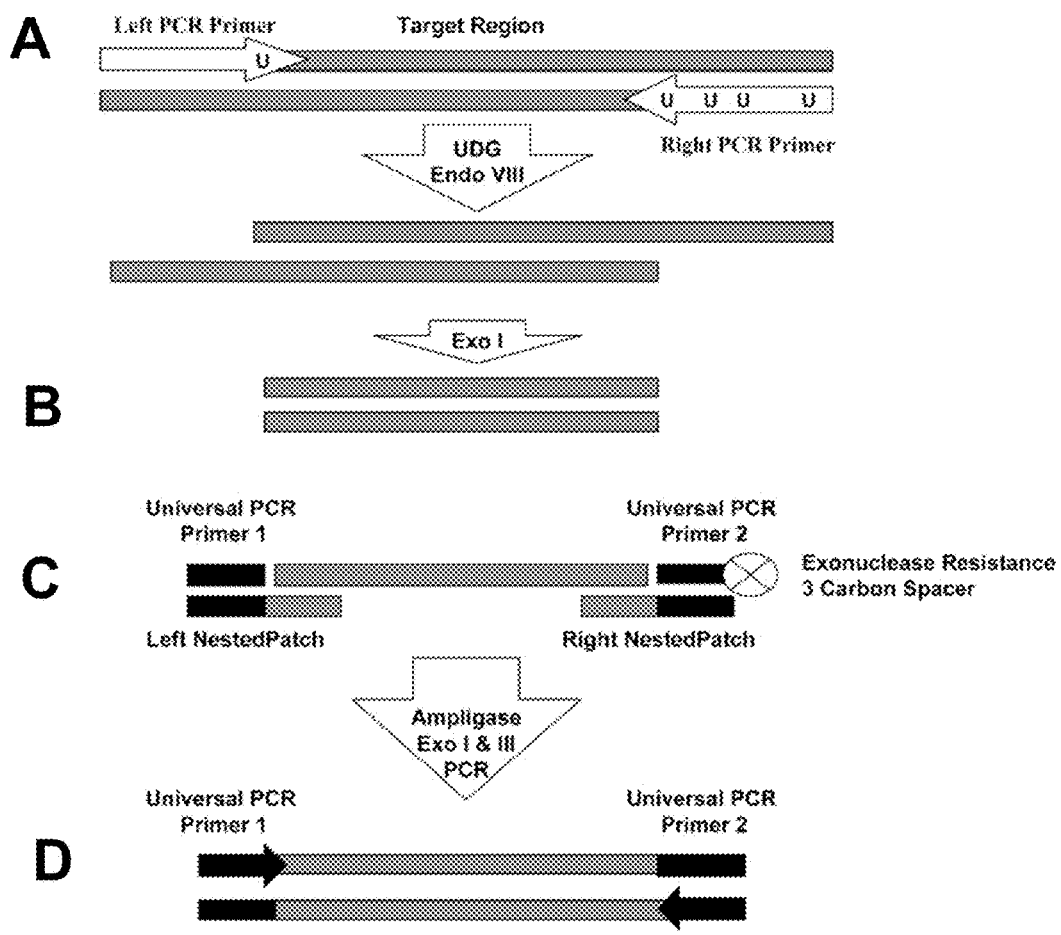
FIG. 1A-D depicts a schematic of nucleic acid patch PCR.

PCR amplifies specific nucleic acid sequences through a series of manipulations including denaturation, annealing of oligonucleotide primer pairs, and extension of the primers with DNA polymerase. These steps can be repeated many times, potentially resulting in large amplification of the number of copies of the original target sequence. Multiplex PCR is a variant of PCR that enables the simultaneous amplification of many targets of interest in one reaction by using more than one pair of primers. However, current multiplex PCR methods are hampered by the amplification of mispriming events and inter-primer interactions that prevent amplification, as more primer pairs are used.

The present invention provides a method of multiplex PCR that affords a high level of specificity. The method also allows for parallel sequencing of multiple PCR amplification samples in a single sequencing run. Additionally, the invention provides uses for the method. Each is described in more detail below.

I. Nucleic Acid Patch PCR Method

Generally speaking, the method comprises defining the ends of at least two nucleic acid sequences, annealing upstream and downstream nucleic acid patches to each nucleic acid sequence, annealing an upstream and a downstream universal primer to each patch, and subsequently ligating the universal primers to each nucleic acid sequence.

The resulting modified nucleic acid sequences may be amplified using primer sequences wherein each primer comprises a nucleic acid sequence tag specific for the sample, and a nucleic acid sequence to prime the sequencing reaction.

(a) Nucleic Acid Template

A method of the invention may be used to amplify nucleic acid sequences. Usually, the nucleic acid sequences may be found in a nucleic acid template. A nucleic acid template may be from any sample that contains nucleic acid molecules. The nucleic acid template may be from humans, animals, plants, microorganisms or viruses. In preferred embodiments, the nucleic acid template is from a human sample. The sample may be fresh, from archeological or forensic samples, or from preserved samples such as paraffin-embedded tissue. The sample may be a solid tissue or a physiological fluid, such as blood, serum, plasma, saliva, ocular lens fluid, cerebral spinal fluid, sweat, urine, milk, ascites fluid, lymphatic fluid, mucous, synovial fluid, peritoneal fluid, or amniotic fluid. Nucleic acid templates may be prepared from the sample using methods well known to those of skill in the art (see, e.g., Sambrook et al. (1989) "Molecular Cloning: A Laboratory Manual," $2^{nd}$ Ed., Cold Spring Harbor Laboratory Press, Cold Spring Harbor). Alternatively, the sample containing the nucleic acid template may be used directly.

The nucleic acid template may be DNA, RNA, or a complementary DNA (cDNA) sequence that is synthesized from a mature messenger RNA. If the nucleic acid template is RNA, the RNA may be reverse transcribed to DNA using methods well known to persons skilled in the art. In a preferred embodiment, the nucleic acid template is DNA.

In some embodiments, suitable quantities of nucleic acid template for the invention may be 10, 9, 8, 7, 6, 5, 4, 3, 2, 1, 0.5, 0.1, 0.05, 0.01, 0.005, 0.001 µg or less. In preferred embodiments, suitable quantities of nucleic acid template for the invention may be 1000, 900, 675, 450, 225, 112, 70, 50, 20, 1.6, 0.8, 0.4 ng or less.

In some embodiments, the nucleic acid template may be treated to prepare the template for specific applications of the invention. In one embodiment, the nucleic acid template may be treated with bisulfite to determine the pattern of methylation. Nucleic acid templates may be treated with bisulfite using methods well known to those of skill in the art, and may be performed using commercially available reagents, following manufacturer's protocols, such as by using the EZ DNA Methylation-Gold Kit™ (Zymo Research), the Imprint™ DNA Modification Kit (Sigma), or the like.

(b) Creation of Nucleic Acid Sequences with Defined Ends

The invention encompasses methods for the creation of nucleic acid sequences with defined ends. As used herein, the phrase "defined ends" refers to a nucleic acid sequence where both the 5' and 3' end of the sequence is known. Generally speaking, at least three, four, five, six, seven, or more than seven bases of the sequence are known. Non-limiting examples of methods for creating defined ends may include amplification (such as multiplex amplification), restriction endonuclease digestion, single strand specific exonuclease degradation, or triplex formation and cleavage. These methods are described in more detail below.

i. Multiplex Amplification from a Nucleic Acid Sample

Figure 15A:
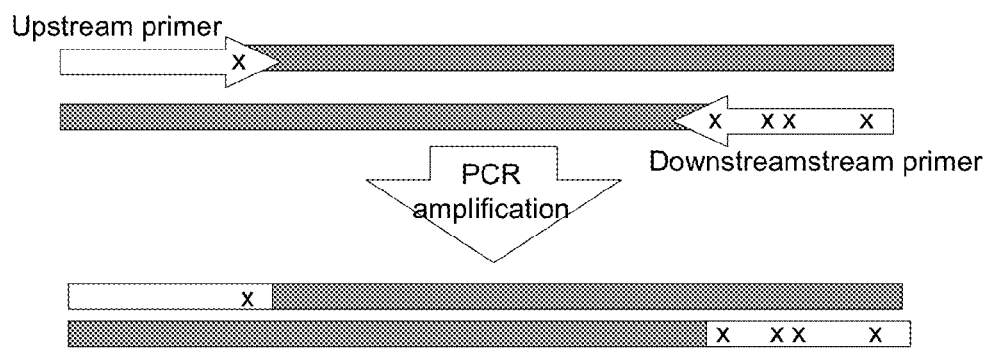
FIG. 15A-G depicts schematic illustrations of various embodiments of the invention.

Creating defined ends by multiplex amplification may consist of a PCR reaction using primer pairs for desired targets on the nucleic acid template. An exemplary example of a multiplex PCR reaction is depicted in FIG. 15A. Components of the multiplex PCR amplification reaction may include the nucleic acid sequence to be amplified (template; see section I(a) above), one or more primer pairs for delineating the target nucleic acid sequence on the template to be amplified (described below), one or more nucleotide polymerase (described below), deoxynucleotides, and salts and buffers essential for optimal activity of the polymerases in the reaction.

A. Primers

In a method for creating defined ends, the oligonucleotide PCR primers may be typically synthesized using the four naturally occurring deoxynucleotides dATP, dTTP, dCTP and dGTP. In some embodiments of this invention, oligonucleotide primers may also incorporate natural or synthetic deoxynucleotide analogs not normally present in DNA. Incorporation of nucleotide analogs, depicted as "x" in the diagram above, allows for the oligonucleotide primers to be selectively removed (see section (b) below) after amplification of the target nucleic acid. In some embodiments of the invention, a primer may be used such that, at one or more positions of the primer, one or more of the four deoxyribonucleotides in the primer may be replaced with one or more nucleotide analogs. Primers with nucleotide analogs located throughout the primer may also be used. In one preferred embodiment, primers may have one of the deoxynucleotides replaced with a nucleotide analog. In another preferred embodiment, 25%, 30%, 35% 40%, 50%, 60%, 70%, 80%, 90% or 100% of either dATP, dTTP, dCTP or dGTP in the primers may be replaced with a nucleotide analog. In yet another preferred embodiment, the nucleotide analog may be at the 3'-terminus of the primer.

PCR primers may be designed using standard primer design computer software techniques known to individuals skilled in the art. The variables considered during PCR primer design may include primer length, GC pair content, melting temperature, and size of the target nucleic acid amplified by the primer pair. Generally speaking, primers should not form hairpin structures or self- or hetero-primer pairs, but in some embodiments a primer forming a hairpin structure may be used. In a preferred embodiment, primers may comprise a sequence of 15, 20, 25, 30, 35, 40, 45, 50 or more bases complementary to a portion of a template. In another preferred embodiment, the primer melting temperature may be 50, 55, 60, 65, 70 or 75° C. In a preferred embodiment, the primer melting temperature may be 61, 62, 63, 64, 65, 66 or 67° C. In one embodiment, the melting temperature of each primer of the primer pair may be the same. In another embodiment, the melting temperature of each primer of the primer pair may be different for each primer. In yet another preferred embodiment, the difference in melting temperatures between each primer of the primer pair may be 1, 2, 3, 4, 5, 6, 7, 8, 9° C. or more. In another preferred embodiment, the maximum difference in melting temperature between primer pairs may be 5° C. In a preferred embodiment, the GC content of primer may be 10, 20, 30, 40, 50, 60, 70 or 80%. In yet another preferred embodiment the primer pair may be designed to amplify nucleic acid target products that may be 30, 40, 50, 60, 70, 80, 90, 100, 200, 300, 400, 500, 600, 700, 800, or more base pairs in length.

B. Nucleotide Polymerases

In one embodiment of a method for creating defined ends, the nucleotide polymerase may be a DNA polymerase. In another embodiment, the nucleotide polymerase may be a thermostable polymerase. In a preferred embodiment, the nucleotide polymerase may be a thermostable DNA polymerase. A thermostable polymerase is an enzyme that is relatively stable to heat and eliminates the need to add enzyme prior to each PCR cycle. Non-limiting examples of thermostable polymerases may include polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus* rubber (Tru polymerase), *Thermus brockianus* (DYNAZYME™ polymerase) *Thermotoga neapolitana* (Tne polymerase), *Thermotoga maritime* (Tma) and other species of the *Thermotoga* genus (Tsp polymerase), and *Methanobacterium thermoautotrophicum* (Mth polymerase). The PCR reaction may contain more than one thermostable polymerase enzyme with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form. Alternatively, the polymerase may be modified to contain a fragment of the enzyme or to contain a mutation that provides beneficial properties to facilitate the PCR reaction. In one embodiment, the thermostable polymerase may be Taq polymerase. Many variants of Taq polymerase with enhanced properties are known and include AmpliTaq™, AmpliTaq™ Stoffel fragment, SuperTaq™, SuperTaq™ plus, LA Taq™, LApro Taq™, and EX Taq™. In a preferred embodiment, the thermostable polymerase used in the multiplex amplification reaction of the invention is the AmpliTaq Stoffel fragment.

C. PCR Reaction Conditions

Buffer conditions for PCR reactions are known to those of ordinary skill in the art. PCR buffers may generally contain about 10-50 mM Tris-HCl pH 8.3, up to about 70 mM KCl, about 1.5 mM or higher $MgCl_2$, to about 50-200 µM each of dATP, dCTP, dGTP and dTTP, gelatin or BSA to about 100 µg/ml, and/or non-ionic detergents such as Tween-20 or Nonidet P-40 or Triton X-100 at about 0.05-0.10% v/v. In some embodiments, betaine may be added to the PCR reactions at about 0.25 to about 1 M. An example of a detailed description of buffer conditions may be found in Example 2.

In some embodiments, the multiplex PCR reaction may contain 30, 40, 50, 60, 70, 80, 90, 100, 200, 300, 400, 500, 600, 700, 800, 900, 1000, 1100, 1200 or more primer pairs. Not all primer pairs will amplify targets with the same efficiency. In some embodiments, PCR primer pairs with similar amplification efficiency may be pooled in separate multiplex PCR reactions to have better representation of all targets. These PCR reactions may be combined after amplification.

In other embodiments, PCR amplification may be performed at a uniform temperature (isothermal PCR). Examples of isothermal PCR methods may include the ramification amplifying method and the helicase-dependent amplification method. In a preferred embodiment of the invention, PCR amplification may be by thermal cycling between a high temperature to melt the nucleic acid strands, a lower temperature to anneal the primers to the target nucleic acid, and an intermediate temperature compatible with the nucleic acid polymerase to elongate the nucleic acid sequence. In one embodiment, the melting temperatures may be about 85, 86, 87, 88, 89, 90, 95, or 100° C. In a preferred embodiment, the melting temperature may be about 90, 91, 92, 93, 94, 95, 96, 97 or 98° C. In another embodiment, the annealing temperatures may be 30, 35, 40, 45, 50, 55, 60, 65, 70, 75° C. or more. In a preferred embodiment, the annealing temperature may be 51, 52, 53, 54, 55, 56, 57, 58, 59, 60, 61, 62, 63, 64, 65, 66, 67, 68, 69 70, 71, or 72° C. In yet another embodiment, the elongation temperature may be 30, 35, 40, 45, 50, 55, 60, 65, 70, 75, 80° C. or more. In a preferred embodiment, the elongation temperature may be 70, 71, 72, 73, 74, 75, 80° C. or more.

In certain embodiments, the PCR reaction may be incubated at the melting temperature for about 5 to about 60 seconds. In a preferred embodiment, the PCR reaction may be incubated at the melting temperature for about 30 seconds. In some embodiments, the PCR reaction may be incubated at the annealing temperature for about 5 to about 60 seconds. In a preferred embodiment, the PCR reaction may be incubated at the annealing temperature for about 30 seconds. In some embodiments, the PCR reaction may be incubated at the elongation temperature for about 1 to about 10 minutes. In a preferred embodiment, the PCR reaction may be incubated at the elongation temperature for about 6 minutes. In some embodiments, the PCR reaction is pre-incubated at the melting temperature for about 1, 2, 3, 4, 5, 6, 7, 8, 9 or 10 minutes before cycling between the melting, annealing and elongation temperatures. In a preferred embodiment, the PCR reaction may be pre-incubated at the melting temperature for about 2 minutes.

In several embodiments, the PCR reactions may be cycled between the melting, annealing and elongation temperatures 2, 5, 10, 15, 20, 25, 30, 35, 40, 45, 50, 55 or more times. In a preferred embodiment, the PCR reactions may be cycled between the melting, annealing and elongation temperatures 2, 3, 4, 5, 6, 7, 8, 9, 10, 11, 12, 13, 14, 15 or more times.

D. Trimming Amplicons

Figure 15B:
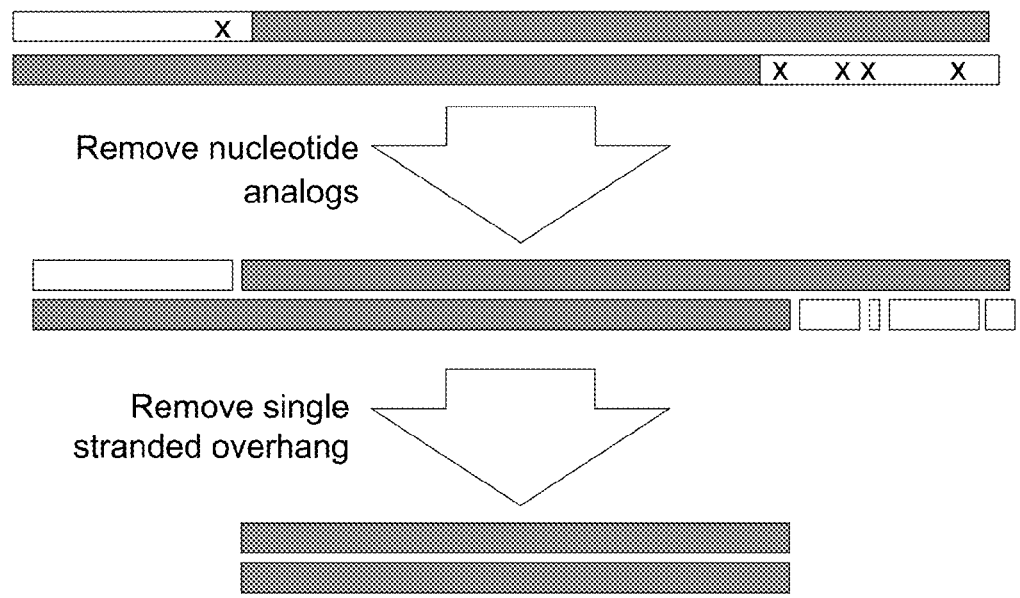

In some embodiments of the invention, the amplified targets from the PCR reaction described above may be trimmed so the ends of the target regions become internal to the PCR primer sequences as depicted in FIG. 15B. The extent of the trimming may generally be defined by synthetic nucleotide analogs incorporated into the primer pairs described above. Treatments that specifically remove synthetic nucleotide analogs have been devised and are well known to those skilled in the art.

In certain embodiments, oligonucleotides containing 5-bromodeoxyuridine (BdUR) or 5-bromodeoxycytidine (BrdC) may be used as the primers of the invention. Primers containing BdUR may be degraded upon exposure to light. In other embodiments, the deoxyinosine may be incorporated into primers of the invention. Primers containing deoxyinosine may be degraded using Endonuclease V, an enzyme that recognizes and cleaves the sugar phosphate backbone at the deoxyinosine residue.

In other embodiments, the base of the synthetic nucleotide is first specifically removed, leaving an apurinic or apyrimidinic site (AP site) and an intact sugar-phosphate backbone. The sugar-phosphate backbone is then cleaved at the AP site, generating a nick in the target, which dictates the nucleic acid sequence to be removed by exonuclease enzymes. In preferred embodiments of the invention, the base of the synthetic nucleotide analog is removed with a DNA glycosylase enzyme. DNA glycosylases are a family of enzymes that can remove the base of some nucleotide analogs. Some examples of nucleotide analogs that may be incorporated into primers and that are substrates for glycosylase enzymes may include deoxyuridine, deoxy-7-methylguanosine, deoxy-5,6-dihydroxythymidine, deoxy-3-methyladenosine, deoxyinosine, 5-methyl-deoxycytidine, O-6-methyl-deoxyguanosine, 5-iodo-deoxyuridine, 8-oxy-deoxyguanine, and 1,$N^6$-ethenoadenine. Glycosylase enzymes that remove bases from nucleotide analogs incorporated into target nucleic acid sequences may include uracyl DNA glycosylase, 7-methylguanine-DNA glycosylase, 5,6-dihydroxythymidine glycosylase, 3-methyladenine glycosylase, hypoxanthine DNA N-glycosylases, 8-oxoguanine-DNA glycosylase, and alkylpurine-DNA-N-glycosylase. In a preferred embodiment, the nucleotide analog may be deoxyuridine. In another preferred embodiment, the DNA glycosylase enzyme may be uracil DNA glycosylase.

In some embodiments, treatments that cleave AP sites may include, but are not limited to, heat, alkaline hydrolysis, tripeptides such as Lys-Trp-Lys and Lys-Tyr-Lys, AP endonucleases such as endonuclease III, endonuclease IV, endonuclease VI, endonuclease VIII, phage T4 UV endonuclease, and the like. In a preferred embodiment, the treatment is endonuclease VIII.

After removing primers from amplified target nucleic acid sequences, the resulting single strand overhanging nucleic acid sequence at the 3' termini may be removed using an enzyme with a 3' to 5' single stranded exonuclease activity as depicted in the diagram above. Commonly used 3' to 5' exonucleases that remove single stranded nucleic acids may include exonuclease I and exonuclease VII. In a preferred embodiment of the invention, the exonuclease is exonuclease I.

After trimming the ends of the amplified target nucleic acids, other manipulations that prepare the reactions for subsequent steps may be performed. For example, removal of unincorporated nucleotides might be required. In some embodiments, this may be accomplished by physical means such as precipitation, filtration, and chromatography. In other embodiments, the unincorporated nucleotides may be diluted to a concentration where they would not interfere in later steps. In preferred embodiments, the unincorporated nucleotides may be removed using enzymes such as apyrase, an ATP diphosphohydrolase that catalyses the removal of the gamma phosphate from ATP and the beta phosphate from ADP.

ii. Restriction Endonuclease Enzymes

In another embodiment, restriction endonuclease enzymes may be used to create nucleic acid sequences with defined ends. Suitable restriction endonuclease enzymes may include type I, type II, type III or type IV restriction endonuclease enzymes. Generally speaking, the restriction enzyme used should have recognition sites that flank, and not bisect, the desired nucleic acid sequence. In some embodiments, the restriction endonuclease enzymes may be type I restriction endonuclease enzymes. Non-limiting examples of Type I restriction endonuclease enzymes may include CfrI, Eco377I, EcoAI, EcoDXXI, EcoKI, Eco124I, KpnAI, and StySPI. In other embodiments, the restriction endonuclease enzymes may be type II restriction endonuclease enzymes. Type II restriction endonuclease enzymes suitable for the methods of the invention may be a restriction endonuclease enzyme of type IIB, type IIE, type IIF, type IIG, type IIM, type IIS, or type IIT. In certain embodiments, Type III restriction endonuclease enzymes may be suitable for the methods of the invention. Non-limiting examples of Type III restriction endonuclease enzymes are known in the art. In alternative embodiments, the restriction endonuclease enzymes may be Type IIS restriction endonuclease enzymes. Non-limiting examples of Type IIS restriction endonuclease enzymes may include FokI, HgaI, EciI, BceAI, BbvI, BtgZI, BsmFI, BpmI, and BsgI. Other restriction endonuclease enzymes are known in the art. For instance, additional non-limiting examples may be found at http://rebase.neb.com/cgi-bin/azlist?re1, http://rebase.neb.com/cgi-bin/azlist?re2, http://rebase.neb.com/cgi-bin/azlist?re3, or http://rebase.neb.com/cgi-bin/azlist?re4.

Figure 15C:
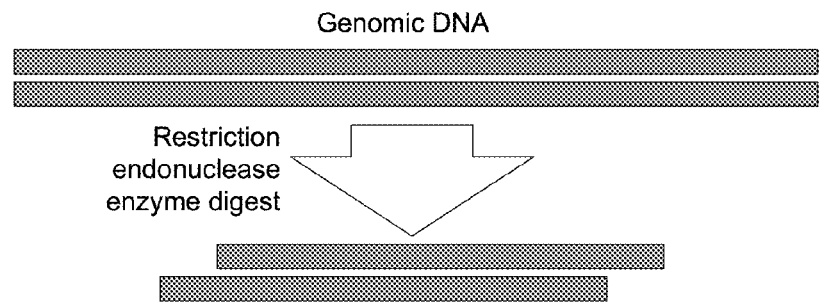

The restriction endonuclease enzyme cut sites may be used to define the ends of nucleic acid templates. An exemplary example of a restriction enzyme reaction creating nucleic acid sequences with defined ends is depicted in FIG. 15C. Components of the restriction enzyme reaction may include the nucleic acid sequence to be digested (template; see section I(a) above), one or more restriction endonucleases, and salts and buffers essential for optimal activity of the enzymes in the reaction. The restriction enzyme reaction may be prepared using methods well known to those of skill in the art (see, e.g., Sambrook et al. (1989) "Molecular Cloning: A Laboratory Manual," $2^{nd}$ Ed., Cold Spring Harbor Laboratory Press, Cold Spring Harbor).

Figure 15D:
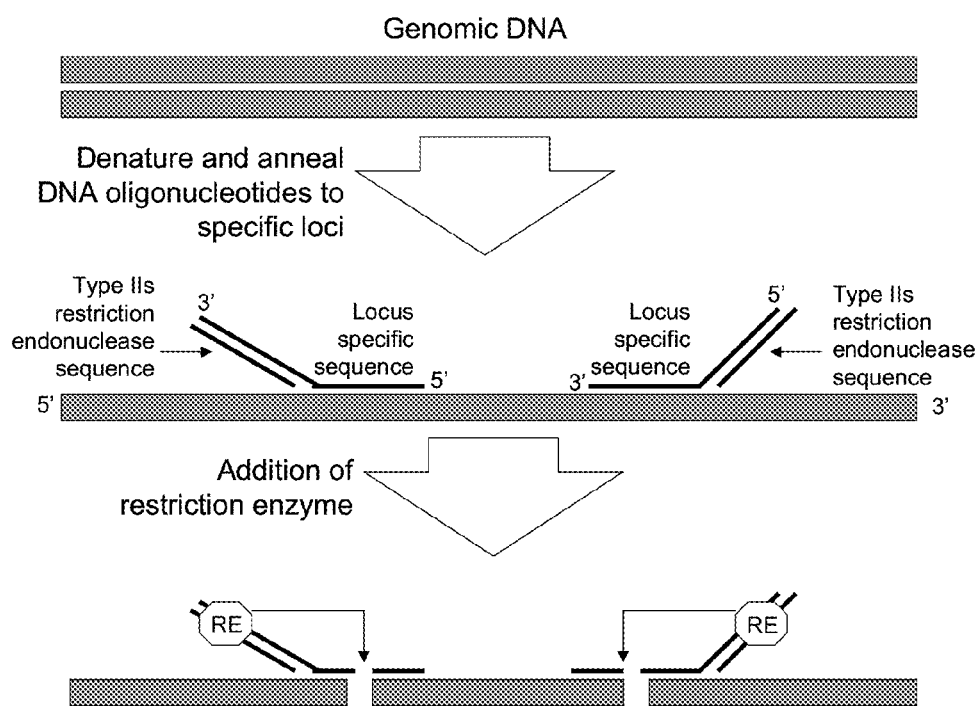

In some embodiments, oligonucleotides may be used to direct Type IIs restriction enzymes to cut at specific sites in the nucleic acid template. As depicted in FIG. 15D, this is facilitated by upstream and downstream oligonucleotides that anneal upstream and downstream of the target nucleic acid sequences and serve as a guide for digestion by the type IIs restriction endonuclease enzyme. Thus, components of the restriction enzyme reaction may include the nucleic acid sequence to be digested (template; see section I(a) above), one or more restriction endonucleases, the oligonucleotides directing the restriction endonuclease cut sites (described below), and salts and buffers essential for optimal activity of the enzymes in the reaction.

A. Oligonucleotides Directing Type IIs Restriction Endonuclease Enzymes

The upstream and downstream restriction enzyme-directing oligonucleotides may be designed using primer length, GC pair content, and melting temperature criteria as described in section I(b)iA above. In some preferred embodiments, the 5' ends of the upstream restriction enzyme-directing oligonucleotides may be complementary to a portion of the desired nucleic acid sequence (e.g. the segment parallel to the genomic DNA in the diagram above), and may be concatenated at the 3' end of the oligonucleotides to double-stranded nucleotide sequences encoding type IIs restriction enzymes. In other preferred embodiments, the 3' ends of the downstream restriction-enzyme-directing oligonucleotides may be complementary to a portion of the desired nucleic acid sequences (e.g. the segment parallel to the genomic DNA in the diagram above), and may be concatenated at the 5' end of the oligonucleotides to double-stranded nucleotide sequences encoding type IIs restriction enzymes.

B. Annealing and Digestion Reaction Conditions

Annealing of the restriction enzyme-directing oligonucleotides to the nucleic acid templates may generally be performed before addition of the restriction enzyme for digestion. In addition to the nucleic acid template, annealing reactions may generally contain about 1 pM to about 500 nM of each restriction enzyme-directing oligonucleotide, and about 0.01 to about 0.9% Tween80. An example of a detailed description of buffer conditions may be found in Example 8.

In some embodiments, annealing of the restriction enzyme-directing oligonucleotides may be performed by melting the nucleic acid strands at a high temperature, followed by a lower temperature suitable for annealing the restriction enzyme-directing oligonucleotides to target nucleic acid sequences. In one embodiment, the melting temperatures may be about 85, 86, 87, 88, 89, 90, 95, or 100° C. In a preferred embodiment, the melting temperature may be about 90, 91, 92, 93, 94, 95, 96, 97 or 98° C. In another embodiment, the annealing temperatures may be about 10, 15, 20, 25, 30, 35, 40, 45, 50, 55° C. or more. In a preferred embodiment, the annealing temperatures may be about 25, 26, 27, 28, 29, 30, 31, 32, 33, 34, 35, 36, 37, 38, 39, 40, 41, 42, 43, 44, 45, 46, 47, 48, 49 50, 51, or 52° C.

In other embodiments, the annealing reactions may be incubated at the melting temperature for about 5 to about 30 minutes. In a preferred embodiment, the annealing reactions may be incubated at the melting temperature for about 10, 11, 12, 13, 14, 15, 16, 17, 18, 19, 20, 21, 22, 23, 24, 25 minutes. In some embodiments, the annealing reactions may be incubated at the annealing temperature for about 1 to about 10 minutes. In a preferred embodiment, the annealing reactions may be incubated at the melting temperature for about 1, 2, 3, 13, 4, 5, 6, 7, 8, 9, 10, 11, 12, 13, 14, or 15 minutes.

After annealing the restriction enzyme-directing oligonucleotides to the template, the type IIs restriction enzyme may be added, and the restriction enzyme reaction may be prepared using methods well known to those of skill in the art (see, e.g., Sambrook et al. (1989) "Molecular Cloning: A Laboratory Manual," 2$^{nd}$ Ed., Cold Spring Harbor Laboratory Press, Cold Spring Harbor).

iii. Single Strand Specific Exonuclease Degradation

Figure 15E:
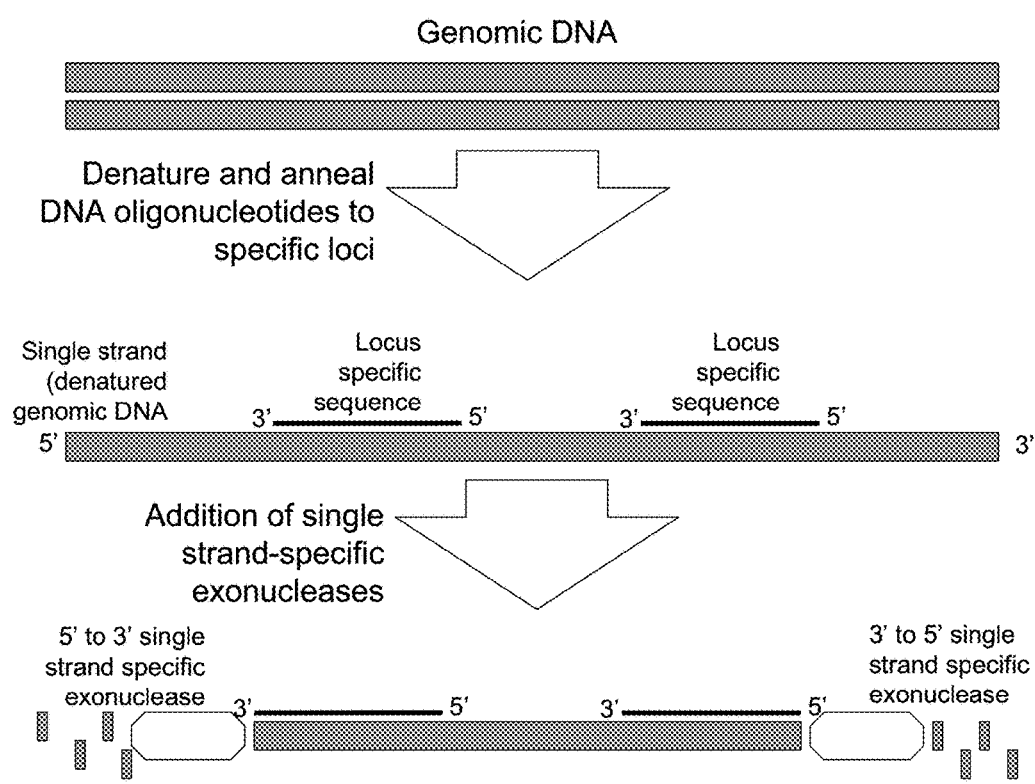

Single strand specific exonuclease enzyme digestion of nucleic acid templates protected by locus-specific oligonucleotides may be used to define ends of the nucleic acid template. As depicted in FIG. 15E, this is facilitated by upstream and downstream oligonucleotides that anneal upstream and downstream of the target nucleic acid sequences and serve as protection against digestion by the single strand specific exonuclease enzymes. Thus, components of the exonuclease reaction may include the nucleic acid sequence to be digested (template; see section I(a) above), one or more single strand specific exonuclease enzymes (described below), the oligonucleotides protecting the nucleic acid template (described below), and salts and buffers essential for optimal activity of the exonucleases in the reaction.

Non-limiting examples of single strand specific exonuclease enzymes suitable for the methods of the invention may be exonuclease VII, exonuclease I, RecJ exonuclease, or Terminator™ 5'-Phosphate-Dependent Exonuclease (Epicentre Biotechnologies). The upstream and downstream oligonucleotides may be designed using primer length, GC pair content, and melting temperature criteria as described in (b)i.A. above.

Annealing of the protecting oligonucleotides to the nucleic acid templates may generally be performed before addition of the exonuclease enzymes. In addition to the nucleic acid template, annealing reactions may generally contain about 1 pM to about 500 nM of each oligonucleotide. In some embodiments, annealing of the oligonucleotides may be performed by melting the nucleic acid strands at a high temperature, followed by a lower temperature suitable for annealing the protecting oligonucleotides to target loci. In one embodiment, the melting temperatures may be about 85, 86, 87, 88, 89, 90, 95, or 100° C. In a preferred embodiment, the melting temperature may be about 90, 91, 92, 93, 94, 95, 96, 97 or 98° C. In another embodiment, the annealing temperatures may be about 10, 15, 20, 25, 30, 35, 40, 45, 50, 55° C. or more. In a preferred embodiment, the annealing temperatures may be about 25, 26, 27, 28, 29, 30, 31, 32, 33, 34, 35, 36, 37, 38, 39, 40, 41, 42, 43, 44, 45, 46, 47, 48, 49 50, 51, or 52° C.

In some embodiments, the annealing reactions may be incubated at the melting temperature for about 5 to about 30 minutes. In a preferred embodiment, the annealing reactions may be incubated at the melting temperature for about 10, 11, 12, 13, 14, 15, 16, 17, 18, 19, 20, 21, 22, 23, 24, 25 minutes. In some embodiments, the annealing reactions may be incubated at the annealing temperature for about 1 to about 10 minutes. In a preferred embodiment, the annealing reactions may be incubated at the melting temperature for about 1, 2, 3, 13, 4, 5, 6, 7, 8, 9, 10, 11, 12, 13, 14, or 15 minutes. After annealing of the protecting oligonucleotides, the exonuclease enzymes may be added for digestion.

iv. Triplex Formation and Cleavage by Endonucleases

The ability of some nucleic acid recombination proteins to direct the formation of triplex nucleic acid structures may be used to create defined ends of a nucleic acid sequence. Triplex DNA structures are induced at specific loci by incubating nucleic acid templates with locus-specific oligonucleotides that have been coated with the recombination protein. The triplex structure then produces a single stranded region of nucleic acid available for cleavage by single strand specific endonucleases. Thus, components of the restriction enzyme reaction may include the nucleic acid sequence to be digested (template; see section I(a) above), one or more recombination proteins, the recombination protein-coated locus-specific oligonucleotides, the endonuclease proteins, and salts and buffers for optimal activity of the enzymes. Non-limiting examples of recombination proteins may include RecA of *Escherichia coli*, or any homologous recombination protein capable of inducing formation of triplex DNA structure. Non-limiting examples of single strand specific endonucleases may include S1 and BAL1 endonucleases.

(c) Nucleic Acid Patch PCR

Figure 15F:
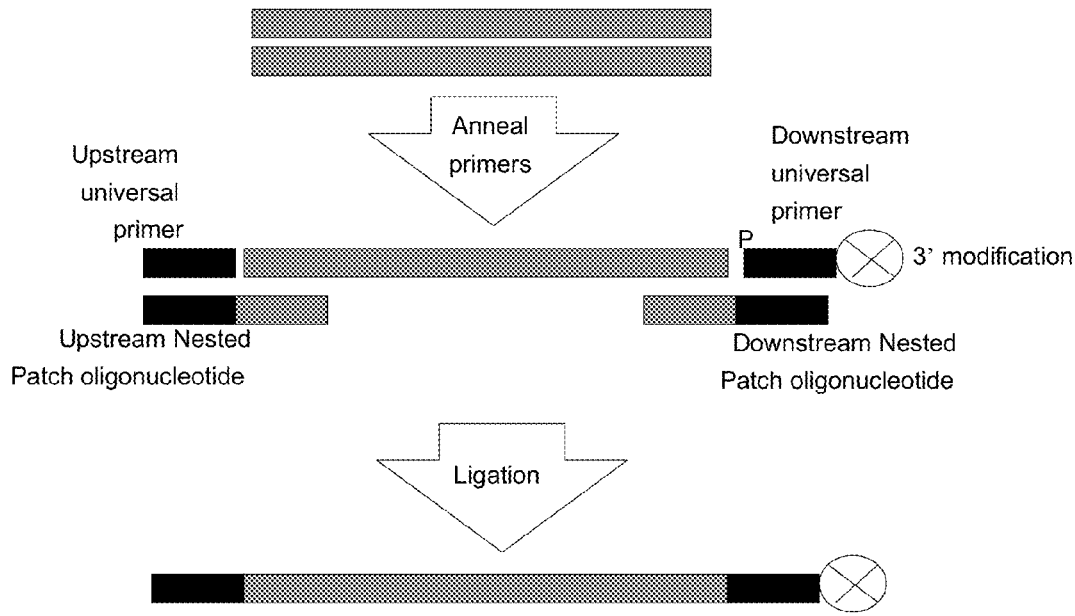

One aspect of the invention is the ligation of universal primer sequences to nucleic acid sequences. As depicted in FIG. 15F, this is facilitated by upstream and downstream nucleic acid patch oligonucleotides that anneal upstream and downstream of the target nucleic acid sequences and serve as a patch between the desired sequence and upstream and downstream universal primers to be ligated. Thus, nucleic acid patch ligation reactions contain the target sequences, the upstream and downstream universal primers to be ligated, the upstream and downstream nucleic acid patch oligonucleotides to guide the specific ligation of the universal primers, and the enzymes and other components needed for the ligation reaction. In preferred embodiments, target sequences may be nucleic acid sequences with defined ends as described above.

i. Universal Primers

The upstream and downstream universal primers may be designed using primer length, GC pair content and melting temperature criteria as described in I(a) above. In some embodiments, the downstream universal primer may be modified to facilitate further steps of the invention. In a specific embodiment, the downstream universal primer may be modified with a 5' phosphate group to enable ligation of the downstream universal primer to the amplicon. In other specific embodiments, the 3' end of the downstream universal primer may be modified for protection against exonuclease digestion. Modifications at the 3' end may be introduced at the time of synthesis or after synthesis through chemical means well know to those of skill in the art. Modifications may be 3' terminal or slightly internal to the 3' end. Some examples of modifications that make nucleic acid sequences exonuclease resistant include, but are not limited to, locked nucleic acids (LNA's), 3'-linked amino groups, 3' phosphorylation, the use of a 3'-terminal cap (e.g., 3'-aminopropyl modification or by using a 3'-3' terminal linkage), phosphorothioate modifications, the use of attachment chemistry or linker modification such as Digoxigenin NHS Ester, Cholesteryl-TEG, biotinylation, thiol modifications, or addition of various fluorescent dyes and spacers such as C3 spacer. In a preferred embodiment, the downstream universal primer is protected from exonuclease digestion by a C3 spacer.

ii. Nucleic Acid Patch Primers

In some embodiments, an upstream and a downstream nucleic acid patch oligonucleotide may be designed for each amplicon (see diagram above). In some preferred embodiments, the 5' ends of the upstream nucleic acid patch oligonucleotides may be complementary to sequences in the amplicons (grey segment of upstream nucleic acid patch oligonucleotide in diagram above), and may be concatenated to upstream nucleotide sequences complementary to the upstream universal primer sequence on the 3' end (black segment of upstream nucleic acid patch oligonucleotide in diagram above). In other preferred embodiments, the 3' ends of the downstream nucleic acid patch oligonucleotides may be complementary to downstream sequences in the amplicons (grey segment of downstream Nucleic acid patch oligonucleotide in diagram above), and may be concatenated to nucleotide sequences complementary to the downstream universal primer sequence on the 5' end (black segment of downstream nucleic acid patch oligonucleotide in diagram above).

iii. Ligation of Universal Primers

In some embodiments, the universal primers may be ligated to nucleic acid sequences. In a process similar to a PCR amplification reaction, multiple cycles of heating and cooling may be used to melt the target nucleic acid sequence, anneal the nucleic acid patch and universal primers, and ligate the universal primers to target nucleic acid sequences.

In some embodiments of the invention, the universal primers of the invention may be ligated to the target nucleic acids using a DNA ligase. The ligase may be theromostable. In preferred embodiments, the ligase is a thermostable DNA ligase. A thermostable DNA ligase is an enzyme that is relatively stable to heat and eliminates the need to add enzyme prior to each ligation cycle. Non-limiting examples of theromostable DNA ligases may include Ampligase® Thermostable DNA Ligase, Taq DNA Ligase from *Thermus aquaticus*, Tfi DNA ligase from *Thermus filiformis*, Tth DNA ligase from *Thermus thermophilus*, Thermo DNA ligase, Pfu DNA ligase from *Pyrococcus furiosus*, and thermostable DNA ligase from *Aquifex pyrophilus*. The thermostable polymerase may be used in its wild type form, modified to contain a fragment of the enzyme, or to contain a mutation that provides beneficial properties to facilitate the ligation reaction. In a preferred embodiment, the thermostable ligase is Ampligase®.

iv. Ligation Reaction Conditions

Ligation reactions may generally contain about 1 pM to about 500 nM of each nucleic acid patch oligo, about 1 pM to about 500 nM of each universal primer, about 3, 4, 5, 6, 7, or 8 units of Ampligase®, and 1× Ampligase Reaction Buffer. An example of a detailed description of buffer conditions may be found in Example 2.

In some embodiments, ligation reactions may be performed by thermal cycling between a high temperature to melt the nucleic acid strands, a sequence of 1, 2, 3, 4 or 5 lower temperatures to anneal the nucleic acid patch oligonucleotides to the target nucleic acid, and a temperature compatible with the ligase to ligate the nucleic acid sequence. In a preferred embodiment, ligation reactions may be performed by thermal cycling between a high temperature to melt the nucleic acid strands, a first lower temperature to anneal the nucleic acid patch oligonucleotides to the target nucleic acid, a second lower temperature to anneal the universal primers to the nucleic acid patch oligonucleotides, and a temperature compatible with the ligase to ligate the nucleic acid sequence. In one embodiment, the melting temperatures may be about 85, 86, 87, 88, 89, 90, 95, or 100° C. In a preferred embodiment, the melting temperature may be about 90, 91, 92, 93, 94, 95, 96, 97 or 98° C. In another embodiment, the Nucleic acid patch oligonucleotide annealing temperatures may be about 30, 35, 40, 45, 50, 55, 60, 65, 70, 75° C. or more. In a preferred embodiment, the nucleic acid patch oligonucleotide annealing temperatures may be about 45, 46, 47, 48, 49, 50, 51, 52, 53, 54, 55, 56, 57, 58, 59, 60, 61, 62, 63, 64, 65, 66, 67, 68, 69 70, 71, or 72° C. In another embodiment, the ligation temperature may be about 30, 35, 40, 45, 50, 55, 60, 65, 70, 75, 80° C. or more. In a preferred embodiment, the ligation temperature may be about 55, 56, 57, 58, 59, 60, 61, 62, 63, 64, 65, 66, 67, 68, 69, 70° C. or more.

In some embodiments, the ligation reactions may be incubated at the melting temperature for about 5 to about 60 seconds. In a preferred embodiment, the ligation reactions may be incubated at the melting temperature for about 30 seconds. In some embodiments, the ligation reactions may be incubated at the nucleic acid patch oligonucleotide annealing temperature for about 1, 2, 3, 4, 5, 6, 7, 8, 9, 10 or more minutes. In a preferred embodiment, the reactions may be incubated at the nucleic acid patch oligonucleotide annealing temperature for about 2 minutes. In some embodiments, the ligation reactions may be incubated at the universal primer annealing temperature for about 30 seconds to about 5 minutes. In a preferred embodiment, the ligation reactions may be incubated at the universal primer annealing temperature for about 1 minute. In some embodiments, the ligation reactions may be incubated at the ligation temperature for about 30 seconds to about 5 minutes. In a preferred embodiment, the ligation reactions may be incubated at the ligation temperature for about 1 minute. In some embodiments, the reactions may be pre-incubated at the melting temperature for about 5, 6, 7, 8, 9, 10, 15, 20 or 25 minutes before cycling between the melting, annealing and ligation temperatures. In a preferred embodiment, the ligation reactions may be pre-incubated at the melting temperature for about 15 minutes.

In some embodiments, the ligation reactions may be cycled between the melting, annealing and ligation temperatures about 10, 50, 100, 150, 200 or more times. In a preferred embodiment, the ligation reactions may be cycled between the melting, annealing and elongation temperatures about 100 times.

(d) Degrade Mispriming Products and Genomic DNA

In some embodiments, exonucleases may be added to the ligation reaction at the completion of the reaction to degrade mispriming products of the multiplex PCR reaction or genomic DNA. In preferred embodiments, exonucleases may be 3' to 5' exonucleases. Exonucleases may be single stranded or double stranded exonucleases. Non-limiting examples of exonucleases suitable for this step of the reaction may include exonuclease I, exonuclease III and mung bean nuclease. One or more exonucleases may be added. In a preferred embodiment, the exonucleases may be exonuclease I and III.

Figure 15G:
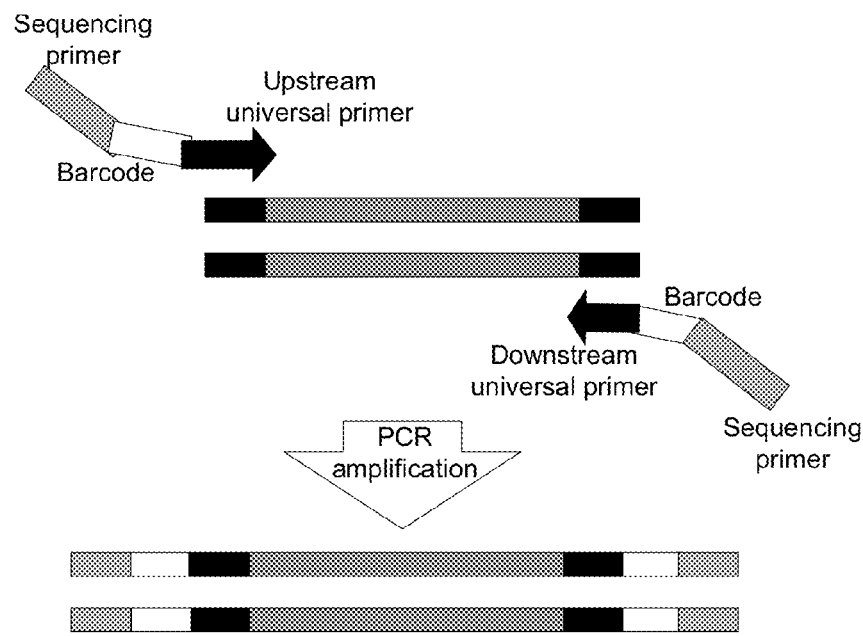

(e) Sample-Specific Barcode PCR and Sequencing of Nucleic Acid Patch Amplicons In some aspects of the invention, nucleic acid samples may be sequenced. In some embodiments, the nucleic acids sequenced may be the amplicons prepared in (a), (b) and (c) above. Sequencing techniques suitable for the invention may be high throughput. High throughput sequencing techniques may include techniques based on chain termination, pyrosequencing (sequence by synthesis), or sequencing by ligation and are well known to those of skill in the art. In some embodiments, high throughput sequencing techniques like true single molecule sequencing (tSMS) may not require amplification of target nucleotide sequences. In preferred embodiments, sequencing may be performed using high throughput sequencing techniques that involve in vitro clonal amplification of the target nucleotide sequence. Non-limiting examples of high throughput sequencing techniques that involve amplification may include solid-phase PCR in polyacrylamide gels, emulsion PCR, rolling-circle amplification, bridge PCR, BEAMing (beads, emulsions, amplification and magnetics)-based cloning on beads, massively parallel signature sequencing (MPSS) to generate clonal bead arrays. In a preferred embodiment, the amplicons may be sequenced using PCR techniques as exemplified by 454 Sequencing™. The PCR amplification for 454 sequencing may be as depicted in FIG. 15G.

In some embodiments, the PCR may use primers complementary to the universal primer sequences described in section I(c)i above, and depicted as black segments in the diagram. In other embodiments, the PCR primers may be coupled to nucleic acid sequences for sequencing (grey segments of the primers in diagram above). In a preferred embodiment, the primers for the final universal PCR may be tailed to 454 sequencing primers A and B (454 Life Sciences, Branford, Conn.). In other embodiments, the primers for the PCR amplification may be complementary to the upstream and downstream universal primer nucleotide sequences ligated in FIG. 15G (black segments of the primers). In additional embodiments, the PCR primers may be coupled to nucleic acid sequence barcodes (white segments of the primers in FIG. 15G). In some embodiments, the nucleic acid barcode may be about 4, 5, 6, 7, 8, 9, 10, or more bases. In a preferred embodiment, the nucleic acid barcode may be about 6 bases. The barcodes may be at the 5' end, the 3' end or, as exemplified in FIG. 15G, internal to the primer sequence.

In some embodiments, nucleic acid sequences amplified in the PCR reactions of more than one sample may be pooled for parallel sequencing of nucleic acids prepared in multiple samples. In some embodiments, about 2, 3, 4, 5, 10, 15, 20, 30, 40, 50, 60, 70, 80, 90, 100, 1000 or more samples may be pooled for sequencing.

(f) Specific Embodiments

In a specific embodiment, restriction endonuclease enzymes may be used to create nucleic acid sequences with defined ends. Suitable restriction endonuclease enzymes may be as described in Section I(b)ii. In a specific embodiment, the restriction endonuclease enzyme may be Type II restriction endonuclease enzymes. In another specific embodiment, the restriction endonuclease enzyme may be Type IIS restriction endonuclease enzymes.

In a specific embodiment, oligonucleotides may be used to direct Type IIS restriction enzymes to cut at specific sites in the nucleic acid template. This is facilitated by upstream and downstream oligonucleotides that anneal upstream and downstream of the target nucleic acid sequences and serve as a guide for digestion by the Type IIS restriction endonuclease enzyme. Thus, components of the restriction enzyme reaction may include the nucleic acid sequence to be digested (template; see section I(a) above), one or more restriction endonucleases, the oligonucleotides directing the restriction endonuclease cut sites, and salts and buffers essential for optimal activity of the enzymes in the reaction.

The upstream and downstream restriction enzyme-directing oligonucleotides may be designed using primer length, GC pair content, and melting temperature criteria as described in section I(b)iA above. In a specific embodiment, the upstream and downstream restriction enzyme-directing oligonucleotides may each form a hairpin structure. Specifically, the 5' ends of the upstream restriction enzyme-directing oligonucleotides may be complementary to a portion of the desired nucleic acid sequence (e.g. the segment parallel to the genomic DNA in FIG. 13), and may form a hairpin structure at the 3' end of the oligonucleotides to generate a double-stranded nucleotide sequence recognized by Type IIS restriction enzymes. Further, the 3' ends of the downstream restriction-enzyme-directing oligonucleotides may be complementary to a portion of the desired nucleic acid sequences (e.g. the segment parallel to the genomic DNA in the diagram above), and may form a hairpin structure at the 5' end of the oligonucleotides to generate a double-stranded nucleotide sequence recognized Type IIS restriction enzymes.

The upstream and downstream restriction enzyme-directing oligonucleotides may comprise a sequence of 10, 15, 20, 25, 30, 35, 40, 45, 50 or more bases complementary to a portion of a template. In a specific embodiment, the upstream and downstream restriction enzyme-directing oligonucleotides may comprise a sequence of 10 or more bases complementary to a portion of a template. In another specific embodiment, the upstream and downstream restriction enzyme-directing oligonucleotides may comprise a sequence of 15 or more bases complementary to a portion of a template. In still another specific embodiment, the upstream and downstream restriction enzyme-directing oligonucleotides may comprise a sequence of 20 or more bases complementary to a portion of a template. In still yet another specific embodiment the upstream and downstream restriction enzyme-directing oligonucleotides may comprise a sequence of 9, 10, 11, 12, 13, 14, 15, 16, 17, 18, 19, or 20 bases complementary to a portion of a template. In an exemplary embodiment the upstream and downstream restriction enzyme-directing oligonucleotides may comprise a sequence of 15, 16, 17, 18, 19, or 20 bases complementary to a portion of a template. It is not necessary that the upstream and downstream restriction enzyme-directing oligonucleotides comprise the same amount of bases complementary to a portion of a template.

The upstream and downstream restriction enzyme-directing oligonucleotides may comprise 20, 25, 30, 35, 40, 45, 50 or more bases. In a specific embodiment, the upstream and downstream restriction enzyme-directing oligonucleotides may comprise 20 or more bases. In another specific embodiment, the upstream and downstream restriction enzyme-directing oligonucleotides may comprise 25 or more bases. In still another specific embodiment, the upstream and downstream restriction enzyme-directing oligonucleotides may comprise 30 or more bases. In still yet another specific embodiment, the upstream and downstream restriction enzyme-directing oligonucleotides may comprise 35 or more bases. It is not necessary that the upstream and downstream restriction enzyme-directing oligonucleotides comprise the same amount of bases.

The annealing and digestion reaction conditions may be as described in section I(b)iiB and the rest of the method may be as described in sections I(c)-(e).

The specific embodiments described above may be used in a method of detecting short tandem repeats (STRs). As used herein, a STR consists of a unit of about two to about 13 nucleotides repeated up to hundreds of times in a row on the DNA. The method of detecting STRs may be used to measure the number of repeating units and/or measure the length of the STR. According to the specific embodiment described above, upstream and downstream restriction enzyme-directing oligonucleotides anneal to regions on the DNA immediately adjacent to the STR and the methodology disclosed herein may be used to detect the number of repeating units in the STR and/or the length of the STR. Such a method may be useful in the field of forensic science. By immediately adjacent is meant that the oligonucleotides anneal to the base directly next to the STR or about 1 or up to 20 bases upstream and downstream from the STR. For example, the oligonucleotides may anneal 1, 2, 3, 4, 5, 6, 7, 8, 9, 10, 11, 12, 13, 14, 15, 16, 17, 18, 19 or 20 bases upstream and downstream from the STR. In a specific embodiment, the oligonucleotides may anneal 1, 2, 3, 4, 5, 6, 7, 8, 9 or 10 bases upstream and downstream from the STR. The upstream oligonucleotide does not have to be the same distance from the STR as the downstream oligonucleotide.

II. Methods of Use

A further aspect of the invention provides uses for the amplification method detailed herein. In some embodiments, a method described herein may be used to detect and discover single nucleotide polymorphisms (SNPs) or mutations. In other embodiments, a method described herein may be used to detect pathogen DNA in a high background of host DNA, detect rare DNA to allow for multiplexed or genome-wide amplification of biomarkers in peripheral samples, or amplify targets from degraded samples to allow for multiplexed or genome-wide amplification. In a specific embodiment, a method described herein may be used to detect rare tumor DNA to allow for multiplexed or genome-wide amplification of biomarkers in peripheral samples such as blood or stool. In yet other embodiments, a PCR method described herein may be used to detect DNA methylation. Other applications that rely heavily on PCR may benefit from higher levels of multiplexing, such as the amplification of all exons or all conserved regions, or the engineered assembly of many DNA fragments simultaneously in synthetic biology experiments, or the analysis of short tandem repeats.

In still other embodiments, the PCR method described herein may be used to detect DNA methylation, detect and/or sequence tumor DNA derived from peripheral samples (blood, stool), amplify all exons in a particular template, or amplify all conserved regions in a particular template. A skilled researcher in the art will appreciate that other methods of use for a method detailed herein may be possible or desirable, and that the methods of use detailed herein are not to be construed as limiting.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1: Nucleic Acid Patch PCR Design

Mispriming events plague standard multiplex PCR reactions as the number of primer pairs increases. Nucleic acid patch PCR was designed to significantly decrease mispriming events, as nucleic acid patch PCR requires four oligonucleotide hybridizations per locus. This results in a more specific amplification than standard multiplex PCR, which requires only two hybridizations per locus. FIG. 1 presents a schematic of the concept of nucleic acid patch PCR.

In the first round of oligonucleotide hybridization, a PCR reaction containing DNA primer pairs for all targets is performed on genomic DNA (FIG. 1A). These DNA primers contain uracil substituted for thymine to facilitate the next step of the process. The PCR is performed for a low number of cycles and serves to define the ends of the target regions. To prepare for the second round of oligonucleotide hybridization, the PCR product generated above is first trimmed to produce a nucleic acid fragment with ends internal to the PCR primer sequences (FIG. 1B). This is accomplished by removing the uracil-containing primers, and trimming the resulting DNA overhangs on the PCR product by an enzyme mix containing uracil DNA glycosylase.

Next, a second round of oligonucleotide hybridization is performed. Nucleic acid patch oligonucleotides are annealed to the target amplicons and serve as a patch between the correct amplicons and universal primers (FIG. 1C). In the third oligonucleotide hybridization, the universal primers are annealed to the nucleic acid patch primers, and then ligated to the amplicons in a reaction containing a thermostable ligase followed by exonucleases I and III. This reaction provides two levels of selection in addition to the oligonucleotide hybridization. First, the thermostable ligase used is sensitive to mismatched bases near the ligation junction (Barany 1991), and second, the exonucleases in the reaction provide an added level of selectively by degrading mispriming products and the genomic DNA. The selected amplicons are protected from the exonuclease in the final reaction by a 3' modification with a 3-carbon spacer on the universal primer. The selected amplicons are then amplified together simultaneously by PCR with the universal primers (FIG. 1D) for the final round of selection.

Figure 2:
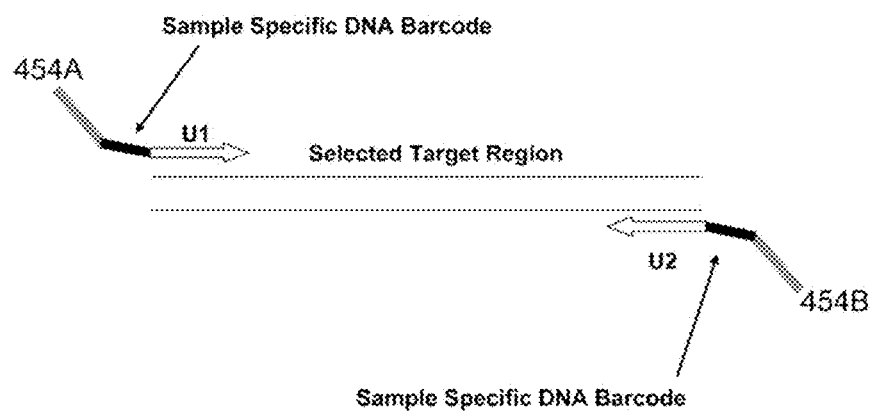
FIG. 2 depicts a schematic of Sample Specific Barcode PCR. Sample-specific DNA barcodes are incorporated into the primers that are used for the final universal PCR. The 5' end of the universal primer (white) is tailed with the sequences for the Roche/454 FLX Machine (grey) and sample-specific DNA sequences (black). When sequencing from either 454A or 454B, the first few bases indicate from which sample the read originated.

The target selection protocol is an addition-only reaction and can be performed in a single tube per sample, making it amenable to automation. To pool and sequence multiple samples, nucleic acid patch PCR is first performed separately for each sample (1 tube per sample). Sample-specific DNA barcodes are then incorporated into the primers used for the final universal PCR by tailing the 5' end with sample-specific DNA sequences and 454 sequencing primers (FIG. 2). Thus, the first few bases indicate from which sample each read originated.

Example 2: Nucleic Acid Patch PCR and Sequencing of Candidate Genes in Colon Cancer To demonstrate the multiplexed selection and amplification of exons by nucleic acid patch PCR described in Example 1, single nucleotide polymorphisms (SNPs) and mutations were analyzed in six nucleotide sequences encoding cancer related proteins: tumor protein p53 (TP53); adenomatous polyposis coli (APC); mutL homolog 1, colon cancer, nonpolyposis type 2 (MLH1); retinoblastoma 1 (RB1); breast cancer 1, early onset protein (BRCA1); and von Hippel-Lindau tumor suppressor protein (VHL) (Marsh and Zori 2002). These targets are located across 4 chromosomes, vary in length from 74 bp to 438 bp, and total 21.6 kbp. Oligonucleotide design, conditions of PCR reactions, sequencing and sequence analysis are described below.

Oligonucleotide Design

Human exon sequence plus 150 bp flanking sequence from the March 2006 assembly was downloaded from the UCSC Genome Browser (www.genome.ucsc.edu). The reference sequences (Refseq) representing the six colon cancer related nucleic acids were: NM_000038 (APC), NM_000546 (TP53), NM_000249 (MLH1), NM_000321 (RB1), NM_007304 (BRCA1), and NM_000551 (VHL).

The convention that exon numbering for each gene begins with zero was maintained throughout the analysis. Primer3 software (http://frodo.wi.mit.edu/) was then used to select primer pairs flanking the exon. The design was constrained to PCR products between 50-500 bp, primer length 20-36 bp, primer melting temperature (Tm)=61-67° C., where the maximum difference in Tm between primer pairs was 5° C., and the GC content of the primer had to be between 10-80%. Four thousand possible primer pairs were generated per exon. Those primer pairs that ended with a T as the 3' base were then selected. Oligonucleotide sequences of the PCR primers are listed in TABLE A. All PCR primer oligonucleotides were synthesized by Sigma-Genosys.

A nucleic acid patch oligonucleotide was then designed by extending into the sequence from the PCR primer until the Tm of the nucleic acid patch oligonucleotide was 62-67° C. The selected oligonucleotides were then aligned against themselves using BLASTN software from the Washington University BLAST Archives WUBLAST (http://blast.wustl.edu) to approximate cross reactivity. For each exon, the oligonucleotide sets with the fewest blastn matches to the entire set were chosen. The PCR primer sequence was substituted with a deoxyuridine in place of every deoxythymidine. The nucleic acid patch oligonucleotides were then concatenated with the complement universal primer sequences to result in the appropriate patch sequence. Sequences of the nucleic acid patch oligonucleotides are listed in TABLE B. All nucleic acid patch oligonucleotides were synthesized by Sigma-Genosys.

Two Universal Primer oligonucleotides were synthesized for the ligation reaction, including the Universal Primer 2, which has a 5' Phosphate and a 3-carbon spacer on the 3' end. The Universal Primer oligonucleotide sequences were then tailed at the 5' end with the sample-specific DNA barcodes and 454 Life Sciences A or B oligonucleotide sequence to result in the Final Universal Primer oligonucleotides for normal samples and colon cancer samples. The Universal Primer oligonucleotides for ligation and the Final Universal primer oligonucleotide sequences for normal and colon cancer samples are listed in TABLE C.

TABLE A

Multiplex PCR

| SEQ ID. NO. | Oligo Name | Sequence |
|---|---|---|
| 1 | 000038_00_PCRleft | TCTTAAGAGTTTTGTTTCCTTTACCCCU |
| 2 | 000038_01_PCRleft | CGTGCTTTGAGAGTGATCTGAATTU |
| 3 | 000038_02_PCRleft | TTGTGGTTAAAATGTAAACCTAATATTTCACU |
| 4 | 000038_03_PCRleft | GGTAGAGAAGTTTGCAATAACAACTGAU |
| 5 | 000038_04_PCRleft | AAATAATTTTCTCATGCACCATGACU |
| 6 | 000038_05_PCRleft | TTAAATGAGAATGATTTGACATAACCCU |
| 7 | 000038_06_PCRleft | AAAAAGCCTTGGGCTAAGAAAGCCU |
| 8 | 000038_07_PCRleft | AATGGTCATACTTTTATGATGTATTTAATTGTTU |
| 9 | 000038_08_PCRleft | GCTTTTGGATATTAAAGTCGTAATTTTGTTU |
| 10 | 000038_09_PCRleft | ATTTGTTGATCCACTAAAATTCCGU |
| 11 | 000038_10_PCRleft | TGATTGTCTTTTTCCTCTTGCCCTU |

TABLE A-continued

Multiplex PCR

| SEQ ID. NO. | Oligo Name | Sequence |
|---|---|---|
| 12 | 000038_11_PCRleft | AAAGCTTGGCTTCAAGTTGTCTTTU |
| 13 | 000038_12_PCRleft | AAAGTGATAGGATTACAGGCGTGAGU |
| 14 | 000038_13_PCRleft | GAAGTTAATGAGAGACAAATTCCAACTCU |
| 15 | 000249_00_PCRleft | CCGTTGAGCATCTAGACGTTTCCU |
| 16 | 000249_01_PCRleft | CCTGTAAGACAAAGGAAAAACACGTTAAU |
| 17 | 000249_02_PCRleft | TGGATTAAATCAAGAAAATGGGAAU |
| 18 | 000249_03_PCRleft | CAGCAGTTCAGATAACCTTTCCCTTU |
| 19 | 000249_04_PCRleft | TGTTGATATGATTTTCTCTTTTCCCCTU |
| 20 | 000249_05_PCRleft | TGGATTCACTATCTTAAGACCTCGCTTU |
| 21 | 000249_06_PCRleft | GGGCTCTGACATCTAGTGTGTGTTU |
| 22 | 000249_07_PCRleft | TCCTTGTGTCTTCTGCTGTTTGTTU |
| 23 | 000249_08_PCRleft | GAGGACCTCAAATGGACCAAGTCU |
| 24 | 000249_09_PCRleft | GGTGATTTCATGACTTTGTGTGAATGU |
| 25 | 000249_10_PCRleft | ATCTTCTGGCCACCACATACACCAU |
| 26 | 000249_11_PCRleft | GCTCCATTTGGGGACCTGTATATCU |
| 27 | 000249_12_PCRleft | GCTCTGTAGAACCAGCACAGAGAAGTU |
| 28 | 000249_13_PCRleft | AGGCTTCTTTGCTTACTTGGTGTCU |
| 29 | 000249_14_PCRleft | TCTCATCCATGTTTCAGGGATTACU |
| 30 | 000249_15_PCRleft | TTGCTCCTTCATGTTCTTGCTTCTU |
| 31 | 000249_16_PCRleft | ATCAAGTAACGTGGTCACCCAGAGU |
| 32 | 000249_17_PCRleft | CAGCAATATTCAGCAGTCCCATTU |
| 33 | 000249_18_PCRleft | ATCAGCCAGGACACCAGTGTATGTU |
| 34 | 000321_00_PCRleft | GAAGTGACGTTTTCCCGCGGU |
| 35 | 000321_01_PCRleft | GATCTTAAAGTATTTAATAATGTTCTTTTTCACAGU |
| 36 | 000321_02_PCRleft | CCATCAGAAGGATGTGTTACAAATATACAGU |
| 37 | 000321_03_PCRleft | AATTCCTTCCAAAGGATATAGTAGTGATTU |
| 38 | 000321_04_PCRleft | TCTTAAAAGAAGATAAATAAAGCATGAGAAAACU |
| 39 | 000321_05_PCRleft | GCACAAAAAGAAACACCCAAAAGAU |
| 40 | 000321_06_PCRleft | CATGCTGATAGTGATTGTTGAATGAAU |
| 41 | 000321_07_PCRleft | GGATGTACAATTGTTCTTATCTAATTTACCACTU |
| 42 | 000321_08_PCRleft | CATGGGGATTGACACCTCTAACU |
| 43 | 000321_09_PCRleft | AAAATTCTTTAATGAAATCTGTGCCTCU |
| 44 | 000321_10_PCRleft | TTATATGATTTTATGAGACAACAGAAGCATU |
| 45 | 000321_11_PCRleft | AACCACAGTCTTATTTGAGGGAATGU |
| 46 | 000321_12_PCRleft | CGACATTGATTTCTGTTTTTACCTCCU |
| 47 | 000321_14_PCRleft | TGAGCCAAGATTGTGCCATU |
| 48 | 000321_15_PCRleft | AATTATCTGTTTCAGGAAGAAGAACGAU |

TABLE A-continued

Multiplex PCR

| SEQ ID. NO. | Oligo Name | Sequence |
|---|---|---|
| 49 | 000321_16_PCRleft | TGGTTTAACCTTTCTACTGTTTTCTTTGTCU |
| 50 | 000321_17_PCRleft | TTCATTCTGACTTTTAAATTGCCACU |
| 51 | 000321_18_PCRleft | TCTGGGTGTACAACCTTGAAGTGTAU |
| 52 | 000321_19_PCRleft | TCTGGGGGAAAGAAAAGAGTGGU |
| 53 | 000321_20_PCRleft | AAAGAAATAACTCTGTAGATTAAACCTTTCTTTU |
| 54 | 000321_21_PCRleft | TTTCCTTTATAATATGTGCTTCTTACCAGU |
| 55 | 000321_22_PCRleft | TCTTCATGCAGAGACTGAAAACAAAU |
| 56 | 000321_23_PCRleft | TTTGGTATTCCTAATAGTTCAGAATGATGU |
| 57 | 000321_24_PCRleft | CTTTGCCTGATTTTTGACACACCU |
| 58 | 000321_25_PCRleft | AATAGCATAAAGTAAGTCATCGAAAGCAU |
| 59 | 000321_26_PCRleft | TGTCAAATACTAGAATGAAGACCACTGCU |
| 60 | 000546_00_PCRleft | GTCTCAGACACTGGCATGGTGU |
| 61 | 000546_01_PCRleft | CATTTTCAGACCTATGGAAACTGTGAGU |
| 62 | 000546_02_PCRleft | ACAACGTTCTGGTAAGGACAAGGGU |
| 63 | 000546_03_PCRleft | AGGTGCTTACGCATGTTTGTTTCTU |
| 64 | 000546_04_PCRleft | AGTCACAGCACATGACGGAGGTU |
| 65 | 000546_05_PCRleft | TGAGCTGAGATCACGCCACU |
| 66 | 000546_06_PCRleft | CTCCAGAAAGGACAAGGGTGGU |
| 67 | 000546_07_PCRleft | TATCACCTTTCCTTGCCTCTTTCCU |
| 68 | 000546_08_PCRleft | TACTTACTTCTCCCCCTCCTCTGTU |
| 69 | 000546_09_PCRleft | CACCATCTTGATTTGAATTCCCGU |
| 70 | 000551_00_PCRleft | CGAGCGCGTTCCATCCTCU |
| 71 | 000551_01_PCRleft | CCCAAAGTGCTGGGATTACAGGU |
| 72 | 000551_02_PCRleft | AAGCCTCTTGTTCGTTCCTTGTACU |
| 73 | 007304_00_PCRleft | GGTTTGTATTATTCTAAAACCTTCCAAATCTU |
| 74 | 007304_01_PCRleft | TTATTGAGCCTCATTTATTTTCTTTTTCU |
| 75 | 007304_02_PCRleft | GCTCTTAAGGGCAGTTGTGAGATTAU |
| 76 | 007304_03_PCRleft | TGCTGAGTGTGTTTCTCAAACAATTU |
| 77 | 007304_04_PCRleft | TCACAGGTAACCTTAATGCATTGTCTU |
| 78 | 007304_05_PCRleft | TCTTCAGGAGGAAAAGCACAGAACU |
| 79 | 007304_06_PCRleft | TTAACTAGCATTGTACCTGCCACAGU |
| 80 | 007304_07_PCRleft | AAAGGAGAGAGCAGCTTTCACTAACU |
| 81 | 007304_08_PCRleft | TGACAATTCAGTTTTTGAGTACCTTGTU |
| 82 | 007304_09_PCRleft | CCAAAGCAAGGAATTTAATCATTTTGU |
| 83 | 007304_10_PCRleft | ATTTTCTTGGTGCCATTTATCGTTU |
| 84 | 007304_11_PCRleft | TCACTATCAGAACAAAGCAGTAAAGTAGATU |
| 85 | 007304_12_PCRleft | TGATCTCTCTGACATGAGCTGTTTCAU |

TABLE A-continued

Multiplex PCR

| SEQ ID. NO. | Oligo Name | Sequence |
|---|---|---|
| 86 | 007304_13_PCRleft | TGTGTAAATTAAACTTCTCCCATTCCTU |
| 87 | 007304_14_PCRleft | GTAGAACGTGCAGGATTGCTACAU |
| 88 | 007304_15_PCRleft | AAATCCAGATTGATCTTGGGAGTGU |
| 89 | 007304_16_PCRleft | AGCCTTATTAAAGGGCTGTGGCTTU |
| 90 | 007304_17_PCRleft | CTAGGATTACAGGGGTGAGCCACU |
| 91 | 007304_18_PCRleft | ATTTTCCTTCTCTCCATTCCCCTGU |
| 92 | 007304_19_PCRleft | CCTTCATCCGGAGAGTGTAGGGU |
| 93 | 007304_20_PCRleft | TCCTACTTTGACACTTTGAATGCTCTU |
| 94 | 007304_21_PCRleft | TTGACACTAATCTCTGCTTGTGTTCTCU |
| 95 | 000038_00_PCRright | AAUGGAUAAACUACAAUUAAAAGUCACAGUCU |
| 96 | 000038_01_PCRright | CACCCAAAUCGAGAGAAGCUGUACU |
| 97 | 000038_02_PCRright | CACAAGGCAAUGUUACUAUAUGAAGAAAAGU |
| 98 | 000038_03_PCRright | AAAGUUCAAAUAAGUUGUACUGCCAAGU |
| 99 | 000038_04_PCRright | UUCGCUGUUUAUCACUUAGAAACAAGU |
| 100 | 000038_05_PCRright | UACCCACAAACAAGAAAGGCAAUUU |
| 101 | 000038_06_PCRright | GACAGCACAUGGUACUGAAUGCUU |
| 102 | 000038_07_PCRright | CCCAAAAUGCUGGGAUACAGGU |
| 103 | 000038_08_PCRright | UUUCUGUUAAAAAUUCACAUUGCUU |
| 104 | 000038_09_PCRright | CAGAGGAAGCAGCUGAUAACAGAAGU |
| 105 | 000038_10_PCRright | GCGAAUGUGAAGCACAGGUUUUAU |
| 106 | 000038_11_PCRright | GGCUGAAGUGGGAGGAUUGCU |
| 107 | 000038_12_PCRright | UGAAUAAUACACAGGUAAGAAAUAGGAAAUCU |
| 108 | 000038_13_PCRright | GCUUAAAACUUCAUGAUAUAUAAAACAUUGCU |
| 109 | 000249_00_PCRright | GCAUGCGCUGUACAUGCCUCU |
| 110 | 000249_01_PCRright | GCCUAGUUCCAGAACAGAGAAAGGU |
| 111 | 000249_02_PCRright | GGAGGAUAUUUACACAUUCUGAAUCUU |
| 112 | 000249_03_PCRright | CACUGGUGUUGAGACAGGAUACUCU |
| 113 | 000249_04_PCRright | GCUUCAACAAUUACUCUCCCAUGU |
| 114 | 000249_05_PCRright | UCUCAGAGACCCACUCCCAGAU |
| 115 | 000249_06_PCRright | GGCUGAGACUGAAACAUCAUAACCUU |
| 116 | 000249_07_PCRright | CAAAUCUGAAGCAUAAAACAAGCCU |
| 117 | 000249_08_PCRright | UUCCAUGGUCCCAUAAAAUCCCU |
| 118 | 000249_09_PCRright | CUGUAAGAAGGGACAGAACAUCCUU |
| 119 | 000249_10_PCRright | AAUAACAGGCAAAAAUCUGGGCUCU |
| 120 | 000249_11_PCRright | GCUGUACUUUCCCAAAAGGCCAU |
| 121 | 000249_12_PCRright | AAACCUGGGCAGUUGAGGCCCUAU |
| 122 | 000249_13_PCRright | GGAUUGAAACCACAUGUGUCUGACU |

TABLE A-continued

Multiplex PCR

| SEQ ID. NO. | Oligo Name | Sequence |
|---|---|---|
| 123 | 000249_14_PCRright | GAAAUUCAGAAGUGAAAAGGAUCUAAACU |
| 124 | 000249_15_PCRright | ACCCCAAGTUAUCUGCCCACCU |
| 125 | 000249_16_PCRright | AAAGGGUGGUCAUUGCCCUUU |
| 126 | 000249_17_PCRright | TUGUAUGAGGUCCUGUCCUAGUCCU |
| 127 | 000249_18_PCRright | UCGGAAUACAGAGAAAGAAGAACACAU |
| 128 | 000321_00_PCRright | ACGGCGGCUCUGCUCGCU |
| 129 | 000321_01_PCRright | TUCAAUUUUGUAUAGUGAUUGAAGTUGTU |
| 130 | 000321_02_PCRright | TUGAGAGGAAAAUCCAGAAUCGTU |
| 131 | 000321_03_PCRright | UGAGCUAACATUAAAAGGGACAAGUCU |
| 132 | 000321_04_PCRright | UCUACACAGGACTUAAAUCUAUGGGCTU |
| 133 | 000321_05_PCRright | GCAGAGAAUGAGGGAGGAGUACAUU |
| 134 | 000321_06_PCRright | AUCAUCCUGUCAGCCUAGAACCAU |
| 135 | 000321_07_PCRright | AAAAACAUGCUCAUAACAAAAGAAGUAAAU |
| 136 | 000321_08_PCRright | GACAATUAUCCUCCCUCCACAGUCU |
| 137 | 000321_09_PCRright | CCUAUAUCUAAAGCAAAUCAAUCAAAUAUACCAU |
| 138 | 000321_10_PCRright | UGAAUACAUAAAGAAACGUGAACAAAUCU |
| 139 | 000321_11_PCRright | UCAAGUUCUUGCCAAGAUAUACAAUAAAUAAU |
| 140 | 000321_12_PCRright | CGAACUGGAAAGAUGCUGCUUUAAU |
| 141 | 000321_14_PCRright | AGCGCACGCCAAUAAAGACAU |
| 142 | 000321_15_PCRright | GCAUCCUUCUCCUAACCUCACACU |
| 143 | 000321_16_PCRright | AGAUGTUAAGAAACACCUCUCACUAACAAU |
| 144 | 000321_17_PCRright | UGCAGUTUGAAUGGUCAACAUAACAU |
| 145 | 000321_18_PCRright | AACAUGAUUGAACCCAGUCAGCCU |
| 146 | 000321_19_PCRright | GAGGAGAGAAGGUGAAGUGCUUGAU |
| 147 | 000321_20_PCRright | UGAAUACCUAUGUAUGUAUGGAUAUGGAUUAU |
| 148 | 000321_21_PCRright | AAGGGCUCGAGGAAUGUGAGGUAU |
| 149 | 000321_22_PCRright | UCAAAAUAAUCCCCCUCUCAUUCUTU |
| 150 | 000321_23_PCRright | UAUGCAAUAUGCCUGGAUGAGGUGU |
| 151 | 000321_24_PCRright | AACTUGGCAUGAAAGAAAUGGUAU |
| 152 | 000321_25_PCRright | AAACAAACCUGCCAACUGAAGAAAU |
| 153 | 000321_26_PCRright | UGUGAGAGACAAUGAAUCCAGAGGU |
| 154 | 000546_00_PCRright | ACAGGUCUCUGCUAGGGGCU |
| 155 | 000546_01_PCRright | GACAGCAUCAAAUCAUCCAUUGCU |
| 156 | 000546_02_PCRright | UCCCAAAGTUCCAAACAAAAGAAAU |
| 157 | 000546_03_PCRright | GCAAAUUCCUUCCACUCGGAU |
| 158 | 000546_04_PCRright | CUCCUCCCAGAGACCCCAGTU |
| 159 | 000546_05_PCRright | GGUCAGAGGCAAGCAGAGGCU |

TABLE A-continued

Multiplex PCR

| SEQ ID. NO. | Oligo Name | Sequence |
|---|---|---|
| 160 | 000546_06_PCRright | GAAUCUGAGGCAUAACUGCACCCU |
| 161 | 000546_07_PCRright | AGCUACAACCAGGAGCCAUGUCUU |
| 162 | 000546_08_PCRright | CAACCUAGGAAGGCAGGGGAGU |
| 163 | 000546_09_PCRright | CGGGACAAAGCAAAUGGAAGU |
| 164 | 000551_00_PCRright | CUUCAGACCGUGCUAUCGUCCCU |
| 165 | 000551_01_PCRright | AAAGAUGGAUAACGUGCCUGACAU |
| 166 | 000551_02_PCRright | GAAACUAAGGAAGGAACCAGUCCUGU |
| 167 | 007304_00_PCRright | CCCAAAUAAUACACUCUGUGCUGACU |
| 168 | 007304_01_PCRright | UGGAGCCACAUAACACAUCAAACU |
| 169 | 007304_02_PCRright | UCUACUUUUCCUACUGUGGUUGCUU |
| 170 | 007304_03_PCRright | AGCACUUGAGUGUCAUUCUUGGGAU |
| 171 | 007304_04_PCRright | GGCUAAGGCAGGAGGACUGCUU |
| 172 | 007304_05_PCRright | UCACCAUAGGGCUCAUAAAAUUCACU |
| 173 | 007304_06_PCRright | GGAAAAUACCAGCUUCAUAGACAAAGGU |
| 174 | 007304_07_PCRright | AACUCUGCCAAGAGAUUUGUGGGU |
| 175 | 007304_08_PCRright | GCUGUAAUGAGCUGGCAUGAGUAUUU |
| 176 | 007304_09_PCRright | UGUGCCAUAAUUCAAAGAGAUGAU |
| 177 | 007304_10_PCRright | AAGGCUCCAUAAUUACCCAUGUGCU |
| 178 | 007304_11_PCRright | CCACAGCAUCUUACAUUGAUGUUCU |
| 179 | 007304_12_PCRright | UGUUUGUCCAAUACAGCAGAUGAAAU |
| 180 | 007304_13_PCRright | UGUUGUUAAGUCUAGUCAUAGGGAGAUACAU |
| 181 | 007304_14_PCRright | CAAAGUGCUGCGAUUACAGGCAU |
| 182 | 007304_15_PCRright | GGUGUAAAAAUGCAAUUCUGAGGUGUU |
| 183 | 007304_16_PCRright | UUUGUGCAUUGUUAAGGAAAGUGGU |
| 184 | 007304_17_PCRright | GGUGGGGUGAGAUUUUUGUCAACUU |
| 185 | 007304_18_PCRright | UCCACUAUGUAAGACAAAGGCUGGU |
| 186 | 007304_19_PCRright | GAGGCUACAGUAGGGGCAUCCAU |
| 187 | 007304_20_PCRright | CAAAAGGACCCCAUAUAGCACAGGU |
| 188 | 007304_21_PCRright | GGGGUCCUGUGGCUCUGUACCU |

TABLE B

Nested Patch

| SEQ ID. NO. | Oligo Name | Sequence |
|---|---|---|
| 189 | 000038_00_PP L | TTAGTGGCTGCTTGTTTTTAAAGAAGATCGGAAGAGCGTCGTGTAGGGAAAGAGTGT |
| 190 | 000038_00_PP R | CAAGCAGAAGACGGCATACGATGATACCTTCATATTAGATGCCTCAGT |
| 191 | 000038_01_PP L | TTTCTTGACATTTAAGTATGCTGAGAAAAGATCGGAAGAGCGTCGTGTAGGGAAAGAGTGT |

TABLE B-continued

Nested Patch

| SEQ ID. NO. | Oligo Name | | Sequence |
|---|---|---|---|
| 192 | 000038_01_PP | R | CAAGCAGAAGACGGCATACGATGGATCTACACACCTAAAGATGACA |
| 193 | 000038_02_PP | L | GCTTTAAGCAGTCTAAAATATTCTTAATGTTATATTATTTTAAGATCGGAAGAGCGTCGTGTAGGGAAAGAGTGT |
| 194 | 000038_02_PP | R | CAAGCAGAAGACGGCATACGATACCTCTCTTTCTCAAGTTCTTCTAAATATC |
| 195 | 000038_03_PP | L | AAGACTGCAGAAGAGCAATACTTACGATCGGAAGAGCGTCGTGTAGGGAAAGAGTGT |
| 196 | 000038_03_PP | R | CAAGCAGAAGACGGCATACGATACTTACATTTTCAGTTAAAGGAAGACTATCT |
| 197 | 000038_04_PP | L | CCAATAAAGAAAATGAATAAGCAAATACGTCGATCGGAAGAGCGTCGTGTAGGGAAAGAGTGT |
| 198 | 000038_04_PP | R | CAAGCAGAAGACGGCATACGAAACTTACCTGTGCTCGTTTTTCCAT |
| 199 | 000038_05_PP | L | TACTATGGCTACCACTTAAAAGCTCGATCGGAAGAGCGTCGTGTAGGGAAAGAGTGT |
| 200 | 000038_05_PP | R | CAAGCAGAAGACGGCATACGAACTAACCTCTGCTTCTGTTGCTTG |
| 201 | 000038_06_PP | L | ACATCAGTACATGCAAAATGGTGTGATCGGAAGAGCGTCGTGTAGGGAAAGAGTGT |
| 202 | 000038_06_PP | R | CAAGCAGAAGACGGCATACGACTGGAAATATGCATTCAGGACTAAGA |
| 203 | 000038_07_PP | L | ACTCCAAATGAAGTGTCTGTATGATGATCGGAAGAGCGTCGTGTAGGGAAAGAGTGT |
| 204 | 000038_07_PP | R | CAAGCAGAAGACGGCATACGAGTGAGCCACTGCACCTGG |
| 205 | 000038_08_PP | L | CACCTGTGGGCCAAATGAGTTTAGGATCGGAAGAGCGTCGTGTAGGGAAAGAGTGT |
| 206 | 000038_08_PP | R | CAAGCAGAAGACGGCATACGATGAAACATGCACTACGATGTACACT |
| 207 | 000038_09_PP | L | GCAGGGATCACTAATATAACCCTAATTCGATCGGAAGAGCGTCGTGTAGGGAAAGAGTGT |
| 208 | 000038_09_PP | R | CAAGCAGAAGACGGCATACGATGGTGGCCTTATATCCTAATTCATC |
| 209 | 000038_10_PP | L | TGGCCTGTAGTCCCCCTAATTTAAAGATCGGAAGAGCGTCGTGTAGGGAAAGAGTGT |
| 210 | 000038_10_PP | R | CAAGCAGAAGACGGCATACGACAGTCATTGTTTAATGAGGAGAGTGA |
| 211 | 000038_11_PP | L | GCCTGTAAATTAAATACAGAATAGAGGATCATTAGATCGGAAGAGCGTCGTGTAGGGAAAGAGTGT |
| 212 | 000038_11_PP | R | CAAGCAGAAGACGGCATACGATGAACCCTGGAGGCAGAGG |
| 213 | 000038_12_PP | L | GAAATTCTGGCTAGCCGTGGTGGATCGGAAGAGCGTCGTGTAGGGAAAGAGTGT |
| 214 | 000038_12_PP | R | CAAGCAGAAGACGGCATACGACATGGCTAAAAGAAGGCAGCAAAAA |
| 215 | 000038_13_PP | L | AGTAAGAAACAGAATATGGGTCATCTAATTGATCGGAAGAGCGTCGTGTAGGGAAAGAGTGT |
| 216 | 000038_13_PP | R | CAAGCAGAAGACGGCATACGATACAATTAGGTCTTTTTGAGAGTATGAATTC |
| 217 | 000249_00_PP | L | TGGCGCCAGAAGAGCCAGATCGGAAGAGCGTCGTGTAGGGAAAGAGTGT |
| 218 | 000249_00_PP | R | CAAGCAGAAGACGGCATACGAGCCCGGGCAAAGAGGC |
| 219 | 000249_01_PP | L | CTCCAAATACAAACAATAGTGCCTCGATCGGAAGAGCGTCGTGTAGGGAAAGAGTGT |
| 220 | 000249_01_PP | R | CAAGCAGAAGACGGCATACGACCTGACTCTTCCATGAAGCGC |
| 221 | 000249_02_PP | L | ATGTTACTCATTTTTCCAAATCTCTTTGAGATCGGAAGAGCGTCGTGTAGGGAAAGAGTGT |
| 222 | 000249_02_PP | R | CAAGCAGAAGACGGCATACGAAGCTTACCTCACCTCGAAAGCC |
| 223 | 000249_03_PP | L | TCACCCACTGTCACCTCACCGATCGGAAGAGCGTCGTGTAGGGAAAGAGTGT |
| 224 | 000249_03_PP | R | CAAGCAGAAGACGGCATACGAGAGACCTAGGCAAAAAATACATTTCAG |
| 225 | 000249_04_PP | L | ATCCAGTAGAGAGATAGATACTAATCCCGATCGGAAGAGCGTCGTGTAGGGAAAGAGTGT |
| 226 | 000249_04_PP | R | CAAGCAGAAGACGGCATACGAACCATTCTTACCGTGATCTGGGTC |
| 227 | 000249_05_PP | L | AAATAAAACCCAAGATGTCCTGGCAGATCGGAAGAGCGTCGTGTAGGGAAAGAGTGT |
| 228 | 000249_05_PP | R | CAAGCAGAAGACGGCATACGATTTGGACTGTACCTGCCAACAACT |

TABLE B-continued

Nested Patch

| SEQ ID. NO. | Oligo Name | | Sequence |
|---|---|---|---|
| 229 | 000249_06_PP | L | CAAAAGAGTAAGAAAAGAGTTGCCAAGATCGGAAGAGCGTCGTGTAGGGAAAGAGTGT |
| 230 | 000249_06_PP | R | CAAGCAGAAGACGGCATACGAATCTCCACCAGCAAACTATTAAAAATC |
| 231 | 000249_07_PP | L | CAGCTACTGTCTCTCCTTGCTGATGATCGGAAGAGCGTCGTGTAGGGAAAGAGTGT |
| 232 | 000249_07_PP | R | CAAGCAGAAGACGGCATACGAGTGTATTTGACTAAAGCAAACTCTTAACA |
| 233 | 000249_08_PP | L | TTTGTGAAATGAGGGCCCCGAGATCGGAAGAGCGTCGTGTAGGGAAAGAGTGT |
| 234 | 000249_08_PP | R | CAAGCAGAAGACGGCATACGAGTGGGTGTTTCCTGTGAGTGGAT |
| 235 | 000249_09_PP | L | GGGGTGAGGTCACAGGTGTGATCGGAAGAGCGTCGTGTAGGGAAAGAGTGT |
| 236 | 000249_09_PP | R | CAAGCAGAAGACGGCATACGATTGCCAGTGGTGTATGGGATTCA |
| 237 | 000249_10_PP | L | AGGGGGAGAAAAAGCCCACATGATCGGAAGAGCGTCGTGTAGGGAAAGAGTGT |
| 238 | 000249_10_PP | R | CAAGCAGAAGACGGCATACGACACGTCTGGCCGGGC |
| 239 | 000249_11_PP | L | AGTGGAGAGACTCAGAATAAGAAGTATGATCGGAAGAGCGTCGTGTAGGGAAAGAGTGT |
| 240 | 000249_11_PP | R | CAAGCAGAAGACGGCATACGAACCTGGGGTTGCTGGAAGTAGG |
| 241 | 000249_12_PP | L | GTTGCATTTTGGAGGAGCAAGCGATCGGAAGAGCGTCGTGTAGGGAAAGAGTGT |
| 242 | 000249_12_PP | R | CAAGCAGAAGACGGCATACGAGCATCCCAGGCAGGCC |
| 243 | 000249_13_PP | L | AAGCACCAGGCACCAGAACTAGGATCGGAAGAGCGTCGTGTAGGGAAAGAGTGT |
| 244 | 000249_13_PP | R | CAAGCAGAAGACGGCATACGACCAAAGCCTGTGCCCTCC |
| 245 | 000249_14_PP | L | AACCAGTTGGGACAAAATGGAGAGATCGGAAGAGCGTCGTGTAGGGAAAGAGTGT |
| 246 | 000249_14_PP | R | CAAGCAGAAGACGGCATACGATACCGATAACCTGAGAACACCAAAA |
| 247 | 000249_15_PP | L | CGGTGCTGGCTCCTAGGGATCGGAAGAGCGTCGTGTAGGGAAAGAGTGT |
| 248 | 000249_15_PP | R | CAAGCAGAAGACGGCATACGACAGCCTCCCAAAGTGCTGG |
| 249 | 000249_16_PP | L | GCCTTGTGCTCCTATCTGCCGATCGGAAGAGCGTCGTGTAGGGAAAGAGTGT |
| 250 | 000249_16_PP | R | CAAGCAGAAGACGGCATACGACCCTCCAGCACACATGCATG |
| 251 | 000249_17_PP | L | TGTGATACTTTAGGCGTTAAAACTGTGATCGGAAGAGCGTCGTGTAGGGAAAGAGTGT |
| 252 | 000249_17_PP | R | CAAGCAGAAGACGGCATACGAGGGGTGCCAGTGTGCATC |
| 253 | 000249_18_PP | L | GCCTCCCTGTTTGCATCCCGATCGGAAGAGCGTCGTGTAGGGAAAGAGTGT |
| 254 | 000249_18_PP | R | CAAGCAGAAGACGGCATACGACCCACAGTGCATAAATAACCATATTT |
| 255 | 000321_00_PP | L | AACTGAGCGCCGCGTCCAGATCGGAAGAGCGTCGTGTAGGGAAAGAGTGT |
| 256 | 000321_00_PP | R | CAAGCAGAAGACGGCATACGACACCTGACGAGAGGCAGGTC |
| 257 | 000321_01_PP | L | TGTTTCAATAGTTTGCACATAACACTGATCGGAAGAGCGTCGTGTAGGGAAAGAGTGT |
| 258 | 000321_01_PP | R | CAAGCAGAAGACGGCATACGATTTAAAATGAGAAAAAAAAATTTCAAAACGTTTTAAG |
| 259 | 000321_02_PP | L | TTTCTTATTCAGCATACAAAATAAATGTTTGTAATGATCGGAAGAGCGTCGTGTAGGGAAAGAGTGT |
| 260 | 000321_02_PP | R | CAAGCAGAAGACGGCATACGATCCTTTTATGGCAGAGGCTTATATT |
| 261 | 000321_03_PP | L | TTCAATTCAAAAGATTATCAGCTCTACATCGATCGGAAGAGCGTCGTGTAGGGAAAGAGTGT |
| 262 | 000321_03_PP | R | CAAGCAGAAGACGGCATACGAAAGAATTAATACTTACTAACTTTACTAAATGTGTTAAATAATT |
| 263 | 000321_04_PP | L | TTTTTAACATTTTTTCGTAATTTAGAAGTCATAGTGATCGGAAGAGCGTCGTGTAGGGAAAGAGTGT |
| 264 | 000321_04_PP | R | CAAGCAGAAGACGGCATACGAAATTTATGAAGTAGCCTGCTATAATCGA |
| 265 | 000321_05_PP | L | TGTATCACTGAAAGAAAGTTTTCCAGATATGATCGGAAGAGCGTCGTGTAGGGAAAGAGTGT |

TABLE B-continued

Nested Patch

| SEQ ID. NO. | Oligo Name | Sequence |
|---|---|---|
| 266 | 000321_05_PP R | CAAGCAGAAGACGGCATACGAACTCAATAAAAATTGGGGAATTTAGTCC |
| 267 | 000321_06_PP L | CGCAGGGTAGAGTATATCCATAAATTTGATCGGAAGAGCGTCGTGTAGGGAAAGAGTGT |
| 268 | 000321_06_PP R | CAAGCAGAAGACGGCATACGAGTTTGGTACCCACTAGACATTCAAT |
| 269 | 000321_07_PP L | ATGGGTATAACAGCTGTTTCTGTAAGATCGGAAGAGCGTCGTGTAGGGAAAGAGTGT |
| 270 | 000321_07_PP R | CAAGCAGAAGACGGCATACGAATTGTTAGGGAGAACTTACATCTAAATCT |
| 271 | 000321_08_PP L | CTTGACTCTTGAACAATGCAGGGTAGATCGGAAGAGCGTCGTGTAGGGAAAGAGTGT |
| 272 | 000321_08_PP R | CAAGCAGAAGACGGCATACGACAAAACATTAATATTTTATTAAATTTCCTTTCAGATTACC |
| 273 | 000321_09_PP L | CATGTCATTACATCTCTCAGCACACGATCGGAAGAGCGTCGTGTAGGGAAAGAGTGT |
| 274 | 000321_09_PP R | CAAGCAGAAGACGGCATACGAGTGCAATACCTGTCTATAGAATCAGT |
| 275 | 000321_10_PP L | TGCTTTATGCATCAAAAAAGCAGTATGATCGGAAGAGCGTCGTGTAGGGAAAGAGTGT |
| 276 | 000321_10_PP R | CAAGCAGAAGACGGCATACGAGAAACACTATAAAGCCATGAATAACAAAATT |
| 277 | 000321_11_PP L | CACTGCCTCCCACTTGTCTCTGATCGGAAGAGCGTCGTGTAGGGAAAGAGTGT |
| 278 | 000321_11_PP R | CAAGCAGAAGACGGCATACGAGTTTCATATATGGCTTACGTTAAAATAGGA |
| 279 | 000321_12_PP L | TTTTGGATTCACTGTGCAGTTCTTTGATCGGAAGAGCGTCGTGTAGGGAAAGAGTGT |
| 280 | 000321_12_PP R | CAAGCAGAAGACGGCATACGAATTATTACTCTATAGTACCACGAATTACAATGA |
| 281 | 000321_14_PP L | TTGCCAGGCTGGGGTGAGATCGGAAGAGCGTCGTGTAGGGAAAGAGTGT |
| 282 | 000321_14_PP R | CAAGCAGAAGACGGCATACGAATGAAAATGTTGTCATTCAGAAGTTTGC |
| 283 | 000321_15_PP L | ACTAAAAGTAAAAAATTTACCTAAAATTTTGAATGGATAGATCGGAAGAGCGTCGTGTAGGGAAAGAGTGT |
| 284 | 000321_15_PP R | CAAGCAGAAGACGGCATACGAATCCCTCTCCCCCGACCA |
| 285 | 000321_16_PP L | TGAGCTAGGTATTTTTTTGGAAGTTATTATCGATCGGAAGAGCGTCGTGTAGGGAAAGAGTGT |
| 286 | 000321_16_PP R | CAAGCAGAAGACGGCATACGAAATTTGTTAGCCATATGCACATGAA |
| 287 | 000321_17_PP L | AGTACTATGAATTTTAGGCACAATTGACGATCGGAAGAGCGTCGTGTAGGGAAAGAGTGT |
| 288 | 000321_17_PP R | CAAGCAGAAGACGGCATACGAATATTTGCTTACATATCTGCTGCAG |
| 289 | 000321_18_PP L | CAAGTTGGCTAAGAATCACAGATTATACGATCGGAAGAGCGTCGTGTAGGGAAAGAGTGT |
| 290 | 000321_18_PP R | CAAGCAGAAGACGGCATACGAAGTTTCAGAGTCCATGCTCTTGAAA |
| 291 | 000321_19_PP L | GTAGCATTTTAACAGAAACCTCTTTTCTGATCGGAAGAGCGTCGTGTAGGGAAAGAGTGT |
| 292 | 000321_19_PP R | CAAGCAGAAGACGGCATACGATTTCTTACTTGGTCCAAATGCCTGT |
| 293 | 000321_20_PP L | AATACCATTTTCTTTCTTTTAGCCTCAAGATCGGAAGAGCGTCGTGTAGGGAAAGAGTGT |
| 294 | 000321_20_PP R | CAAGCAGAAGACGGCATACGACAAAAAAACTTACTATGGAAAATTACCTACCT |
| 295 | 000321_21_PP L | ACCTTTAGATTTTCTTTTCTAATAGTTTATAATACTTTTTGGATCGGAAGAGCGTCGTGTAGGGAAAGAGTGT |
| 296 | 000321_21_PP R | CAAGCAGAAGACGGCATACGATGGTGACAAGGTAGGGGGC |
| 297 | 000321_22_PP L | CCTGGTGGAAGCATACTGCAAAATGATCGGAAGAGCGTCGTGTAGGGAAAGAGTGT |
| 298 | 000321_22_PP R | CAAGCAGAAGACGGCATACGAACTACTTCCCTAAAGAGAAAACACAC |
| 299 | 000321_23_PP L | ACAATTTTGCAGAGATGAGCATAAATGATCGGAAGAGCGTCGTGTAGGGAAAGAGTGT |
| 300 | 000321_23_PP R | CAAGCAGAAGACGGCATACGATTGAATAACTGCATTTGGAAATTCAAATTAT |
| 301 | 000321_24_PP L | CATAGTTAGCAACCTCAAGTTATAGTTTGGATCGGAAGAGCGTCGTGTAGGGAAAGAGTGT |
| 302 | 000321_24_PP R | CAAGCAGAAGACGGCATACGAAAGCCAGGAGCAGTGCTGA |

TABLE B-continued

Nested Patch

| SEQ ID. NO. | Oligo Name | Sequence |
|---|---|---|
| 303 | 000321_25_PP L | TGGAAAACTCAAATTTCCAGTAACTATGGATCGGAAGAGCGTCGTGTAGGGAAAGAGTGT |
| 304 | 000321_25_PP R | CAAGCAGAAGACGGCATACGATATACATTCTTTTATATAACGAAAAGACTTCTTGC |
| 305 | 000321_26_PP L | GCGCTCAGGACCTTGCAAAGATCGGAAGAGCGTCGTGTAGGGAAAGAGTGT |
| 306 | 000321_26_PP R | CAAGCAGAAGACGGCATACGAGTACACAGTGTCCACCAAGGTC |
| 307 | 000546_00_PP L | GGAACCCCCTCCCCCAGATCGGAAGAGCGTCGTGTAGGGAAAGAGTGT |
| 308 | 000546_00_PP R | CAAGCAGAAGACGGCATACGAGGGGTTGGGGTGGGG |
| 309 | 000546_01_PP L | CCTGCCCTTCCAATGGATCCGATCGGAAGAGCGTCGTGTAGGGAAAGAGTGT |
| 310 | 000546_01_PP R | CAAGCAGAAGACGGCATACGATGGGACGGCAAGGGGG |
| 311 | 000546_02_PP L | CCAGGTCCCCAGCCCAGATCGGAAGAGCGTCGTGTAGGGAAAGAGTGT |
| 312 | 000546_02_PP R | CAAGCAGAAGACGGCATACGAGCAGGGGATACGGCCA |
| 313 | 000546_03_PP L | CAACTGGAAGACGGCAGCAGATCGGAAGAGCGTCGTGTAGGGAAAGAGTGT |
| 314 | 000546_03_PP R | CAAGCAGAAGACGGCATACGAAAGATGCTGAGGAGGGCC |
| 315 | 000546_04_PP L | GGGGCAGCGCCTCACGATCGGAAGAGCGTCGTGTAGGGAAAGAGTGT |
| 316 | 000546_04_PP R | CAAGCAGAAGACGGCATACGAGCAAACCAGACCTCAGGCG |
| 317 | 000546_05_PP L | GCCCAGGCTGGAGTGCGATCGGAAGAGCGTCGTGTAGGGAAAGAGTGT |
| 318 | 000546_05_PP R | CAAGCAGAAGACGGCATACGAGGGGCACAGCAGGCC |
| 319 | 000546_06_PP L | ACCAGGCTCCATCTACTCCCAGATCGGAAGAGCGTCGTGTAGGGAAAGAGTGT |
| 320 | 000546_06_PP R | CAAGCAGAAGACGGCATACGATGGTCTCCTCCACCGCTTC |
| 321 | 000546_07_PP L | GGTGTTGTTGGGCAGTGCTGATCGGAAGAGCGTCGTGTAGGGAAAGAGTGT |
| 322 | 000546_07_PP R | CAAGCAGAAGACGGCATACGATGAGGCATCACTGCCCCC |
| 323 | 000546_08_PP L | GCCCACGGATCTGCAGCGATCGGAAGAGCGTCGTGTAGGGAAAGAGTGT |
| 324 | 000546_08_PP R | CAAGCAGAAGACGGCATACGAAGGGCCAGGAAGGGGC |
| 325 | 000546_09_PP L | GGGCCTAAGGCTGGGACAGATCGGAAGAGCGTCGTGTAGGGAAAGAGTGT |
| 326 | 000546_09_PP R | CAAGCAGAAGACGGCATACGACCTGGGTGCTTCTGACGC |
| 327 | 000551_00_PP L | TCTTCGCGCGCTCGGTGATCGGAAGAGCGTCGTGTAGGGAAAGAGTGT |
| 328 | 000551_00_PP R | CAAGCAGAAGACGGCATACGAGCTGGGTCGGGCCTAAG |
| 329 | 000551_01_PP L | GGCACGGTGGCCCACGATCGGAAGAGCGTCGTGTAGGGAAAGAGTGT |
| 330 | 000551_01_PP R | CAAGCAGAAGACGGCATACGACAGGCAAAAATTGAGAACTGGGCTT |
| 331 | 000551_02_PP L | CTCAGTGGCAGACTAGGGTCTCGATCGGAAGAGCGTCGTGTAGGGAAAGAGTGT |
| 332 | 000551_02_PP R | CAAGCAGAAGACGGCATACGAATCTAGATCAAGACTCATCAGTACCA |
| 333 | 007304_00_PP L | ATGACAACTTCATTTTATCATTTTAAAATAAAGTAAATTTGATCGGAAGAGCGTCGTGTAGGGAAAGAGTGT |
| 334 | 007304_00_PP R | CAAGCAGAAGACGGCATACGATACCAGATGGGACACTCTAAGATTT |
| 335 | 007304_01_PP L | CTAGCAGGGTAGGGGGGGATCGGAAGAGCGTCGTGTAGGGAAAGAGTGT |
| 336 | 007304_01_PP R | CAAGCAGAAGACGGCATACGATACTTGCAAAATATGTGGTCACACT |
| 337 | 007304_02_PP L | TCAAAAGGCAAATAGCCATGAAAAGGATCGGAAGAGCGTCGTGTAGGGAAAGAGTGT |
| 338 | 007304_02_PP R | CAAGCAGAAGACGGCATACGACCAACCTAGCATCATTACCAAATTATATAC |
| 339 | 007304_03_PP L | TACTTTCTTGTAGGCTCCTGAAATTGATCGGAAGAGCGTCGTGTAGGGAAAGAGTGT |

TABLE B-continued

Nested Patch

| SEQ ID. NO. | Oligo Name | Sequence |
|---|---|---|
| 340 | 007304_03_PP R | CAAGCAGAAGACGGCATACGAATTCAACACTTACACTCCAAACCTG |
| 341 | 007304_04_PP L | CCCTATGTATGCTCTTTGTTGTGTTGATCGGAAGAGCGTCGTGTAGGGAAAGAGTGT |
| 342 | 007304_04_PP R | CAAGCAGAAGACGGCATACGACTAGCCTGGGCCACAGAG |
| 343 | 007304_05_PP L | AAGAACAGTCAAGCAATTGTTGGCCGATCGGAAGAGCGTCGTGTAGGGAAAGAGTGT |
| 344 | 007304_05_PP R | CAAGCAGAAGACGGCATACGATCCCAAAGCTGCCTACCACAAATA |
| 345 | 007304_06_PP L | AGATATTCAACTAGAAATATTTACTGAGCATCTGATCGGAAGAGCGTCGTGTAGGGAAAGAGTGT |
| 346 | 007304_06_PP R | CAAGCAGAAGACGGCATACGATCTCTTTGACTCACCTGCAATAAGT |
| 347 | 007304_07_PP L | GATTACAGAAAGCTGACCAATCTTATTTGATCGGAAGAGCGTCGTGTAGGGAAAGAGTGT |
| 348 | 007304_07_PP R | CAAGCAGAAGACGGCATACGATGTAAAGGTCCCAAATGGTCTTCAG |
| 349 | 007304_08_PP L | TCACAAGCAGCTGAAAATATACAAAAATGATCGGAAGAGCGTCGTGTAGGGAAAGAGTGT |
| 350 | 007304_08_PP R | CAAGCAGAAGACGGCATACGAGTGCCACATGGCTCCACATG |
| 351 | 007304_09_PP L | AGGACTGGATTTACTTTCATGTCACGATCGGAAGAGCGTCGTGTAGGGAAAGAGTGT |
| 352 | 007304_09_PP R | CAAGCAGAAGACGGCATACGAGTCAGCAAACCTAAGAATGTGGGAT |
| 353 | 007304_10_PP L | TTGCATGGTATCCCTCTGCTTCAAGATCGGAAGAGCGTCGTGTAGGGAAAGAGTGT |
| 354 | 007304_10_PP R | CAAGCAGAAGACGGCATACGAGAGCAAGGATCATAAAATGTTGGAG |
| 355 | 007304_11_PP L | ACTGCTTTAAATGGAATGAGAAAACAGATCGGAAGAGCGTCGTGTAGGGAAAGAGTGT |
| 356 | 007304_11_PP R | CAAGCAGAAGACGGCATACGATACCTTTCCACTCCTGGTTCTTTAT |
| 357 | 007304_12_PP L | GCTGGGCAGCCAAAGCATAAGATCGGAAGAGCGTCGTGTAGGGAAAGAGTGT |
| 358 | 007304_12_PP R | CAAGCAGAAGACGGCATACGAATTACCTAGATCTTGCCTTGGCAAG |
| 359 | 007304_13_PP L | CAGGTAAGGGGTTCCCTCTGAGATCGGAAGAGCGTCGTGTAGGGAAAGAGTGT |
| 360 | 007304_13_PP R | CAAGCAGAAGACGGCATACGAATGGATACACTCACAAATTCTTCTGG |
| 361 | 007304_14_PP L | ATTCCACCATGGCATATGTTTACCTGATCGGAAGAGCGTCGTGTAGGGAAAGAGTGT |
| 362 | 007304_14_PP R | CAAGCAGAAGACGGCATACGAGCGCCACCGTGCCTC |
| 363 | 007304_15_PP L | AGAAGCTAAAGAGCCTCAGTTTTTTGATCGGAAGAGCGTCGTGTAGGGAAAGAGTGT |
| 364 | 007304_15_PP R | CAAGCAGAAGACGGCATACGAAAAGGGAGGAGGGGAGAAATAGTAT |
| 365 | 007304_16_PP L | CAGAGGAGAGGTCCTTCCCTCTGATCGGAAGAGCGTCGTGTAGGGAAAGAGTGT |
| 366 | 007304_16_PP R | CAAGCAGAAGACGGCATACGAGCATTGATGGAAGGAAGCAAATACA |
| 367 | 007304_17_PP L | CATTCAGGCCAGGCGCGATCGGAAGAGCGTCGTGTAGGGAAAGAGTGT |
| 368 | 007304_17_PP R | CAAGCAGAAGACGGCATACGAGAGGGAGGGAGCTTTACCTTTCTG |
| 369 | 007304_18_PP L | TGGAAGAAGAGAGGAAGAGAGAGGGGATCGGAAGAGCGTCGTGTAGGGAAAGAGTGT |
| 370 | 007304_18_PP R | CAAGCAGAAGACGGCATACGAGCTGGAACTCTGGGGTTCTCC |
| 371 | 007304_19_PP L | GCATACTTAACCCAGGCCCTCTGATCGGAAGAGCGTCGTGTAGGGAAAGAGTGT |
| 372 | 007304_19_PP R | CAAGCAGAAGACGGCATACGAAGGGACTGACAGGTGCCAG |
| 373 | 007304_20_PP L | CCTGGATCCCCAGGAAGGAGATCGGAAGAGCGTCGTGTAGGGAAAGAGTGT |
| 374 | 007304_20_PP R | CAAGCAGAAGACGGCATACGAACATGCAGGCACCTTACCATG |
| 375 | 007304_21_PP L | CATCTGCCCAATTGCTGGAGACGATCGGAAGAGCGTCGTGTAGGGAAAGAGTGT |
| 376 | 007304_21_PP R | CAAGCAGAAGACGGCATACGAGTGGCTGGCTGCAGTCAG |

TABLE C

| SEQ ID. NO. | Oligo Name | Sequence |
|---|---|---|
| 377 | Upstream Universal Primer For Ligation | ACACTCTTTCCCTACACGACGCTCTTCCGATC |
| 378 | Downstream Universal Primer For Ligation | 5' Phosphate TCGTATGCCGTCTTCTGCTTG 3' |
| 379 | Final Universal PCR Barcode Forward Primer for Normal Sample | GCCTCCCTCGCGCCATCAGCTACACGACGCTCTTCCGATC |
| 380 | Final Universal PCR Barcode Reverse Primer for Normal Sample | GCCTTGCCAGCCCGCTCAGCAAGCAGAAGACGGCATACGA |
| 381 | Final Universal PCR Barcode Forward Primer for Colon Cancer Sample | GCCTCCCTCGCGCCATCAGGTCACACTACACGACGCTCTTCCGATC |
| 382 | Final Universal PCR Barcode Reverse Primer for Colon Cancer Sample | GCCTTGCCAGCCCGCTCAGCAGTCACAAGCAGAAGACGGCATACGA |

Nucleic Acid Patch PCR

Genomic DNA from a moderately differentiated colon adenocarcinoma primary tumor and adjacent normal tissue from an 81-year-old male (Biochain catalog # D8235090-PP-10) was used as template for the first PCR. Targets were amplified in a reaction containing 1 µg human genomic DNA, 50 nM each of 94 Forward PCR primers, 50 nM each of 94 Reverse PCR primers, 5 units of AmpliTaq Polymerase Stoffel Fragment (Applied Biosystems), 200 µM each dNTP, 2 mM $MgCl_2$, 20 mM Tris-HCl pH 8.4 and 50 mM KCl in a total volume of 10 µl. This reaction was incubated at 94° C. for 2 min followed by (94° C. for 30 sec, 56° C. for 30 sec, 72° C. for 6 min)×10 cycles, and then held at 4° C.

To prepare for the next round of oligonucleotide hybridization, the uracil-containing primers from the first reaction were cleaved from the amplicons by the addition of 1 unit heat labile Uracil-DNA Glycosylase (USB), 10 units of Endonuclease VIII (NEB), and 10 units of Exonulcease I (USB). This mix was incubated at 37° C. for 2 hours followed by heat inactivation at 95° C. for 20 minutes, and held at 4° C. To remove the unincorporated nucleotide from the mix, 0.05 U Apyrase (NEB) was added to the reaction and incubated at 30° C. for 30 minutes.

Nucleic acid patch-driven ligation of the universal primers to correct amplicons is performed by addition of more reactants to the initial tube to result in the following final concentrations: 20 nM each nucleic acid patch oligonucleotide, 40 nM Universal Primer 1, 40 nM Universal Primer 2 with 5' phosphate and 3' three carbon spacer, 5 U Ampligase (Epicentre), and 1× Ampligase Reaction Buffer (Epicentre) in a total volume of 25 µl. This reaction was incubated at 95° C. for 15 min followed by (94° C. for 30 sec, 65° C. for 2 min, 55° C. for 1 min, 60° C. for 5 min) for 100 cycles, and held at 4° C.

Incorrect products, template genomic DNA and excess primer were degraded by the addition of 10 U Exonuclease I (USB) and 200 U Exonuclease III (Epicentre). This mix was incubated at 37° C. for 2 hours followed by heat inactivation at 95° C. for 20 minutes, and held at 4° C. Each selection reaction was purified using a Qiaquick Spin Column (Qiagen) and the final elution was performed with 30 µl elution buffer (EB).

For the final PCR using the universal primers, reagents were added to the elution to result in these final concentrations in 50 µl: 0.5 µM each Tailed Universal Primer (see below), 10 U Platinum Taq Polymerase (Invitrogen) 0.5 mM each dNTP, 2 mM $MgCl_2$, 0.5 M Betaine to improve the amplification of GC-rich sequences, 20 mM Tris-HCl pH 8.4 and 50 mM KCl. This reaction was incubated at 93° C. for 2 min followed by (93° C. for 30 sec, 60° C. for 6 min) for 27 cycles, and held at 4° C. The universal PCR used the Final Universal PCR primers tailed with 454 Life Sciences A or B oligonucleotide at the 5' end, followed by a sample-specific 6 bp sequence and ending at the 3' end with the same universal primer sequence ligated to the amplicons in the nucleic acid patch PCR procedure. The PCR product smear between the expected sizes was confirmed by running on a 3% Metaphor Agarose gel (Lonza). The reactions were then purified on a Qiaquick Spin Column (Qiagen). The eluted DNA was quantified on a Nanodrop spectrophotometer (ThermoFisher Scientific Inc.), and the same quantity of DNA was pooled together from the two separate samples. This pooled sample was sequenced using the 454 sequencing system on the 454 Life Sciences/Roche FLX machine.

Sequence Analysis

To determine which sequences matched the intended targets, the reads were aligned against a database of reference target sequences for each target using the BLASTN software at the Washington university in St. Louis BLAST archives (http://blast.wustl.edu). The number of reads that matched significantly to each exon was determined ($p<0.02$). The first six bases of sequence from each read, the sample specific DNA barcode, was used to determine whether the sequence came from the tumor sample or the normal sample. The number of reads that did not match targeted sequence was determined, and those sequences were aligned to a database of nucleic acid patch oligonucleotide sequence to identify what fraction was due to primer artifacts. For each exon, CLUSTALW was used to generate a multiple sequence alignment of all of the reads against the reference sequence (Larkin, Blackshields, Brown, Chenna, McGettigan, McWilliam, Valentin, Wallace, Wilm, Lopez et al. 2007). The majority of the differences from the reference sequence were insertion or deletion mutations (indels) adjacent to stretches of identical nucleotides (homopolymers), which is a known error-prone feature for 454 sequencing (Ronaghi, Uhlen and Nyren 1998). To filter these out, all the positions that did not match the reference sequence but were in greater than 30% of the reads were examined.

Results

Oligonucleotides were designed for 94 of the 96 exons from the six nucleotide sequences encoding colon-cancer related proteins. Attempts to design oligonucleotides to two of the 96 exons failed; the last exon of APC failed because of length (~6000 bp) and an exon in RB1 failed due to the presence of Alu repeat elements surrounding the exon.

55,068 sequencing reads were obtained. At least one read from each sample was mapped to 90 of the 94 exons (95.7%). The 4 exons that failed to amplify were due to imperfect primer/patch design. Two of the loci could not be amplified in separate individual PCR reactions, indicating PCR primer failure. The other 2 loci failed because their patch oligonucleotides bound to multiple locations in the genome. This problem could be avoided by more careful primer design. Ninety percent of all reads (49553 reads) mapped to one of the targeted exons. Thus, a 125,000-fold enrichment was achieved with nucleic acid patch PCR from genomic DNA (90% specificity×total possible fold enrichment). When selecting a fraction of the genome this small, the total possible enrichment is 138,888 fold ($3 \times 10^9$ bp genome/21.6 kbp targeted). Of the remaining 10% of reads that did not match the targeted regions, most (85%) appear to be due to concatamers of nucleic acid patch oligonucleotides that contain Alu elements. It is likely that designing oligonucleotides that do not overlap repetitive genomic elements could reduce this background.

These results demonstrate that nucleic acid patch PCR can be performed on multiple samples in parallel, which can then be labeled with sample-specific DNA barcodes and sequenced as a pool. The choice of targets and target boundaries is flexible, and a wide range of sizes can be amplified simultaneously (here, 74 bp to 438 bp). Nucleic acid patch PCR is robust and sensitive, as this method was able to amplify 90 of the 94 targeted exons.

Example 3: Uniformity of Nucleic Acid Patch PCR Per Exon in Each Sample

Figure 3A:
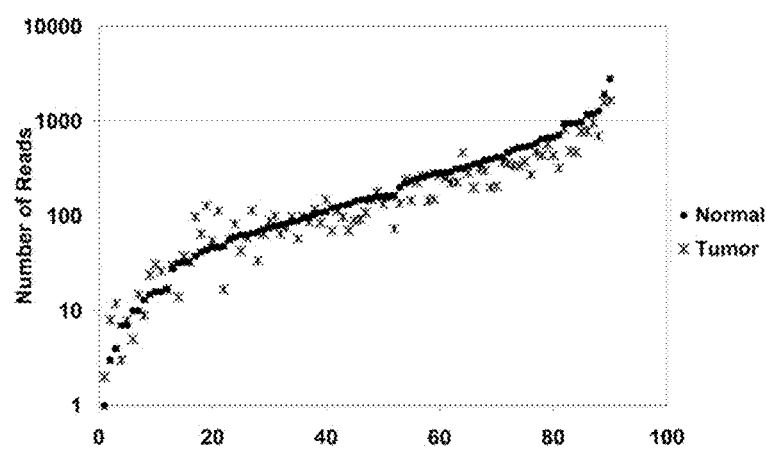
FIG. 3A-C shows the quantification of the abundance and reproducibility of nucleic acid patch PCR per exon in each sample.
Figure 3:
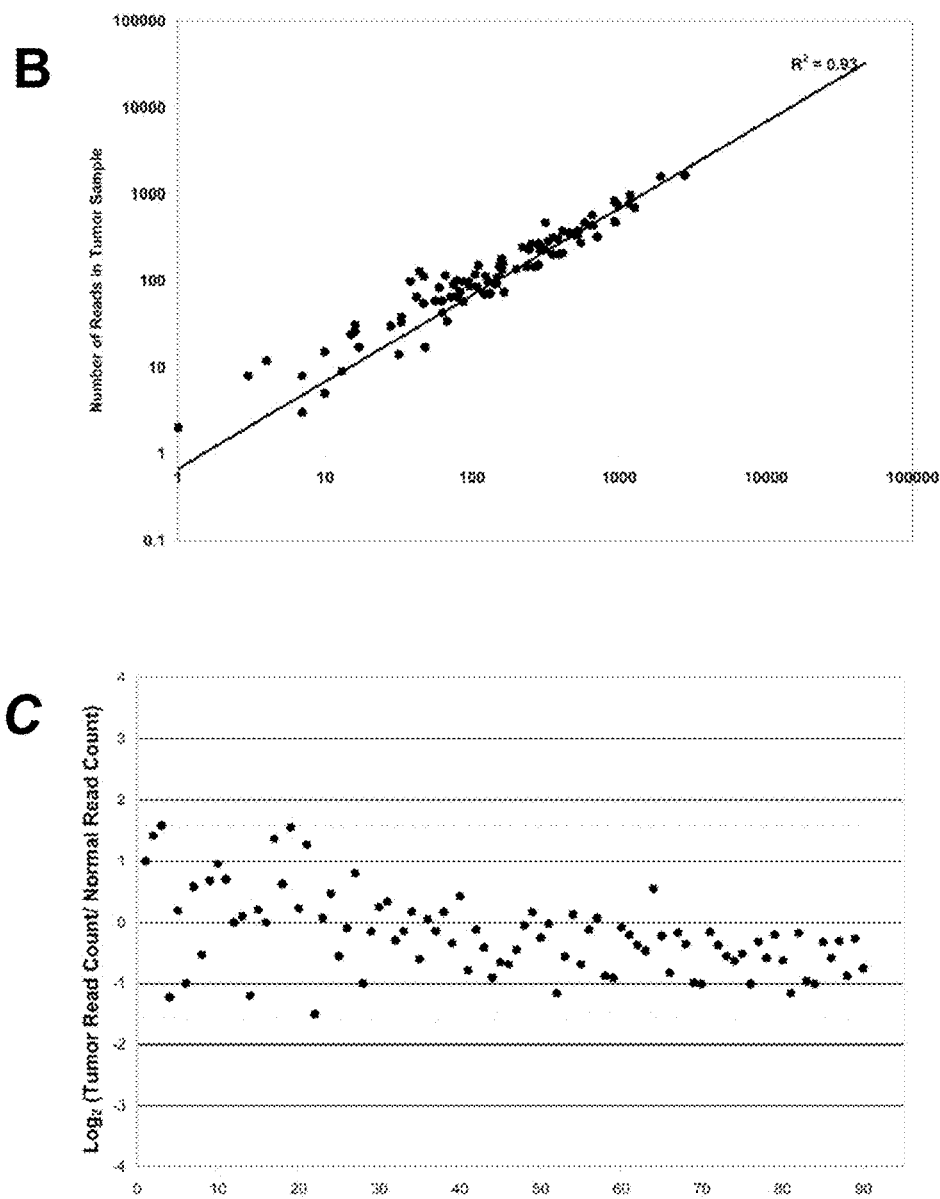

Ideally for any multiplexed PCR method, all targeted regions would be uniformly amplified within each reaction by all primer pairs, and across samples from different templates. To analyze the uniformity of amplification of the 90 regions generated by nucleic acid patch PCR in Example 2, the number of reads obtained for each targeted was graphed (FIG. 3A). The number of sequencing reads obtained for each exon is also presented numerically in TABLE D. Sequence coverage ranged over 2-3 logs (base 10), with 75% (68/90) of exons having between 10 and 500 reads in both samples (50 fold abundance range). The median number of reads per exon was 145. Seventy-six percent of all exons fell within 5-fold coverage of this median (29-725 reads). There were no parameters found that explain the non-uniformity. Exon non-uniformity did not correlate with the gene, the size of the amplicon, nor the GC content of the oligonucleotides.

TABLE D

Reads Per Exon in Tumor and Normal Samples

| RefSeq _ Exon Number | Number of Reads in Normal Sample | Number of Reads in Tumor Sample |
|---|---|---|
| NM_000551_1 | 1 | 2 |
| NM_000321_22 | 3 | 8 |
| NM_000546_5 | 4 | 12 |
| NM_007304_0 | 7 | 3 |
| NM_007304_2 | 7 | 8 |
| NM_000546_3 | 10 | 5 |
| NM_000546_9 | 10 | 15 |
| NM_000321_16 | 13 | 9 |
| NM_007304_4 | 15 | 24 |
| NM_000038_8 | 16 | 31 |
| NM_000321_20 | 16 | 26 |
| NM_000249_8 | 17 | 17 |
| NM_000321_9 | 28 | 30 |
| NM_000321_26 | 32 | 14 |
| NM_000321_17 | 33 | 38 |
| NM_007304_10 | 33 | 33 |
| NM_000321_14 | 38 | 98 |
| NM_000321_24 | 42 | 65 |
| NM_000321_1 | 44 | 129 |
| NM_000038_2 | 47 | 55 |
| NM_000551_2 | 47 | 113 |
| NM_000321_7 | 48 | 17 |
| NM_000038_7 | 56 | 59 |
| NM_000321_2 | 60 | 83 |
| NM_000249_17 | 63 | 43 |
| NM_000546_8 | 63 | 59 |
| NM_007304_21 | 66 | 115 |
| NM_000038_11 | 68 | 34 |
| NM_000321_4 | 72 | 65 |
| NM_000321_5 | 75 | 89 |
| NM_000321_6 | 79 | 100 |
| NM_000321_10 | 80 | 65 |
| NM_000038_12 | 83 | 75 |
| NM_000321_18 | 87 | 98 |
| NM_007304_7 | 88 | 58 |
| NM_007304_9 | 95 | 98 |
| NM_007304_14 | 96 | 87 |
| NM_007304_16 | 105 | 118 |
| NM_000546_0 | 108 | 85 |
| NM_000249_1 | 111 | 150 |
| NM_000038_13 | 121 | 70 |
| NM_007304_8 | 124 | 114 |
| NM_000321_11 | 129 | 97 |
| NM_000038_5 | 133 | 71 |
| NM_000249_12 | 143 | 91 |
| NM_000546_1 | 148 | 92 |
| NM_007304_15 | 149 | 109 |
| NM_000249_7 | 154 | 149 |
| NM_007304_20 | 159 | 178 |
| NM_000249_19 | 160 | 134 |
| NM_007304_13 | 162 | 160 |
| NM_007304_11 | 165 | 74 |
| NM_000249_10 | 200 | 136 |
| NM_000321_3 | 222 | 243 |
| NM_000249_0 | 235 | 146 |
| NM_007304_17 | 247 | 227 |
| NM_000321_15 | 253 | 265 |
| NM_000249_15 | 267 | 145 |
| NM_000546_6 | 283 | 151 |
| NM_007304_12 | 286 | 270 |
| NM_000249_2 | 288 | 249 |
| NM_000249_9 | 292 | 225 |
| NM_000038_4 | 314 | 227 |
| NM_000321_19 | 317 | 464 |
| NM_000038_3 | 332 | 284 |
| NM_000249_13 | 353 | 199 |
| NM_000038_9 | 356 | 316 |
| NM_000321_25 | 386 | 301 |
| NM_000546_7 | 396 | 200 |
| NM_000546_4 | 415 | 206 |
| NM_000321_21 | 416 | 373 |
| NM_007304_5 | 464 | 358 |
| NM_000249_18 | 498 | 340 |
| NM_000038_10 | 524 | 338 |
| NM_007304_18 | 532 | 373 |
| NM_000038_0 | 549 | 273 |
| NM_000249_6 | 587 | 470 |
| NM_000249_3 | 648 | 433 |
| NM_000249_4 | 660 | 574 |
| NM_000321_12 | 670 | 434 |

TABLE D-continued

Reads Per Exon in Tumor and Normal Samples

| RefSeq_Exon Number | Number of Reads in Normal Sample | Number of Reads in Tumor Sample |
|---|---|---|
| NM_000038_1 | 713 | 320 |
| NM_007304_3 | 940 | 833 |
| NM_000249_14 | 942 | 483 |
| NM_000249_16 | 948 | 471 |
| NM_007304_6 | 975 | 779 |
| NM_000038_6 | 1170 | 780 |
| NM_000321_23 | 1198 | 967 |
| NM_000321_8 | 1283 | 697 |
| NM_007304_1 | 1932 | 1605 |
| NM_000249_5 | 2813 | 1665 |

To test the reproducibility of the nucleic acid patch PCR method, the number of reads per exon from the tumor and normal samples were correlated. The correlation was high ($R^2$ of 93%), indicating high reproducibility (FIG. 4A). In fact, 85% (77/90) of exons displayed at most a 2 fold difference in abundance between samples, and all exons were within 3 fold relative abundance between samples (FIG. 4B).

These results demonstrate that even though the abundance of PCR products varies between exons, the abundance of each exon is highly reproducible across different reactions and samples.

Example 4: SNP and Mutation Discovery and Validation

The variants from the reference sequence identified by nucleic acid patch PCR and 454 FLX sequencing in Example 2 were validated by performing individual PCR reactions for each variant locus, cloning the amplicons into E. coli, and sequencing 12 clones for each variant. Sequence variants were then analyzed for novelty and whether they affected the translation product of that nucleotide sequence.

Methods

The PCR for each locus in each sample was performed in a total volume of 50 µl. The reaction contained 1×PCR buffer lacking $MgCl_2$ (Invitrogen, Carlsbad, Calif.), 10 units Platinum Taq Polymerase (Invitrogen Carlsbad, Calif.), 0.5 mM each dNTP, 0.5 M Betaine, 0.5 µM Forward Primer, 0.5 µM Reverse Primer, and 100 ng genomic DNA from either the colon tumor or the adjacent normal tissue (Biochain catalog # D8235090-PP-10). This reaction was incubated at 93° C. for 2 minutes, followed by (93° C. for 30 sec, 55° C. for 6 minutes)×30 cycles, and held at 4° C. One fifth of the PCR reaction was verified by electrophoresis on a 2% agarose gel. The PCR products were ligated into the pGEM-T Easy Vector using Rapid Ligation Buffer according to the manufacturer's instructions (Promega, Madison, Wis.), transformed into GC10 Competent Cells (Gene Choice) and grown overnight on LB-agar (Luria-Broth) plates containing standard concentrations of carbenicillin, X-gal and IPTG. After overnight growth, at least 12 colonies were picked from the plates and added to 50 µl colony PCR reactions containing 1×PCR Reaction Buffer (Sigma, St. Louis, Mo.), 2 units Jumpstart Taq Polymerase (Sigma), 0.2 mM each dNTP, 0.5 µM M13 Forward Primer (5' CGCCAGGGTTTTCCCAGTCACGAC 3')(SEQ ID NO:383), 0.5 µM M13 Reverse Primer (5' TCACACAGGAAA CAGCTATGAC 3')(SEQ ID NO:384), and 0.01% Tween. The reaction was incubated at 94° C. for 10 minutes, followed by (94° C. for 1 min 30 sec, 55° C. for 1 min, 72° C. for 1 min)×35 cycles, and held at 4° C. These reactions were then treated with 10 µl Exo-SAP to degrade the remaining primers and nucleotides by adding 0.2 units Exonuclease I (USB, Cleveland, Ohio) and 0.2 units Shrimp Alkaline Phosphatase (SAP) (Promega, Madison, Wis.) in 1×SAP buffer (Promega, Madison, Wis.), incubating at 37° C. for 30 min, then by 80° C. for 30 min. The Sanger sequencing/cycle sequencing reactions were 20 ul and contained 1.5 µl Exo-SAP Treated colony PCR, 1 µl Big Dye Terminator v3.1 RR-100 Mix (Applied Biosystems, Foster City, Calif.), 2 mM $MgCl_2$, and 0.16 µM M13 Forward Primer. They were incubated at 96° C. for 1 min, followed by (96° C. for 10 sec, 50° C. for 5 sec, 60° C. for 4 min)×24 cycles, and held at 4° C. The reactions were ethanol precipitated with sodium acetate and submitted to the Washington University Genome Sequencing Center to load on the ABI 3730 (Applied Biosystems, Foster City, Calif.). Trace files were analyzed using the Phred software (Ewing and Green 1998; Ewing, Hillier, Wendl and Green 1998), and the resulting sequencing reads were aligned to the reference sequence using the BLAT software on the UCSC Genome Browser (Kent 2002; Kent, Sugnet, Furey, Roskin, Pringle, Zahler and Haussler 2002).

Sequence variants for each exon were identified, and the UCSC Genome browser was used to determine the presence of these variants in the NCBI database of SNPs (dbSNP, www.ncbi.nlm.nih.gov/projects/SNP/index.html), and whether they disrupted a codon. To determine if the tumor specific mutation identified in this analysis had been previously reported, the Catalog of Somatic Mutations in Cancer (www.sanger.ac.uk/genetics/CGP/cosmic/) was searched.

Results

Seven variants from the reference sequence were identified (TABLE E). The SNPs and mutations identified by nucleic acid patch PCR and 454 FLX sequencing were validated by performing individual PCR reactions from the original patient samples, cloning the amplicons, and sequencing at least 8 clones per locus using standard Sanger sequencing. Five of these variants were already in the NCBI database of SNPs (dbSNP; http://www.ncbi.nlm.nih.gov/SNP/). The individual sequenced was germline homozygous at three of these SNPs (rs17883323, rs185587, rs3020646) and was germline heterozygous at two other SNPs in the database, rs2229992 and rs351771. The A allele of the SNP rs2229992 was in 54% of reads from the tumor sample and 54% of reads from normal sample. The C allele of the SNP rs351771 was in 48% of reads from the tumor sample and 47% of reads from normal sample. The ability to detect both alleles of these known polymorphisms at near equal frequency indicates that nucleic acid patch PCR provides high allele sensitivity that is reproducible across samples. SNP in an intron of APC that was not yet in dbSNP (rs62626346) was also discovered. The sequenced individual was heterozygous in both the tumor and normal samples at this intronic position. A novel germline SNP was discovered in the sequenced individual in one of the most extensively surveyed genes, APC. This illustrates that medical resequencing of well-characterized candidate genes will yield more insight into genetic variation in individuals.

TABLE E

Mutation and SNPs discovered. Bold mutation is tumor specific.

| Protein | Ref Seq ID | Exon number | Location* | Reference Base | Variant | Amino Acid Change | Fraction of Reads with Variant | | | |
|---------|------------|-------------|-----------|----------------|---------|-------------------|---|---|---|---|
| | | | | | | | Colon Adenocarcinoma Tissue | | Adjacent Normal Tissue | |
| APC | NM_000038 | 10 | rs2229992 | T | C | none | 143/301 | 48% | 222/468 | 47% |
| APC | NM_000038 | 12 | rs351771 | G | A | none | 37/68 | 54% | 43/79 | 54% |
| APC | NM_000038 | 12 | chr5: 112192485 | C | T | Arg-> STOP | 23/68 | 33% | 3/80 | 4% |
| APC | NM_000038 | 13 | rs62626346 † | T | C | intronic | 17/29 | 59% | 27/50 | 54% |
| TP53 | NM_000546 | 1 | rs17883323 | G | T | intronic | 41/41 | 100% | 50/50 | 100% |
| RB1 | NM_000321 | 11 | rs185587 | G | T | intronic | 79/79 | 100% | 102/102 | 100% |
| RB1 | NM_000321 | 24 | rs3020646 | C | T | intronic | 24/24 | 100% | 18/18 | 100% |

*Location is according to the March 2006 human genome assembly from the UCSC Genome Browser
† Novel germline SNP A tumor-specific nonsense mutation was also discovered. It is a C to T substitution in the APC gene at chr5:112192485 that results in a codon for arginine changing to a stop codon. This is likely a significant mutation in this individual's colon tumor because it is a nonsense mutation in a gene that is already known to cause colon cancer. This mutation was in 33% of reads from the tumor sample. This mutation is adjacent to a heterozygous SNP, and we discovered that 62% of the SNP A allele reads had the nonsense mutation, and 0% of the SNP G allele reads had the nonsense mutation. This indicates that the nonsense mutation occurred on the A allele during the clonal expansion of the tumor. This mutation was previously observed in an ovarian endometrioid adenocarcinoma and is Mutation ID #19040 in the Catalog of Somatic Mutations in Cancer (http://www.sanger.ac.uk/genetics/CGP/cosmic/).

In summary, this method has the allele sensitivity necessary for variant discovery in personal genome sequencing since both alleles of heterozygous SNPs were identified at near-even frequencies. Indeed, the utility of nucleic acid patch PCR is best illustrated by the fact that a novel, cancer-specific mutation was discovered in this pilot study.

Example 5: SNP Sensitivity Analysis

To determine the sensitivity of the nucleic acid patch PCR method coupled with 454 sequencing, each exon analyzed in examples 2 to 5 was individually amplified by PCR from the same colon cancer and adjacent normal tissue samples as used above. Direct Sanger sequencing was then performed. The sequences obtained were then compared to sequences generated using nucleic acid patch PCR and 454 sequencing.

The PCR for each locus in each sample was performed in a total volume of 50 ul. The reaction contained 1×PCR Buffer—MgCl2 (Invitrogen, Carlsbad, Calif.), 5 units Platinum Taq Polymerase (Invitrogen Carlsbad, Calif.), 0.5 mM each dNTP, 0.5 M Betaine, 0.5 µM Locus Specific Forward Primer, 0.5 µM Locus Specific Reverse Primer, and 20 ng genomic DNA from the adjacent normal tissue (Biochain catalog # D8235090-PP-10). This reaction was incubated at 93° C. for 2 min, followed by (93° C. for 30 sec, 55° C. for 6 min)×30 cycles, and held at 4° C. One fifth of the PCR reaction was verified by electrophoresis on a 2% agarose gel. These reactions were then treated with 10 µl Exo-SAP to degrade the remaining primers and nucleotides by adding 0.2 units Exonuclease I (USB, Cleveland, Ohio) and 0.2 units Shrimp Alkaline Phosphatase (SAP) (Promega, Madison, Wis.) in 1×SAP buffer (Promega, Madison, Wis.), incubating at 37° C. for 30 min, then by 80° C. for 30 min. The Sanger sequencing/cycle sequencing reactions were 20 µl and contained 1.5 µl ExoSAP-treated individual exon PCR, 1 µl Big Dye Terminator v3.1 RR-100 Mix (Applied Biosystems, Foster City, Calif.), 2 mM MgCl2, and 0.16 µM Forward or Reverse PCR Primer. They were incubated at 96° C. for 1 min, followed by (96° C. for 10 sec, 50° C. for 5 sec, 60° C. for 4 min)×24 cycles, and held at 4° C. The reactions were ethanol precipitated with sodium acetate and submitted to the Washington University Genome Sequencing Center to load on the ABI 3730 (Applied Biosystems, Foster City, Calif.). Trace files from both forward and reverse reads were analyzed for SNPs using PolyPhred and manual inspection (Nickerson, Tobe and Taylor 1997).

No additional SNPs were identified in the DNA sample beyond the six germline SNPs already identified. Thus, in this experiment, the sensitivity of the method is 100%.

REFERENCES FOR EXAMPLES 1-5

1. Akhras, M. S., Thiyagarajan, S., Villablanca, A. C., Davis, R. W., Nyren, P., and Pourmand, N. 2007a. PathogenMip assay: a multiplex pathogen detection assay. PLoS ONE 2: e223.
2. Akhras, M. S., Unemo, M., Thiyagarajan, S., Nyren, P., Davis, R. W., Fire, A. Z., and Pourmand, N. 2007b. Connector inversion probe technology: a powerful one-primer multiplex DNA amplification system for numerous scientific applications. PLoS ONE 2: e915.
3. Albert, T. J., Molla, M. N., Muzny, D. M., Nazareth, L., Wheeler, D., Song, X., Richmond, T. A., Middle, C. M., Rodesch, M. J., Packard, C. J. et al. 2007. Direct selection of human genomic loci by microarray hybridization. Nature methods 4: 903-905.
4. Barany, F. 1991. Genetic disease detection and DNA amplification using cloned thermostable ligase. Proceedings of the National Academy of Sciences of the United States of America 88: 189-193.
5. Bashiardes, S., Veile, R., Helms, C., Mardis, E. R., Bowcock, A. M., and Lovett, M. 2005. Direct genomic selection. Nature methods 2: 63-69.
6. Dahl, F., Gullberg, M., Stenberg, J., Landegren, U., and Nilsson, M. 2005. Multiplex amplification enabled by selective circularization of large sets of genomic DNA fragments. Nucleic acids research 33: e71.
7. Dahl, F., Stenberg, J., Fredriksson, S., Welch, K., Zhang, M., Nilsson, M., Bicknell, D., Bodmer, W. F., Davis, R. W., and Ji, H. 2007. Multigene amplification and massively parallel sequencing for cancer mutation discovery. Proceedings of the National Academy of Sciences of the United States of America 104: 9387-9392.
8. Elnifro, E. M., Ashshi, A. M., Cooper, R. J., and Klapper, P. E. 2000. Multiplex PCR: optimization and application in diagnostic virology. Clinical microbiology reviews 13: 559-570.
9. Ewing, B. and Green, P. 1998. Base-calling of automated sequencer traces using phred. II. Error probabilities. Genome research 8: 186-194.
10. Ewing, B., Hillier, L., Wendl, M. C., and Green, P. 1998. Base-calling of automated sequencer traces using phred. I. Accuracy assessment. Genome research 8: 175-185.
11. Fackler, M. J., Malone, K., Zhang, Z., Schilling, E., Garrett-Mayer, E., Swift-Scanlan, T., Lange, J., Nayar, R., Davidson, N. E., Khan, S. A. et al. 2006. Quantitative multiplex methylation-specific PCR analysis doubles detection of tumor cells in breast ductal fluid. Clin Cancer Res 12: 3306-3310.
12. Fan, J. B., Chee, M. S., and Gunderson, K. L. 2006. Highly parallel genomic assays. Nature reviews 7: 632-644.
13. Forster, A. C. and Church, G. M. 2007. Synthetic biology projects in vitro. Genome research 17: 1-6.
14. Fredriksson, S., Baner, J., Dahl, F., Chu, A., Ji, H., Welch, K., and Davis, R. W. 2007. Multiplex amplification of all coding sequences within 10 cancer genes by Gene-Collector. Nucleic acids research 35: e47.
15. Greenman, C., Stephens, P., Smith, R., Dalgliesh, G. L., Hunter, C., Bignell, G., Davies, H., Teague, J., Butler, A., Stevens, C. et al. 2007. Patterns of somatic mutation in human cancer genomes. Nature 446: 153-158.
16. Han, J., Swan, D. C., Smith, S. J., Lum, S. H., Sefers, S. E., Unger, E. R., and Tang, Y. W. 2006. Simultaneous amplification and identification of 25 human papillomavirus types with Templex technology. Journal of clinical microbiology 44: 4157-4162.
17. Hodges, E., Xuan, Z., Balija, V., Kramer, M., Molla, M. N., Smith, S. W., Middle, C. M., Rodesch, M. J., Albert, T. J., Hannon, G. J. et al. 2007. Genome-wide in situ exon capture for selective resequencing. Nature genetics 39: 1522-1527.
18. Kent, W. J. 2002. BLAT—the BLAST-like alignment tool. Genome research 12: 656-664.
19. Kent, W. J., Sugnet, C. W., Furey, T. S., Roskin, K. M., Pringle, T. H., Zahler, A. M., and Haussler, D. 2002. The human genome browser at UCSC. Genome research 12: 996-1006.
20. Larkin, M. A., Blackshields, G., Brown, N. P., Chenna, R., McGettigan, P. A., McWilliam, H., Valentin, F., Wallace, I. M., Wilm, A., Lopez, R. et al. 2007. Clustal W and Clustal X version 2.0. Bioinformatics (Oxford, England) 23: 2947-2948.
21. Marsh, D. and Zori, R. 2002. Genetic insights into familial cancers—update and recent discoveries. Cancer letters 181: 125-164.
22. Marsh, S. and McLeod, H. L. 2006. Pharmacogenomics: from bedside to clinical practice. Human molecular genetics 15 Spec No 1: R89-93.
23. Metzker, M. L. 2005. Emerging technologies in DNA sequencing. Genome research 15: 1767-1776.
24. Meuzelaar, L. S., Lancaster, O., Pasche, J. P., Kopal, G., and Brookes, A. J. 2007. MegaPlex PCR: a strategy for multiplex amplification. Nature methods 4: 835-837.
25. Nickerson, D. A., Tobe, V. O., and Taylor, S. L. 1997. PolyPhred: automating the detection and genotyping of single nucleotide substitutions using fluorescence-based resequencing. Nucleic acids research 25: 2745-2751.
26. Okou, D. T., Steinberg, K. M., Middle, C., Cutler, D. J., Albert, T. J., and Zwick, M. E. 2007. Microarray-based genomic selection for high-throughput resequencing. Nature methods 4: 907-909.
27. Parameswaran, P., Jalili, R., Tao, L., Shokralla, S., Gharizadeh, B., Ronaghi, M., and Fire, A. Z. 2007. A pyrosequencing-tailored nucleotide barcode design unveils opportunities for large-scale sample multiplexing. Nucleic acids research 35: e130.
28. Porreca, G. J., Zhang, K., Li, J. B., Xie, B., Austin, D., Vassallo, S. L., LeProust, E. M., Peck, B. J., Emig, C. J., Dahl, F. et al. 2007. Multiplex amplification of large sets of human exons. Nature methods 4: 931-936.
29. Reisinger, S. J., Patel, K. G., and Santi, D. V. 2006. Total synthesis of multi-kilobase DNA sequences from oligonucleotides. Nature protocols 1: 2596-2603.
30. Ronaghi, M., Uhlen, M., and Nyren, P. 1998. A sequencing method based on real-time pyrophosphate. Science (New York, N.Y 281: 363, 365.
31. Sjoblom, T., Jones, S., Wood, L. D., Parsons, D. W., Lin, J., Barber, T. D., Mandelker, D., Leary, R. J., Ptak, J., Silliman, N. et al. 2006. The consensus coding sequences of human breast and colorectal cancers. Science (New York, N.Y 314: 268-274.
32. Weinstein, L. B. 2007. Selected genetic disorders affecting Ashkenazi Jewish families. Family & community health 30: 50-62.
33. Wood, L. D., Parsons, D. W., Jones, S., Lin, J., Sjoblom, T., Leary, R. J., Shen, D., Boca, S. M., Barber, T., Ptak, J. et al. 2007. The genomic landscapes of human breast and colorectal cancers. Science (New York, N.Y 318: 1108-1113.

Example 6: Bisulfite Nucleic Acid Patch PCR Proof of Concept

Figure 4:
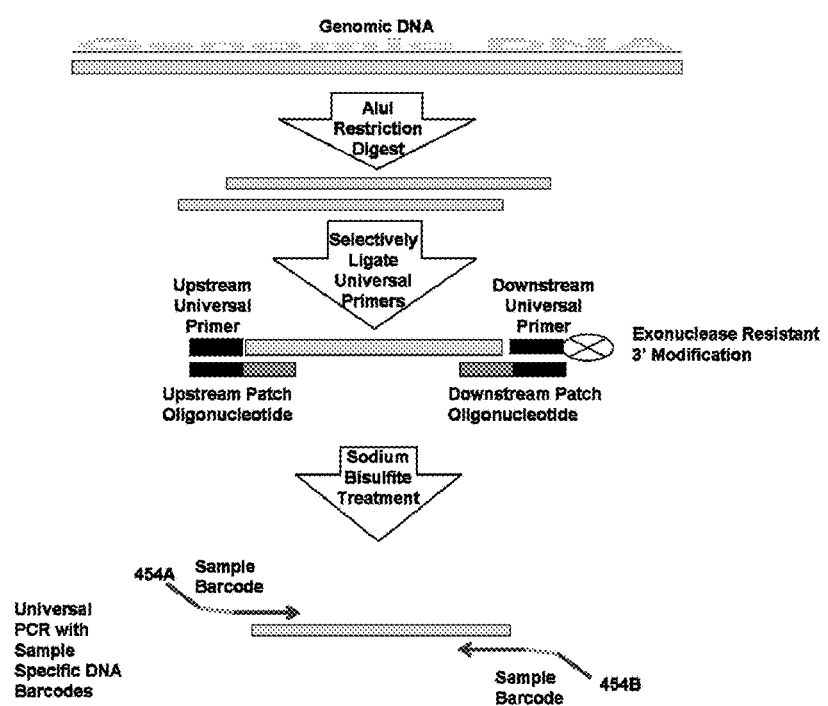
FIG. 4 depicts a schematic of bisulfite nucleic acid patch PCR with ends defined by AluI digest. Genomic DNA is digested with AluI restriction enzyme. Nucleic acid patch oligonucleotides are then annealed to the target amplicons and serve as a patch between the correct amplicons and universal primers. The universal primers are then ligated to the amplicons. The universal primer on the 3' end of the amplicon is modified with a 3 carbon spacer that protects the selected amplicon from the final exonuclease reaction that degrades nonspecific products. The reactions are then treated with sodium bisulfite to convert unmethylated cytosines to uracil. The selected amplicons are then amplified together simultaneously by PCR with universal primers.

In this example, various features of the method of the invention are demonstrated including: 1. Creating nucleic acid template with defined ends using AluI restriction digest. 2. Treatment with sodium bisulfite to detect DNA methylation by sequencing. 3. Using small quantities of DNA. The method is depicted in FIG. 4.
Template Preparation
Genomic DNA from breast and colon cancer and adjacent normal tissue was digested with the AluI restriction endonuclease in 10 ul total volume reaction containing genomic DNA, 10 U AluI enzyme (NEB), and 1× NEBuffer 2 (NEB). This reaction was incubated at 37° C. for 1 hour, followed by heat inactivation of the enzyme at 65° C. for 20 min, and held at 4° C. until the subsequent step. To demonstrate the efficacy of this method with small quantities of DNA, multiple reactions were performed using decreasing quantities of genomic DNA including 900, 675, 450, 250, 225, 112, 70, 50, 20, 1.6, 0.8, and 0.4 ng genomic DNA. A control reaction lacking genomic DNA was also prepared.
Nucleic Acid Patch Ligation
Nucleic acid patch oligos were designed as described in Example 2 but were designed to anneal adjacent to the AluI restriction enzyme site upstream and downstream of promoters of a select 94 gene in the human genome. These loci were selected because they are the promoters of genes frequently mutated in cancer. Nucleic acid patch driven ligation of the universal primers to selected fragments was performed by addition of more reactants to the initial tube to result in the following final concentrations: 2 nM each nucleic acid patch oligo, 200 nM Universal Primer 1, 200 nM Universal Primer 2 with 5' phosphate and 3' three carbon spacer, 5 U Ampligase (Epicentre), and 1× Ampligase Reaction Buffer (Epicentre) in a total volume of 25 ul. This reaction was incubated at 95° C. for 15 minutes followed by (94° C. for 30 sec, 65° C. for 8 min) for 100 cycles, and held at 4° C.

Incorrect products, template genomic DNA and excess primer were degraded as described in Example 2. In brief, 10 U Exonuclease I (USB) and 200 U Exonuclease III (Epicentre) were added to the reaction. This mix was incubated at 37° C. for 1 hour followed by heat inactivation at 95° C. for 20 minutes, and held at 4° C.

Sodium Bisulfite Treatment

The reactions were then treated with sodium bisulfite to convert unmethylated cytosines to uracil. This was achieved by using the EZ DNA Methylation Gold Bisulfite Treatment Kit (Zymo Research) following the manufacture's instructions. Since the sample volume after the exonuclease treatment was 27 ul, the CT Conversion Reagent from the kit was made by adding 830 ul dH2O instead of 900 ul dH2O. The DNA was eluted from the column in the final step with 10 ul M-Elution buffer.

PCR Amplification

The universal primers were then used to PCR amplify the selected bisulfite converted loci from each sample. For the PCR, reagents were added to the last 10 ul column elution to result in these final concentrations in 50 ul: 0.5 uM each tailed Universal Primer, 10 U Platinum Taq Polymerase (Invitrogen), 0.5 mM each dNTP, 2 mM $MgCl_2$, 0.5M Betaine, 20 mM Tris-HCl pH 8.4 and 50 mM KCl. This reaction was incubated at 93° C. for 2 minutes followed by (93° C. for 30 sec, 57° C. for 6 min) for 29 cycles, and held at 4° C. As described in Example 2, the universal PCR used primers tailed with 454 Life Sciences A or B oligo at the 5' end, followed by a sample specific DNA sequence and ending at the 3' end with the nucleic acid patch universal primer sequence. The PCR product smear between the expected sizes was confirmed by running on a 3% Metaphor Agarose gel (Lonza). The reactions were then purified on a Qiaquick Spin Column (Qiagen). An aliquot of the reactions was analyzed by gel elctrophoresis on an agrose gel (Lonza).

The eluted DNA of the reactions using 250 ng of genomic DNA was quantified on the Nanodrop (www.nanodrop.com) and the same quantity of DNA was pooled together from each of the separate samples. This pooled sample was submitted for sequencing on the 454 Life Sciences/Roche FLX machine. Sequence and data analysis were as described in Example 2.

Results

Figure 5:
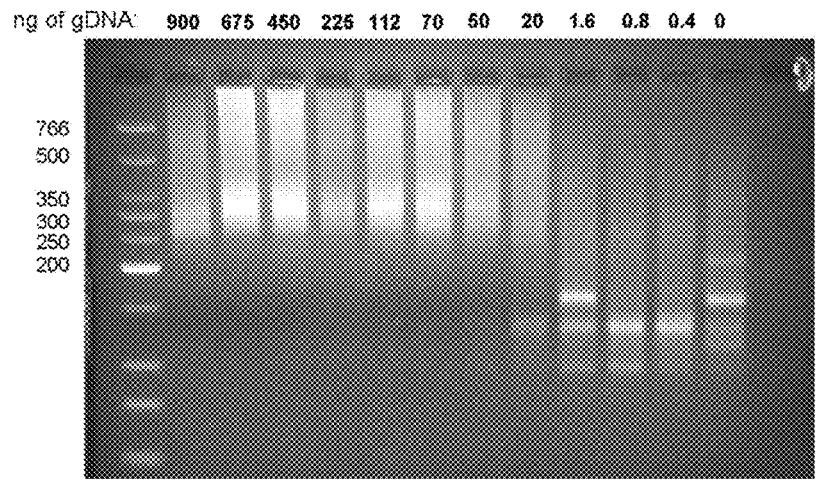
FIG. 5 shows an image of the agarose gel electrophoresis of the final Universal PCR products of bisulfite nucleic acid patch PCR with ends defined by AluI digest. Each reaction was performed using decreasing quantities of starting human genomic DNA, as labeled in the figure. The expected smear of products is seen in the lanes that contained 900, 675, 450, 225, 112, 70, 50, and 20 ng of genomic DNA. The first lane contains Low Molecular Weight Ladder (NEB), with band sizes denoted on the left.

Highly multiplexed bisulfite PCR was successful even when small quantities of genomic DNA were used (FIG. 5). The expected smear of products is seen in the lane that contained 900 ng DNA, and the reaction generates the expected products even when as little as 20 ng of genomic DNA is used. Using less than 20 ng of genomic DNA might also have been successful, but the sensitivity of the imaging was not sufficient to reliably detect it.

Figure 6:
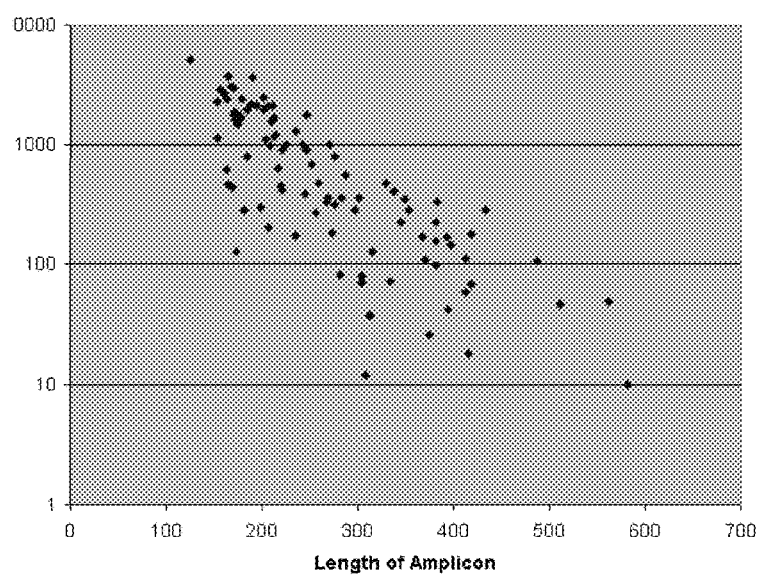
FIG. 6 depicts the sequencing results of bisulfite nucleic acid patch PCR with ends defined by AluI digest. The Y axis on the graph represents the number of reads obtained for each promoter. The promoters are order by length (bp) on the X axis.

Sequence analysis of the reactions performed using 250 ng of human tumor genomic DNA demonstrated that 100% of the targeted regions were successfully amplified and sequenced. All of the 94 targeted promoters were sequenced at least once (FIG. 6). The method was also very specific, with 90% of all reads matching the targeted promoters.

In summary, digesting genomic DNA with AluI successfully defined the ends of nucleic acid templates even when a very small quantity of genomic DNA treated with sodium bisulfite was used.

Example 7: Bisulfite Nucleic Acid Patch PCR and Tumor Analysis

Inappropriate CpG DNA methylation has been found in most types of cancers[1]. Genes that participate in numerous pathways involved in malignancy can acquire aberrant promoter methylation[2]. Tumor suppressor genes frequently exhibit promoter hypermethylation, an epimutation that is associated with inappropriate gene silencing[2]. A recent study has found that several key tumor suppressor genes exhibit promoter hypermethylation more often than genetic disruption, suggesting this mechanism is an important driver of tumorigenesis[3]. Oncogenes can exhibit hypomethylation of their promoters which is associated with inappropriate expression[4]. More complicated mis-regulation of a gene can also be caused by aberrant methylation; a recent report found that hypermethylation of a p53 binding site blocked binding of the repressor, resulting in overexpression of the survivin oncogene[5].

The identification of gene promoters that are aberrantly methylated during tumor development is valuable because it can provide insights into pathways that are commonly disrupted during tumorigenesis that can serve as drug targets[6,7]. Analysis of promoter methylation can also classify distinct subtypes of cancers that may have differential clinical characteristics in order to personalize treatment[8,9]. Finally, loci that are hypermethylated in tumors are often detected in peripheral samples (e.g. blood or stool) and may serve as diagnostic or prognostic biomarkers[10].

Many techniques have been developed to detect DNA methylation including methods based on microarrays[11], quantitative PCR[12], mass-spectrometry[13] and DNA sequencing[14]. The method that is the most direct and has the highest resolution involves treatment of genomic DNA with sodium bisulfite (which converts unmethylated cytosines to uracil, while leaving methylated cytosines intact) followed by sequencing of single molecules. Not only does this method determine the methylation state at each CpG position across a single molecule, but it also detects sequence variants. This cis information makes it possible to distinguish allele specific methylation[14], and is also valuable for quantifying densely methylated molecules in a background of unmethylated or sparsely methylated molecules.

The recent introduction of second-generation DNA sequencing technologies has significantly reduced the cost required to sequence DNA. This has led to several new approaches for studying aberrant methylation using bisulfite PCR and sequencing. Methods for genome-wide surveys of methylation in a small number of samples have been developed including whole genome bisulfite sequencing[15], bisulfite sequencing large fractions of restriction digested genomic DNA[16], padlock probe based strategies[17,18] and array-based hybridization capture[19]. In contrast, methods for the detailed study of a few loci across many samples have been described that involve amplifying each locus individually, labeling with sample-specific barcodes and performing ultra-deep bisulfite sequencing[20-22]. These methods are limited to a small number of loci because the amplification of each locus separately is laborious and requires a significant amount of patient DNA per locus queried. There is still a need for a method that enables the intermediate experiment to be performed. That is, the targeted multiplexed bisulfite PCR and sequencing of an intermediate number of loci (100-1000) across a large number of samples. In cancer research this experiment is crucial since the discoveries made in genome wide profiling of a few samples need to be validated and followed-up across large numbers of patient samples.

We sought to develop a method to perform highly multiplexed bisulfite sequencing across many patient samples simultaneously. Bisulfite treatment significantly reduces the complexity of DNA sequence by converting most Cs to Ts. It also results in molecules from the same locus having different sequences depending on their methylation state. Therefore we perform the oligo hybridization and ligation based selection of the targeted loci before bisulfite treatment. The selection is highly sensitive and specific and only one pair of oligos per locus is needed, even when selecting CpG rich loci. The PCR amplification of selected loci is performed after bisulfite. Therefore the universal primers used to amplify all loci simultaneously had to be designed to exclude C's, so that they would remain unchanged through bisulfite conversion. Since the major application of this method is likely to be in clinical specimens, we optimized the method so that it didn't require large quantities of starting genomic DNA and was compatible with the DNA degradation inherit in sodium bisulfite treatment.

We designed the method to be easy to implement in any lab with standard molecular biology techniques and reagents. We also tested that it would scale up well to process many patient samples in 96-well format. We integrated sample-specific DNA barcodes into the multiplexed amplification so that many patient samples can be pooled and sequenced simultaneously on second-generation sequencing machines. Here we present a proof-of-principle experiment in which we amplified promoter regions from 94 targeted loci simultaneously and sequenced these loci across 48 samples including colon and breast tumor and adjacent normal tissue samples. In this experiment, we characterized the promoter methylation of genes that are known to be frequently mutated in cancer. We identified several novel loci that undergo frequent tumor-specific promoter methylation, and we observed allele-specific methylation patterns that occur during tumor development. We demonstrated that this method utilizes the power of next-generation sequencing to study DNA methylation at many loci across many patient samples.

Results

Overview of Bisulfite Patch PCR

Figure 7F:
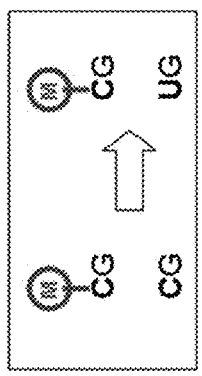
Figure 7G:
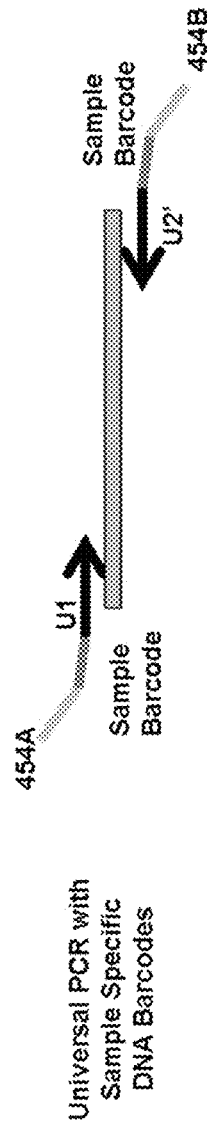

Bisulfite Patch PCR begins with a restriction digest of human genomic DNA to define the ends of the fragments that will be selected (FIGS. 7A & B). Targeted loci are then selected from the genomic restriction fragments by annealing patch oligos to the ends of the targeted genomic fragments. These oligos serve as a patch between the correct fragments and universal primers (U1 & U2) (FIG. 7C). The universal primers are then ligated to the genomic fragments using a thermostable ligase (FIG. 7D). Unselected genomic DNA is then degraded with exonucleases to gain additional selectively (FIG. 7E). Selected fragments are protected from degradation by a 3' modification on the universal primer U2 (FIG. 7E). Next, the selected fragments are treated with sodium bisulfite to convert unmethylated cytosines to uracil, leaving methylated bases intact (FIG. 7F). The universal primers do not contain cytosine bases so that the sequence remains unchanged through the bisulfite conversion. The bisulfite treated selected fragments are then all amplified together simultaneously by PCR with the universal primers (U1 & U2') (FIG. 7G). Sample-specific DNA barcodes are incorporated into the universal primers by tailing the 5' end with a DNA sequence that is specific to each sample and the sequencing platform primers (454 sequencing primers) (FIG. 7G). The final PCR amplicons from each of the samples can be pooled together for sequencing because the first few bases of each sequencing read will identify the sample from which that sequence originated.

Figure 8:
FIG. 8 depicts a photograph of an agarose gel showing that multiplexed bisulfite PCR works from small quantities of human genomic DNA. Image of the final universal PCR products by 3% Metaphor agarose gel electrophoresis. Each reaction was performed on a different amount of starting human genomic DNA, as labeled at the top of the figure. The expected smear of products is seen in the lanes that contained between 900 ng and 20 ng DNA. The gel image demonstrates that the reaction generates the expected products when as little as 20 ng of genomic DNA is used. A faint smear is visible in the lane that started with 1.6 ng in images taken at higher exposure.

Highly Multiplexed Bisulfite Sequencing of CAN Gene Promoters in Colon and Breast Cancer To test the performance of Bisulfite Patch PCR we analyzed the promoter methlyation of 94 genes that are frequently mutated in breast and colon cancers ('CAN genes')[24]. We designed the patch oligos to select AluI restriction digest fragments containing at least three CpG positions within 700 bp upstream of the transcription start site. We chose 42 colon CAN gene promoters, 44 breast CAN gene promoters, 4 gene promoters that were identified as both colon and breast CAN genes, and 4 controls. The four controls include an imprinted locus, a housekeeping gene promoter, and 2 neutral loci that accumulate methylation with mitotic cell division[25]. These targeted promoter regions ranged in length from 125 bp to 581 bp and totaled 25.4 Kbp (SEQ ID NOs xx-xx). To determine the amount of genomic DNA required for the Bisulfite Patch PCR, we performed gel electrophoresis of the PCR products generated with different amounts of starting DNA. We observed DNA within the expected size range from reactions that started with as much as 1 microgram and as little as 20 nanograms (ng) of human genomic DNA (FIG. 8).

We performed Bisulfite Patch PCR on 250 ng of genomic DNA from each of 48 samples in parallel in a 96-well plate. The genomic DNA was isolated from a panel of 12 colon tumors, 12 matched adjacent normal colon tissues, 12 breast tumors and 12 matched adjacent normal breast tissues (TABLE F). We incorporated a 5-bp sample-specific DNA barcode in the final PCR, pooled the amplicons from all of the samples, and sequenced the pool using the Roche/454 FLX sequencer. We obtained 97,115 reads and aligned these to the in silico bisulfite treated reference sequences of our targeted loci. We successfully amplified all 94 (100%) of the targeted loci, indicating that the method is highly sensitive. Ninety percent (87,458 reads) of all reads mapped to one of the targeted promoters, demonstrating that the method is highly specific. These results demonstrate the Bisulfite Patch PCR enables highly multiplexed bisulfite sequencing.

TABLE F

| Lot Number | Tissue | Tumor or Normal | Age | Sex | Pathological Diagnosis | DNA Barcode | Patient Number |
|---|---|---|---|---|---|---|---|
| A811018 | Breast | T | 34 | F | invasive ductal carcinoma | GAGAC | 1 |
|  | Breast | N |  |  |  | GACAT | 1 |
| A704203 | Breast | T | 36 | F | invasive ductal carcinoma | GTCGT | 2 |
|  | Breast | N |  |  |  | CAGAT | 2 |
| A810202 | Breast | T | 41 | F | invasive ductal carcinoma | AGAGC | 3 |
|  | Breast | N |  |  |  | AGCAT | 3 |

TABLE F-continued

| Lot Number | Tissue | Tumor or Normal | Age | Sex | Pathological Diagnosis | DNA Barcode | Patient Number |
|---|---|---|---|---|---|---|---|
| A811022 | Breast | T | 46 | F | invasive ductal carcinoma | GTGTA | 4 |
|  | Breast | N |  |  |  | GTCAC | 4 |
| A810219 | Breast | T | 47 | F | invasive ductal carcinoma | ATAGA | 5 |
|  | Breast | N |  |  |  | ATATC | 5 |
| A811019 | Breast | T | 47 | F | invasive ductal carcinoma | GACGA | 6 |
|  | Breast | N |  |  |  | GCAGA | 6 |
| A810210 | Breast | T | 48 | F | invasive ductal carcinoma | ACGAT | 7 |
|  | Breast | N |  |  |  | ACTAG | 7 |
| A810220 | Breast | T | 48 | F | invasive ductal carcinoma | ATCAG | 8 |
|  | Breast | N |  |  |  | ATCGC | 8 |
| A811021 | Breast | T | 50 | F | invasive ductal carcinoma | GCTGT | 9 |
|  | Breast | N |  |  |  | GTGAG | 9 |
| A810208 | Breast | T | 55 | F | invasive ductal carcinoma | AGCGA | 10 |
|  | Breast | N |  |  |  | ACAGT | 10 |
| A810213 | Breast | T | 58 | F | invasive ductal carcinoma, Poorly Differentiated | ACTGC | 11 |
|  | Breast | N |  |  |  | ACTCT | 11 |
| A811020 | Breast | T | 77 | F | invasive ductal carcinoma | GCACG | 12 |
|  | Breast | N |  |  |  | GCTAC | 12 |
| B108099 | Colon | T | 37 | M | Adenocarcinoma, mucinous | CTCAT | 1 |
|  | Colon | N |  |  |  | CTCGA | 1 |
| A811012 | Colon | T | 40 | M | Adenocarcinoma, Ulcer | TATAC | 2 |
|  | Colon | N |  |  |  | TATGT | 2 |
| B105050 | Colon | T | 52 | F | Adenocarcinoma, Moderately Differentiated | CGTGT | 3 |
|  | Colon | N |  |  |  | CTAGC | 3 |
| B105051 | Colon | T | 56 | F | Adenocarcinoma, Ulcer, Moderately Differentiated | CTACT | 4 |
|  | Colon | N |  |  |  | CTGAC | 4 |
| A709116 | Colon | T | 57 | M | Adenocarcinoma, Moderately Differentiated | CGAGA | 5 |
|  | Colon | N |  |  |  | CGCAG | 5 |
| A709121 | Colon | T | 57 | M | Adenocarcinoma, Moderately Differentiated | CGCGC | 6 |
|  | Colon | N |  |  |  | CGTAC | 6 |
| A811013 | Colon | T | 62 | F | Adenocarcinoma | TGCAC | 7 |
|  | Colon | N |  |  |  | TGCGT | 7 |
| A811015 | Colon | T | 65 | M | Adenocarcinoma | TGTCG | 8 |
|  | Colon | N |  |  |  | TCAGC | 8 |
| A811010 | Colon | T | 71 | F | Adenocarcinoma, Ulcer | TACAG | 9 |
|  | Colon | N |  |  |  | TACGC | 9 |
| A811016 | Colon | T | 75 | M | Adenocarcinoma | TCGAC | 10 |
|  | Colon | N |  |  |  | TCGTG | 10 |
| A811014 | Colon | T | 79 | M | Adenocarcinoma, Ulcer | TGTAT | 11 |
|  | Colon | N |  |  |  | TGTGA | 11 |
| A704198 | Colon | T | 81 | M | Adenocarcinoma, Moderately Differentiated | CATAG | 12 |
|  | Colon | N |  |  |  | CATGC | 12 |

Coverage of Promoters and Reproducibility

Figure 9A:
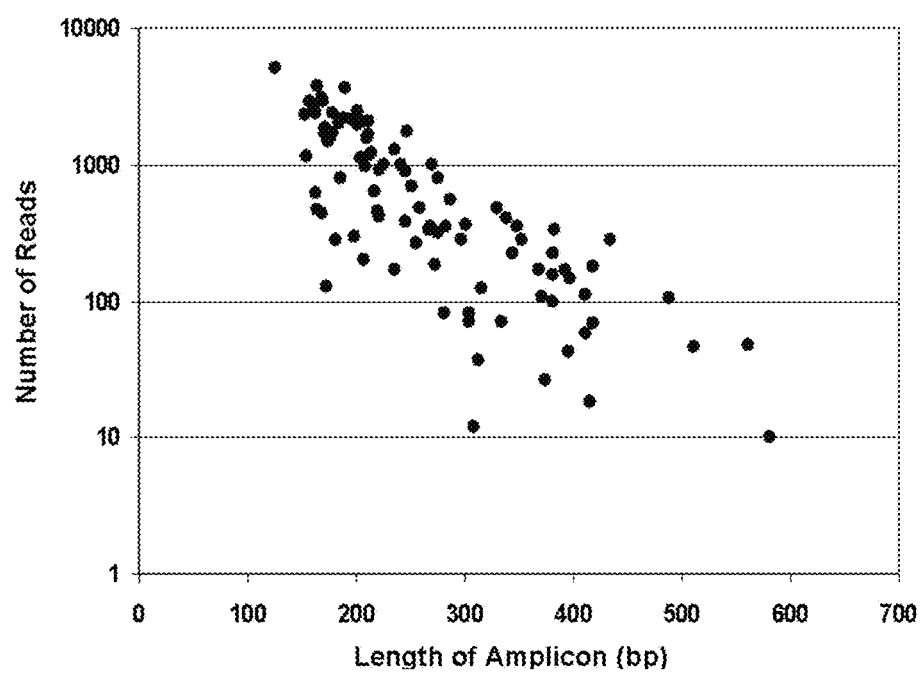
FIG. 9A-B depicts two graphs showing the bisulfite method performance.

To analyze the uniformity of the sequence coverage, we graphed the number of reads obtained for each targeted promoter versus the length of the targeted region. (FIG. 9A; TABLE G). The abundance of each promoter ranged from 10 to 5114 reads. We calculated that 93% of promoters have coverage within 10 fold of the median coverage (444 reads). There is a strong inverse correlation between amplicon length and the number of reads (linear regression $R^2$=0.42). This correlation indicates that longer amplicons are less abundant in the reaction. If we had restricted our design to a maximum target length of 300 bp, then 92% (57/62) of those promoters would have coverage within 5 fold of the median coverage (1051 reads). These calculations indicate that approximately half of the difference in abundance of the loci is attributable to length bias. While length bias can occur in multiplex PCR, in previous versions of this universal PCR used in nested patch PCR we did not observe a correlation between amplification efficiency and length[23]. Since the main difference between these methods is the sodium bisulfite treatment, we suspect that longer loci were more likely to be damaged during bisulfite conversion[26], and thus are less abundant in the reaction.

Figure 9B:
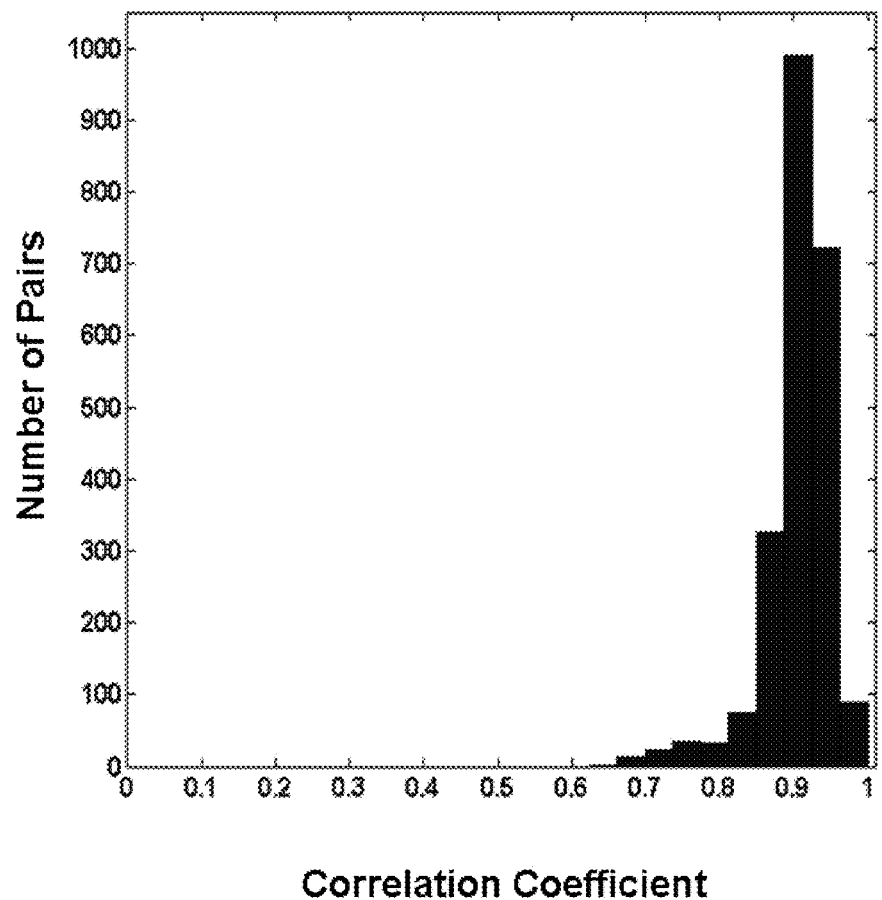

To test if bisulfite patch PCR reproducibly amplifies selected loci, we calculated the number of reads per locus in each of the 48 samples that were prepared in parallel. We then calculated the correlation coefficient, r, for the number of reads per locus between all possible pairs of samples. The histogram of r values obtained for the pair-wise correlations between all 48 samples is depicted in FIG. 9B. The mean r value is 0.91, indicating that the number of reads per locus is highly reproducible across patient samples. This indicates that the abundance of each locus in the reaction is not stochastic, but represents something intrinsic to the locus, including the length, as discussed above.

TABLE G

| CAN Gene Type | Gene | Accession | # of Reads | Length of Amplicon (bp) | Number of CGs per Amplicon | Methylated | BT | BN | CT | CN |
|---|---|---|---|---|---|---|---|---|---|---|
| Breast | DPYD | NM_000110 | 1207 | 214 | 6 | N | (0%)0/12 | (0%)0/12 | (0%)0/12 | (0%)0/12 |
| Breast | XDH | NM_000379 | 313 | 276 | 3 | N | (0%)0/12 | (0%)0/12 | (0%)0/12 | (0%)0/12 |
| Breast | CYP1A1 | NM_000499 | 478 | 259 | 23 | N | (0%)0/12 | (0%)0/12 | (0%)0/11 | (0%)0/12 |
| Breast | DPAGT1 | NM_001382 | 278 | 182 | 7 | N | (0%)0/12 | (0%)0/11 | (0%)0/12 | (0%)0/10 |
| Breast | CLCN3 | NM_001829 | 2405 | 163 | 15 | N | (0%)0/12 | (0%)0/12 | (0%)0/12 | (0%)0/12 |
| Breast | MYH9 | NM_002473 | 167 | 368 | 31 | N | (0%)0/11 | (0%)0/12 | (0%)0/12 | (0%)0/12 |
| Breast | PRPF4B | NM_003913 | 997 | 225 | 10 | N | (0%)0/12 | (0%)0/12 | (0%)0/12 | (0%)0/12 |
| Breast | TIMELESS | NM_003920 | 12 | 308 | 17 | N | (0%)0/4 | (0%)0/2 | (0%)0/2 | (0%)0/2 |
| Breast | LRRFIP1 | NM_004735 | 464 | 165 | 14 | N | (0%)0/12 | (0%)0/12 | (0%)0/12 | (0%)0/12 |
| Breast | NUP214 | NM_005085 | 1963 | 201 | 12 | N | (0%)0/12 | (0%)0/12 | (0%)0/12 | (0%)0/12 |
| Breast | TLN1 | NM_006289 | 282 | 297 | 22 | N | (0%)0/12 | (0%)0/11 | (0%)0/12 | (0%)0/12 |
| Breast | ABCB8 | NM_007188 | 2390 | 179 | 8 | N | (0%)0/12 | (0%)0/12 | (0%)0/12 | (0%)0/12 |
| Breast | ZNF646 | NM_014699 | 2451 | 202 | 7 | N | (0%)0/12 | (0%)0/12 | (0%)0/12 | (0%)0/12 |
| Breast | PDCD11 | NM_014976 | 891 | 246 | 17 | N | (0%)0/12 | (0%)0/12 | (0%)0/12 | (0%)0/12 |
| Breast | MAPKBP1 | NM_014994 | 221 | 382 | 26 | N | (0%)0/12 | (0%)0/12 | (0%)0/12 | (0%)0/12 |
| Breast | C14orf100 | NM_016475 | 556 | 287 | 34 | N | (0%)0/12 | (0%)0/12 | (0%)0/12 | (0%)0/12 |
| Breast | NOTCH1 | NM_017617 | 81 | 282 | 34 | N | (0%)0/9 | (0%)0/10 | (0%)0/12 | (0%)0/7 |
| Breast | SULF2 | NM_018837 | 2094 | 211 | 21 | N | (0%)0/12 | (0%)0/12 | (0%)0/12 | (0%)0/12 |
| Breast | KIAA0999 | NM_025164 | 682 | 252 | 13 | N | (0%)0/12 | (0%)0/12 | (0%)0/12 | (0%)0/12 |
| Breast | PLEKHA8 | NM_032639 | 71 | 334 | 40 | N | (0%)0/9 | (0%)0/10 | (0%)0/7 | (0%)0/9 |
| Breast | FLJ40869 | NM_182625 | 385 | 245 | 31 | N | (0%)0/11 | (0%)0/12 | (0%)0/12 | (0%)0/12 |
| Breast | TMEM123 | NM_052932 | 329 | 383 | 11 | N | (0%)0/12 | (0%)0/12 | (0%)0/12 | (0%)0/12 |
| Breast | KIAA0427 | NM_014772 | 450 | 220 | 15 | N | (8%)1/12 | (8%)1/12 | (17%)2/12 | (8%)1/12 |
| Breast | VEPH1 | NM_024621 | 1563 | 210 | 5 | N | (8%)1/12 | (8%)1/12 | (8%)1/12 | (0%)0/12 |
| Breast | SLC8A3 | NM_182932 | 70 | 304 | 9 | N | (0%)0/10 | (0%)0/8 | (0%)0/11 | (0%)0/10 |
| Breast | RGL1 | NM_015149 | 10 | 581 | 60 | N | (0%)0/2 | (0%)0/3 | (0%)0/3 | (0%)0/2 |
| Colon | ERCC6 | NM_000124 | 1784 | 171 | 15 | N | (0%)0/12 | (0%)0/12 | (0%)0/12 | (0%)0/12 |
| Colon | NF1 | NM_000267 | 293 | 198 | 19 | N | (0%)0/12 | (0%)0/11 | (0%)0/12 | (0%)0/12 |
| Colon | PTEN | NM_000314 | 111 | 412 | 20 | N | (0%)0/11 | (0%)0/9 | (0%)0/12 | (0%)0/9 |
| Colon | GALNS | NM_000512 | 1005 | 242 | 26 | N | (0%)0/12 | (0%)0/12 | (0%)0/12 | (0%)0/12 |
| Colon | GUCY1A2 | NM_000855 | 37 | 313 | 15 | N | (0%)0/6 | (17%)1/6 | (0%)0/4 | (0%)0/7 |
| Colon | UQCRC2 | NM_003366 | 610 | 163 | 10 | N | (0%)0/12 | (0%)0/12 | (0%)0/12 | (0%)0/12 |
| Colon | MCM3AP | NM_003906 | 105 | 488 | 20 | N | (0%)0/8 | (0%)0/11 | (0%)0/8 | (0%)0/11 |
| Colon | EPHB6 | NM_004445 | 1842 | 172 | 13 | N | (0%)0/11 | (0%)0/11 | (0%)0/12 | (0%)0/12 |
| Colon | KRAS | NM_004985 | 18 | 415 | 53 | N | (0%)0/3 | (0%)0/5 | (0%)0/4 | (0%)0/3 |
| Colon | ZNF262 | NM_005095 | 359 | 302 | 21 | N | (0%)0/12 | (0%)0/12 | (0%)0/12 | (0%)0/12 |
| Colon | SMAD4 | NM_005359 | 634 | 217 | 21 | N | (0%)0/12 | (0%)0/12 | (0%)0/12 | (0%)0/12 |
| Colon | SFRS6 | NM_006275 | 402 | 338 | 35 | N | (0%)0/12 | (0%)0/12 | (0%)0/12 | (0%)0/12 |
| Colon | SMTN | NM_006932 | 145 | 397 | 34 | N | (0%)0/12 | (0%)0/12 | (0%)0/11 | (0%)0/10 |
| Colon | KIAA0556 | NM_015202 | 281 | 353 | 38 | N | (0%)0/12 | (0%)0/12 | (0%)0/12 | (0%)0/12 |
| Colon | ADARB2 | NM_018702 | 26 | 374 | 7 | N | (0%)0/2 | (17%)1/6 | (0%)0/6 | (0%)0/5 |
| Colon | FBXW7 | NM_033632 | 1097 | 204 | 24 | N | (0%)0/12 | (0%)0/12 | (0%)0/12 | (0%)0/12 |
| Colon | DTNB | NM_183361 | 2195 | 189 | 19 | N | (0%)0/12 | (0%)0/12 | (0%)0/12 | (0%)0/12 |
| Colon | RET | NM_020975 | 58 | 412 | 46 | N | (0%)0/8 | (0%)0/6 | (0%)0/6 | (0%)0/8 |
| Colon | KIAA0367 | NM_015225 | 170 | 235 | 18 | N | (8%)1/12 | (0%)0/11 | (8%)1/12 | (0%)0/10 |
| Colon | SH3TC1 | NM_018986 | 2876 | 157 | 10 | N | (8%)1/12 | (0%)0/12 | (0%)0/12 | (0%)0/12 |
| Colon | TIAM1 | NM_003253 | 354 | 283 | 40 | N | (0%)0/12 | (0%)0/12 | (8%)1/12 | (0%)0/12 |
| Colon | C13orf7 | NM_024546 | 351 | 269 | 10 | N | (0%)0/12 | (0%)0/12 | (8%)1/12 | (17%)2/12 | (0%)0/12 |
| Control | HSP | NM_007355 | 155 | 381 | 21 | N | (0%)0/11 | (0%)0/12 | (0%)0/10 | (0%)0/11 |
| Dual | TP53 | NM_000546 | 1132 | 154 | 6 | N | (0%)0/12 | (0%)0/12 | (0%)0/12 | (0%)0/12 |
| Dual | PIK3CA | NM_006218 | 989 | 270 | 15 | N | (0%)0/12 | (0%)0/12 | (0%)0/12 | (0%)0/12 |
| Breast | TECTA | NM_005422 | 168 | 393 | 7 | Y | (100%)11/11 | (100%)11/11 | (100%)12/12 | (91%)10/11 |
| Breast | KIAA0467 | NM_015284 | 332 | 267 | 6 | Y | (100%)12/12 | (100%)12/12 | (92%)11/12 | (100%)10/10 |
| Breast | RP1L1 | NM_178857 | 416 | 221 | 7 | Y | (100%)12/12 | (100%)12/12 | (100%)12/12 | (100%)12/12 |
| Breast | LOC340156 | NM_001012418 | 1481 | 175 | 3 | Y | (100%)12/12 | (100%)12/12 | (83%)10/12 | (100%)12/12 |
| Breast | DBN1 | NM_004395 | 3750 | 165 | 3 | Y | (100%)12/12 | (100%)12/12 | (100%)12/12 | (92%)11/12 |
| Breast | CENTG1 | NM_014790 | 3613 | 190 | 3 | Y | (100%)12/12 | (100%)12/12 | (92%)11/12 | (100%)12/12 |
| Breast | KIAA1946 | NM_177454 | 1667 | 212 | 5 | Y | (100%)12/12 | (100%)12/12 | (100%)12/12 | (100%)12/12 |
| Breast | CMYA1 | NM_194293 | 127 | 173 | 4 | Y | (100%)11/11 | (83%)8/9 | (83%)10/12 | (70%)7/10 |
| Breast | AEGP | NM_206920 | 902 | 221 | 6 | Y | (83%)10/12 | (100%)12/12 | (83%)10/12 | (100%)12/12 |
| Breast | TAF1 | NM_004606 | 2315 | 153 | 12 | Y | (58%)7/12 | (67%)8/12 | (25%)3/12 | (25%)3/12 |
| Breast | RPGRIP1 | NM_020366 | 48 | 562 | 7 | Y | (88%)7/8 | (100%)7/7 | (100%)9/9 | (43%)3/7 |
| Breast | SLC9A10 | NM_183061 | 2096 | 195 | 3 | Y | (100%)12/12 | (100%)12/12 | (33%)4/12 | (75%)9/12 |
| Breast | COL19A1 | NM_001858 | 3069 | 168 | 4 | Y | (58%)7/12 | (58%)7/12 | (33%)4/12 | (8%)1/12 |
| Breast | ABP1 | NM_001091 | 200 | 207 | 5 | Y | (36%)4/11 | (67%)8/12 | (64%)7/11 | (58%)7/12 |
| Breast | CSPP1 | NM_024790 | 476 | 330 | 3 | Y | (17%)2/12 | (42%)5/12 | (15%)3/12 | (67%)8/12 |
| Breast | NCB5OR | NM_016230 | 282 | 434 | 6 | Y | (42%)5/12 | (17%)2/12 | (50%)6/12 | (18%)2/11 |
| Colon | ITGAE | NM_002208 | 348 | 349 | 9 | Y | (100%)12/12 | (100%)12/12 | (100%)12/12 | (100%)12/12 |
| Colon | TGM3 | NM_003245 | 178 | 418 | 5 | Y | (100%)10/10 | (100%)12/12 | (100%)11/11 | (100%)10/12 |
| Colon | DSCAML1 | NM_020693 | 2052 | 205 | 7 | Y | (100%)12/12 | (100%)12/12 | (100%)12/12 | (100%)12/12 |
| Colon | TNN | NM_022093 | 2659 | 161 | 3 | Y | (100%)12/12 | (100%)12/12 | (100%)12/12 | (100%)12/12 |
| Colon | ACSL5 | NM_016234 | 1280 | 235 | 5 | Y | (100%)12/12 | (100%)12/12 | (83%)10/12 | (92%)11/12 |
| Colon | SEC8L1 | NM_021807 | 221 | 345 | 4 | Y | (82%)9/11 | (100%)10/10 | (100%)12/12 | (100%)12/12 |
| Colon | PCDHA9 | NM_014005 | 1761 | 247 | 4 | Y | (83%)10/12 | (92%)11/12 | (83%)10/12 | (100%)12/12 |

TABLE G-continued

| CAN Gene Type | Gene | Accession | # of Reads | Length of Amplicon (bp) | Number of CGs per Amplicon | Methylated | BT | BN | CT | CN |
|---|---|---|---|---|---|---|---|---|---|---|
| Colon | C1QR1 | NM_012072 | 1646 | 172 | 8 | Y | (100%)12/12 | (83%)10/12 | (67%)8/12 | (50%)6/12 |
| Colon | STAB1 | NM_015136 | 46 | 511 | 16 | Y | (86%)6/7 | (100%)9/9 | (70%)7/10 | (50%)4/6 |
| Colon | HAPLN1 | NM_001884 | 108 | 371 | 11 | Y | (91%)10/11 | (83%)5/6 | (30%)3/10 | (55%)6/11 |
| Colon | BCL9 | NM_004326 | 266 | 256 | 5 | Y | (67%)8/12 | (64%)7/11 | (0%)0/12 | (25%)3/12 |
| Colon | SCN3B | NM_018400 | 98 | 382 | 11 | Y | (27%)3/11 | (13%)1/8 | (0%)0/11 | (10%)1/10 |
| Colon | GPR158 | NM_020752 | 125 | 315 | 37 | Y | (8%)1/12 | (11%)1/9 | (27%)3/11 | (0%)0/9 |
| Colon | HIST1H1B | NM_005322 | 962 | 208 | 3 | Y | (25%)3/12 | (17%)2/12 | (25%)3/12 | (8%)1/12 |
| Colon | NUP210 | NM_024923 | 68 | 419 | 24 | Y | (0%)0/8 | (25%)2/8 | (11%)1/9 | (20%)2/10 |
| Control | NKX2-5 | NM_004387 | 1980 | 184 | 10 | Y | (100%)12/12 | (100%)12/12 | (100%)12/12 | (92%)11/12 |
| Control | SOX10 | NM_006941_1 | 1170 | 213 | 22 | Y | (100%)12/12 | (67%)8/12 | (100%)12/12 | (100%)12/12 |
| Control | H19 | AK311497 | 1614 | 177 | 9 | Y | (58%)7/12 | (83%)10/12 | (75%)9/12 | (92%)11/12 |
| Breast | ICAM5 | NM_003259 | 1717 | 178 | 11 | Y | (33%)4/12 | (8%)1/12 | (58%)7/12 | (0%)0/12 |
| Breast | PPM1E | NM_014906 | 2932 | 170 | 10 | Y | (25%)3/12 | (0%)0/12 | (42%)5/12 | (0%)0/12 |
| Colon | IGFBP3 | NM_000598 | 791 | 276 | 25 | Y | (67%)8/12 | (8%)1/12 | (75%)9/12 | (25%)3/12 |
| Colon | UHRF2 | NM_152896 | 800 | 185 | 10 | Y | (58%)7/12 | (8%)1/12 | (50%)6/12 | (8%)1/12 |
| Colon | KCNQ5 | NM_019842 | 181 | 273 | 21 | Y | (0%)0/10 | (0%)0/12 | (92%)11/12 | (33%)4/12 |
| Colon | CLSTN2 | NM_022131 | 80 | 304 | 35 | Y | (0%)0/8 | (10%)1/10 | (56%)5/9 | (0%)0/10 |
| Colon | APC | NM_000038 | 42 | 395 | 16 | Y | (29%)2/7 | (0%)0/3 | (0%)0/8 | (0%)0/6 |
| Dual | LAMA1 | NM_005559 | 438 | 169 | 14 | Y | (50%)6/12 | (8%)1/12 | (67%)8/12 | (17%)2/12 |
| Dual | SORL1 | NM_003105 | 5114 | 125 | 3 | Y | (33%)4/12 | (92%)11/12 | (0%)0/12 | (42%)5/12 |

Allele Sensitivity at Imprinted Locus

Figure 10:
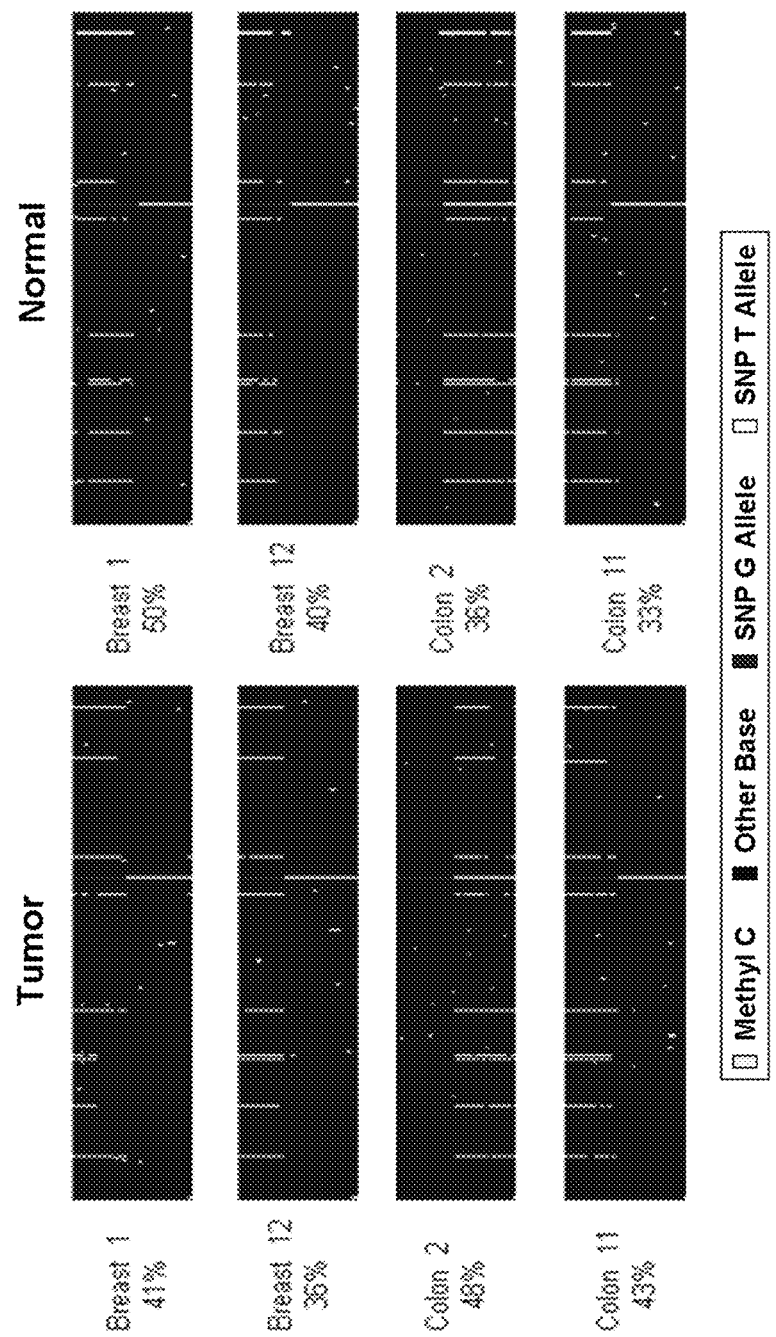
FIG. 10 depicts an illustration of methylation at the H19 imprinted locus. Data from four patients who were germline heterozygous for a SNP (rs2251375) in this locus. The sequencing reads are aligned as rows in each panel. Each base in the read is color coded to indicate the sequence, yellow indicates a methylated cytosine, blue indicates all other bases. The position of the SNP is indicated by the red and white column, where a red base indicates reads from the G allele, and a white base indicates reads from the T allele. The percent of reads for each patient that are from the G allele is listed below the patient identifier for each sample. As expected for an imprinted locus, methylation is observed on one allele in both the tumor (left panels) and adjacent normal tissue (right panels) for each patient. Both alleles and both methylated and unmethylated molecules were amplified and sequenced efficiently from this locus in all samples.
Figure 11A:
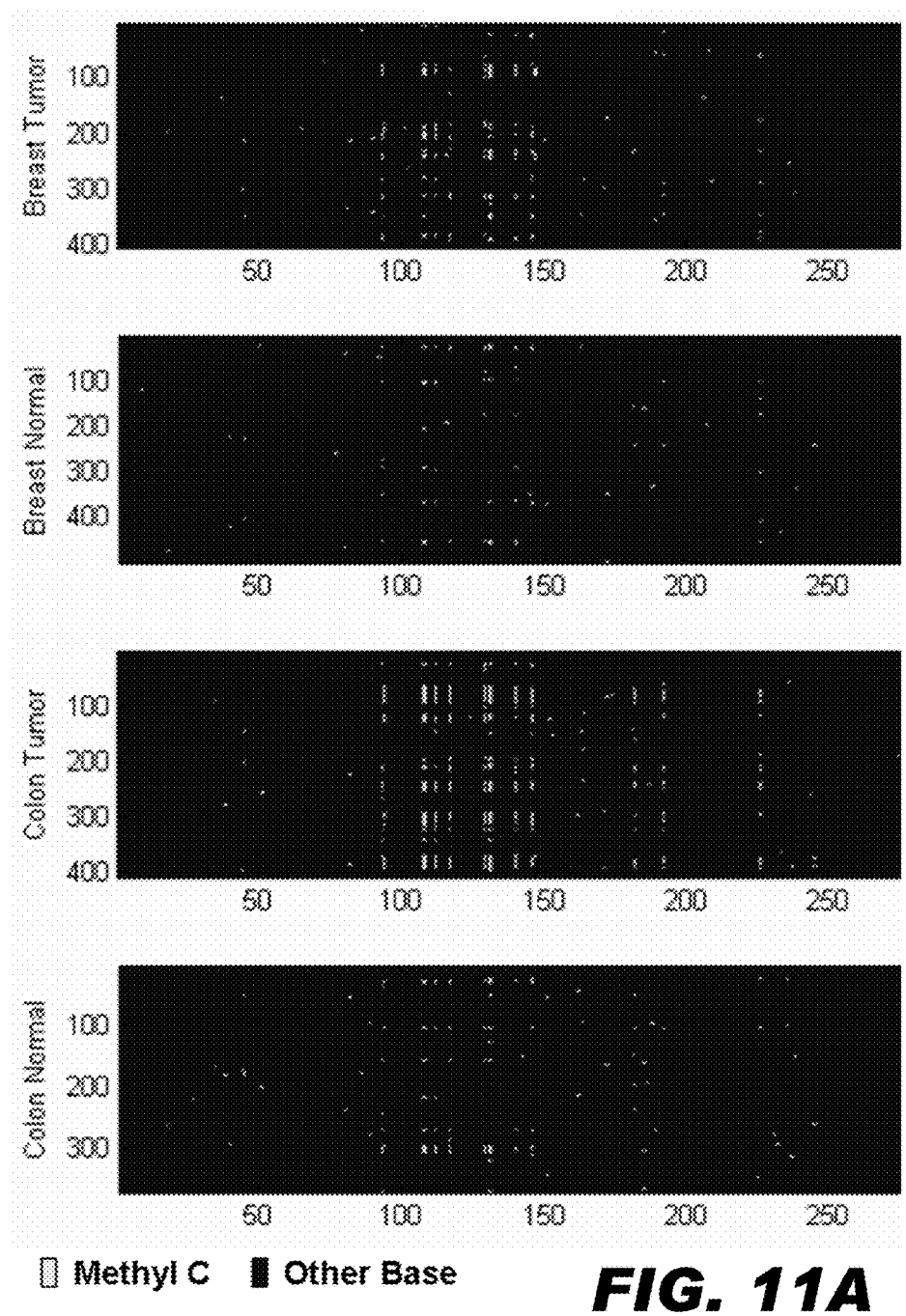
FIG. 11A-D depicts an illustration of four promoters that exhibit tumor specific methylation. Sequencing reads from all patients for each type of tissue are grouped together in panels; breast tumors, adjacent normal breast tissues, colon tumors, and adjacent normal colon tissues. The sequencing reads are aligned as rows in each panel, and grouped by patient. Each base in the read is color coded to indicate the sequence, yellow indicates a methylated cytosine, blue indicates all other bases.
Figure 11B:
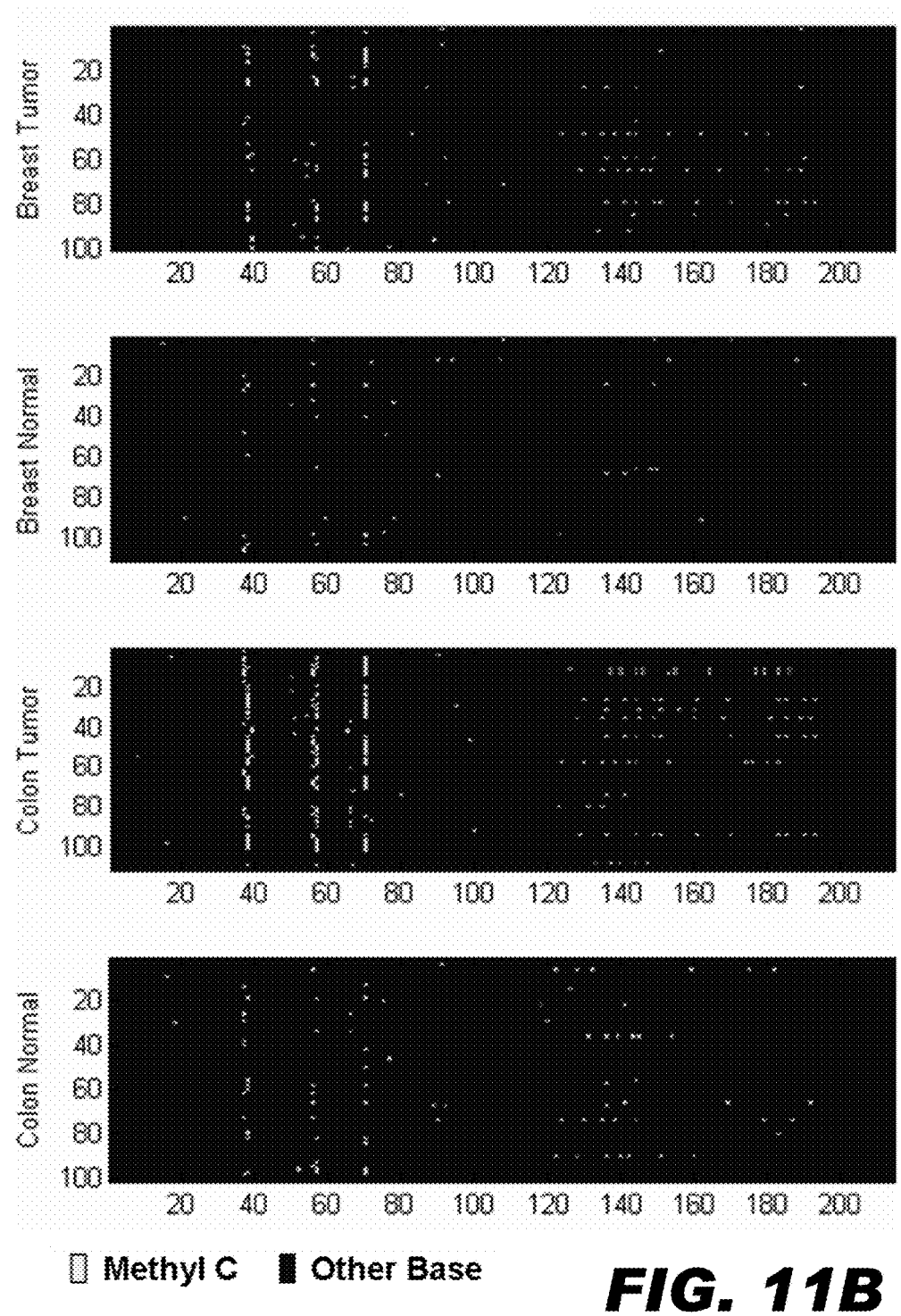
Figure 11C:
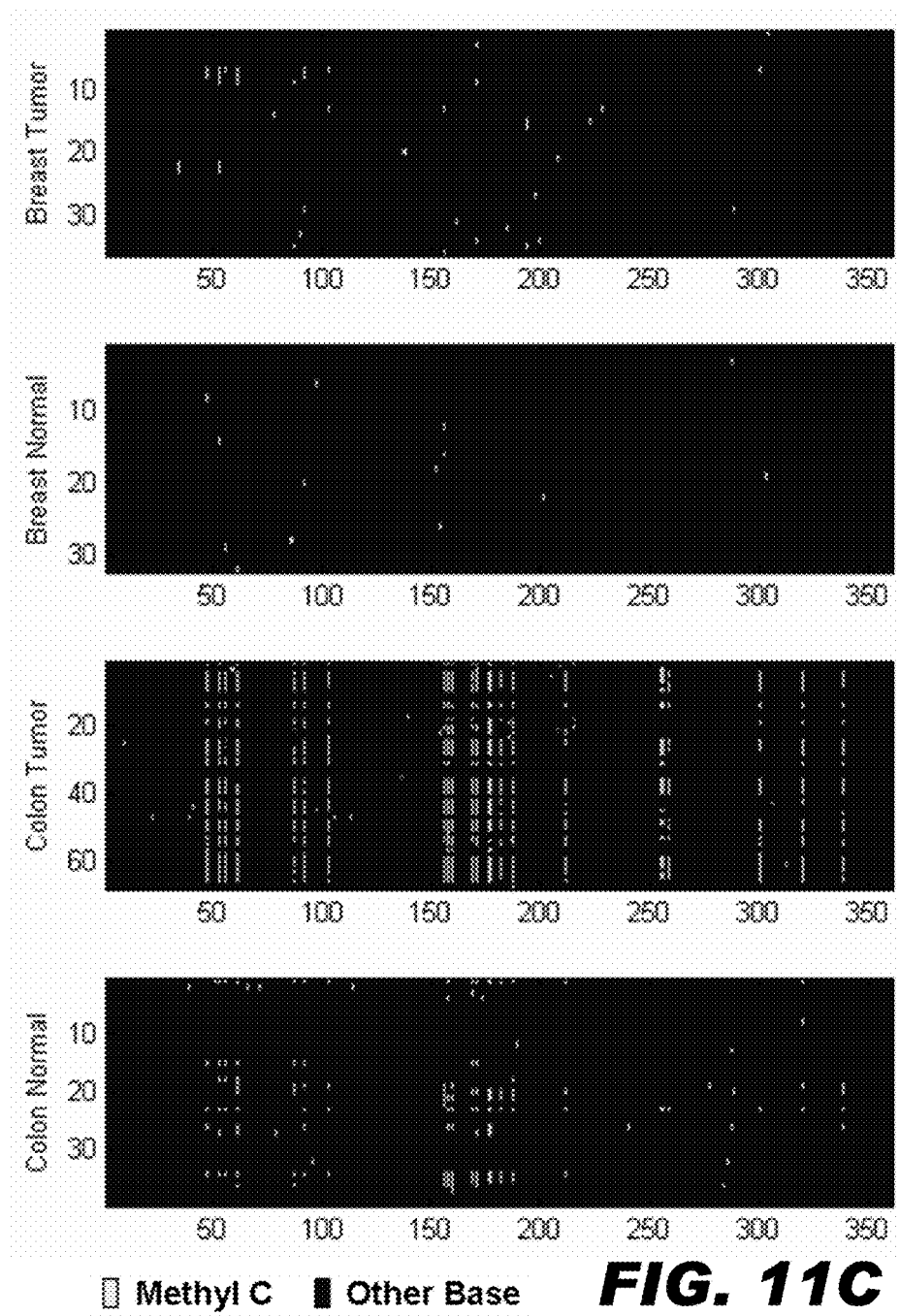
Figure 11D:
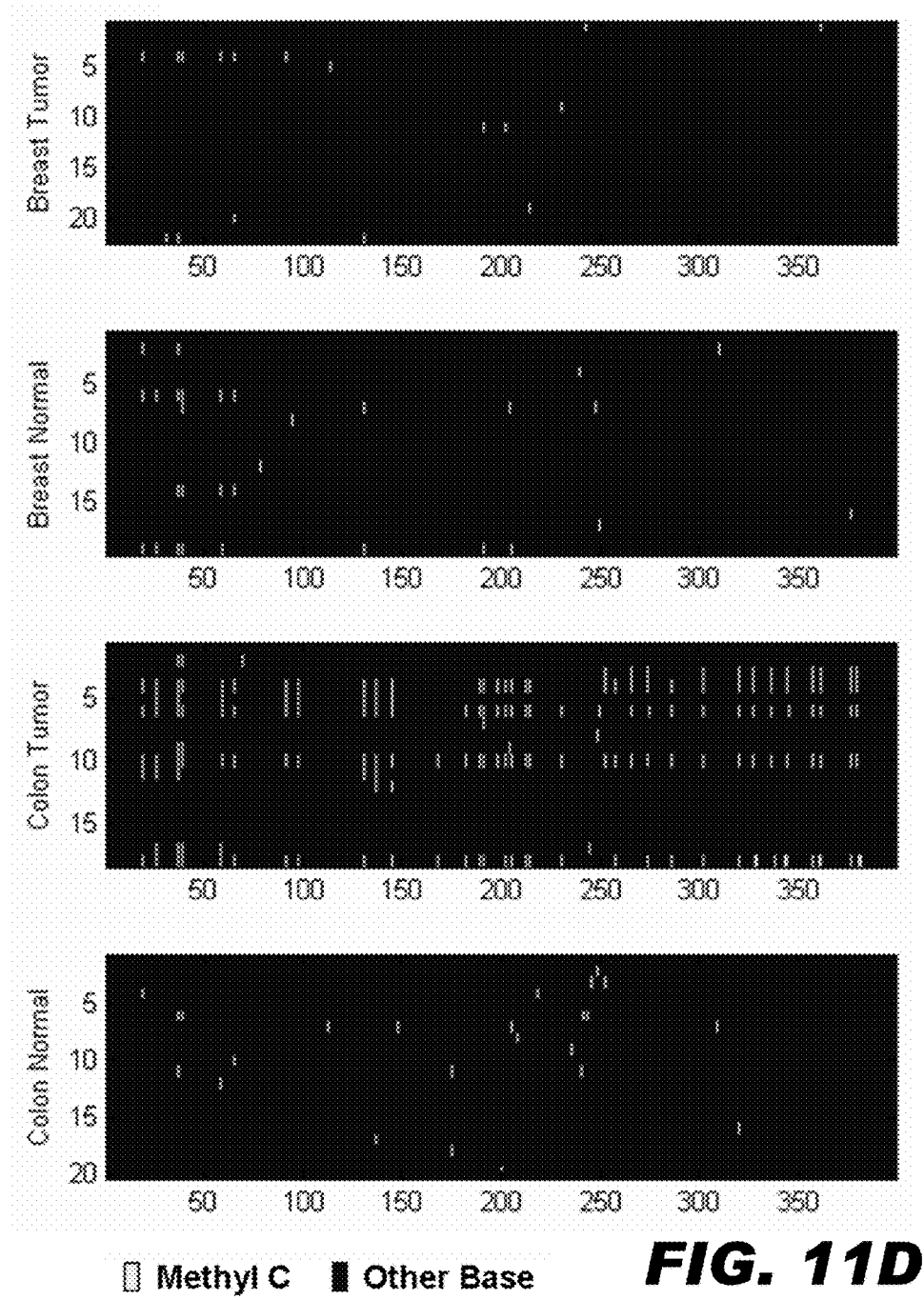

We next sought to determine if methylated and unmethylated molecules from the same locus are amplified with similar efficiencies. This is requisite if the method is to be used to make quantitative measurements of promoter methylation. The imprinted region from the H19 locus (AK311497), which was included as a control, allows the direct comparison of the amplification efficiency of methylated and unmethylated alleles. We identified nine patients in our panel who were heterozygous for a SNP (rs2251375) in the H19 locus. We used this SNP to identify allele-specific methylation and to quantify the number of sequencing reads obtained for each allele. Allele specific methylation was observed, and both alleles were amplified with nearly equal efficiencies (FIG. 10). Imprinting methylation was observed on either allele in different individuals, consistent with the parent-of-origin determining which allele is methylated, and both alleles were represented at similar frequencies—on average 42% of the sequencing reads corresponded to the 'G' allele, 58% to the 'T' allele. Thus, our method amplifies methylated and unmethylated molecules from the same locus with nearly equal efficiency, which is crucial for quantifying heterogeneous methylation within tumors.

CAN Gene Promoter Methylation

We next examined the methylation patterns found at the targeted CAN gene promoters to determine if they exhibited tumor specific methylation. Since these genes were previously shown to be frequently mutated in colon and breast tumors[24], we hypothesized that the promoters of these genes might also be frequently hyper- or hypomethylated in these cancers. (TABLE H, Detailed in TABLE G).

Approximately half, (51/94), of all the promoters were unmethylated in all tissue types that we tested, including, the negative control promoter of the housekeeping gene HSP90AB1 (NM_007355). Approximately one third, (34/94), of all promoters were methylated in both cancer and normal tissue including all 3 (100%) of the positive control gene promoters, the H19 imprinted promoter (AK311497) and two neutral loci that accumulated DNA methylation with mitotic division (NM_006941 Exon 2, and NM_004387 3' UTR)[25]. The remaining nine promoters exhibited tumor-specific aberrant methylation.

TABLE H

| | Colon CAN genes | Breast CAN genes | Dual CAN genes | Controls | Total |
|---|---|---|---|---|---|
| Unmethylated | 22 | 26 | 2 | 1 | 51 |
| Methylated In Tumor and Normal Tissues | 15 | 16 | 0 | 3 | 34 |
| Tumor Specific Methylation: Breast & Colon | 2 | 2 | 2 | 0 | 6 |
| Tumor Specific Methylation: Colon | 2 | 0 | 0 | 0 | 2 |
| Tumor Specific Methylation: Breast | 1 | 0 | 0 | 0 | 1 |
| Total | 42 | 44 | 4 | 4 | 94 |

Tumor Specific Promoter Methylation

Of the nine promoters that exhibited tumor specific methylation, 5 were promoters from colon CAN genes, 2 were promoters from breast CAN genes, and 2 were promoters from genes that were frequently mutated in both colon and breast cancer ('dual CAN genes') (TABLE H, Detailed in TABLE G).

Five promoters exhibited tumor-specific hypermethylation in both breast and colon tumors (IGFBP3, UHRF2, LAMA1, ICAM5, PPM1E). One promoter (SORL1) exhibited tumor-specific hypomethylation in both types of cancer. The methylation patterns of ICAM5 and LAMA1 are depicted in FIG. 11 Panels A and B, respectively. Tumor specific promoter methylation of ICAM5[3] and IGFBP3[27] was recently reported in different cohorts of breast and colon cancers. The other three loci are novel observations of aberrant tumor methylation. The frequent hypermethylation of these five loci in both types of tumors indicates that common molecular defects are shared between colon and breast cancer. The molecular defect could be an error in both types of tumors that directs methylation to these loci or it could suggest that the inactivation of these genes is a key step in tumorigenesis in both tissues.

These five loci that are hypermethylated in both breast and colon cancer are methylated in 25% to 75% of tumors (TABLE I). Loci that exhibit frequent tumor-specific methylation are often useful as clinical biomarkers. A valuable biomarker would occur frequently in patients' tumors and would be easily distinguished from normal samples. We calculated the sensitivity and specificity of these loci across our samples. The presence of aberrant methylation at two or more of these five methylated markers is found in 9 out of 12 breast tumors (75%), 11 out of 12 colon tumors (92%), 1 of 12 normal breast (8%) and 1 of 12 normal colon (8%). These strong classifiers of cancer vs. normal samples are good candidates for follow-up studies to evaluate their potential as biomarkers for stratifying disease subtypes or as diagnostic biomarkers that can be detected in peripheral specimens. The frequency of aberrant methylation at these loci approaches the significance of even the most common genetic mutations such as APC or TP53 mutations, which are reported to occur in 40-80% of tumors[28]. This supports the previously proposed hypothesis that epigenetic defects at CAN genes may be more frequent than genetic mutations[3].

Three of the CAN gene promoters show tumor specific methylation in only one type of cancer. Colon tumor specific methylation was found in the promoters of KCNQ5 (NM_019842) and CLSTN2 (NM_022131), and those methylation patterns are depicted in FIG. 11 Panels C and D, respectively. Breast tumor specific methylation was found in the promoter of APC (NM_000038). The frequency of these aberrant events in each tumor type is cataloged in TABLE I and suggests that these loci may represent frequent tumor-specific epimutations which merit follow up investigation in a larger cohort of tumors, adjacent normal and cancer-free patient's tissue.

bi-allelic methylation would indicate that both copies of the gene are inactive. Some patients exhibit different allelic methylation patterns between their tumor and adjacent normal tissue: Colon Cancer Patient 12 has methylation on their A allele across all CpGs in both the tumor and the adjacent normal tissue, but as the tumor formed the C allele acquired methylation, specifically in the region of the promoter most distal from the SNP. This suggests that the accumulation of methylation on each allele can occur in different regions of the locus and can occur at different times in tumor development. This type of allelic analysis is useful for resolving intra-tumor heterogeneity of DNA methylation, identifying heterozygous and homozygous epimutations, and understanding the accumulation of aberrant DNA methylation in different tumors.

Discussion

We have developed a method to perform highly multiplexed bisulfite sequencing of many loci across many patient samples simultaneously. This method is highly sensitive and specific and integrates sample specific DNA barcodes into the library construction so that many samples can be pooled to fully utilize the power of next-generation sequencing. Many methods are being developed to perform genome-wide profiling of DNA methylation in individual samples. Bisulfite Patch PCR provides an efficient workflow to utilize second-generation sequencing to follow up and validate aberrant methylation at many loci across large numbers of samples.

In this proof-of-principle experiment, we applied this method to characterize the promoter methylation of genes

TABLE I

Promoters Exhibiting Tumor Specific Methylation

| Gene | Accession # | Methylated Breast Tumor | Methylated Breast Normal | Methylated Colon Tumor | Methylated Colon Normal |
|---|---|---|---|---|---|
| IGFBP3 | NM_000598 | 8/12 (67%) | 1/12 (8%) | 9/12 (75%) | 3/12 (25%) |
| UHRF2 | NM_152896 | 7/12 (58%) | 1/12 (8%) | 6/12 (50%) | 1/12 (8%) |
| LAMA1 | NM_005559 | 6/12 (50%) | 1/12 (8%) | 8/12 (67%) | 2/12 (17%) |
| ICAM5 | NM_003259 | 4/12 (33%) | 1/12 (8%) | 7/12 (58%) | 0/12 (0%) |
| PPM1E | NM_014906 | 3/12 (25%) | 0/12 (0%) | 5/12 (42%) | 0/12 (0%) |
| KCNQ5* | NM_019842 | 0/10 (0%) | 0/12 (0%) | 11/12 (92%) | 4/12 (33%) |
| CLSTN2* | NM_022131 | 0/8 (0%) | 1/10 (10%) | 5/9 (56%) | 0/10 (0%) |
| APC* | NM_000038 | 2/7 (29%) | 0/3 (0%) | 0/8 (0%) | 0/6 (0%) |
| SORL1** | NM_003105 | 4/12 (33%) | 11/12 (92%) | 0/12 (0%) | 5/12 (42%) |

Gene promoters exhibiting tumor specific hyper- methylation in both breast and colon tumors are not indicated by an * or **.
*Gene promoters exhibiting tumor specific hyper- methylation in one tumor type.
**Gene promoters exhibiting tumor specific hypo- methylation in both breast and colon tumors.

Allelic Tumor Methylation

Figure 12:
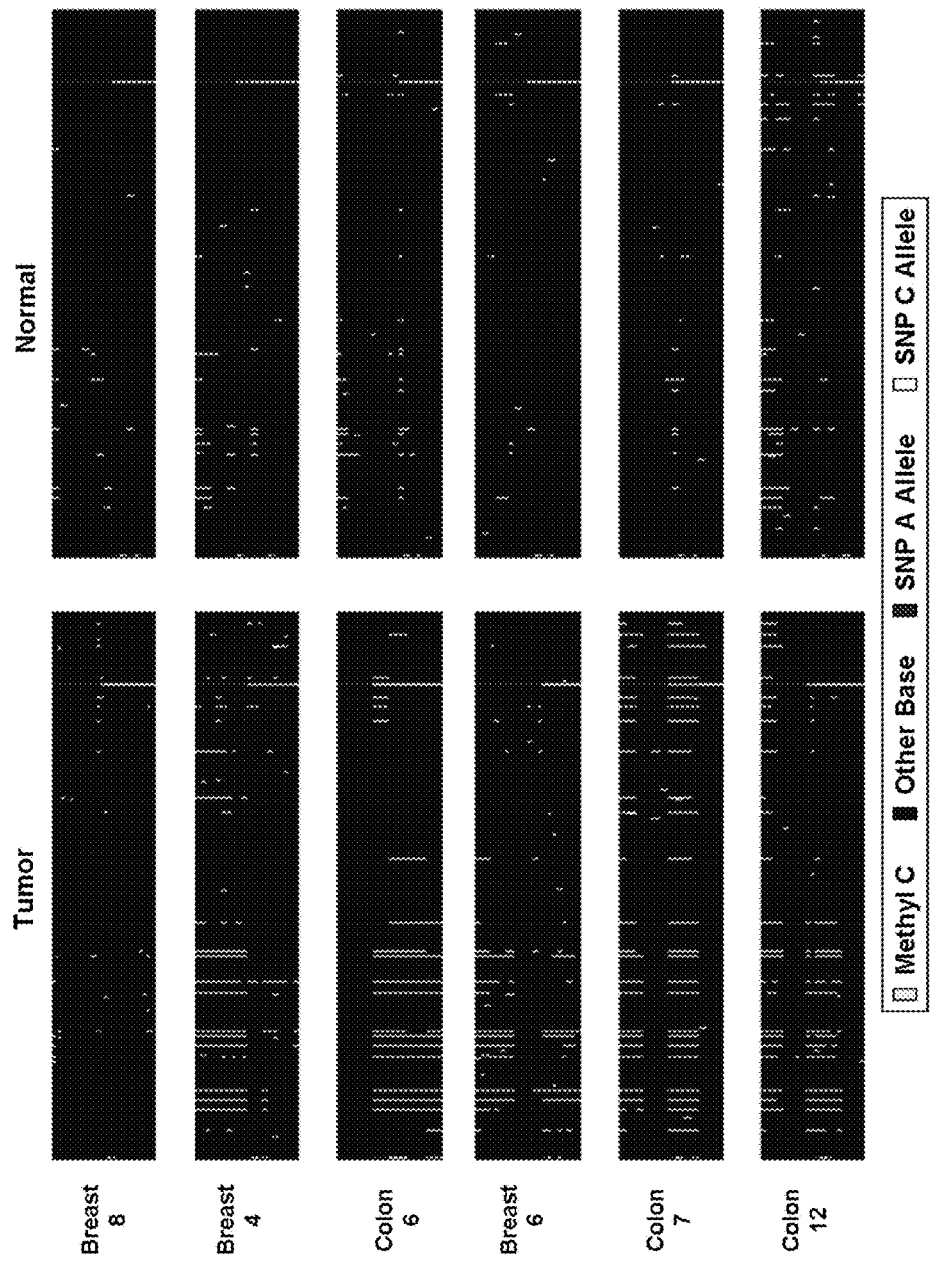
FIG. 12 depicts an illustration of allelic tumor specific methylation. Data from six patients who are germline heterozygous for a SNP (rs2854744) in IGFBP3 promoter. The sequencing reads are aligned as rows in each panel. Each base in the read is color coded to indicate the sequence, yellow indicates a methylated cytosine, blue indicates all other bases. The position of the SNP is indicated by the red and white column, where red indicates reads from the A allele, and the C allele is indicated by yellow, if methylated, or white, if unmethylated and converted to a T. Patient 'Breast 8' is unmethylated on both alleles in both the tumor (left column) and normal tissue (right column). Patients 'Breast 4' and 'Colon 6' display tumor-specific methylation on only one allele, and the methylated allele differs between them. Patients 'Colon 7' and 'Colon 12' display tumor specific methylation on both alleles. Patient 'Colon 12' displays different patterns of methylation on each allele in the tumor.

The single molecule resolution of bisulfite sequencing allows us to simultaneously assess methylation status and identify single nucleotide polymorphisms (SNPs). As seen in FIG. 12, we can distinguish whether tumor specific methylation is occurring on one allele or on both alleles in individuals that are heterozygous for the SNP (rs2854744) in IGFBP3 (NM_000598). Although some aberrant promoter methylation events are known to always occur on both alleles, such as MLH1 promoter methylation[29], we found examples in which aberrant methylation was observed on only one allele: Breast Cancer Patient 4 acquired tumor-specific methylation primarily on the A allele, while Colon Cancer Patient 6 acquired tumor-specific methylation primarily on the C allele (FIG. 12). However, other patients acquired aberrant methylation on both alleles during tumorigenesis, such as Breast Cancer Patient 6 and Colon Cancer Patient 7 (FIG. 12). If associated with silencing, this that are frequently mutated in cancer. From the 94 gene promoters that we analyzed we found that approximately 10% showed tumor specific DNA methylation in breast or colon cancer when compared to adjacent normal tissue. Our data support the previously proposed hypothesis that a relatively small set of genes that are important for tumorigenesis are disrupted in multiple ways in cancers, including frequent epigenetic defects[3]. We found five loci that can be used to classify tumor and normal samples with high sensitivity (9/12 breast tumors, 11/12 colon tumors) and high specificity (1/12 adjacent normal breast tissues, 1/12 adjacent normal colon tissues). In some samples we observed very low-frequency methylation of these loci in the adjacent normal tissue that may represent a field defect surrounding the tumor, or it may be a part of normal variation between individuals. Follow-up studies that include larger cohorts, cancer-free control patients and peripheral samples from patients with cancer will help determine if these new molecular defects can be useful biomarkers in the clinic. We also utilized SNPs in the sequencing data to observe allele-specific methylation patterns that provide insights into the accumulation of aberrant DNA methylation during tumor development. This method would be valuable for comparing the allelic accumulation of methylation across tumors with different stages and grades to understand the timing of aberrant methylation.

The method presented here fills a gap in the arsenal of tools for the characterization of aberrant DNA methylation. It provides the high resolution of bisulfite sequencing with the throughput of sampling many loci across many samples. This enables an experimental scale that promises to be useful in the effort to understand cancer.

Methods

Design of Patch Oligonucleotides

Human promoter sequence between the transcription start site (TSS) and 700 bp upstream of the TSS was downloaded from the March 2006 assembly on the UCSC Genome Browser (www.genome.ucsc.edu) for the RefSeq genes listed in SEQ ID NOs 582-675. These sequences were then scanned for AluI restriction enzyme recognition sequences, and AluI restriction fragments that were between 125 bp and 600 bp in length and containing at least 3CpG positions were selected. A patch oligo was then designed by sequentially including base pairs from the AluI restriction site into the fragment sequence until the Tm of the patch oligo was between 62° C. and 67° C. Any fragment whose patch oligos contained repetitive elements according to the repeat masker track on the UCSC Genome Browser (www.genome.ucsc.edu) were excluded. The patch oligos were then appended with the complement universal primer sequences to result in the appropriate patch sequence. Patch oligonucleotides were synthesized by SigmaGenosys http://www.sigmaaldrich.com/Brands/Sigma_Genosys.html). Ninety-four pairs of patch oligos were ordered in a 96-well plate. The patch oligos for two loci were duplicated on the plate so that when equimolar portions were pooled from each well these two loci were twice as concentrated in the pool. This was used to measure how the concentration of patch oligos affected amplification efficiency during protocol development. Two universal primer sequences were synthesized by IDT (www.idtdna.com), including U2, which has a 5' phosphate and a 3 carbon spacer on the 3' end. Oligonucleotide sequences are listed in TABLE J.

TABLE J

Patch Oligonucleotide Sequences Naming: Refseq Accession Number of Locus, L (left) or R (right) side

| SEQ ID NO: | Oligo Name | Sequence (universal sequence and AluI restricition site in capitals) |
|---|---|---|
| 385 | NM_000110 L | taggtgggcggggtttgAGATCACCAACTACCCACACACC |
| 386 | NM_015149 L | gcaccggcgcggAGATCACCAACTACCCACACACC |
| 387 | NM_015284 L | ttgcccacctggagagcAGATCACCAACTACCCACACACC |
| 388 | NM_182625 L | ggggagaggtctggggaaAGATCACCAACTACCCACACACC |
| 389 | NM_000379 L | attctcagagtcactgctaatagAGATCACCAACTACCCACACACC |
| 390 | NM_177454 L | gcatcaccgccatcattgcttAGATCACCAACTACCCACACACC |
| 391 | NM_004735 L | cctcaggccacgctgAGATCACCAACTACCCACACACC |
| 392 | NM_194293 L | ggggaaacagaggggagaAGATCACCAACTACCCACACACC |
| 393 | NM_183061 L | gggacagtggatttctgacaaagAGATCACCAACTACCCACACACC |
| 394 | NM_024621 L | cttttttcgttatttgctgggaAGATCACCAACTACCCACACACC |
| 395 | NM_001829 L | cagcgtccgggagcAGATCACCAACTACCCACACACC |
| 396 | NM_004395 L | ccattctcagcccctacccAGATCACCAACTACCCACACACC |
| 397 | NM_001012418 L | tgtcaatactctcggatttacaaAGATCACCAACTACCCACACACC |
| 398 | NM_003913 L | aatgcttaaccatctcgctagacAGATCACCAACTACCCACACACC |
| 399 | NM_001858 L | ggtaattggcttttttaacggttgAGATCACCAACTACCCACACACC |
| 400 | NM_016230 L | cactgggaattgtgtactgatgcAGATCACCAACTACCCACACACC |
| 401 | NM_032639 L | tctagtccctattcttgttccaaAGATCACCAACTACCCACACACC |
| 402 | NM_001091 L | gaaggacttggctgggagaaAGATCACCAACTACCCACACACC |
| 403 | NM_007188 L | ccgactggccctccaAGATCACCAACTACCCACACACC |
| 404 | NM_024790 L | gaaagtcagtgccaaaacagcaAGATCACCAACTACCCACACACC |
| 405 | NM_178857 L | ggaggcccgaaagaagcAGATCACCAACTACCCACACACC |
| 406 | NM_005085 L | ttagatgtaggttggctattggtAGATCACCAACTACCCACACACC |
| 407 | NM_017617 L | cgggcggggagcAGATCACCAACTACCCACACACC |

TABLE J-continued

Patch Oligonucleotide Sequences Naming: Refseq
Accession Number of Locus, L (left) or R (right) side

| SEQ ID NO: | Oligo Name | Sequence (universal sequence and AluI restricition site in capitals) |
|---|---|---|
| 408 | NM_006289 L | gtgcccgaggcctacAGATCACCAACTACCCACACACACC |
| 409 | NM_206920 L | aggactcaaccagtccagcAGATCACCAACTACCCACACACACC |
| 410 | NM_004606 L | cgtaaattatacaggcattcccgAGATCACCAACTACCCACACACACC |
| 411 | NM_014976 L | cctcttttcttctgtatgtccatAGATCACCAACTACCCACACACACC |
| 412 | NM_052932 L | tgctcagaactctgaagtgacatAGATCACCAACTACCCACACACACC |
| 413 | NM_025164 L | cttgaggccacaaatgcaggaatAGATCACCAACTACCCACACACACC |
| 414 | NM_001382 L | cacaactcagttcccggaaacaaAGATCACCAACTACCCACACACACC |
| 415 | NM_005422 L | ctggatttcctaattttcactacAGATCACCAACTACCCACACACACC |
| 416 | NM_003920 L | gttttatttgggaggaagtaaagAGATCACCAACTACCCACACACACC |
| 417 | NM_014770 L | tacgatgtaaccctttttcaggcAGATCACCAACTACCCACACACACC |
| 418 | NM_020366 L | tagaactactatgtaaacttgggAGATCACCAACTACCCACACACACC |
| 419 | NM_182932 L | ttgtgagagacgcttgggtgAGATCACCAACTACCCACACACACC |
| 420 | NM_016475 L | ggtcctagtcccgagcgAGATCACCAACTACCCACACACACC |
| 421 | NM_014994 L | ggcccgagggaccgtAGATCACCAACTACCCACACACACC |
| 422 | NM_00499 L | cagagcccgggcgactAGATCACCAACTACCCACACACACC |
| 423 | NM_014699 L | cgggaactttcccttccttcctAGATCACCAACTACCCACACACACC |
| 424 | NM_014906 L | ctaccctcacgtggttaagagtgAGATCACCAACTACCCACACACACC |
| 425 | NM_014772 L | tgtgctaatggcagatgaaaaggAGATCACCAACTACCCACACACACC |
| 426 | NM_003259 L | ctggctgagatgccatgataataAGATCACCAACTACCCACACACACC |
| 427 | NM_018837 L | gccgcgacccgcAGATCACCAACTACCCACACACACC |
| 428 | NM_002473 L | tcggggcgcggagAGATCACCAACTACCCACACACACC |
| 429 | NM_005095 L | caagtctctttgctgccagcAGATCACCAACTACCCACACACACC |
| 430 | NM_004326 L | aaaggaaaaagcaaagtcccattAGATCACCAACTACCCACACACACC |
| 431 | NM_022093 L | ccacacgccaacagtacaagAGATCACCAACTACCCACACACACC |
| 432 | NM_183361 L | ccccgtgaactccgcaAGATCACCAACTACCCACACACACC |
| 433 | NM_024923 L | ctcagccagagagccccaAGATCACCAACTACCCACACACACC |
| 434 | NM_015136 L | cagcccatgctcagccAGATCACCAACTACCCACACACACC |
| 435 | NM_022131 L | ctccactccgactctcggaaaAGATCACCAACTACCCACACACACC |
| 436 | NM_006218 L | ttctacgagcagcaggcgAGATCACCAACTACCCACACACACC |
| 437 | NM_018986 L | ccgcagccggttgatcattAGATCACCAACTACCCACACACACC |
| 438 | NM_033632 L | cacgggacgaggcagaAGATCACCAACTACCCACACACACC |
| 439 | NM_001884 L | acaatgatgatagtggcacataaAGATCACCAACTACCCACACACACC |
| 440 | NM_000038 L | gaattaaaaatagttaccagaaaAGATCACCAACTACCCACACACACC |
| 441 | NM_014005 L | cttctgtccttgattactgcaggAGATCACCAACTACCCACACACACC |
| 442 | NM_005322 L | caagtaacacaggcacaggacAGATCACCAACTACCCACACACACC |
| 443 | NM_019842 L | ctggcaggggctttgcAGATCACCAACTACCCACACACACC |
| 444 | NM_021807 L | attgatgaagaaaagacagtataAGATCACCAACTACCCACACACACC |

TABLE J-continued

Patch Oligonucleotide Sequences Naming: Refseq
Accession Number of Locus, L (left) or R (right) side

| SEQ ID NO: | Oligo Name | Sequence (universal sequence and AluI restriction site in capitals) |
|---|---|---|
| 445 | NM_000598 L | cattcgtgtgtacctcgtggAGATCACCAACTACCCACACACACC |
| 446 | NM_004445 L | ctaaaacagtggggctcctactcAGATCACCAACTACCCACACACACC |
| 447 | NM_015225 L | ccggggaggcactcAGATCACCAACTACCCACACACACC |
| 448 | NM_152896 L | caccgcgctcaacaggaaAGATCACCAACTACCCACACACACC |
| 449 | NM_018702 L | acaatgacacaaaaggaagagaaAGATCACCAACTACCCACACACACC |
| 450 | NM_020752 L | gaggaaagccagtttaaagaggcAGATCACCAACTACCCACACACACC |
| 451 | NM_000314 L | ggctcgtttgccctaaaaatgaaAGATCACCAACTACCCACACACACC |
| 452 | NM_016234 L | caggggggccctggAGATCACCAACTACCCACACACACC |
| 453 | NM_020975 L | caggaggcggggaagAGATCACCAACTACCCACACACACC |
| 454 | NM_000124 L | gcgagcagggcgagaaAGATCACCAACTACCCACACACACC |
| 455 | NM_000855 L | cccatcctgctggagcAGATCACCAACTACCCACACACACC |
| 456 | NM_020693 L | tgtcttcacctacccaccccctatAGATCACCAACTACCCACACACACC |
| 457 | NM_018400 L | attagccactccctagtcctagcAGATCACCAACTACCCACACACACC |
| 458 | NM_024546 L | cacgtttcaattttttttcaaaacAGATCACCAACTACCCACACACACC |
| 459 | NM_003366 L | ggctacatagaatataaaaacttAGATCACCAACTACCCACACACACC |
| 460 | NM_015202 L | cgcacccgggcatcAGATCACCAACTACCCACACACACC |
| 461 | NM_000512 L | aggaggccttcgccgAGATCACCAACTACCCACACACACC |
| 462 | NM_002208 L | cacagaacacgccgttgacAGATCACCAACTACCCACACACACC |
| 463 | NM_000267 L | ctggcgctgggctcAGATCACCAACTACCCACACACACC |
| 464 | NM_005559 L | gattccgagaaactatgtgcccAGATCACCAACTACCCACACACACC |
| 465 | NM_005359 L | caaggagcgcgggagAGATCACCAACTACCCACACACACC |
| 466 | NM_003245 L | ccacccctctcaactcacaaAGATCACCAACTACCCACACACACC |
| 467 | NM_012072 L | ggggctaggaactcgaggaAGATCACCAACTACCCACACACACC |
| 468 | NM_006275 L | tctttcttggagccctggcAGATCACCAACTACCCACACACACC |
| 469 | NM_003253 L | agggagcccctaacaaagcAGATCACCAACTACCCACACACACC |
| 470 | NM_003906 L | gggcgctgccacgaAGATCACCAACTACCCACACACACC |
| 471 | NM_006932 L | cccttctcgcgtcagtgtttaAGATCACCAACTACCCACACACACC |
| 472 | NM_004985 L | CTGACCGGTCTCCACAGAGAAGATCACCAACTACCCACACACACC |
| 473 | NM_007355 L | ccgaaaaagagcggaggcAGATCACCAACTACCCACACACACC |
| 474 | AK311497 L | gattcccatccagttgaccgAGATCACCAACTACCCACACACACC |
| 475 | NM_004387 L | CCCCCGAGAGTCAGGGAGATCACCAACTACCCACACACACC |
| 476 | NM_006941_1 L | CTCCTTCTTGACCTTGCCCAGATCACCAACTACCCACACACACC |
| 477 | NM_005559 L | gattccgagaaactatgtgcccAGATCACCAACTACCCACACACACC |
| 478 | NM_006218 L | ttctacgagcagcaggcgAGATCACCAACTACCCACACACACC |
| 479 | NM_003105 L | ACAGCAAAAACTACCCTTGATCAAGATCACCAACTACCCACACACACC |
| 480 | NM_000546 L | GGTGGAAAATTCTGCAAGCCAGAGATCACCAACTACCCACACACACC |
| 481 | NM_000110 R | CTACCCCACCTTCCTCATTCTCTCTaggcaggcggggc |

TABLE J-continued

Patch Oligonucleotide Sequences Naming: Refseq
Accession Number of Locus, L (left) or R (right) side

| SEQ ID NO: | Oligo Name | Sequence (universal sequence and AluI restricition site in capitals) |
|---|---|---|
| 482 | NM_015149 R | CTACCCCACCTTCCTCATTCTCTCTttttggccctccctctcg |
| 483 | NM_015284 R | CTACCCCACCTTCCTCATTCTCTCTtaccttgtgccgggcc |
| 484 | NM_182625 R | CTACCCCACCTTCCTCATTCTCTCTgcggcggtgttcatgg |
| 485 | NM_000379 R | CTACCCCACCTTCCTCATTCTCTCTtcagggcatgaagagttcttgg |
| 486 | NM_177454 R | CTACCCCACCTTCCTCATTCTCTCTggtagaccctcacagcgtc |
| 487 | NM_004735 R | CTACCCCACCTTCCTCATTCTCTCTccacccgcagggg |
| 488 | NM_194293 R | CTACCCCACCTTCCTCATTCTCTCTgcctttatcttgctggctagtg |
| 489 | NM_183061 R | CTACCCCACCTTCCTCATTCTCTCTtcaggcccatcatctcttactt |
| 490 | NM_024621 R | CTACCCCACCTTCCTCATTCTCTCTtcattaacacttccctctccct |
| 491 | NM_001829 R | CTACCCCACCTTCCTCATTCTCTCTcacgtcagtcactcacgca |
| 492 | NM_004395 R | CTACCCCACCTTCCTCATTCTCTCTtcagccccatgcttagcac |
| 493 | NM_001012418 R | CTACCCCACCTTCCTCATTCTCTCTgttgccttcttagtcagatggg |
| 494 | NM_003913 R | CTACCCCACCTTCCTCATTCTCTCTcttcagtcaatgctagaaatgg |
| 495 | NM_001858 R | CTACCCCACCTTCCTCATTCTCTCTgggagtaatgcctttcaggttt |
| 496 | NM_016230 R | CTACCCCACCTTCCTCATTCTCTCTgttccttagccttggtgctga |
| 497 | NM_032639 R | CTACCCCACCTTCCTCATTCTCTCTgccggtcgcaggc |
| 498 | NM_001091 R | CTACCCCACCTTCCTCATTCTCTCTgacagatggaccagggcag |
| 499 | NM_007188 R | CTACCCCACCTTCCTCATTCTCTCTgtgattggaggatatgttgtca |
| 500 | NM_024790 R | CTACCCCACCTTCCTCATTCTCTCTtaggaacagtgtaagagcctgg |
| 501 | NM_178857 R | CTACCCCACCTTCCTCATTCTCTCTcccaccctgttccagttgt |
| 502 | NM_005085 R | CTACCCCACCTTCCTCATTCTCTCTgggctgagtagtggc |
| 503 | NM_017617 R | CTACCCCACCTTCCTCATTCTCTCTgagccgcgcgtcc |
| 504 | NM_006289 R | CTACCCCACCTTCCTCATTCTCTCTtggggtagaaggcggag |
| 505 | NM_206920 R | CTACCCCACCTTCCTCATTCTCTCTcccacctgcccgg |
| 506 | NM_004606 R | CTACCCCACCTTCCTCATTCTCTCTgctcgagtcacgtggctta |
| 507 | NM_014976 R | CTACCCCACCTTCCTCATTCTCTCTagaaaaaacgaggggcgcaag |
| 508 | NM_052932 R | CTACCCCACCTTCCTCATTCTCTCTgacagatttgttgcttaaatt |
| 509 | NM_025164 R | CTACCCCACCTTCCTCATTCTCTCTggcggtgggaaccttc |
| 510 | NM_001382 R | CTACCCCACCTTCCTCATTCTCTCTaaagggcccgtacctctcc |
| 511 | NM_005422 R | CTACCCCACCTTCCTCATTCTCTCTtgccagagtaaacagaacacca |
| 512 | NM_003920 R | CTACCCCACCTTCCTCATTCTCTCTggaccggtccccg |
| 513 | NM_014770 R | CTACCCCACCTTCCTCATTCTCTCTaggtccgaggtgcaatcctaaa |
| 514 | NM_020366 R | CTACCCCACCTTCCTCATTCTCTCTgtaagagatcccagaggacact |
| 515 | NM_182932 R | CTACCCCACCTTCCTCATTCTCTCTccaggcagcaggcg |
| 516 | NM_016475 R | CTACCCCACCTTCCTCATTCTCTCTgcgggaccgtactcgt |
| 517 | NM_014994 R | CTACCCCACCTTCCTCATTCTCTCTatggtggcacgatcggc |
| 518 | NM_000499 R | CTACCCCACCTTCCTCATTCTCTCTccatcctggggcgc |

TABLE J-continued

Patch Oligonucleotide Sequences Naming: Refseq
Accession Number of Locus, L (left) or R (right) side

| SEQ ID NO: | Oligo Name | Sequence (universal sequence and AluI restriction site in capitals) |
|---|---|---|
| 519 | NM_014699 R | CTACCCCACCTTCCTCATTCTCTCTgagcatggccttttgtcctc |
| 520 | NM_014906 R | CTACCCCACCTTCCTCATTCTCTCTcagcccacgctgccta |
| 521 | NM_014772 R | CTACCCCACCTTCCTCATTCTCTCTgccaagacagcccagtctag |
| 522 | NM_003259 R | CTACCCCACCTTCCTCATTCTCTCTggcaggagtgagcgac |
| 523 | NM_018837 R | CTACCCCACCTTCCTCATTCTCTCTggagggagccaaatgttcc |
| 524 | NM_002473 R | CTACCCCACCTTCCTCATTCTCTCTcggctcctcgccg |
| 525 | NM_005095 R | CTACCCCACCTTCCTCATTCTCTCTtctgagatcccacgggtcc |
| 526 | NM_004326 R | CTACCCCACCTTCCTCATTCTCTCTagttgctgctgcactggtg |
| 527 | NM_022093 R | CTACCCCACCTTCCTCATTCTCTCTcttctgacttccctcctccttc |
| 528 | NM_183361 R | CTACCCCACCTTCCTCATTCTCTCTggctccatccaggcttct |
| 529 | NM_024923 R | CTACCCCACCTTCCTCATTCTCTCTgagggagaaggcttgggg |
| 530 | NM_015136 R | CTACCCCACCTTCCTCATTCTCTCTcaccccacaggaaccc |
| 531 | NM_022131 R | CTACCCCACCTTCCTCATTCTCTCTcgccggcagcagc |
| 532 | NM_006218 R | CTACCCCACCTTCCTCATTCTCTCTgaggaggggcagagcc |
| 533 | NM_018986 R | CTACCCCACCTTCCTCATTCTCTCTggacggagcaggcag |
| 534 | NM_033632 R | CTACCCCACCTTCCTCATTCTCTCTtggttggggcccg |
| 535 | NM_001884 R | CTACCCCACCTTCCTCATTCTCTCTctgtgcccagaccttgtaaag |
| 536 | NM_000038 R | CTACCCCACCTTCCTCATTCTCTCTgcttctctctccgcttccc |
| 537 | NM_014005 R | CTACCCCACCTTCCTCATTCTCTCTatgcttgagattcttttcctga |
| 538 | NM_005322 R | CTACCCCACCTTCCTCATTCTCTCTttttcataagaatccattgggct |
| 539 | NM_019842 R | CTACCCCACCTTCCTCATTCTCTCTcgaattctaaatccggacctg |
| 540 | NM_021807 R | CTACCCCACCTTCCTCATTCTCTCTtttttcagtttccttgctttta |
| 541 | NM_000598 R | CTACCCCACCTTCCTCATTCTCTCTgagactcgcccggg |
| 542 | NM_004445 R | CTACCCCACCTTCCTCATTCTCTCTcctgcctgggctcg |
| 543 | NM_015225 R | CTACCCCACCTTCCTCATTCTCTCTgctgcaaccatggacagc |
| 544 | NM_152896 R | CTACCCCACCTTCCTCATTCTCTCTgaggggcgggtg |
| 545 | NM_018702 R | CTACCCCACCTTCCTCATTCTCTCTgccctgctcagaaagaca |
| 546 | NM_020752 R | CTACCCCACCTTCCTCATTCTCTCTgctgctgctgctgc |
| 547 | NM_000314 R | CTACCCCACCTTCCTCATTCTCTCTgagatgggtgcgttgagc |
| 548 | NM_016234 R | CTACCCCACCTTCCTCATTCTCTCTgcctgccttggtctctgaa |
| 549 | NM_020975 R | CTACCCCACCTTCCTCATTCTCTCTcagtgcgggacgcg |
| 550 | NM_000124 R | CTACCCCACCTTCCTCATTCTCTCTcaaccatagacaccgccc |
| 551 | NM_000855 R | CTACCCCACCTTCCTCATTCTCTCTcgggtcggactgaggg |
| 552 | NM_020693 R | CTACCCCACCTTCCTCATTCTCTCTgcccttccaacccctc |
| 553 | NM_018400 R | CTACCCCACCTTCCTCATTCTCTCTcttttcaggcaatgatgtcatct |
| 554 | NM_024546 R | CTACCCCACCTTCCTCATTCTCTCTgcaagattcctgcgaatgtgta |
| 555 | NM_003366 R | CTACCCCACCTTCCTCATTCTCTCTccgtgaaacaggggcct |

TABLE J-continued

Patch Oligonucleotide Sequences Naming: Refseq
Accession Number of Locus, L (left) or R (right) side

| SEQ ID NO: | Oligo Name | Sequence (universal sequence and AluI restriction site in capitals) |
|---|---|---|
| 556 | NM_015202 R | CTACCCCACCTTCCTCATTCTCTCTccacttactgagcccgc |
| 557 | NM_000512 R | CTACCCCACCTTCCTCATTCTCTCTgtgtgcggatggggc |
| 558 | NM_002208 R | CTACCCCACCTTCCTCATTCTCTCTtccagcccagggtcctc |
| 559 | NM_000267 R | CTACCCCACCTTCCTCATTCTCTCTagagattgagagcgcggct |
| 560 | NM_005559 R | CTACCCCACCTTCCTCATTCTCTCTtggcctctgggtccc |
| 561 | NM_005359 R | CTACCCCACCTTCCTCATTCTCTCTttcctttctcccggctgc |
| 562 | NM_003245 R | CTACCCCACCTTCCTCATTCTCTCTtggggagaaggggggcag |
| 563 | NM_012072 R | CTACCCCACCTTCCTCATTCTCTCTctgccgggtccctgg |
| 564 | NM_006275 R | CTACCCCACCTTCCTCATTCTCTCTcgggaggcgggct |
| 565 | NM_003253 R | CTACCCCACCTTCCTCATTCTCTCTccgattgggccgcc |
| 566 | NM_003906 R | CTACCCCACCTTCCTCATTCTCTCTatgttctgctacaagtctaaga |
| 567 | NM_006932 R | CTACCCCACCTTCCTCATTCTCTCTgcccgtccagccg |
| 568 | NM_004985 R | CTACCCCACCTTCCTCATTCTCTCTATCGATGCGTTCCGCG |
| 569 | NM_007355 R | CTACCCCACCTTCCTCATTCTCTCTactgcgtgccccaagtc |
| 570 | AK311497 R | CTACCCCACCTTCCTCATTCTCTCTgcgggtccctggg |
| 571 | NM_004387 R | CTACCCCACCTTCCTCATTCTCTCTAAGACACCAGGCTGCAGGAT |
| 572 | NM_006941_1 R | CTACCCCACCTTCCTCATTCTCTCTTCCTGCGCGCTGC |
| 573 | NM_005559 R | CTACCCCACCTTCCTCATTCTCTCTtggcctctgggtccc |
| 574 | NM_006218 R | CTACCCCACCTTCCTCATTCTCTCTgaggaggggcagagcc |
| 575 | NM_003105 R | CTACCCCACCTTCCTCATTCTCTCTCCTAGAACGCAACCAACAAGA |
| 576 | NM_000546 R | CTACCCCACCTTCCTCATTCTCTCTGGACAGTCGCCATGACAA |
| | Universal Primers | |
| 577 | U1 | GGT GTG TGT GGG TAG TTG GTG AT |
| 578 | U2 | /5Phos/AGA GAA TGA GGA AGG TGG GGT AG/3SpC3/ |
| 579 | U2' | CTA CCC CAC CTT CCT CAT TCT CT |
| 580 | 454A: Sample Specific Barcode: U1 | GCC TCC CTC GCG CCA TCA G (5bp barcode) GGT GTG TGT GGG TAG TTG GTG AT |
| 581 | 454B: Sample Specific Barcode: U2' | GCC TTG CCA GCC CGC TCA G (5bp barcode) CTA CCC CAC CTT CCT CAT TCT CT |

Bisulfite Patch PCR

Genomic DNA from cancer and adjacent normal tissue was obtained from Biochain (www.biochain.com) for both breast (catalog number D8235086) and colon (catalog number 8235090). Patient information and lot numbers are listed in TABLE F. Each patient sample was aliquoted into a well of a 96-well plate and digested with the AluI restriction endonuclease in 10 ul total volume reaction containing 250 ng DNA, 10 units (U) AluI enzyme (NEB), and 1× NEBuffer 2 (NEB). This reaction was incubated at 37° C. for 1 hour, followed by heat inactivation of the enzyme at 65° C. for 20 min, and held at 4° C. until the subsequent step.

Patch driven ligation of the universal primers to selected fragments was performed by addition of more reactants to the initial tube to result in the following final concentrations: 2 nM each Patch oligo, 200 nM U1 primer, 200 nM U2 primer (contains 5' phosphate and 3' three carbon spacer), 5 U Ampligase (Epicentre), and 1× Ampligase Reaction Buffer (Epicentre) in a total volume of 25 ul. This reaction was incubated at 95° C. for 15 minutes followed by (94° C. for 30 sec, 65° C. for 8 min) for 100 cycles, and held at 4° C.

Incorrect products, template genomic DNA and excess primer were degraded by the direct addition of 10 U Exonuclease I (USB) and 200 U Exonuclease III (Epicentre) to the reaction. This mix was incubated at 37° C. for 1 hour followed by heat inactivation at 95° C. for 20 minutes, and held at 4° C.

The reactions were then treated with sodium bisulfite to convert unmethylated cytosines to uracil. This was achieved by using the EZ DNA Methylation Gold Bisulfite Treatment Kit (Zymo Research) following the manufacturer's instructions, with one exception. Since the sample volume after the exonuclease treatment is 27 ul, the CT Conversion Reagent from the kit is made by adding 830 ul dH2O instead of 900 ul dH2O. The DNA is eluted from the columns in the final step with 10 ul M-Elution buffer.

The universal primers are then used to PCR amplify the selected bisulfite converted loci from each sample. A different pair of universal primers is used to PCR amplify each sample, and they are distinguished by a five base-pair sample-specific DNA barcode that resides between the universal primer sequence and the 454 machine specific sequence (TABLE J). There are 1,024 possible 5 bp DNA sequences, and we selected 48 sample-specific barcodes, one for each sample, that did not contain homopolymers and had the least sequence similarity to each other (The barcodes used for each patient are listed in TABLE F). For the PCR we added reagents to the last 10 ul column elution to result in these final concentrations in 50 ul: 0.5 uM each Barcoded U1, 0.5 uM each Barcoded U2', 10 U Platinum Taq Polymerase (Invitrogen), 0.5 mM each dNTP, 2 mM $MgCl_2$, 0.5M Betaine, 20 mM Tris-HCl pH 8.4 and 50 mM KCl. This reaction was incubated at 93° C. for 2 minutes followed by (93° C. for 30 sec, 57° C. for 6 min) for 35 cycles, and held at 4° C. The PCR product smear between the expected sizes was confirmed by running 20 ul of the PCR product from each sample on a 3% Metaphor Agarose gel (Lonza). We then pooled 5 ul from each sample into a single tube and purified this pool on a Qiaquick Spin Column (Qiagen). The eluted DNA was quantified on the Nanodrop (www.nanodrop.com) as well as on a plate reader (BioTek Synergy HT) using PicoGreen (Invitrogen) following the manufacturer's instructions. This pooled sample was then prepared and sequenced on the 454 Life Sciences/Roche FLX machine following the manufacturer's instructions.

Sequencing Data Analysis

We obtained 97,115 sequencing reads. To determine which sequences matched our targets, we aligned the reads against a database of reference sequences for each target using WU-BLASTN (http://blast.wustl.edu). Since the sequences are sodium bisulfite treated, we substituted a T in place of C in the genomic sequence at non-CpG positions in the reference sequences. We then determined how many reads matched significantly to each promoter (BLAST smallest sum probability (P)<0.001), and put all reads from each promoter in a separate file. We computed the correlation between the number of reads and the amplicon length for each promoter using linear regression. We identified which sample each read came from by matching the first five bases of the read to the list of sample-specific barcode and corresponding patients. To determine the reproducibility of the method, we computed number of reads for each locus in each sample, and calculated the squared correlation coefficient ($R^2$) between two samples for all possible pairs of samples. The mean of these correlation coefficients represents the average correlation between the number of reads per locus across samples. For each promoter, we used CLUSTALW to generate a multiple sequence alignment of all of the reads and the reference sequence (Larkin et al. 2007). We identified germline SNPs in the sequences by looking for variants in the reads and comparing these to known SNPs reported on the UCSC Genome Browser (www.genome.ucsc.edu). To visualize these multiple sequence alignments we create one matrix per promoter where the first column identifies the sample from which the read originated (1-48), and the remaining columns are coded for the base in the read, where C's are replaced with 8, the two alleles at SNP positions are replaced with 5 and 12, and the remaining bases are converted to 0. This matrix was then visualized as an image using the Matlab software package (The Mathworks). The matrix was sorted by sample type (the first column) and further calculations regarding the amount of methylation per read and per sample were computed using Matlab (The MathWorks Inc.).

To quantify the sensitivity and specificity of each locus exhibiting tumor-specific methylation we used a threshold to classify a locus as methylated or unmethylated in each sample. We queried many CpGs for each locus with the bisulfite sequencing. We used this information to find the optimal classifier of DNA methylation to distinguish tumor and normal samples. We search across all possible values for two parameters: % of CpGs per molecule and % of reads per sample. We found that the optimal classifier between tumor and normal was to classify a sample as 'methylated' if more than 20% of CpG positions per molecule were methylated in more than 35% of molecules. The fraction of samples that were classified as methylated is listed in TABLE I for each locus.

REFERENCES FOR EXAMPLE 7

1. Lyko, F. & Brown, R. DNA methyltransferase inhibitors and the development of epigenetic cancer therapies. J Natl Cancer Inst 97, 1498-1506 (2005).
2. Baylin, S. B., Herman, J. G., Graff, J. R., Vertino, P. M. & Issa, J. P. Alterations in DNA methylation: a fundamental aspect of neoplasia. Adv Cancer Res 72, 141-196 (1998).
3. Chan, T. A. et al. Convergence of mutation and epigenetic alterations identifies common genes in cancer that predict for poor prognosis. PLoS medicine 5, e114 (2008).
4. Jun, H. J. et al. Epigenetic regulation of c-ROS receptor tyrosine kinase expression in malignant gliomas. Cancer research 69, 2180-2184 (2009).
5. Nabilsi, N. H., Broaddus, R. R. & Loose, D. S. DNA methylation inhibits p53-mediated survivin repression. Oncogene 28, 2046-2050 (2009).
6. Klarmann, G. J., Decker, A. & Farrar, W. L. Epigenetic gene silencing in the Wnt pathway in breast cancer. Epigenetics 3, 59-63 (2008).
7. Suzuki, H. et al. Frequent epigenetic inactivation of Wnt antagonist genes in breast cancer. Br J Cancer 98, 1147-1156 (2008).
8. Esteller, M. et al. Inactivation of the DNA-repair gene MGMT and the clinical response of gliomas to alkylating agents. The New England journal of medicine 343, 1350-1354 (2000).
9. Widschwendter, M. et al. Association of breast cancer DNA methylation profiles with hormone receptor status and response to tamoxifen. Cancer research 64, 3807-3813 (2004).
10. Laird, P. W. Cancer epigenetics. Hum Mol Genet 14 Spec No 1, R65-76 (2005).
11. Ushijima, T. Detection and interpretation of altered methylation patterns in cancer cells. Nat Rev Cancer 5, 223-231 (2005).

12. Eads, C. A. et al. MethyLight: a high-throughput assay to measure DNA methylation. Nucleic acids research 28, E32 (2000).
13. Ehrich, M. et al. Quantitative high-throughput analysis of DNA methylation patterns by base-specific cleavage and mass spectrometry. Proceedings of the National Academy of Sciences of the United States of America 102, 15785-15790 (2005).
14. Frommer, M. et al. A genomic sequencing protocol that yields a positive display of 5-methylcytosine residues in individual DNA strands. Proceedings of the National Academy of Sciences of the United States of America 89, 1827-1831 (1992).
15. Cokus, S. J. et al. Shotgun bisulphite sequencing of the Arabidopsis genome reveals DNA methylation patterning. Nature 452, 215-219 (2008).
16. Meissner, A. et al. Genome-scale DNA methylation maps of pluripotent and differentiated cells. Nature 454, 766-770 (2008).
17. Ball, M. P. et al. Targeted and genome-scale strategies reveal gene-body methylation signatures in human cells. Nature biotechnology 27, 361-368 (2009).
18. Deng, J. et al. Targeted bisulfite sequencing reveals changes in DNA methylation associated with nuclear reprogramming. Nature biotechnology 27, 353-360 (2009).
19. Hodges, E. et al. High definition profiling of mammalian DNA methylation by array capture and single molecule bisulfite sequencing. Genome research (2009).
20. Korshunova, Y. et al. Massively parallel bisulphite pyrosequencing reveals the molecular complexity of breast cancer-associated cytosine-methylation patterns obtained from tissue and serum DNA. Genome research 18, 19-29 (2008).
21. Taylor, K. H. et al. Ultradeep bisulfite sequencing analysis of DNA methylation patterns in multiple gene promoters by 454 sequencing. Cancer research 67, 8511-8518 (2007).
22. Varley, K. E., Mutch, D. G., Edmonston, T. B., Goodfellow, P. J. & Mitra, R. D. Intra-tumor heterogeneity of MLH1 promoter methylation revealed by deep single molecule bisulfite sequencing. Nucleic acids research (2009).
23. Varley, K. E. & Mitra, R. D. Nested Patch PCR enables highly multiplexed mutation discovery in candidate genes. Genome research 18, 1844-1850 (2008).
24. Wood, L. D. et al. The genomic landscapes of human breast and colorectal cancers. Science 318, 1108-1113 (2007).
25. Kim, J. Y., Tavare, S. & Shibata, D. Human hair genealogies and stem cell latency. BMC biology 4, 2 (2006).
26. Munson, K., Clark, J., Lamparska-Kupsik, K. & Smith, S. S. Recovery of bisulfite-converted genomic sequences in the methylation-sensitive QPCR. Nucleic acids research 35, 2893-2903 (2007).
27. Tomii, K. et al. Aberrant promoter methylation of insulin-like growth factor binding protein-3 gene in human cancers. International journal of cancer 120, 566-573 (2007).
28. Sjoblom, T. et al. The consensus coding sequences of human breast and colorectal cancers. Science (New York, N.Y 314, 268-274 (2006).
29. Veigl, M. L. et al. Biallelic inactivation of hMLH1 by epigenetic gene silencing, a novel mechanism causing human MSI cancers. Proceedings of the National Academy of Sciences of the United States of America 95, 8698-8702 (1998).
30. Comprehensive genomic characterization defines human glioblastoma genes and core pathways. Nature 455, 1061-1068 (2008).

Figure 13:
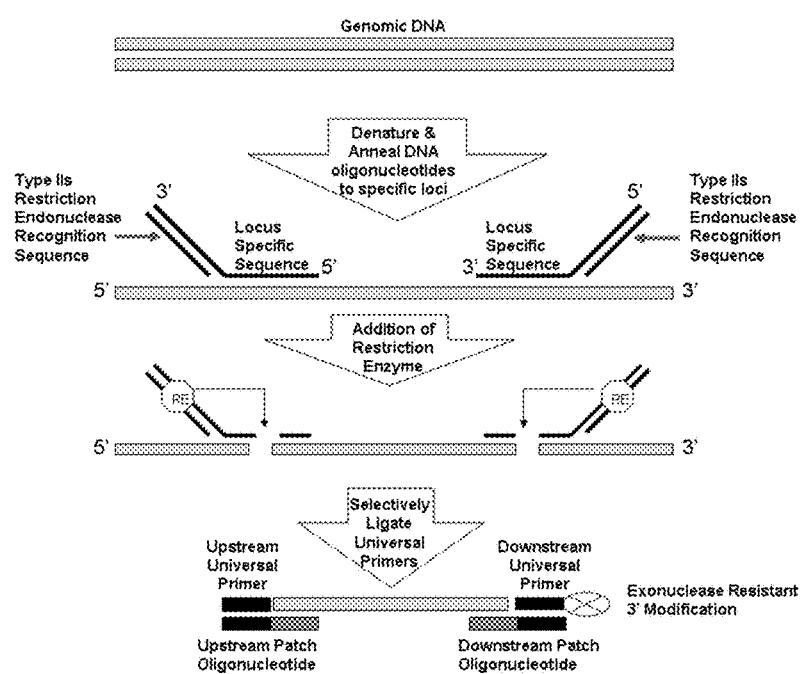
FIG. 13 depicts a schematic of nucleic acid patch PCR with ends defined by oligo-directed FokI digestion. FokI-directing DNA oligonucleotides anneal upstream and downstream of target nucleic acid sequence in genomic DNA. These oligonucleotides contain a FokI restriction endonuclease recognition sequence, which directs FokI digestion of genomic DNA, defining the ends of the PCR template. Nucleic acid patch oligonucleotides are then annealed to the target amplicons and serve as a patch between the correct amplicons and universal primers. The universal primers are then ligated to the amplicons. The universal primer on the 3' end of the amplicon is modified with a 3 carbon spacer that protects the selected amplicon from the final exonuclease reaction that degrades nonspecific products. The selected amplicons are then amplified together simultaneously by PCR with universal primers.

Example 8: Nucleic Acid Patch PCR with Ends Defined by Oligonucleotide-Directed FokI Digestion This example details creating defined ends of a nucleic acid sequence by using oligonucleotide-directed digestion on nucleic acid templates. The method is depicted in FIG. 13.

Template Preparation

FokI-directing DNA oligonucleotides were designed to anneal upstream and downstream of each of 96 targeted exons in the human genome. These loci were selected because they are genes implicated in pediatric acute lymphoblastic leukemia. The oligos contained the recognition sequence of the FokI restriction endonuclease. Human genomic DNA from the blood of healthy individuals (Promega) was incubated with FokI-directing oligonucleotides in a reaction containing appropriate buffer for the FokI enzyme, NEBuffer3 (NEB) and a final concentration of 0.1% Tween80 (Sigma) in a total volume of 9 ul. This mixture was denatured at 98° C. for 15 minutes and held at 37° C. for 5 minutes. FokI enzyme (NEB) was then added to the reaction so that there was 4 U of enzyme in a 10 ul reaction. The reaction was incubated at 37° C. for 1 hour, followed by heat inactivation of the enzyme at 65° C. for 20 min, and held at 4° C. until the subsequent step. Control reactions lacking Tween80, FokI-directing oligonucleotides, FokI enzyme, or genomic DNA were also performed.

Nucleic Acid Patch Ligation

Nucleic acid patch oligos were designed as described in Example 2 but were designed to anneal adjacent to the FokI-digested cut sites upstream and downstream of a targeted 96 exons in the human genome. Nucleic Acid Patch driven ligation of the universal primers to selected fragments was performed essentially as in Example 2. Briefly, the following reactants were added to the FokI digest to result in the following final concentrations: 2 nM each Nucleic Acid Patch oligo, 200 nM Universal Primer 1, 200 nM Universal Primer 2 with 5' phosphate and 3' three carbon spacer, 5 U Ampligase (Epicentre), and 1× Ampligase Reaction Buffer (Epicentre) in a total volume of 25 ul. This reaction was incubated at 95° C. for 15 minutes followed by (94° C. for 30 sec, 65° C. for 8 min) for 100 cycles, and held at 4° C.

Incorrect products, template genomic DNA and excess primer were degraded by the direct addition of 10 U Exonuclease I (USB) and 200 U Exonuclease III (Epicentre) to the reaction. This mix was incubated at 37° C. for 1 hour followed by heat inactivation at 95° C. for 20 minutes and then held at 4° C.

PCR Amplification

The universal primers were then used to PCR amplify the selected loci from each sample. For the PCR, reagents were added to the reactions to result in these final concentrations in 50 ul: 0.5 uM each Universal Primer, 10 U Platinum Taq Polymerase (Invitrogen), 0.5 mM each dNTP, 2 mM MgCl2, 0.5M Betaine, 20 mM Tris-HCl pH 8.4 and 50 mM KCl.

This reaction was incubated at 93° C. for 2 minutes followed by (93° C. for 30 sec, 57° C. for 6 min) for 35 cycles, and held at 4° C. An aliquot of the reactions was analyzed by gel elctrophoresis on a 2% agarose gel (Lonza).

Results

Figure 14:
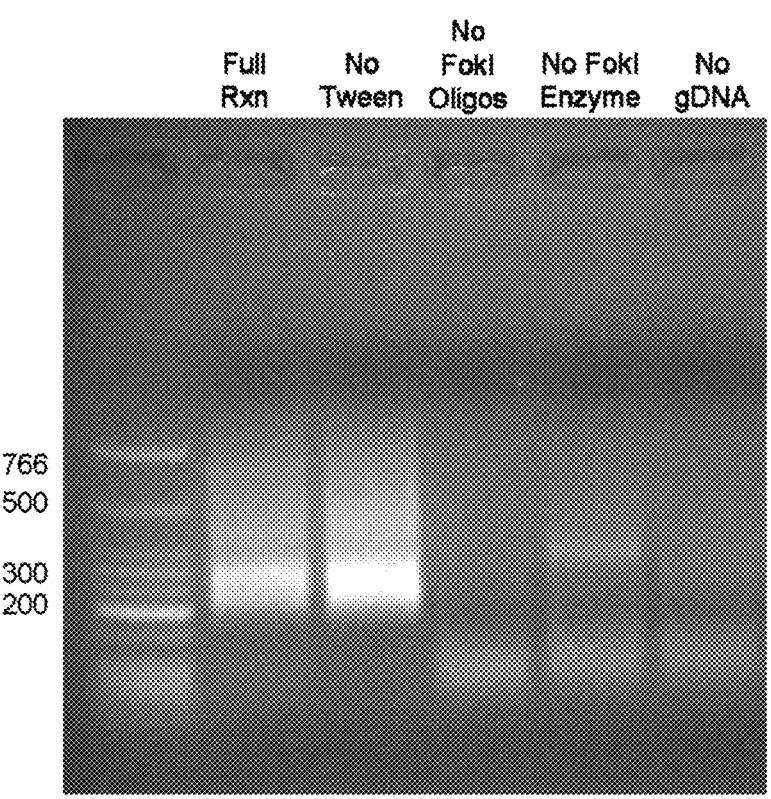
FIG. 14 shows an image of the agarose gel electrophoresis of the final Universal PCR products of nucleic acid patch PCR with ends defined by oligo-directed FokI digestion. The first lane contains Low Molecular Weight Ladder (NEB), with band sizes denoted on the left. The second lane contains the full reaction and a smear of products in the expected size range is achieved. The remaining lanes are each missing a component of the reaction, demonstrating that all components of the reactions (except Tween) are required to obtain the expected products.

Defining template ends using oligo-directed FokI digestion was successful (FIG. 14). A smear of PCR products of the expected sizes was detected on the agarose gel.

What is claimed is:

1. A method of amplifying at least two different nucleic acid sequences, the method comprising:
   a) creating known 5' and 3' ends of at least two nucleic acid sequences by:
      i) annealing oligonucleotides to the at least two nucleic acid sequences, wherein the oligonucleotides comprise a locus specific sequence and form a hairpin structure comprising a Type IIS restriction enzyme recognition sequence, and
      ii) contacting the at least two nucleic acid sequences with a Type IIS restriction enzyme, under conditions suitable for the enzymes to cleave the at least two nucleic acid sequences creating known 5' and 3' ends,
   b) annealing an upstream and a downstream nucleic acid patch to each nucleic acid sequence of known ends from step (a), and annealing an upstream universal primer to the upstream patch, and a downstream universal primer to the downstream patch;
   c) ligating the upstream universal primer and the downstream universal primer to each nucleic acid sequence; and
   d) amplifying the nucleic acid sequences of step (c).

2. The method of claim 1, wherein each nucleic acid sequence is encoded by genomic DNA.

3. The method of claim 1, wherein the downstream universal primer comprises a protecting group.

4. The method of claim 1, further comprising sequencing the products of step (d).

5. The method of claim 4, wherein the amplifying of step (d) is performed with an upstream and a downstream amplification primer, wherein the upstream amplification primer comprises a first universal sequence and a sequence corresponding to the upstream universal primer of step (b), and wherein the downstream amplification primer comprises a second universal sequence and a sequence corresponding to the downstream universal primer of step (b), wherein the products of step (d) are sequenced using an upstream and a downstream sequencing primer corresponding to the first and second universal sequences, respectively.

6. The method of claim 1, wherein step (c) additionally includes treating the ligated nucleic acid sequences with bisulfite, wherein the amplifying of step (d) amplifies the bisulfite-treated nucleic acid sequences.

7. The method of claim 1, wherein the oligonucleotides comprise a locus specific sequence comprising 10 or more bases.

8. A method of amplifying at least two different nucleic acid sequences, the method comprising:
   a) creating known 5' and 3' ends of at least two nucleic acid sequences by:
      i) annealing oligonucleotides to the at least two nucleic acid sequences, wherein the oligonucleotides comprise a locus specific sequence comprising 10 or more bases and a Type IIS restriction enzyme recognition sequence, and ii) contacting the at least two nucleic acid sequences with a Type IIS restriction enzyme, under conditions suitable for the enzymes to cleave the at least two nucleic acid sequences creating known 5' and 3' ends, b) annealing an upstream and a downstream nucleic acid patch to each nucleic acid sequence of known ends from step (a), and annealing an upstream universal primer to the upstream patch, and a downstream universal primer to the downstream patch;

c) ligating the upstream universal primer and the downstream universal primer to each nucleic acid sequence; and d) amplifying the nucleic acid sequences of step (c).

9. The method of claim 8, wherein each nucleic acid sequence is encoded by genomic DNA.

10. The method of claim 8, wherein the downstream universal primer comprises a protecting group.

11. The method of claim 8, further comprising sequencing the products of step (d).

12. The method of claim 11, wherein the amplifying of step (d) is performed with an upstream and a downstream amplification primer, wherein the upstream amplification primer comprises a first universal sequence and a sequence corresponding to the upstream universal primer of step (b), and wherein the downstream amplification primer comprises a second universal sequence and a sequence corresponding to the downstream universal primer of step (b), wherein the products of step (d) are sequenced using an upstream and a downstream sequencing primer corresponding to the first and second universal sequences, respectively.

13. The method of claim 8, wherein step (c) additionally includes treating the ligated nucleic acid sequences with bisulfite, wherein the amplifying of step (d) amplifies the bisulfite-treated nucleic acid sequences.

14. The method of claim 8, wherein the oligonucleotides form a hairpin structure comprising the Type IIS restriction enzyme recognition sequence.

15. A method of detecting short tandem repeats, the method comprising:

a) creating known 5' and 3' ends of at least two nucleic acid sequences, wherein the known 5' and 3' ends are immediately adjacent to a short tandem repeat, by:

i) annealing oligonucleotides to the at least two nucleic acid sequences, wherein the oligonucleotides comprise a locus specific sequence and a Type IIS restriction enzyme recognition sequence, and ii) contacting the at least two nucleic acid sequences with a Type IIS restriction enzyme, under conditions suitable for the enzymes to cleave the at least two nucleic acid sequences creating known 5' and 3' ends, b) annealing an upstream and a downstream nucleic acid patch to each nucleic acid sequence of known ends from step (a), and annealing an upstream universal primer to the upstream patch, and a downstream universal primer to the downstream patch;

c) ligating the upstream universal primer and the downstream universal primer to each nucleic acid sequence;

d) amplifying the nucleic acid sequences of step (c); and e) sequencing the products of step (d) to detect the length of the short tandem repeat.

16. The method of claim 15, wherein each nucleic acid sequence is encoded by genomic DNA.

17. The method of claim 15, wherein the downstream universal primer comprises a protecting group.

18. The method of claim 15, wherein the amplifying of step (d) is performed with an upstream and a downstream amplification primer, wherein the upstream amplification primer comprises a first universal sequence and a sequence corresponding to the upstream universal primer of step (b), and wherein the downstream amplification primer comprises a second universal sequence and a sequence corresponding to the downstream universal primer of step (b), wherein the products of step (d) are sequenced using an upstream and a downstream sequencing primer corresponding to the first and second universal sequences, respectively.

19. The method of claim 15, wherein step (c) additionally includes treating the ligated nucleic acid sequences with bisulfite, wherein the amplifying of step (d) amplifies the bisulfite-treated nucleic acid sequences.

20. The method of claim 15, wherein the oligonucleotides form a hairpin structure comprising the Type IIS restriction enzyme recognition sequence.

21. The method of claim 15, wherein the oligonucleotides comprise a locus specific sequence comprising 10 or more bases.

* * * * *

UNITED STATES PATENT AND TRADEMARK OFFICE
CERTIFICATE OF CORRECTION

PATENT NO. : 9,909,170 B2
APPLICATION NO. : 14/599056
DATED : March 6, 2018
INVENTOR(S) : Robi M. Mitra and Katherine E. Varley Page 1 of 1

It is certified that error appears in the above-identified patent and that said Letters Patent is hereby corrected as shown below:

In the Specification

Column 1, Lines 16-20 delete the following heading and paragraph:
"GOVERNMENTAL RIGHTS
This invention was made with government support under tP50HG003170-0 awarded by the National Institutes of Health. The government has certain rights in the invention."

Signed and Sealed this
Fifth Day of May, 2020

Andrei Iancu
*Director of the United States Patent and Trademark Office*